United States Patent [19]

Aono et al.

[11] Patent Number: 5,753,664

[45] Date of Patent: May 19, 1998

[54] HETEROCYCLIC COMPOUNDS, THEIR PRODUCTION AND USE

[75] Inventors: Tetsuya Aono, Kyoto; Shogo Marui, Hyogo; Fumio Itoh, Osaka; Masuo Yamaoka, Hyogo; Masafumi Nakao, Nara, all of Japan

[73] Assignee: Takeda Chemical Industries, Ltd., Osaka, Japan

[21] Appl. No.: 614,893

[22] Filed: Mar. 13, 1996

[30] Foreign Application Priority Data

Mar. 16, 1995 [JP] Japan .................. 7-056869
Jul. 27, 1995 [JP] Japan .................. 7-191770

[51] Int. Cl.$^6$ .................. C07D 239/00; C07D 239/72; A61K 31/505; A61K 31/435

[52] U.S. Cl. .................. 514/258; 544/282; 544/295; 544/296; 544/283; 544/284; 544/285; 544/286; 544/287; 544/288; 544/289; 544/290; 544/291; 544/292; 544/293; 544/255; 544/281; 544/253; 544/224; 544/238; 544/233; 544/234; 514/259; 514/260

[58] Field of Search .................. 544/282; 514/258

[56] References Cited

U.S. PATENT DOCUMENTS

| | | |
|---|---|---|
| 4,342,870 | 8/1982 | Kennis et al. .................. 544/282 |
| 5,324,729 | 6/1994 | Allen et al. .................. 514/258 |
| 5,486,525 | 1/1996 | Summers, Jr. et al. .................. 514/303 |

FOREIGN PATENT DOCUMENTS

| | | |
|---|---|---|
| 0339105 | 11/1989 | European Pat. Off. . |
| 0339976 | 11/1989 | European Pat. Off. . |
| 0492316 | 7/1992 | European Pat. Off. . |
| 0530537 | 3/1993 | European Pat. Off. . |
| 0530579 | 3/1993 | European Pat. Off. . |
| WO 07869 | 4/1994 | WIPO . |

*Primary Examiner*—Matthew V. Grumbling
*Attorney, Agent, or Firm*—Fitzpatrick, Cella, Harper & Scinto

[57] ABSTRACT

A novel compound of the formula:

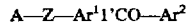

$$A-Z-Ar^1-CO-Ar^2$$

wherein A is a condensed pyrimidinone or condensed pyridazinone ring; $Ar^1$ and $Ar^2$ are independently a ring; Z is a divalent group, or a salt thereof which have an excellent antitumor activity.

6 Claims, No Drawings

HETEROCYCLIC COMPOUNDS, THEIR PRODUCTION AND USE

BACKGROUND OF THE INVENTION

1. Field of the Invention

The present invention relates to novel ketone derivatives and salts thereof having antitumor activity, their production and pharmaceutical use thereof.

2. Description of the Prior Art

Pancreas cancer, which has been known as a refractory solid cancer, tends to have caused metastasis or cancerous peritonitis by the time it is discovered and, therefore, can hardly be treated by surgery. If the cancer is resectable, the prognosis is often poor. Such malignant or postperative cancer patients receive mono-drug therapies of 5-fluorouracil (5-FU) alone or multiple-drugs therapies in combination with some chemotherapeutic agents such as 5-FU and mitomycin. In case of non-hormone dependent cancer (e.g. prostate cancer, brest cancer, etc.) which has been known as a refractory solid cancer and its recurrent or metastatic cancer, mono-drug or multiple-drugs therapies using various chemotherapeutic agents such as adriamycin, cisplatin, mitomycin, 5-FU, etc. have been practiced. For treatment of lung cancer, multiple-drug therapies using cisplatin, carboplatin, etoposide, mitomycin, cyclophosphamide, etc. are being relied on. However, therapies using these drugs have not been rewarded with satisfactory results.

Diarylketone derivatives have been developed as clinical drugs as antiphlogistic, analgesic, antipyretic (ketoprofen, tiaprofenic acid) and antihyperlipemic agents (fenofibrate). Diarylketone denvatives are described as miticidal and insecticidal agents in JP06-762-B, JP60-54370-A, JP61-112057-A, JP61-112058-A, EP-183212, EP-210647, EP-339105, JP64-34971, EP-302346, JP03-220717-A, and described as antiallergic agents in JP61-260018-A. Pyrimidine derivatives are described as insecticidal and miticidal agents in JP01-190670-A, JP01-261371-A, and is described as a herbicidal agent in JP06-73022-A. Pyrimidinone derivatives are disclosed as pesticides in US 4,908,379. Azole derivatives are disclosed as antiprotozoal agents in US-3833603, US-4472421, and described as a fungicide in GB-1504016. Imidazole derivatives are described as angiotensin II inhibitors in EP-253310, EP-515548, as antifungal agents in U.S. Pat. No. 4239767, U.S. Pat. No. 4,073,921, U.S. Pat. No. 4,105,762, as anticoccidial agents in EP-113570, and as diuretic-antiinflammatory agents in EP-324377. Triazole derivatives are disclosed as fungicidal agents in U.S. Pat. No. 4,151,287, EP-10691 and as anticoccidial agents in EP-151529. Pyridine derivatives are described as insecticides in EP-407346, as polymerization initiators in JP05-255256-B, as antiviral agents in EP-72529, and as hypoglycemic agents in U.S. Pat. No. 4,036,844, U.S. Pat. No. 4,053,607. Pyrazolopyrimidine derivatives are described as antihyperlipemic agents in JP63-246377-A. Tetrazole derivatives are described as antihypertensive, antiedema and antihyperuricemic agents in U.S. Pat. No. 410,712. Pyrazole derivatives are described as herbicidal agents in GB-1463473 and as fungicides in EP-433899. Oxadiazole derivatives are described as herbicidal agents in JP62-164673-A. Thiadiazole derivatives are discribed as antimycotic -agents in JP61-802927-A. Nicotine derivatives are described as antihyperlipemic agents in GB-2041937. Piperazine derivatives are described as anti-inflammatory agents in EP-5091. Phenoxyacetic acid derivatives are described as antihypertensive, antiedema and antirheumatic agent in U.S. Pat. No. 4,058,559, U.S. Pat. No. 4,166,819. Uracil derivatives are described as insecticidal-miticidal agents in JP05-43555-A. Also known are compounds described in GB-1519495, EP-242989, EP-258391, JP53-124682-A, EP-451556, EP-462812, JPO6-135977-A. Compounds having antitumoral activity are described in WO 9418168 (indole derivatives), EP-304221 (triazole derivatives), U.S. Pat. No. 5,045,543 (triazole derivatives), EP-337928, EP-337928, (imidazole derivatives), EP-180897 (5-fluorouracil derivatives).

Because of the insufficient therapeutic efficacy of the known antitumor compounds, drugs of different chemical structures are sought which display excellent efficacy in the therapy of refractory solid cancers such as pancreas cancer, prostate cancer, breast cancer, lung cancer, etc. and in the prevention of remote metastasis of such cancers to other organs.

SUMMARY OF THE INVENTION

An object of the present invention is to provide novel ketone derivatives of the formula:

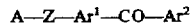

$$A-Z-Ar^1-CO-Ar^2 \qquad [I]$$

wherein ring A is an optionally substituted condensed pyrimidinone or condensed pyridazinone ring; $Ar^1$ and $Ar^2$ are independently an optionally substituted ring; Z is a divalent group, or salts thereof. Unexpectedly, these compounds have been found to have excellent antitumor activity and exhibit excellent cell-growth inhibiting effects against carcinoma cells such as pancreas cancer cells, prostate cancer cells, breast cancer cells, lung cancer cells, etc. As a result, these compounds are useful as a prophylactic or for the treatment of a refractory solid cancer.

DETAILED DESCRIPTION OF THE INVENTION

The present invention is directed to: (1) a compound of the formula [I] or a salt thereof, (2) a compound according to (1), ring A is an optionally substituted condensed pyrimidinone or condensed pyridazinane ring, which is condensed between (i) a $C_{6-14}$ aromatic hydrocarbon, $C_{5-10}$ cycloalkane or mono- or di-heterocyclic ring which contains 1 to 4 hetero atoms selected from nitrogen, oxygen and sulfur and (ii) a pyrimidinone or pyridazinone ring, (3) a compound according to (1), ring A is an optionally substituted pyrrolo[2,3-d]pyrimidin-4-one, pyrrolo[3,2-d]pyrimidin-4-one, pyrrolo[3,4-d]pyrimidin-4-one, pyrazolo[3,4-d]pyrimidin-4-one, pyrazolo[4,3-d]pyrimidin-7-one, 6-oxopurine, imidazo[1,2-a]pyrimidin-5-one, imidazo[1,2-a]pyrimidin-7-one, thieno[2,3-d]pyrimidin-4-one, thieno[3,4-d]pyrimidin-4-one, thieno[3,2-d]pyrimidin-4-one, furo[2,3-d]pyrimidin-4-one, furo[3,4-d]pyrimidin-4-one, furo[3,2-d]pyrimidin-4-one, isoxazolo[5,4-d]pyrimidin-4-one, isoxazolo[4,5-d]pyrimidin-7-one, oxazolo[5,4-d]pyrimidin-4-one, oxazolo[4,5-d]pyrimidin-7-one, thiazolo[5,4-d]pyrimidin-4-one, thiazolo[4,5-d]pyrimidin-7-one, isothiazolo[5,4-d]pyrimidin-4-one, isothiazolo[4,5-d]pyrimidin-7-one, triazolo[4,5-d]pyrimidin-4-one, 1,2,4-triazolo[1,5-a]pyrimidin-7-one, dihydrocyclopenta[d]pyrimidin-4-one, 5H- or 7H-cyclopenta[d]pyrimidin-4-one, pyrido[2,3-d]pyrimidin-4-one, pyrido[3,2-d]pyrimidin-4-one, pyrido[4,3-d]pyrimidin-4-one, pyrido[3,4-d]pyrimidin-4-one, pteridin-4-one, quinazolin-4-one, pyrido[1,2-a]pyrimidin-4-one, pyrimido[1,2-a]pyrimidin-4-one, thiazolo[3,2-a]pyrimidin-5-one, oxazolo[3,2-a]pyrimidin-5-one, pyrrolo[1,2-a]pyrimidin-4-one, pyrimido[3,4-a]pyrimidin-4-one, pyrimido[4,5-d]pyrimidin-4-one, pyrimido[5,4-d]pyrimidin-4-one, pyridazino[2,3-a]pyrimidin-4-one, pyridazino[4,3-d]pyrimidin-4-one, pyridazino[3,4-d]pyrimidin-4-one, xanthine, uric acid, pyrrolo[3,2-d]pyrimidin-2,4-dione, pyrrolo[2,3-d]pyrimidin-2,4-dione, pyrrolo[3,4-d]pyrimidin-2,4-dione, pyrimido[2,1-b][1,3]thiazin-6-one, pyrimido[2,1-b][1,3]oxazin-6-one, imidazo[2,1-b]quinazolin-5-one, cyclopento[d]imidazo[1,2-a]pyrimidin-5-one, cyclopento[d]imidazo[1,2-a]pyrimidin-5-one, pyridazino[4,5-b]-1,5-oxazepin-9(8H)-one, pyridazino[4,5-b]-1,4-oxazin-8(7H)-one, pyrrolo[3,4-d]pyridazin-4(5H)-one, pyrrolo[2,3-d]pyridazin-7(6H)-one, pyrrolo[2,3-d]pyridazin-4(5H)-one, imidazo[4,5-d]pyridazin-4(5H)-one, imidazo[4,5-c]pyridazin-4(5H)-one, pyrazolo[4,3-d]pyridazin-4(5H)-one, pyrazolo[3,4-d]pyridazin-4(5H)-one, triazolo[4,5-d]pyridazin-4(5H)-one, pyrido[2,3-d]pyridazin-5(6H)-one or thiazolo[4,5-d]pyridazin-7(6H)-one, which may be partially reduced, (4) a compound according to (1), wherein ring A is an optionally substituted condensed pyrimidione ring which is condensed between (i) a $C_{6-14}$ aromatic hydrocarbon, $C_{5-10}$ cycloalkane or mono- or di-heterocyclic ring which contain 1 to 4 hetero atoms selected from nitrogen, oxygen and sulfur in addition to carbon as ring member and (ii) a pyrimidione ring, (5) a compound according to (4), wherein the condensed pyrimidinone ring is pyrrolo[2,3-d]pyrimidin-4-one, quinazolin-4-one, pyrido[1,2-a]pyrimidin-4-one, thiazolo[3,2-a]pyrimidin-5-one, pyrimido[2,1-b]thiadin-6-one or imidazo[2,1-b]quinazolin-5-one, which may be partially reduced, (6) a compound according to (1), wherein Z is a divalent $C_{16}$ aliphatic hydrocarbon group which may contain —NH—, —O— or —S—, (7) a compound according to (1), wherein $Ar^1$ and $Ar^2$ are independently an optionally substituted aromatic ring, (8) a compound according to (1), wherein $Ar^1$ is a para-substituted benzene or para-disubstituted benzene, (9) a compound according to (1), wherein $Ar^2$— is an optionally substituted phenyl, pyridyl, indolyl, pyrrolyl, thienyl, piperidino, piperazino or morpholino group, (10) a compound according to (8), wherein $Ar^2$— is an optionally substituted phenyl group, (11) a compound according to (1), wherein $Ar^2$— is an optionally substituted piperidino, piperazino or morpholino group, (12) a compound according to (1), wherein $Ar^2$ may have 1 to 5 substituents selected from the group consisiting of a halogen, $C_{1-10}$ alkyl, $C_{2-10}$ alkenyl, $C_{2-10}$ alkynyl, $C_{3-10}$ cycloalkyl, $C_{3-6}$ cycloalkyl-$C_{1-6}$ alkyl, $C_{1-10}$ alkoxy, $C_{2-10}$ alkenyloxy, $C_{2-10}$ alkynyloxy, $C_{6-14}$ aryloxy, $C_{7-16}$ aralkyloxy, $C_{1-10}$ alkylthio, $C_{2-10}$ alkenylthio, $C_{2-10}$ alkynylthio, $C_{6-14}$ arylthio, $C_{7-16}$ aralkylthio, $C_{1-10}$ alkylsulfinyl, $C_{2-10}$ alkenylsulfinyl, $C_{2-10}$ alkynylsulfinyl, $C_{6-14}$ arylsulfinyl, $C_{1-10}$ alkylsulfonyl, $C_{2-10}$ alkenylsulfonyl, $C_{2-10}$ alkynylsulfonyl, $C_{6-14}$ arylsulfonyl, carbamoyloxy, mono- or di-$C_{1-10}$ alkylcarbamoyloxy, phosphonooxy, mono- or di-$C_{1-10}$ alkylphosphonooxy, oxo, nitro, cyano, sulfo, hydroxyl, amino, mono- or di-$C_{1-10}$ alkylamino, mono- or di-$C_{7-16}$ aralkylamino, cyclic amino, carboxyl, mercapto, carbamoyl, mono- or di-$C_{1-10}$ alkylcarbamoyl, mono- or di-$C_{6-14}$ arylcarbamoyl, $C_{1-10}$ alkoxy-carbonyl, $C_{2-10}$ alkenyloxy-carbonyl, $C_{2-10}$ alkynyloxy-carbonyl, $C_{6-14}$ aryloxy-carbonyl, $C_{1-10}$ alkylsulfonylamino, $C_{7-16}$ aralkyl, $C_{6-14}$ aryl, styryl, $C_{6-14}$ arylimino, aromatic heterocyclic, formyl, $C_{1-10}$ alkyl-carbonyl, $C_{2-10}$ alkenyl-carbonyl, $C_{2-10}$ alkynyl-carbonyl, $C_{6-14}$ aryl-carbonyl, $C_{1-10}$ acylamino, —CO—Q (Q is a substituted amino) and $C_{1-10}$ acyloxy group, which may be substituted by 1 to 3 substituents selected from the group consisting of a halogen, $C_{1-6}$ alkyl, $C_{2-6}$ alkenyl, $C_{2-6}$ alkynyl, $C_{3-6}$ cycloalkyl, carboxyl, hydroxyl, cyano, nitro, sulfo, phosphono, oxo, $C_{1-6}$ alkoxy, $C_{1-3}$ alkylenedioxy, $C_{6-10}$ aryloxy, $C_{7-14}$ aralkyloxy, mercapto, $C_{1-6}$ alkylthio, $C_{6-10}$ arylthio, $C_{7-14}$ aralkylthio, carbamoyl, mono- or di-$C_{1-6}$ alkylcarbamoyl, amino, mono- or di-$C_{1-6}$ alkylamino, cyclic amino, mono- or di-$C_{7-14}$ aralkylamino, $C_{6-10}$ aryl, $C_{7-14}$ aralkyl, formyl, $C_{1-6}$ alkyl-carbonyl, $C_{6-10}$ aryl-carbonyl, $C_{1-6}$ alkoxy-carbonyl, $C_{1-6}$ acyloxy, aromatic heterocyclic and aromatic heterocyclic thio, and further which may be substituted by 1 to 3 substituents selected from the group consisting of a halogen, $C_{1-6}$ alkyl, $C_{2-6}$ alkenyl, $C_{2-6}$ alkynyl, $C_{3-6}$ cycloalkyl, carboxyl, hydroxyl, cyano, nitro, sulfo, phosphono, oxo, $C_{1-6}$ alkoxy, $C_{1-3}$ alkylenedioxy, $C_{6-10}$ aryloxy, $C_{7-14}$ aralkyloxy, mercapto, $C_{1-6}$ alkylthio, $C_{6-10}$ arylthio, $C_{7-14}$ aralkylthio, carbamoyl, mono- or di-$C_{1-6}$ alkylcarbamoyl, amino, mono- or di-$C_{1-6}$ alkylamino, cyclic amino, mono- or di-$C_{7-14}$ aralkylamino, $C_{6-10}$ aryl, $C_{7-14}$ aralkyl, formyl, $C_{1-6}$ alkyl-carbonyl, $C_{6-10}$ aryl-carbonyl, $C_{1-6}$ alkoxy-carbonyl, $C_{1-6}$ acyloxy, aromatic heterocyclic and aromatic heterocyclic thio, (13) a compound of the formula:

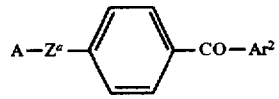

wherein ring A is an optionally substituted condensed pyrimidinone or condensed pyridazinone ring; $Ar^2$ is an optionally substituted ring; $Z^a$ is a divalent $C_{1-6}$ aliphatic hydrocarbon group which may contain —NH—, —O— or —S—, or a salt thereof, (14) a compound according to (13), wherein the moiety of A— is a moiety:

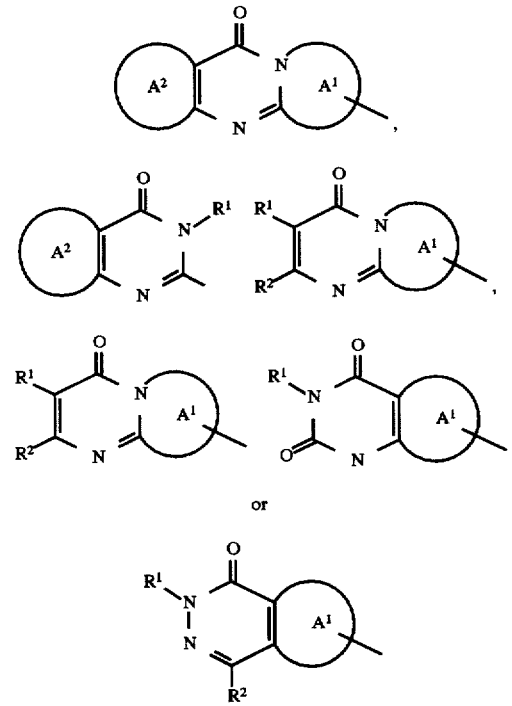

wherein $A^1$ and $A^2$ are independently an optionally substituted 5- to 8- membered carbocyclic or heterocyclic ring; R and R2 are independently a hydrogen, halogen, $C_{1-6}$ alkyl, halo-$C_{1-6}$ alkyl, hydroxyl, $C_{1-6}$ alkoxy, halo-$C_{1-6}$ alkoxy, $C_{1-6}$ alkylthio or halo-$C_{1-6}$ alkylthio group, (15) a compound according to (13), wherein the moiety of A— is a moiety:

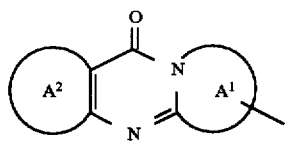

or

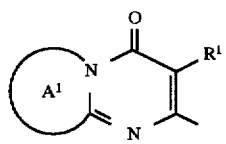

wherein all symbols are of the same meanings as defined in (14), (16) a compound according to (14), wherein the moiety of A— is a moiety:

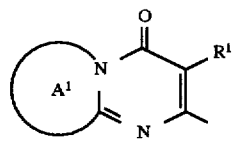

wherein all symbols are of the same meanings as defined in (14), (17) a compound according to (14), wherein $R^1$ and $R^2$ are independently a hydrogen or a $C_{16}$ alkyl, (18) a compound according to (14), wherein the 5- to 8-membered carbocyclic or heterocyclic ring is 5- to 8-membered ring optionally containing 1 to 4 hetero atoms selected from nitrogen, oxygen and sulfur, (19) a compound according to (18), the 5- to 8-membered ring is (i) a cyclopentane, cyclohexane, cycloheptane, benzene or (ii) an imidazole, pyridine, thiadine, thiazole, oxazole, thiophene, pyrrole, pyrazole, pyrazine, pyrimidine which may be partially reduced, (20) a compound according to (13), wherein $Z^a$ is a $C_{1-6}$ alkylene which may contain —O— or —S—, (21) a compound according to (13), wherein $Ar^2$— is an optionally substituted phenyl, pyridyl, indolyl, pyrrolyl, thienyl, piperidino, piperazino or morpholino group, (22) a compound according to (13), wherein $Ar^21'$ is an optionally substituted phenyl group, (23) a compound according to (13), wherein $Ar^2$— is an optionally substituted piperidino, piperazino or morpholino group, (24) a compound according to (13), wherein the moiety of A— is a moiety:

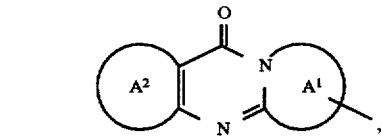

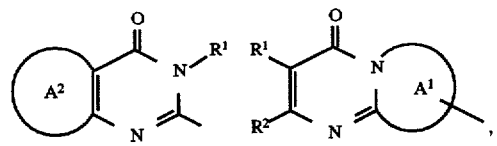

-continued

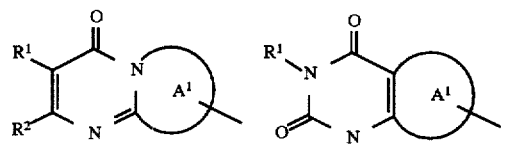

or

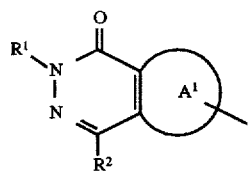

wherein all symbols are of the same meanings as defined in (14); $Z^a$ is a $C_{1-6}$ alkylene which may contain —O— or —S—; $Ar^2$— is an optionally substituted phenyl group, (25) a compound according to (24), wherein $Z^a$ is —O—$CH_2$— or —$CH_2$—, (26) a compound according to (13), wherein the moiety of A— is a moiety:

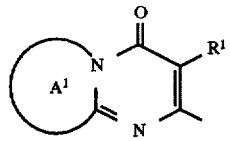

wherein all symbols are of the same meaning as defined in (14); $Z^a$ is a $C_{1-6}$ alkylene which may contain —O— or —S—; $Ar^2$— is an optionally substituted phenyl group, (27) a compound according to (26), wherein Za is —O—$CH_2$— or —$CH_2$—, (28) a compound according to (13) of the formula:

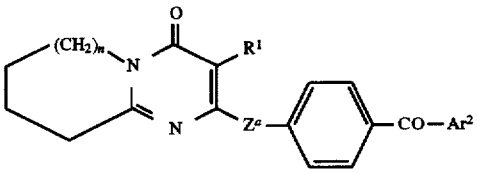

or

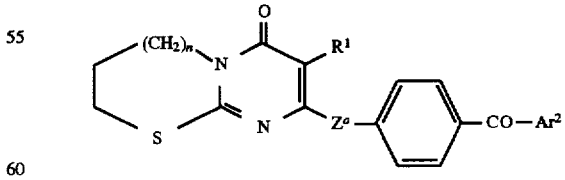

wherein n is 0 to 3, the other symbols are of the same meanings as defined in (13), (29) a compound according to (28), wherein n is 1 to 3, (30) a compound according to (28) of the formula:

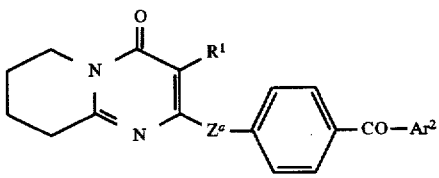

wherein all symbols are of the same meanings as defined in (13), (31) a compound according to (28), wherein $Ar^2$— is an optionally substituted phenyl group, (32) a compound according to (31), wherein the optionally substituted phenyl group is a phenyl group which may be substituted by 1 to 5 substituents selected from the group consisting of a $C_{1-6}$ alkyl, halo-$C_{1-6}$ alkyl, $C_{1-6}$ alkoxy, halo-$C_{1-6}$ alkoxy, $C_{1-6}$ alkylthio, halo-$C_{1-6}$ alkylthio, halo, amino, mono- or di-$C_{1-6}$ alkylamino, $C_{1-6}$ acylamino, $C_{1-6}$ alkyl-carbonyl, $C_{6-10}$ aryl-carbonyl, $C_{7-14}$ aralkyl-carbonyl, $C_{1-6}$ alkoxy-carbonyl, $C_{1-6}$ acyloxy, carbamoyloxy, mono- or di-$C_{1-6}$ alkylcarbamoyloxy, cyano, nitro, carbamoyl and mono- or di-$C_{1-6}$ alkyl-carbamoyl, (33) a compound according to (28), wherein $Ar^2$— is an optionally substituted piperidino or piperazino group, (34) a compound according to (28), wherein the moiety of $Ar^2$— is a moiety:

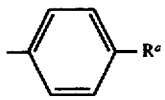

wherein $R^a$ is a substituent group, (35) a compound according to (34), wherein $R^a$ is a halogen, $C_{1-6}$ alkyl, halo-$C_{1-6}$ alkyl, $C_{1-6}$ alkoxy or halo-$C_{1-6}$ alkoxy, (36) a compound according to (35), wherein $Z^a$ is —O— $CH_2$—, (37) a compound according to (36), wherein $R^1$ is methyl group, (38) a compound according to (13) of the formula:

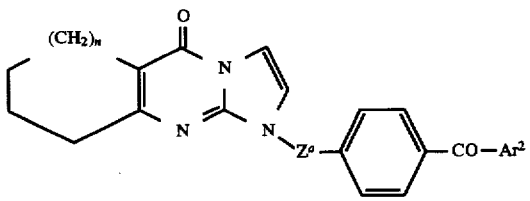

wherein n is 0 to 3, the other symbols are of the same meanings as defined in (13), (39) a compound according to (38), wherein $Ar^2$— is an optionally substituted phenyl group, (40) a compound according to (39), wherein the optionally substituted phenyl group is a phenyl group which may be substituted by 1 to 5 substituents selected from the group consisting of a halogen, $C_{1-6}$ alkyl, halo-$C_{1-6}$ alkyl, $C_{1-6}$ alkoxy, halo-$C_{1-6}$ alkoxy, $C_{1-6}$ alkylthio, halo-$C_{1-6}$ alkylthio, amino, mono- or di-$C_{1-6}$ alkylamino, $C_{1-6}$ acylamino, $C_{1-6}$ alkyl-carbonyl, $C_{6-10}$ aryl-carbonyl, $C_{7-14}$ aralkyl-carbonyl, $C_{1-6}$ alkoxy-carbonyl, $C_{1-6}$ acyloxy, carbamoyloxy, mono- or di-$C_{1-6}$ alkylcarbamoyloxy, cyano, nitro, carbamoyl and mono- or di-$C_{1-6}$ alkyl-carbamoyl, (41) a compound according to (38), wherein $Ar^2$— is an optionally substituted piperidino or piperazino group, (42) a compound according to (38), wherein the moiety of $Ar^2$— is a moiety:

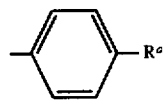

wherein $R^a$ is a substituent group, (43) a compound according to (42), wherein $R^a$ is a halogen, $C_{1-6}$ alkyl, halo-$C_{1-6}$ alkyl, $C_{1-6}$ alkoxy or halo-$C_{1-6}$ alkoxy, (44) a compound according to (38), wherein $Z^a$ is —$CH_2$—, (45) a compound according to (38), wherein n is 1, (46) a compound according to (1) of the formula:

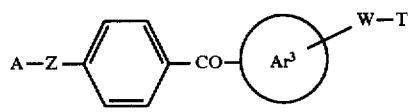

wherein $Ar^3$ is a ring; W is a bond, a carbonyl or a divalent $C_{1-6}$ aliphatic hydrocarbon group which may contain —$NR^3$— (R is a hydrogen or $C_{1-6}$ alkyl group), —O— or —S—;T is an optionally substituted amino group, and the other symbols are of the same meanings as defined in (1), (47) a compound according to (46), T is a piperidino, piperazino or morpholino which may be substituted by 1 to 3 substituents selected from the group consisting of a halogen, $C_{1-6}$ alkyl, $C_{2-6}$ alkenyl, $C_{2-6}$ alkynyl, $C_{3-6}$ cycloalkyl, carboxyl, hydroxyl, cyano, nitro, sulfo, phosphono, oxo, $C_{1-6}$ alkbxy, $C_{1-3}$ alkylenedioxy, $C_{6-10}$ aryloxy, $C_{7-14}$ aralkyloxy, mercapto, $C_{1-6}$ alkylthio, $C_{6-10}$ arylthio, $C_{7-14}$ aralkylthio, carbamoyl, mono- or di-$C_{1-6}$ alkylcarbamoyl, amino, mono- or di-$C_{1-6}$ alkylamino, pyrrolidino, piperidino, piperazino, morpholino, mono- or di-$C_{7-14}$ aralkylamino, $C_{6-10}$ aryl, $C_{7-4}$ aralkyl, formyl, $C_{1-6}$ alkyl-carbonyl, $C_{6-10}$ aryl-carbonyl, $C_{1-6}$ alkoxy-carbonyl, $C_{1-6}$ acyloxy, aromatic heterocyclic and aromatic heterocyclic thio, (48) a compound according to (46), wherein W is a bond, carbonyl, —$(CH_2)_{1-3}$— or —O—$(CH_2)_{1-3}$—, (49) a compound according to (46), wherein the moiety of A— is a moiety:

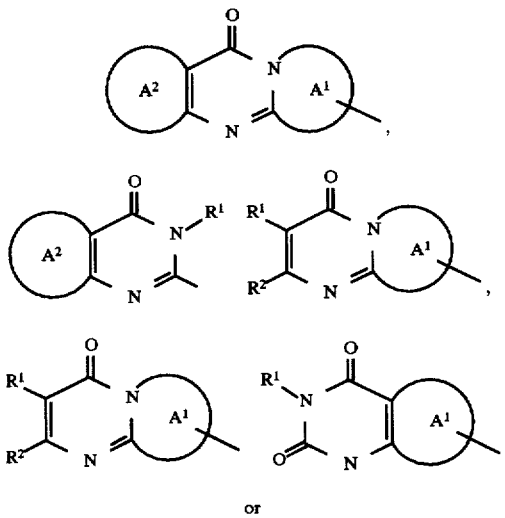

or

-continued

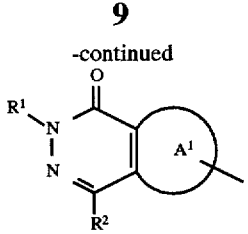

wherein all symbols are of the same meanings as defined in (14), (50) a compound according to (46), wherein Z is a divalent $C_{1-6}$ aliphatic hydrocarbon group which may contain —O— or —S—, (51) a compound according to (46), wherein the moiety of $Ar^3$ is a moiety:

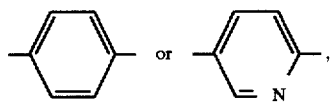

(52) a compound according to (1) of the formula:

wherein ring D is an optionally substituted quinazolin-5-one, pyrido[1,2-a]pyrimidin-4-one, imidazo[1,2-a]pyrimidin-5-one, thiazolo[3,2-a]pyrimidin-5-one, oxazolo[3,2-a]pyrimidin-5-one or pyrido[1,2-a]pyrimidin-4-one, which may be partially reduced; Alk is $C_{1-3}$ alkylene; E is a bond, —S—, —O—, —NR—, —S—$CH_2$—, —O—$CH_2$— or —NR—$CH_2$— (R is hydrogen, $C_{1-6}$ alkyl or $C_{2-6}$ alkenyl); the other symbols are of the same meanings as defined in (1), (53) 1-[4-(4-Chlorobenzoyl)benzyl]-6,7,8,9-tetrahydroimidazo[2,1-b]quinazolin-5(1H)-one, or a salt thereof, (54) 3-Methyl-2-[4-(4-trifluoromethylbenzoyl)benzyloxy]-6,7,8,9-tetrahydro-4H-pyrido[1,2-a]pyrimidin-4-one, or a salt thereof, (55) 7-[4-(4-Methoxybenzoyl)benzyloxy]-6-methyl-2,3-dihydro-5H-thiazolo[1,2-a]pyrimidin-5-one, or a salt thereof, (56) a process for producing a compound of (1), which comprises reacting a) A—$Y^a$, or a salt thereof with Y—$Ar^1$—CO—$Ar^2$, or a salt thereof, b) A, or a salt thereof with X—Z—$Ar^1$—CO—$Ar^2$, or a salt thereof, c) A—X, or a salt thereof with HZ—$Ar^1$—CO—$Ar^2$, or a salt thereof, d) $A^a$, or a salt thereof with $A^b$—Z—$Ar^1$—CO—$Ar^2$, or a salt thereof or e) A—Z—$Ar^1$, or a salt thereof with X—CO—$Ar^2$, or a salt thereof wherein Y and $Y^a$ react to form the group represented by Z; $A^a$ and $A^b$ are, taken together, an optionally substituted condensed pyridazinone or condensed pyrimidinone represented by A; X is a reactive group and the other symbols are defined as in (1), 5 (57) a composition comprising an effective amount of a compound according to (1) with a pharmaceutically acceptable carrier or diluent, (58) method for treating a tumor in mammals which comprises administrating to a subject in need an effective amount of a compound according to (1), and (59) use of a compound according to (1) for the manufacture of a medicament for the treatment of a tumor, and so on.

In the above formula [I], "A" represents an optionally substituted condensed pyrimidinone or condensed pyridazinone ring.

The "condensed pyrimidinone ring" represented by the ring A, includes a condensed pyrimidinone ring condensed between (i) a cyclic hydrocarbon and/or heterocyclic ring and (ii) a pyrimidinone ring. A condensed pyrimidinone ring consisting of 9 to 14 atoms selected from carbon, nitrogen, oxygen and sulfur is preferable.

The term "cyclic hydrocarbon" represents a 5- to 10-membered mono-cyclic hydrocarbon, or a condensed bicyclic hydrocarbon.

The preferable examples of the cyclic hydrocarbon are a $C_{6-14}$ aromatic hydrocarbon (e.g. benzene, naphthalene), a $C_{5-10}$ cycloalkane (e.g. cyclopentane, cyclohexane, cycloheptane, indan, tetralin), and so on.

The "heterocyclic ring" represents a 5- to 10-membered heterocyclic ring which contains one or two species, preferably .1 to 4 heteroatoms selected from among nitrogen, oxygen and sulfur or a condensed hetero-bicyclic ring. The preferable examples of the heterocyclic ring are an imidazole, thiazole, oxazole, pyrrole, isoxazole, isothiazole, pyrazole, triazole, pyridine, pyrimidine, pyridazine, pyrazine, thiophene, furan, thiazine, indole, isoindole, purine, quinoline, isoquinoline, and which may be partially or all reduced.

The examples of said "condensed pyrimidinone ring" includes pyrrolo[2,3-d]pyrimidin-4-one, pyrrolo[3,2-d]pyrimidin-4-one, pyrrolo[3,4-d]pyrimidin-4-one, pyrazolo[3,4-d]pyrimidin-4-one, pyrazolo[4,3-d]pyrimidin-7-one, 6-oxopurine, imidazo[1,2-a]-pyrimidin-5-one, imidazo[1,2-a]pyrimidin-7-one, thieno-[2,3-d]pyrimidin-4-one, thieno[3,4-d]pyrimidin-4-one, thieno[3,2-d]pyrimidin-4-one, furo[2,3-d]pyrimidin-4-one, furo[3,4-d]pyrimidin-4-one, furo[3,2-d]pyrimidin-4-one, isoxazolo[5,4-d]pyrimidin-4-one, isoxazolo[4,5-d]pyrimidin-7-one, oxazolo[5,4-d]pyrimidin-4-one, oxazolo[4,5-d]pyrimidin-7-one, thiazolo[5,4-d]pyrimidin-4-one, thiazolo[4,5-d]pyrimidin-7-one, isothiazolo[5,4-d]pyrimidin-4-one, isothiazolo[4,5-d]pyrimidin-7-one, triazolo[4,5-d]pyrimidin-4-one, 1,2,4-triazolo[1,5-a]pyrimidin-7-one, dihydrocyclopenta[d]pyrimidin-4-one, 5H- or 7H-cyclopenta[d]pyrimidin-4-one, pyrido[2,3-d]pyrimidin-4-one, pyrido[3,2-d]pyrimidin-4-one, pyrido[4,3-d]pyrimidin-4-one, pyrido[3,4-d]pyrimidin-4-one, puteridin-4-one, quinazolin-4-one, pyrido[1,2-*a]pyrimidin-4-one, pyrimido[1,2-a]pyrimidin-4-one, thiazolo[3,2-a]pyrimidin-5-one, oxazolo[3,2-a]pyrimidin-5-one, pyrrolo[1,2-a]pyrimidin-4-one, pyrimido[3,4-a]pyrimidin-4-one, pyrimido[4,5-d]pyrimidin-4-one, pyrimido[5,4-d]pyrimidin-4-one, pyridazino[2,3-a]pyrimidin-4-one, pyridazino[4,3-d]pyrimidin-4-one, pyridazino[3,4-d]pyrimidin-4-one, xanthine, uric acid, pyrrolo[3,2-d]pyrimidin-2,4-dione, pyrrolo[2,3-d]pyrimidin-2,4-dione, pyrrolo[3,4-d]-pyrimidin- 2,4-dione, pyrimido[2,1-b][1,3]thiazin-6-one, pyrimido[2,1-b][1,3]oxazin-6-one, imidazo[2,1-b]quinazolin-5-one, cyclopento[d]imidazo[1,2-a]pyrimidin-5-one, cyclohepto[d]imidazo[1,2-a]pyrimidin-5-one, and so on.

The "condensed pyridazinone ring" represented by the ring A, includes a condensed pyridazinone ring condensed between (i) a cyclic hydrocarbon and/or heterocyclic ring and (ii) a pyridazinone ring. A condensed pyridazinone ring consisting of 9 to 14 atoms selected from carbon, nitrogen, oxygen and sulfur is preferable.

The "cyclic hydrocarbon" and "heterocyclic ring" can be used the same one mentioned hereinabove.

The examples of said "condensed pyridazinone ring" includes pyridazino[4,5-b]-1,5-oxazepin-9(8H)-one, pyridazino[4,5-b]-1,4-oxazin-8(7H)-one, pyrrolo[3,4-d]pyridazin-4(5H)-one, pyrrolo[2,3-d]pyridazin-7(6H)-one, pyrrolo[2,3-d]pyridazin-4(5H)-one, imidazo[4,5-d]pyridazin-4(5H)-one, imidazo[4,5-c]pyridazin-6(5H)-one, pyrazolo[4,3-d]pyridazin-4(5H)-one, pyrazolo[3,4-d]pyridazin-4(5H)-one, triazolo[4,5-d]pyridazin-4(5H)-one, pyrido[2,3-d]pyridazin-5(6H)-one, thiazolo[4,5-d]pyridazin-7(6H)-one, and so on.

The "condensed pyrimidinone" and "condensed pyridazinone" rings may be partially reduced.

The substituent or substituents (designated by -L) that may be substituted on said "condensed pyrimidin-one" or "condensed pyridazinone" ring include halogen, alkyl, alkenyl, alkynyl, cycloalkyl, cycloalkyl-alkyl, alkoxy, alkenyloxy, alkynyloxy, aryloxy, aralkyloxy, alkylthio, alkenylthio, alkynylthio, arylthio, aralkylthio, alkylsulfinyl, alkenylsulfinyl, alkynylsulfinyl, arylsulfinyl, alkylsulfonyl, alkenyl-sulfonyl, alkynylsulfonyl, arylsulfonyl, carbamoyloxy, mono- or di-alkylcarbamoyloxy, phosphonooxy, mono- or di-alkylphosphonooxy, oxo, nitro, cyano, sulfo, hydroxyl, amino, mono- or di-alkylamino, mono- or di-aralkylamino, cyclic amino, carboxyl, mercapto, carbamoyl, mono- or di-alkylcarbamoyl, mono- or di-arylcarbamoyl, alkoxy-carbonyl, alkenyloxy-carbonyl, alkynyloxy-carbonyl, aryloxy-carbonyl, alkylsulfonylamino, aralkyl, aryl, styryl, arylimino, aromatic heterocyclic, formyl, alkyl-carbonyl, alkenyl-carbonyl, alkynyl-carbonyl, aryl-carbonyl, acylamino, —CO—Q (Q is a substituted amino) and acyloxy, and so on. These substituent groups may be substituted in substitutable positions on the "condensed pyrimidinone" and "condensed pyridazinone" rings, and may number 1 through 5, preferably 1 through 3, per ring. Moreover, where two or more substituents are substituted, they may be similar or different to each other. Representative species of such substituents on the "condensed pyrimidinone" and "condensed pyridazinone" rings are listed below.

The "halogen" includes fluorine, chlorine, bromine and iodine.

The "alkyl" includes $C_{1-10}$ alkyl groups such as methyl, ethyl, propyl, isopropyl, butyl, isobutyl, secbutyl, tert-butyl, pentyl, isopentyl, neopentyl, hexyl, 2-methylpentyl, 1,1-dimethylbutyl, 2,2-dimethylbutyl, etc.

The "alkenyl" includes $C_{2-10}$ alkenyl groups such as vinyl, allyl, 2-butenyl, isopropenyl, 2-pentenyl, 3-pentenyl, 4-pentenyl, 2-hexenyl, 3-hexenyl, 4-hexenyl, 5-hexenyl, etc.

The "alkynyl" includes $C_{2-10}$ alkynyl groups such as ethynyl, 1-propynyl, propargyl, 1-hexynyl, 2-hexynyl, 3-hexynyl, 4-hexynyl, etc.

The "cycloalkyl" includes $C_{3-10}$ cycloalkyl groups such as cyclopropyl, cyclobutyl, cyclopentyl, cyclohexyl, etc.

The "cycloalkyl-alkyl" includes $C_{3-6}$ cycloalkyl-$C_{1-6}$ alkyl groups such as cyclopropylmethyl, etc.

The "alkoxy" includes $C_{1-10}$ alkoxy groups such as methoxy, ethoxy, propoxy, isopropoxy, butoxy, isobutoxy, sec-butoxy, pentyloxy, hexyloxy, etc.

The "alkenyloxy" includes $C_{2-10}$ alkenyloxy groups such as allyloxy, isopropenyloxy, etc.

The "alkynyloxy" includes $C_{2-10}$ alkynyloxy groups such as propargyloxy etc.

The "aryloxy" includes $C_{6-14}$ aryloxy groups such as phenoxy, etc.

The "aralkyloxy" includes $C_{7-16}$ aralkyloxy groups such as benzyloxy, etc.

The "alkylthio" includes $C_{1-10}$ alkylthio groups such as methylthio, ethylthio, propylthio, isopropylthio, butylthio, pentylthio, hexylthio, etc.

The "alkenylthio" includes $C_{2-10}$ alkenylthio groups such as allylthio, isopropenylthio, etc.

The "alkynylthio" includes $C_{2-10}$ alkynylthio groups such as propargylthio, etc.

The "arylthio" includes $C_{6-14}$ arylthio groups such phenylthio, etc.

The "aralkylthio" includes $C_{7-10}$ aralkylthio groups such as benzylthio, etc.

The "alkylsulfinyl" includes $C_{1-10}$ alkylsulfinyl groups such as methylsulfinyl, ethylsulfinyl, etc.

The "alkenylsulfinyl" includes $C_{2-10}$ alkenylsulfinyl groups such as allylsulfinyl, isopropenylsulfinyl, etc.

The "alkynylsulfinyl" includes $C_{2-10}$ alkynylsulfinyl groups such as propargylsulfinyl etc.

The "arylsulfinyl" includes $C_{6-14}$ arylsulfinyl groups such as benzenesulfinyl etc.

The "alkylsulfonyl" includes $C_{1-10}$ alkylsulfonyl groups such as methylsulfonyl, ethylsulfonyl, propylsulfonyl, etc.

The "alkenylsulfonyl" includes $C_{2-10}$ alkenylsulfonyl groups such as allylsulfonyl, isopropenylsulfonyl, etc.

The "alkynylsulfonyl" includes $C_{2-10}$ alkynylsulfonyl groups such as propargylsulfonyl, etc.

The "arylsulfonyl" includes $C_{6-14}$ arylsulfonyl groups such as benzenesulfonyl, etc.

The "mono- or di-alkylcarbamoyloxy" includes mono- or di-$C_{1-6}$ alkylcarbamoyloxy groups such as methylcarbamoyloxy, ethylcarbamoyloxy, dimethylcarbamoyloxy, diethylcarbamoyloxy, etc.

The "mono- or di-alkylphosphonooxy" includes mono- or di-$C_{1-6}$ alkylphosphonooxy groups such as methylphosphonooxy, dimethylphosphonooxy, diethylphosphonooxy, etc.

The "mono- or di-alkylamino" includes mono- or di-$C_{1-10}$ alkylamino groups such as methylamino, ethylamino, propylamino, dimethylamino, diethylamino, etc.

The "mono- or di-aralkylamino" includes mono- or di-$C_{7-16}$aralkylamino groups such as benzylamino, dibenzylamino, etc.

The "cyclic amino" includes 5- or 6-membered cyclic amino groups such as pyrrolidino, piperidino, piperazino, morpholino, etc.

The "mono- or di-alkylcarbamoyl" includes mono- or di-$C_{1-10}$ alkylcarbamoyl groups such as methylcarbamoyl, ethylcarbamoyl, dimethylcarbamoyl, diethylcarbamoyl, etc.

The "mono- or di-arylcarbamoyl" includes mono- or di-$C_{6-14}$ aryl-carbamoyl groups such as phenylcarbamoyl, diphenylcarbamoyl, etc.

The "alkoxy-carbonyl" includes $C_{1-10}$ alkoxy-carbonyl groups such as methoxycarbonyl, ethoxycarbonyl, propoxycarbonyl, isopropoxycarbonyl, butoxycarbonyl, etc.

The "alkenyloxy-carbonyl" includes $C_{2-10}$ alkenyloxy-carbonyl groups such as allyloxycarbonyl, isopropenyloxycarbonyl, etc.

The "alkynyloxy-carbonyl" includes $C_{2-10}$ alkynyloxy-carbonyl groups such as propargyloxycarbonyl, etc.

The "aryloxy-carbonyl" includes $C_{6-14}$ aryloxycarbonyl groups such as phenoxycarbonyl, etc.

The "alkylsulfonylamino" includes $C_{1-10}$ alkylsulfonylamino groups such as methylsulfonylamino, ethylsulfonylamino, propylsulfonylamino, butylsulfonylamino, etc.

The "aralkyl" includes $C_{7-16}$ aralkyl groups such as benzyl, phenethyl, diphenylmethyl, triphenylmethyl, 1-naphthylmethyl, 2-naphthylmethyl, 2-diphenylethyl, 3-phenylpropyl, 4-phenylbutyl, 5-phenylpentyl, etc.

The "aryl" includes $C_{6-14}$ aryl groups such as phenyl, 1-naphthyl, 2-naphthyl, biphenyl, 2-anthryl, etc.

The "arylimino" includes $C_{6-14}$ arylimino groups such as phenylimino, etc.

The "aromatic heterocyclic" includes 5- to 10-membered aromatic heterocyclic groups containing 1 to 4 hetero-atoms selected from nitrogen, oxygen and sulfur and aromatic hetero-bicyclic groups, thus including 2-thienyl, 3-thienyl, 2-pyridyl, 3-pyridyl, 4-pyridyl, 2-furyl, 3-furyl, 2-quinolyl, 4-quinolyl, 8-quinolyl, 3-isoquinolyl, 4-isoquinolyl, pyrazinyl, 2-pyrimidinyl, 3-pyrrolyl, 1-imidazolyl, 2-imidazolyl, 1-pyrazolyl, 2-thiazolyl, 4-thiazolyl, 5-thiazolyl, 3-isothiazolyl, 4-isothiazolyl, 3-isoxazolyl, 3-pyridazinyl, 2-pyridon-1-yl, 3-pyridon-1-yl, 1-isoindolyl, 2-isoindolyl, 1-indolyl, 3-indolyl, 1-tetrazolyl, 2-tetrazolyl, 5-tetrazolyl, 2-pyrimidinyl, 4-pyrimidinyl, 5-pyrimidinyl, 2-purinyl, 6-purinyl, 7-purinyl, 8-purinyl, 9-purinyl, 1-xanthinyl, 3-xanthinyl, 7-xanthinyl, 8-xanthinyl, 2-quinazolinyl, 4-quinazolinyl, 5-quinazolinyl, 6-quinazolinyl, 7-quinazolinyl, 8-quinazolinyl, 4(3H)-quinazolinon-2-yl, 4(3H)-quinazolinon-3-yl, 4(3H)-quinazolinon-5-yl, 4(3H)-quinazolinon-6-yl, 4(3H)-quinazolinon-7-yl, 4(3H)-quinazolinon-8-yl, and so on.

The "alkyl-carbonyl" includes $C_{1-10}$ alkyl-carbonyl groups such as acetyl, propionyl, butyryl, valeryl, etc.

The "alkenyl-carbonyl" includes $C_{2-10}$ alkenyl-carbonyl groups such as acryloyl, etc.

The "alkynyl-carbonyl" includes $C_{2-10}$ alkynyl-carbonyl groups such as propioloyl, etc.

The "aryl-carbonyl" includes $C_{6-14}$ aryl-carbonyl groups such as benzoyl, etc.

The "acylamino" includes $C_{1-10}$ acylaminb groups such as formylamino, acetylamino, propionylamino, butyrylamino, benzoylamino, etc.

The "substituted amino" represented by Q in "CO—Q" includes mono- or di-$C_{1-6}$ alkylamino groups (e.g. methylamino, ethylamino, dimethylamino, diethylamino, etc.) and cyclic amino groups (e.g. 5- to 8-membered cyclic amino groups such as pyrrolidino, piperidino, piperazino, morpholino, etc.).

The "acyloxy" includes $C_{1-10}$ acyloxy groups such as formyloxy, acetoxy, propionyloxy, etc.

The above substituents (-L) may also have 1 to 3 substituents (designated by -M) in substitutable positions, selected from halogen (e.g. fluorine, chlorine, bromine, iodine), $C_{1-6}$ alkyl (e.g. methyl, ethyl, propyl, isopropyl, etc.), $C_{2-6}$ alkenyl (e.g. vinyl, allyl, etc.), $C_{2-6}$ alkynyl (e.g. ethynyl, propargyl, etc.), $C_{3-6}$ cycloalkyl (e.g. cyclopropyl, cyclopentyl, cyclohexyl, etc.), carboxyl, hydroxyl, cyano, nitro, sulfo, phosphono, oxo, $C_{1-6}$ alkoxy (e.g. methoxy, ethoxy, propoxy, isopropoxy, etc.), $C_{1-3}$ alkylenedioxy (e.g. methylenedioxy, ethylenedioxy), $C_{6-10}$ aryloxy (e. g. phenoxy, etc.), $C_{7-14}$ aralkyloxy (e.g. benzyloxy, etc.), mercapto, $C_{1-6}$ alkylthio (e.g. methylthio, ethylthio, propylthio, isopropylthio, etc.), $C_{6-10}$ arylthio (e.g. phenylthio, etc.), $C_{7-14}$ aralkylthio (e.g. benzylthio, etc.), carbamoyl, mono- or di- $C_{1-6}$ alkylcarbamoyl (e.g. methylcarbamoyl, dimethylcarbamoyl, etc.), amino, mono- or di-$C_{1-6}$ alkylamino (e.g. methylamino, ethylamino, di-methylamino, diethylamino, etc.), cyclic amino (e.g. pyrrolidino, piperidino, piperazino, morpholino, etc.), mono- or di- $C_{7-14}$ aralkylamino (e.g. benzylamino, dibenzylamino, etc.), $C_{6-10}$ aryl (e.g. phenyl, 1-naphthyl, 2-naphthyl, etc.), $C_{7-14}$ aralkyl (e.g. benzyl, etc.), formyl, $C_{1-6}$ alkyl-carbonyl (e.g. acetyl, propionyl, butyryl, valeryl, etc.), $C_{6-10}$ aryl-carbonyl (e.g. benzoyl, etc.), $C_{1-6}$ alkoxy-carbonyl (e.g. methoxycarbonyl, ethoxycarbonyl, propoxycarbonyl, isopropoxycarbonyl, butoxycarbonyl, etc.), $C_{1-6}$ acyloxy (e.g. formyloxy, acetoxy, etc.) and aromatic heterocyclic or aromatic heterocyclicthio, wherein the aromatic heterocyclic is a 5- to 10-membered aromatic heterocyclic ring containing 1 to 4 hetero-atoms selected from nitrogen, sulfur and oxygen, thus including 2-thienyl, 3-thienyl, 2-pyridyl, 3-pyridyl, 4-pyridyl, 2-furyl, 3-furyl, 2-quinolyl, 4-quinolyl, 8-quinolyl, 3-isoquinolyl, 4-isoquinolyl, pyrazinyl, 2-pyrimidinyl, 3-pyrrolyl, 1-imidazolyl, 2-imidazolyl, 1-pyrazolyl, 2-thiazolyl, 4-thiazolyl, 5-thiazolyl, 3-isothiazolyl, 4-isothiazolyl, 3-isoxazolyl, 3-pyridazinyl, 2-pyridon-1-yl, 3-pyridon-1-yl, 1-isoindolyl, 2-isoindolyl, 1-indolyl, 3-indolyl, 1-tetrazolyl, 2-tetrazolyl, 5-tetrazolyl, 2-pyrimidinyl, 4-pyrimidinyl, 5-pyrimidinyl, 2-purinyl, 6-purinyl, 7-purinyl, 8-purinyl, 9-purinyl, 1-xanthinyl, 3-xanthinyl, 7-xanthinyl, 8-xanthinyl, 2-quinazolinyl, 4-quinazolinyl, 5-quinazolinyl, 6-quinazolinyl, 7-quinazolinyl, 8-quinazolinyl, 4(3H)-quinazolinon-2-yl, 4(3H)-quinazolinon-3-yl, 4(3H)-quinazolinon-5-yl, 4(3H)-quinazolinon-6-yl, 4(3H)-quinazolinon-7-yl, 4(3H)-quinazolinon-8-yl, and so on. These substituent groups (—M), in turn, may have a substituent or substituents to form (—M—M). In other words, "A" may be substituted by —L—M—M.

Where the ring A has a hydroxyl group or a mercapto group, the keto or thione of these tautomeric body form also falls within the scope of the present invention.

In the above formula [I], $Ar^1$ and $Ar^2$ independently represent an optionally substituted ring.

The "ring" of the term "optionally substituted ring" includes a cyclic hydrocarbon or a heterocyclic ring, for instance.

The "cyclic hydrocarbon" includes a monocyclic or polycyclic hydrocarbon which consists of 6 to 14 carbon atoms. The examples are a $C_{6-10}$ aromatic hydrocarbon (e.g. benzene, naphthalene), a $C_{6-10}$ cycloalkane (e.g. cyclohexene) and preferably benzene.

The "heterocyclic ring" includes a mono heterocyclic ring which contains one or two species, 1 to 4 heteroatoms selected from nitrogen, oxygen and sulfur, and di- or tricondensed heterocyclic ring in which a heterocycle is fused with another ring (e.g. benzene). The examples of mono heterocyclic ring are a 5- or 6-membered heterocyclic ring (e.g. furan, thiophene, pyrrole, pyridine, pyrazole, imidazole, oxazole, thiazole, pyrazine, pyrimidine, pyridazine, isoxazole, isothiazole, triazole, etc.) and a 5- or 6-membered cyclic amino (e.g. pyrrolidine, imidazolidine, pyrazolidine, piperidine, piperazine, morpholine, etc.). The examples of di- or tri-heterocyclic ring are a benzofuran, indole, purine, indazole, quinoline, benzothiazole, coumarin, isoquinoline, etc. Preferable examples of the heterocyclic ring are a pyridine, piperidine, piperazine, morpholine, etc. $Ar^1$ and $Ar^2$ may be the same or different.

The substituent or substituents which may be substituted on the "ring" of said "optionally substituted ring" represented by the symbols $Ar^1$ and $Ar^2$ are the same substituent or substituents that may be substituted on said "condensed pyrimidinone ring" or "condensed pyridazinone ring" represented by the ring A, mentioned hereinabove. These substituents may be present in substitutable positions on the ring, and may number 1 through 5, preferably 1 through 3, per ring. Where the number of substituents is not less than 2, they may be similar to or different from each other. The total number of substituents for Arl and $Ar^2$ combined is preferably not greater than 5. $Ar^2$ may preferably have 1 to 5 substituents selected from the group consisiting of a halogen, $C_{1-10}$ alkyl, $C_{2-10}$ alkenyl, $C_{1-10}$ alkoxy, $C_{6-14}$ aryloxy, $C_{7-16}$ aralkyloxy, $C_{14\,10}$ alkylthio, carbamoyloxy, mono- or di-$C_{1-10}$ alkylcarbamoyloxy, phosphonooxy, mono- or di-$C_{1-10}$ alkylphosphonooxy, nitro, cyano, hydroxyl, amino, mono- or di-$C_{1-10}$ alkylamino, cyclic amino, carboxyl, mercapto, carbamoyl, mono- or di-$C_{1-10}$ alkylcarbamoyl, $C_{1-10}$ alkoxy-carbonyl, $C_{6-14}$ aryloxycarbonyl, $C_{7-16}$ aralkyl, $C_{6-14}$ aryl, formyl, $C_{1-10}$ alkyl-carbonyl, $C_{6-14}$ aryl-carbonyl, $C_{1-10}$ acylamino and $C_{1-10}$ acyloxy group, which may be substituted by 1 to 3 substituents selected from the group consisting of a halogen, $C_{1-6}$ alkyl, carboxyl, hydroxyl, oxo, $C_{1-6}$ alkoxy, $C_{1-3}$ alkylenedioxy, $C_{6-10}$ aryloxy, $C_{7-14}$ aralkyloxy, mercapto, $C_{1-6}$ alkylthio, carbamoyl, mono- or di-$C_{1-6}$ alkylcarbamoyl, amino, mono- or di-$C_{1-6}$ alkylamino, cyclic amino, $C_{6-10}$ aryl, $C_{7-14}$ aralkyl, formyl, $C_{1-6}$ alkyl-carbonyl, $C_{6-10}$ arylcarbonyl, $C_{1-6}$ alkoxy-carbonyl, $C_{1-6}$ acyloxy, aromatic heterocyclic and aromatic heterocyclic thio, and further which may be substituted by 1 to 3 substituents selected from the group consisting of a halogen, $C_{-6}$ alkyl, oxo, $C_{1-6}$ alkoxy, amino and mono- or di-$C_{1-6}$ alkylamino.

In the above formula [I], Z represents a divalent group. The "divalent group" is a group connecting the condensed pyrimidinone or condensed pyridazinone ring to the ring ($Ar^1$) and contains 1 to 5 (preferably 1 to 3) atoms selected from carbon, nitrogen, oxygen and sulfur. The group includes a divalent aliphatic group (e.g. straight-chain or branched aliphatic group consisting of 1 to 6 carbon atoms) which contains —NH—, —O— or —S— in the suitable positions. The divalent aliphatic group is a $C_{1-6}$ alkylene (e.g. methylene, ethylene, trimethylene, tetramethylene) or a $C_{2-6}$ alkenylene (e.g. vinylene, propenylene). Thus, for example, Z may be —CH$_2$—, —NH—, —O—, —S—, —CH$_2$CH$_2$—, —CH$_2$— NH—, —CH$_2$—O—, —CH$_2$—S—, —CH$_2$CH$_2$CH$_2$—, —NH—CH$_2$CH$_2$—, —CH$_2$—NH— CH$_2$—, —O—CH$_2$CH$_2$—, —CH$_2$—O—CH$_2$—, —S—CH$_2$CH$_2$—, —CH$_2$—S—CH$_2$—, etc.

Said "divalent group" may have 1 to 3 substituents selected from $C_{1-6}$ alkyl (e.g. methyl, ethyl, propyl, isopropyl, butyl, isobutyl, sec-butyl, tert-butyl, etc.), $C_{2-6}$ alkenyl (e.g. vinyl, allyl, isopropenyl, etc.), $C_{2-6}$ alkynyl (e.g. propargyl, ethynyl, etc.), $C_{1-6}$ alkoxy (e.g. methoxy, ethoxy, propoxy, isopropoxy, etc.), $C_{1-6}$ alkylthio (e.g. methylthio, ethylthio, propylthio, isopropylthio, etc.), $C_{1-6}$ acyl (e.g. formyl, acetyl, etc.), amino, halogen (e.g. fluorine, chlorine, bromine, iodine), hydroxy, mercapto and oxo, etc.

Where the "divalent group" represented by the symbol Z, contains carbon atoms in directly adjacent positions, the carbon-to-carbon linkage may be an unsaturated bond (e.g. double bond). Preferable examples are —CH=CH—, —CH$_2$—CH=CH—, etc.

The preferable examples of the symbols A, $Ar^1$, $Ar^2$ and Z are as follows:

The ring A: (A-1) an optionally substituted condensed pyrimidinone ring, wherein "the optionally substituted condensed pyrimidinone" is of the same meaning as defind hereinabove, (A-2) an optionally substituted pyrrolo[2,3-d]pyrimidin-4-one, quinazolin-4-one, pyrido[1,2-a]pyrimidin-4-one, thiazolo[3,2-a]pyrimidin-5-one, pyrimido[2,1-b]thiadin-6-one or imidazo[2,1-b]quinazolin-5-one, which may be partially reduced, wherein the term "optionally substituted" is of the same meaning as defined "optionally substituted" of the above "condensed pyrimidinone", (A-3) a moiety:

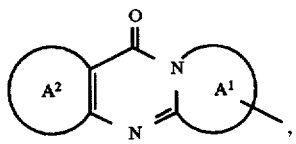

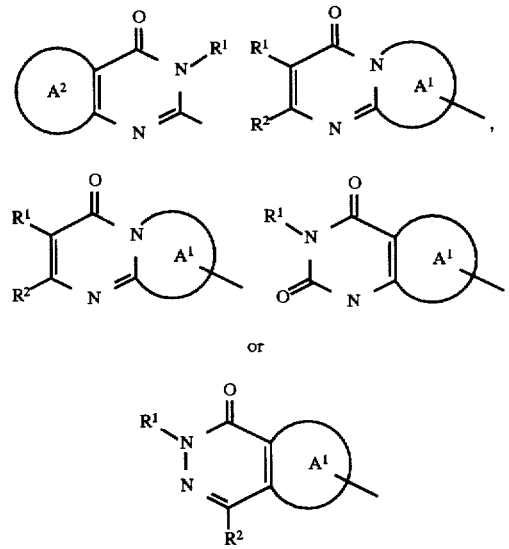

or

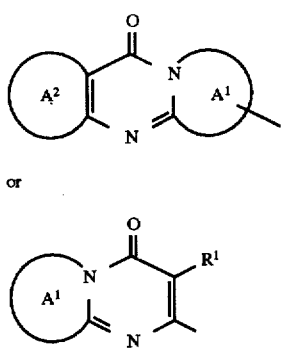

wherein $A^1$ and $A^2$ are independently an optionally substituted 5- to 8- membered carbocyclic or heterocyclic ring which may contain 1 to 4 hetero atoms selected from nitrogen, oxygen and sulfur (e.g. cyclopentane, cyclohexane, cycloheptane, benzene or an imidazole, pyridine, thiadine, thiazole, oxazole, thiophene, pyrrole, pyrazole, pyrazine, pyrimidine which may be partially reducted, etc.) which may have 1 to 3 substituents such as $R^1$ and $R^2$; $R^1$ and $R^2$ are independently a hydrogen, halogen (e.g. fluorine, chlorine, bromine, iodine), $C_{1-6}$ alkyl (e.g. methyl, ethyl, propyl, isopropyl), halogeno-$C_{1-6}$ alkyl (e.g. trifluoromethyl), hydroxyl, $C_{1-6}$ alkoxy (e.g. methoxy, ethoxy, propoxy, isopropoxy), halogeno-$C_{1-6}$ alkoxy (e.g. trifuluoromethoxy), $C_{1-6}$ alkylthio (e.g. methylthio, ethylthio, propylthio, isopropylthio) or halogeno-$C_{1-6}$ alkylthio (e.g. trifluoromethylthio), preferably the hydrogen or $C_{1-6}$ alkyl, (A-4) a moiety:

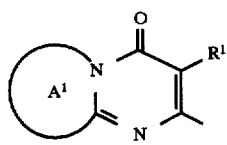

or wherein the symbols $A^1$, $A^2$ and $R^1$ are defined as in (A-3), (A-5) a moiety:

wherein the symbols $A^1$ and $R^1$ are defined as in (A-3), (A-6) a moiety:

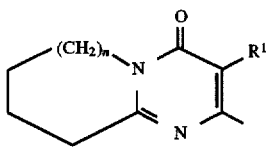

or

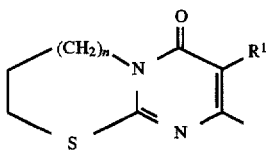

wherein n is 0 to 3, and the symbol R¹ is defined as in (A-3), (A-7) a moiety:

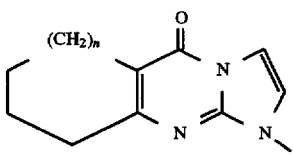

wherein n is 0 to 3, (A-8) a moiety:

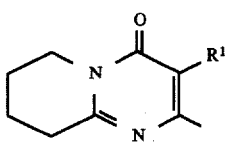

wherein R¹ is defined as in (A-3),

The symbol Z (B-1) a divalent $C_{1-6}$ aliphatic hydrocarbon group which may contain —NH—, —O— or —S—, (which is represented by $Z^a$), wherein the divalent $C_{1-6}$ aliphatic is a $C_{1-6}$ alkylene (e.g. methylene, ethylene, trimethylene, tertamethylene) or $C_{2-6}$ alkenylene (e.g. vinylene, propenylene), (B-2) a divalent $C_{1-6}$ aliphatic hydrocarbon group which may contain —O— or —S—, wherein the divalent $C_{1-6}$ aliphatic is a $C_{1-6}$ alkylene or $C_{2-6}$ alkenylene as defined in above, (B-3) a $C_{1-6}$ alkylene which may contain —O— or —S—, wherein the $C_{1-6}$ alkylene is preferably methylene, (B-4) a $C_{1-6}$ alkylene which may contain —O—, wherein the $C_{1-6}$ alkylene is preferably methylene, (B-5) a $C_{2-6}$ alkenylene (e.g. vinylene), (B-6) —S—CH₂—, —O—CH₂— or —CH₂—, (B-7) —O—CH₂— or —CH₂—, The symbol Ar¹ (C-1) an optionally substituted aromatic ring, wherein the aromatic ring is $C_{6-10}$ aryl (e.g. benzene, naphthalene) or pyridine; the term "optionally substituted" is defined as in the symbol A, (C-2) a para-substituted benzene or para-disubstituted benzene, The symbol Ar² (D-1) an optionally substituted aromatic ring, wherein the aromatic ring is $C_{6-10}$ aryl (e.g. benzene, naphthalene), pyridine, indole, pyrrole, imidazole, thiophene, pyrazine, pyrimidine, purine, quinoline or isoquinoline; the term "optionally substituted" is defined as in the ring A, (D-2) an optionally substituted phenyl, pyridyl, indolyl, pyrrolyl, thienyl, piperidino, piperazino or morpholinogroup, wherein the term "optionally substituted" is defined as in the ring A, (D-3) an optionally substituted phenyl group, wherein the term "optionally substituted" is defined as in the .ring A, (D-4) an optionally substituted piperizino, piperadino or morpholino group, wherein the term "optionally substituted" is defined as in the ring A, (D-5) an optionally substituted piperidino or piperazino group, wherein the term "optionally substituted" is defined as in the ring A. (D-6) a phenyl group which may be substituted by 1 to 5 substituents selected from the group consisting of a $C_{1-6}$ alkyl (e.g. methyl, ethyl, propyl, isopropyl), halo-$C_{1-6}$ alkyl (e.g. trifluoromethyl), $C_{1-6}$ alkoxy (e.g. methoxy, ethoxy, propoxy, isopropoxy), halo-$C_{1-6}$ alkoxy (e.g. trifluoromethoxy), $C_{1-6}$ alkylthio (e.g. .methylthio, ethylthio, propylthio, isopropylthio), halo-$C_{1-6}$ alkylthio (e.g. trifluoromethylthio), halogen (e.g. fluorine, chlorine, bromine, iodine), amino, mono- or di-$C_{1-6}$ alkylamino (e.g. methylamino, ethylamino, dimethylamino, diethylamino), $C_{1-6}$ acylamino (e.g. formylamino, acetylamino), $C_{1-6}$ alkyl-carbonyl (e.g. acetyl, propyonyl), $C_{6-10}$ aryl-carbonyl (e.g. benzoyl), $C_{7-11}$ aralkyl-carbonyl (e.g. benzylcarbonyl), $C_{1-6}$ alkoxy-carbonyl (e.g. methoxycarbonyl, ethoxycarbonyl, propoxycarbonyl, isopropoxycarbonyl), $C_{1-6}$ acyloxy (e.g. formyloxy, acetoxy), carbamoyloxy, mono- or di-$C_{1-6}$ alkylcarbamoyl (e.g. methylcarbamoyloxy, dimethylcarbamoyloxy), cyano, nitro, carbamoyl and mono- or di-$C_{1-6}$ alkyl-carbamoyl (e.g. methylcarbamoyl, ethylcarbamoyl, dimethylcarbamoyl, diethylcarbamoyl), (D-7) a moiety:

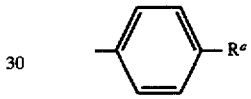

wherein $R^a$ is a substituent group which is defined as the substituent of the ring A, preferably a halogen (e.g. fluorine, chlorine, bromine, iodine), $C_{1-6}$ alkyl (e.g. methyl, ethyl, propyl, isopropyl), halo-$C_{1-6}$ alkyl (e.g. trifluoromethyl), $C_{1-6}$ alkoxy (e.g. methoxy, ethoxy, propoxy, isopropoxy) or halo-$C_{1-6}$ alkoxy (e.g. trifuluoromethoxy), (D-8) a moiety:

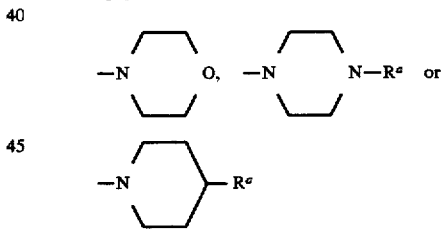

wherein $R^a$ is defined as above, (D-9) a moiety:

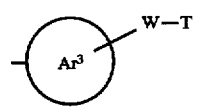

wherein Ar³ is a ring; W is a bond, a carbonyl or a divalent $C_{1-6}$ aliphatic hydrocarbon group which may contains —NR³— (R³ is a hydrogen or a $C_{1-6}$ alkyl group (e.g. methyl)), —O— or —S—; T is an optionally substituted amino group.

The term 'ring' represented by Ar³ is of the same meaning as defined in Ar¹ and Ar². The preferable examples are piperidino, piperazino, phenyl or pyridyl, and more preferably a moiety:

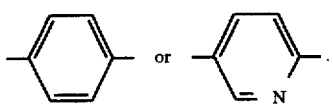

The term "divalent $C_{1-6}$ aliphatic hydrocarbon group" is defined as in (B-1), preferably —$CH_2$—, —$CH_2CH_2$—, —O—$CH_2CH_2$—.

The term "amino group" includes a primary to tertiary amino group such as a mono- or di-$C_{1-6}$ alkylamino (e.g. methylamino, ethylamino, dimethylamino, diethylamino), a mono- or di-$C_{6-10}$ arylamino (e.g. phenylamino, diphenylamino), a cyclic amino (e.g. piperidino, piperazino, morpholino), and so on. The preferable examples are a cyclic amino (e.g. piperidino, piperazino). The "amino group" may have 1 to 3 substituents such as —M defined hereinabove.

The preferable combinations are as follow: (A-1),(B-1), (C-1),(D-1)/(A-2),(B-1),(C-2),(D-1) (A-3),(B-1),(C-2),(D-1)/(A-4),(B-1), (C-2),(D-1)/(A-5),(B-1),(C-2),(D-1)/ (A-6), (B-1),(C-2),(D-1)/(A-7),(B-2),(C-2),(D-1)/(A-2),(B-2),(C-2),(D-1)/(A-3),(B-2),(C-2),(D-1)/(A-4),(B-2),(C-2),(D-1)/ (A-5),(B-2),(C-2),(D-1)/(A-6),(B-2),(C-2),(D-1)/(A-7),(B-2),(C-2),(D-1)/(A-2),(B-3),(C-2),(D-1)/(A-3),(B-3),(C-2), (D-1)/(A-4),(B-3),(C-2),(D-1)/(A-5),(B- 3),(C-2),(D-1)/(A-6),(B-3),(C-2),(D-1)/(A-7),(B-3),(C-2),(D-1)/(A-2),(B-4), (C-2),(D-1)/(A-3),(B-4),(C-2),(D-1)/(A-4),(B-4),(C-2),(D-1)/(A-5),(B-4),(C-2),(D-1)/(A-6),(B-4),(C-2),(D-1)/(A-7), (B-4),(C-2),(D-1)/(A-2),(B-5),(C-2),(D-1)/(A-3),(B-5),(C-2),(D-1)/(A-4),(B-5),(C-2),(D-1)/(A-5),(B-5),(C-2),(D-1)/ (A-6),(B-5),(C-2),(D-1)/(A-7),(B-5),(C-2),(D-1)/(A-3),(B-3),(C-2),(D-2)/(A-4),(B-3),(C-2),(D-2)/(A-4),(B-3),(C-2), (D-2)/(A-5),(B-3),(C-2),(D-2)/(A-6),(B-3),(C-2),(D-2)/(A-7),(B-3),(C-2),(D-2)/(A-3),(B-5),(C-2),(D-2)/(A-4),(B-5), (C-2),(D-2)/(A-5),(B-5),(C-2),(D-2)/(A-6),(B-5),(C-2),(D-2)/(A-7),(B-5),(C-2),(D-2)/(A-3),(B-3),(C-2),(D-3)/(A-3), (B-3),(C-2),(D-4)/(A-4),(B-3),(C-2),(D-3)/(A-4),(B-3),(C-2),(D-4)/(A-5),(B-3),(C-2),(D-3)/(A-5),(B-3),(C-2),(D-4)/ (A-6),(B-3),(C-2),(D-6)/(A-7),(B-3),(C-2),(D-6)/(A-6),(B-4),(C-2),(D-6)/(A-7),(B-4),(C-2),(D-6)/(A-6),(B-6),(C-2), (D-5)/(A-7),(B-6),(C-2),(D-5)/(A-6),(B-7),(C-2),(D-6)/(A-7),(B-7),(C-2),(D-6)/(A-6),(B-7),(C-2),(D-7)/(A-7),(B-7), (C-2),(D-7)/(A-6),(B-7),(C-2),(D-8)/(A-7),(B-7),(C-2),(D-8)/(A-1),(B-1),(C-1),(D-9)/(A-2),(B-1),(C-2),(D-9)/(A-3), (B-1),(C-2),(D-9)/(A-4),(B-1),(C-2),(D-9)/(A-5),(B-1),(C-2),(D-9)/(A-6),(B-1),(C-2),(D-9)/(A-7),(B-1),(C-2),(D-9)/ (A-8),(B-1),(C-2),(D-9)/(A-3),(B-2),(C-2),(D-9)/(A-4),(B-2),(C-2),(D-9)/(A-5),(B-2),(C-2),(D-9)/(A-6),(B-2),(C-2), (D-9)/(A-7),(B-2),(C-2),(D-9)/(A-8),(B-2),(C-2),(D-9)/(A-3),(B-4),(C-2),(D-9)/(A-4),(B-4),(C-2),(D-9)/(A-5),(B-4), (C-2),(D-9)/(A-6),(B-4),(C-2),(D-9)/(A-7),(B-4),(C-2),(D-9)/(A-8),(B-4),(C-2),(D-9)/(A-3),(B-6),(C-2),(D-9)/(A-4), (B-6),(C-2),(D-9)/(A-5),(B-6),(C-2),(D-9)/(A-6),(B-6),(C-2),(D-9)/(A-7),(B-6),(C-2),(D-9)/(A-8),(B-6),(C-2),(D-9)/ (A-3),(B-7),(C-2),(D-9)/(A-4),(B-7),(C-2),(D-9)/(A-5),(B-7),(C-2),(D-9)/(A-6),(B-7),(C-2),(D-9)/(A-7),(B-7),(C-2), (D-9)/(A-8),(B-7),(C-2),(D-9) and so on.

The following are examples of preferred compounds [I] or salts thereof.

(1) Compounds of the formula:

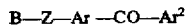

B—Z—Ar—CO—$Ar^2$  [I-a]

wherein ring B represents an optionally substituted, (1) pyrrolo[2,3-d]pyrimidin-4-one, (2) pyrrolo[3,2-d]-pyrimidin-4-one, (3) pyrrolo[3,4-d]pyrimidin-4-one, (4) pyrazolo[3,4-d]pyrimidin-4-one, (5) pyrazolo[4,3-d]-pyrimidin-7-one, (6) $^6$-oxopurine, (7) thieno[2,3-d]-pyrimidin-4-one, (8) thieno[3,4-d]pyrimidin-4-one, (9) thieno[3,2-d]pyrimidin-7-one, (10) furo[2,3-d]pyrimidin-4-one, (11) furo[3,4-d]pyrimidin-4-one, (12) furo[3,2-d]pyrimidin-7-one, (13) isoxazolo[5,4-d]pyrimidin-4-one, (14) isoxazolo[4,5-d]pyrimidin-7-one, (15) oxazolo[5,4-d]pyrimidin-4-one, (16) oxazolo[4,5-d]pyrimidin-7-one, (17) thiazolo[5,4-d]pyrimidin-4-one, (18) thiazolo[4,5-d]pyrimidin-7-one, (19) isothiazolo[5,4-d]pyrimidin-4-one, (20) isothiazolo[4,5-d]pyrimidin-7-one, (21) triazolo[4,5-d]pyrimidin-4-one, (22) $1,2,4$-triazolo[1,5-a]pyrimidin-7-one, (23) dihydrocyclopenta[d]pyrimidin-4-one, (24) 5H- or $^7$H-cyclopenta[d]pyrimidin-4-one, (25) pyrido-[2,3-d]pyrimidin-4-one, (26) pyrido[3,2-d]pyrimidin-4-one, (27) pyrido[4,3-d]pyrimidin-4-one, (28) pyrido[3,4-d]pyrimidin-4-one, (29) puteridin-4-one, (30) pyrrolo[1,2-a]pyrimidin-4-one, (31) pyrimido[3,4-a]pyrimidin-4-one, (32) pyrimido[4,5-d]pyrimidin-4-one, (33) pyrimido[5,4-d]pyrimidin-4-one, (34) pyridazino-[2,3-a]pyrimidin-4-one, (35) pyridazino[4,3-d]pyrimidin-4-one, (36) pyridazino[3,4-d]pyrimidin-4-one, (37) xanthine, (38) uric acid, (39) pyrrolo[3,2-d]pyrimidine-2,4-dione, (40) pyrrolo[2,3-d]pyrimidine-2,4-dione, (41) pyrrolo[3,4-d]pyrimidine-2,4-dione, (42) pyridazino[4,5-b]-1,5-oxazepin-9(8H)-one, (43) pyridazino[4,5-b]-1,4-oxazin-8(7H)-one, (44) pyrrolo[3,4-d]pyridazin-4(5H)-one, (45) pyrrolo[2,3-d]-pyridazin-7(6H)-one, (46) pyrrolo[2,3-d]pyridazin-4(5H)-one, (47) imidazo[4,5-d]pyridazin-4(5H)-one, (48) imidazo[4,5-c]pyridazin-6(5H)-one, (49) pyrazolo[4,3-d]pyridazin-4(5H)-one, (50) pyrazolo[3,4-d]pyridazin-4(5H)-one, (51) triazolo[4,5-d]pyridazin-4(5H)-one, (52) pyrido[2,3-d]pyridazin-5(6H)-one or (53) thiazolo[4,5-d]pyridazin-7(6H)-one; the other symbols are defined as hereinbefore, or salts thereof.

The substituent or substituents which may be substituted on B are the same as the substituent or substituents substituted on A.

(2) Compounds of the formula:

D—Alk—E—$Ar^1$—CO—$Ar^2$  [I-b]

wherein ring D represents an optionally substituted, (1) quinazolin-5-one, (2) pyrido[1,2-a]pyrimidin-4-one, (3) imidazo[1,2-a]pyrimidin-5-one, (4) thiazolo[3,2-a]-pyrimidin-5-one, (5) oxazolo[3,2-a]pyrimidin-5-one or pyrido[1,2-a]pyrimidin-4-one; Alk represents a C1≡3 alkylene (e.g. —$CH_2$—, —$CH_2CH_2$—, etc.); E represents a bond, —S—, —O—, —NR—, —S—$CH_2$—, —O—$CH_2$—, —NR—$CH_2$— [R represents hydrogen, $C_{1-6}$ alkyl (e.g. methyl, ethyl, propyl, isopropyl, etc.) or $C_{2-6}$ alkenyl (e.g. vinyl, allyl, etc.; the other symbols are of the same meanings as defined hereinbefore.

The substituent or substituents which may be substituted on D are the same as the substituent or substituents substituted on ring A.

(3) Compounds having a —Z—Arl—CO—$Ar^2$ moiety in position-1 of the imidazo[1,2-a]pyrimidin-5-one ring that may be substituted, or salts thereof.

The substituent or substituents that may be substituted on said imidazo[1,2-a]pyrimidin-5-one are the same as the substituent or substituents substituted on ring A. The symbols Z, $Ar^1$ and $Ar^2$ are defined as hereinbefore.

Compound [I] or a salt thereof can be typically produced in accordance with the following reaction schemes.

Reaction Schemes (Scheme 1)

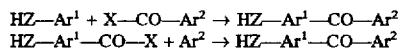

(Scheme 2)

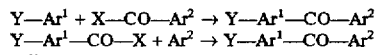

(Scheme 3)

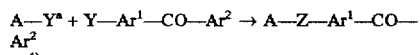

(Scheme 4)

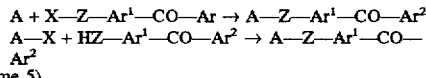

(Scheme 5)

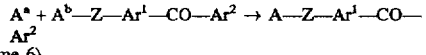

(Scheme 6)

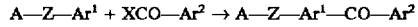

In the above reaction schemes, —CO—X represents a reactive derivative of a reactive carboxyl group; Y and ya react to form the group represented by Z on mutual reaction; X—Z— represents a reactive derivative of Z; $A^a$ and $A^b$, taken together, represents a condensed pyrimidinone or condensed pyridazinone ring A as formed on mutual reaction; X represents a reactive group.

Referring to the above (Scheme 1), the reactive derivative of a carboxyl group as represented by —CO—X includes acid halides (e.g. acid chloride, acid bromide, etc.) and acid anhydrides (e.g. the anhydride of $Ar^2COOH$ and a mixed acid anhydride with a different acid such as formic acid). The reaction is generally carried out in the presence of a Lewis acid (e.g. aluminum chloride, aluminum bromide, tin chloride, antimony chloride, titanium chloride, boron trifluoride, etc.). The reaction solvent can be virtually any solvent that is indifferent to the reaction, typically carbon disulfide or a halogenated hydrocarbon. Where HZ-$Ar^1$ or $Ar^2$ is liquid, HZ-$Ar^1$ or $Ar^2$ can be used as the solvent as well. The reaction temperature may range from 0° C. to the boiling point of the solvent but is generally 20° C. to 80° C. The reaction time is about 1–12 hours. Though it depends on the substrate, the amount of the catalyst is 1–5 times relative to the reactive derivative of the carboxyl compound. The reaction according to (Scheme 2) also proceeds under similar conditions to those used in the reaction according to (Scheme 1). Referring to the above (Scheme 2) and (Scheme 3), Y and $Y^a$ are the groups forming the divalent group Z by carbon-carbon bonding reaction, nitrogen-carbon bonding reaction, oxygen-carbon bonding reaction, sulfur-carbon bonding reaction or the like. The specific reactions giving the divalent group Z from Y and $Y^a$ include the Witting reaction, Grignard reaction, aldol reaction, Claisen reaction, carbon-carbon bonding reaction with the aid of a transition metal, nitrogen-carbon bonding reaction through alkylation or arylation of the amino group, oxygen-carbon bonding reaction by O-alkylation of the alcohol, and sulfur-carbon bonding reaction by S-alkylation of mercaptan, among other reactions. The alkylation of the amino group, alcohol and mercaptan can be invariably carried out advantageously in the presence of a base. The base that can be used includes sodium hydroxide, potassium hydroxide, sodium carbonate, potassium carbonate, sodium hydride, sodium methoxide and sodium ethoxide. The reaction solvent that can be used for the alkylation of the amino group or mercaptan includes alcohols (e.g. methanol, ethanol, propanol, etc.), amides (e.g. dimethylformamide, dimethylacetamide, 1-methyl-2-pyrrolidone, etc.), and dimethyl sulfoxide. For alkylation of the alcohol, an amide or dimethyl sulfoxide can be used on a routine basis. These reactions proceed in the temperature range of 0° C. to the boiling point of the solvent used, preferably at room temperature to the boiling point of the solvent, and goes to completion in 1 to 10 hours, generally in about 5 hours. Where one of Y and $Y^a$ is an amino compound and the other is a carboxylic acid or a reactive derivative thereof, Z may be produced by amide bond formation. The reaction technology that can be used for this purpose is the usual amidation reaction. (Scheme 4), presented hereinbefore, is relevant to the case in which the fused pyrimidinone or fused pyridazinone ring A has an amino group and represents the reaction for bonding Z to the amino group. The reactive derivative of Z as represented by X—Z— includes one in which X is a halogen atom (e.g. chlorine, bromine, iodine, etc.), an alkyl group or an arylsulfonyloxy group (e.g. methanesulfonyloxy, p-toluenesulfonyloxy, etc.), for instance. This reaction is generally carried out in the presence of a base. The base that can be used for this purpose includes but is not limited to sodium hydroxide, potassium hydroxide, sodium carbonate, potassium carbonate, sodium hydride, sodium methoxide and sodium ethoxide. The solvent may be any solvent that is inert to the reaction, thus including methanol, ethanol, dimethyl sulfoxide, N,N-dimethylformamide and dimethylacetamide, to mention but a few examples. The reaction temperature may range from 0° C. to the boiling point of the solvent and the reaction goes to completion in 1–10 hours, usually in about 5 hours. (Scheme 5), given hereinbefore, represents the reaction for forming the fused pyrimidinone or fused pyridazinone ring A and is relevant to the case in which the ring precursor compound $A^a$ or A already has a —Z—$Ar^1$—CO—$Ar^2$ moiety. It should be understood that, as shown in (Scheme 6), the sequence of first synthesizing the A—Z—$Ar^1$ moiety and adding a —CO—$Ar^2$ moiety thereto can also be employed.

The starting compounds and intermediate compounds either mentioned or inferred herein may each be used in the form of a salt, and the type of salt is not particularly critical as far as the production stage is concerned. Thus, for example, salts with various inorganic acids (e.g. hydrochloric acid, sulfuric acid, phosphoric acid, etc.), organic acids (e.g. acetic acid, propionic acid, citric acid, tartaric acid, malic acid, oxalic acid, etc.), alkali metals (e.g. sodium, potassium, etc.), alkaline earth metals (e.g. calcium, magnesium, etc.) and organic bases (e.g. triethylamine, piperidine, etc.) can be employed.

In the above reactions according to the present invention and the reactions for synthesizing the starting compounds used there, where any starting material compound has an amino group, a carboxyl group and/or a hydroxyl group as a substituent, such functional group or groups may be previously blocked or masked using protective groups which are conventionally used in peptide chemistry and the objective compound can then be obtained by eliminating the protective group or groups after the intended reaction.

The protective group that can be used for masking an amino group includes $C_{1-6}$ alkyl-carbonyl (e.g. formyl, acetyl, ethylcarbonyl, etc.), benzyl, tert-butyloxycarbonyl, benzyloxycarbonyl, 9-fluorenylmethyloxycarbonyl, allyloxycarbonyl, phenylcarbonyl, $C_{1-6}$ alkyloxycarbonyl (e.g. methoxycarbonyl, ethoxycarbonyl, etc.), $C_{7-10}$ aralkylcarbonyl (e.g. benzylcarbonyl etc.), trityl, phthaloyl, N,N-dimethylaminomethylene, etc. These groups may have 1–3 substituent groups such as halogen (e.g. fluorine, chlorine, bromine, iodine) and nitro.

The protective group for masking a carboxyl group includes $C_{1-6}$ alkyl (e.g. methyl, ethyl, n-propyl, iso-propyl, butyl, tert-butyl, etc.), phenyl, silyl, benzyl and allyl, to name but a few examples. These groups may have 1–3 substituents, which may for example be halogen (e.g. fluorine, chlorine, bromine, iodine) and nitro.

The protective group for a hydroxyl group includes methoxymethyl, allyl, tert-butyl, $C_{7-10}$ aralkyl (e.g. benzyl etc.), $C_{1-6}$ alkyl-carbonyl (e.g. formyl, acetyl, ethylcarbonyl, etc.), benzoyl, $C_{7-10}$ aralkyl-carbonyl (e.g. benzylcarbonyl etc.), pyranyl, furanyl, trialkyl-silyl, etc. These groups, in turn, may have 1–3 substituents, typically halogen (e.g. fluorine, chlorine, bromine, iodine), $C_{1-6}$ alkyl (e.g. methyl, ethyl, n-propyl, etc.), phenyl, $C_{7-10}$ aralkyl (e.g. benzyl etc.), and nitro.

Removal of such protective groups can be carried out by techniques either known per se or analogous to known techniques. By way of illustration, a method using an acid or a base, reductive deprotection, and a technique using any of ultraviolet light, hydrazine, phenylhydrazine, sodium N-methyldithiocarbamate, tetrabutylammonium fluoride, palladium acetate, etc. can be mentioned.

Where any of the above reactions yields the objective compound in its free form, it may be converted to a salt in the conventional manner. Conversely where a salt is obtained, it can be converted to the free compound or a different salt species. The resulting compound [I] or salt can be separated and purified from the reaction mixture by any known procedures such as redistribution, concentration, solvent extraction, fractional distillation, crystallization, recrystallization, chromatography, etc.

Further, where compound [I] or a salt thereof exists as diastereomers or conformers, the respective isomers can be fractionally isolated by the same separation and purification procedures as mentioned above. Where compound [I] or salt is a racemic compound, it can be resolved into d- and l-isomers by optical resolution procedures known per se.

Where compound [I] contains a basic group, it can be isolated in the form of an acid addition salt, preferably as a pharmacologically acceptable acid addition salt. The acid that can be used for this purpose includes inorganic acids (e.g. hydrochloric acid, sulfuric acid, phosphoric acid, etc.) and organic acids (e.g. acetic acid, propionic acid, citric acid, tartaric acid, malic acid, oxalic acid, etc.). Where compound [I] contains an acidic group, it can be provided in the form of a salt using a base, particularly a pharmacologically acceptable base. The base that can be used for this purpose includes alkali metals (e.g. sodium, potassium, etc.), alkaline earth metals (e.g. calcium, magnesium, etc.), and organic bases (e.g. triethylamine, piperidine, etc.).

Compound [I], inclusive of its salt, has an excellent antineoplastic activity with a low toxic potential and a low risk of side effects and, therefore, can be used as an antineoplastic drug against primary cancer such as prostate cancer, pancreatic cancer and lung cancer in mammalian animals (e.g. man, cow, ox, horse, dog, cat, monkey, mouse, rat, etc.). In addition, because of its antimetastatic action, postoperative recurrence-preventing action, and action to alleviate neoplasm-associated symptoms (such as pain, cachexia, etc.), the compound has a high clinical utility value. Moreover, additive or synergistic effects can be expected by using compound [I] or a salt thereof in combination with other drugs (e.g. alkylating agents such as ifosfamide, estramustine sodium phosphate, nimustine hydrochloride., etc.; antimetabolic agents such as 5-fluorouracil, tegafur, etc.; anibiotics such as mitomycin C, doxorubicin hydrochloride, bleomycin, peplomycin sulfate, aclarubicin hydrochloride, neocarzinostatin, etc.; cisplatin and carboplatin; among others), BRM (IL-2, IFN-α, IFN-β, IFN-γ, TNF-α, etc.), neo-vascularization inhibitors, etc., thermotherapy, and, in the treatment of prostate cancer, hormone therapies (orchiectomy, estrogen therapy, and administration of diethylstilbestrol diphosphate, LHRH-agonists, LHRH-antagonists, etc.).

And, the compound [I] or a salt thereof has also an excellent activity in the eradication of Helicobacter pylori, and therefore can be used for prevention and treatment of infections caused by Helicobacter pylori. The infections caused by Helicobacter pylori include duodenal ulcer, gastric ulcer, oesophagitis, gastritis, gastric cancer, and so on.

A combination of the compound [I] or a salt thereof and one to three agents selected from the group consisting of an anti-ulcer agent and an anti-microbial agent is a preferable therapy against diseases of systema digestorium caused by Helicobacter pylori. The anti-ulcer agents include proton pump inhibitor (e.g. lansoprazole, omeprazole, pantoprazole, pariprazole, leminoprazole, etc.), $H_2$-receptor antagonist (e.g. cimetidine, ranitidine, famotidine, etc.), and so on. The anti-microbial agents include amoxicillin, clarithromycin, tetracycline, metronidazole, tinidazole, and so on. The diseases of systema digestrium include duodenal ulcer, gastric ulcer, oesophagitis, gastritis, gastric cancer, and so on.

Compound [I] or a salt thereof can be safely administered, whether orally or otherwise, either as it is or as a pharmaceutical composition or dosage form prepared using pharmaceutically acceptable carriers in accordance with a per se known manufacturing protocol (as described inter alia in Japanese Pharmacopoeia XII), the pharmaceutical composition or dosage form including but being not limited to tablets (inclusive of dragees, film-coated tablets, etc.), powders, granules, kaoucels, capsules (inclusive of soft capsules), solutions, drip injections, injections, dosage forms for external use (e.g. transnasal and transdermal dosage forms), suppositories (e.g. rectal suppositories and vaginal suppositories), and controlled release preparations, among other drug delivery systems. The dosage depends on the subject, administration route, and type of disease, among other factors. Taking oral administration to an adult patient with cancer of the prostate gland as an example, the recommended dosage should be 0.1 to 20 mg/kg, preferably 0.2 to 10 mg/kg, as active ingredient (compound [I] or salt), to be administered in a single dose or in a few divided doses daily.

The pharmaceutically acceptable carriers mentioned above can be selected from among those organic and inorganic carriers which are conventionally used in pharmaceutical practice. Thus, these substances are incorporated in solid dosage forms as the excipient, lubricant, binder, disintegrator, thickener, etc. or in liquid dosage forms as the solvent, dispersant, solubilizer, suspending agent, isotonizing agent, buffer, soothing (local anesthetic) agent, etc. Where necessary, such other additives as preservatives, antioxidants, coloring agents, sweeteners, etc. can be incorporated. Preferred examples of the excipient are lactose, sucrose, D-mannitol, starch, crystalline cellulose, light silicic anhydride, etc. Preferred examples of the lubricant are magnesium stearate, calcium stearate, talc, colloidal silica, etc. The binder is preferably selected from among crystalline cellulose, sucrose, D-mannitol, dextrin, hydroxypropylcellulose, hydroxypropylmethylcellulose, and polyvinylpyrrolidone, to name but a few. The disintegrator includes such preferred species as starch, carboxymethylcellulose, carboxymethylcellulose calcium, croscarmellose sodium, carboxymethylstarch sodium, etc. The thickener or viscosity builder includes such preferred species as natural gums, cellulose derivatives, and acrylic polymers, among others. The solvent is preferably selected from among water for injection, alcohol, propylene glycol, macrogols, sesame oil, corn oil and so forth. The dispersant includes such preferred species as Tween 80, HCO 60, polyethylene glycol, carboxymethylcellulose, sodium alginate, etc. Among preferred examples of the solubilizer are polyethylene glycol, polypropylene glycol, D-mannitol, benzyl benzoate, ethanol, trisaminomethane, cholesterol, triethanolamine, sodium carbonate and sodium citrate. The preferred suspending agent includes surfactants such as stearyltriethanolamine, sodium lauryl sulfate, lauryl-aminopropionic acid, lecithin, benzalkonium chloride, benzethonium chloride, glycerin monostearate, etc., and hydrophilic macromolecular substances such as polyvinyl alcohol, polyvinylpyrrolidone, carboxymethylcellulose sodium, methylcellulose, hydroxymethylcellulose, hydroxyethylcellulose, hydroxypropylcellulose, etc. The preferred isotonizing agent includes sodium chloride, glycerol, D-mannitol and so forth. The preferred buffer includes phosphate, acetate, carbonate, citrate and other buffer solutions. A preferred example of the soothing agent is benzyl alcohol. The preferred preservative includes p-hydroxybenzoic esters, chlorobutanol, benzyl alcohol, phenethyl alcohol, dehydroacetic acid, and sorbic acid, among others. Preferred examples of the antioxidant are sulfites and ascorbic acid.

Typical dosage forms according to the present invention are now described.

(1) Tablets, powders, granules and kaoucels:

These dosage forms can be manufactured by adding an excipient, a disintegrator, a binder, a lubricant, etc. to compound [I] or a salt thereof and compression-molding the mixture, followed where necessary by masking the taste and applying an enteric or sustained-release coat.

(2) Injections:

An aqueous injection can be manufactured by adding compound [I] or a salt thereof as well as a dispersant, a preservative, an isotonizing agent, etc. to an aqueous medium. An oily injection can be manufactured by dissolving, suspending or emulsifying compound [I] or a salt thereof in a vegetable oil, such as olive oil, sesame oil, cottonseed oil, corn oil, etc., propylene glycol, or the like.

(3) Dosage forms for external application

Dosage forms of this type can be manufactured by processing compound [I] or a salt thereof into solid, semisolid or liquid dosage forms. For example, a solid dosage form can be manufactured by pulverizing compound [I] or a salt thereof either alone or together with an excipient, a thickener, etc. to provide a powdery preparation. A liquid dosage form can be manufactured by formulating compound [I] or a salt thereof into an oily or aqueous suspension in substantially the same manner as the liquid dosage form mentioned above. The semi-solid dosage form is preferably a water-based or oil-based gel or ointment. These dosage forms may contain buffers, preservatives and the like.

(4) Suppositories:

Suppositories can be manufactured by processing compound [I] or a salt thereof into an oil-based or water-based solid, semisolid or liquid composition. The oleaginous base that can be used in such dosage forms includes higher fatty acid glycerides (e.g caccao butter, Witepsol, etc.), medium-chain fatty acids (e.g. Migryol etc.), and vegetable oils (e.g. sesame oil, soybean oil, cottonseed oil, etc.). The hydrogel base that can be used includes natural gums, cellulose derivatives, vinyl polymers, acrylic polymers, and so forth.

EXAMPLES

The following reference examples, examples, formulation examples, and test examples are intended to describe the present invention in further detail and should by no means be construed as defining the invention. Moreover, many changes and modifications can be made without departing from the scope of the invention. The abbreviations used in the reference examples and examples have the following meanings. s: singlet, d: doublet, t: triplet, q: quartet, dd: double doublet, dt: double triplet, m: multiplet, br: broad, J: coupling constant, room temperature: 0°–30° C.

REFERENCE EXAMPLE 1

2-Mercapto-3-methyl-6,7-dihydro-5H-cyclopenta[d]-pyrimidin-4-one

Five (5) drops of concentrated sulfuric acid were added to a mixture of 2-ethoxycarbonylcyclopentanone (31.2 g) and methylthiourea (18.0 g) and the mixture was heated at 100° C. for 2 days. The resulting precipitate was collected by filtration, rinsed with ethanol, and dried to provide the title compound as colorless powder (10.2 g).
$^1$H-NMR (DMSO-$d_6$) δ1.98(2H,m), 2.55(2H,t,J=7.2Hz), 2.74(2H,t,J=7.8Hz), 3.52(3H,s).

REFERENCE EXAMPLE 2

1,7-Dimethyl-2-mercapto-6-oxopurine

A mixture of 1,7-dimethylxanthine (500 mg) and phosphorus oxychloride (10 ml) was refluxed for 5 hours and then concentrated and the residue was dissolved in ethanol (15 ml). To this solution was added thiourea (1.06 g) and the mixture was refluxed for 15 hours. After cooling, the resulting precipitate was collected by filtration, rinsed with ethanol, and dried to provide the title compound (290 mg) as yellow solid. $^1$H-NMR (DMSO-$d_6$) δ3.60(3H,s), 3.89(3H,s), 8.07(1H,s), 13.54(1H,brs).

REFERENCE EXAMPLE 3

9-Hydroxy-2,3-dimethyl-4H-pyrido[1,2-a]pyrimidin-4-one

A mixture of 2-amino-3-hydroxypyridine (11 g), ethyl 2-methylacetoacetate (14.4 g), polyphosphoric acid (20 ml), and acetic acid (40 ml) was heated at 100° C. with stirring for 4 hours. The reaction mixture was poured in ice-water, adjusted to pH 4 with aqueous sodium hydroxide solution and then to pH 7 with potassium carbonate. The resulting precipitate was extracted with chloroform and the extract was washed with water, dried, and concentrated to provide the title compound (3.63 g) as brown solid. $^1$H-NMR (DMSO-$d_6$) δ: 2.25(3H,s), 2.49(3H,s), 6.97(1H,dd,J=7.4, 6.8Hz), 7.05(1H,dd,J=7.4,1.6Hz), 8.47(1H,dd,J=6.8,1.6Hz).

REFERENCE EXAMPLE 4

7-(4-(4-Chlorobenzoyl)benzyl)-2,6-dichloropurine

To a solution of 2,6-dichloropurine (3.25 g) in DMF (34 ml) was added potassium carbonate (2.85 g) as well as 4-(4-chlorobenzoyl)benzyl bromide (5.32 g) and the mixture was stirred at room temperature for 24 hours. This reaction mixture was diluted with water and extracted with ethyl acetate and the extract was washed with saturated aqueous NaCl solution and dried over anhydrous sodium sulfate. The solvent was then distilled off and the residue was purified by silica gel column chromatography (hexane: ethyl acetate= 1:1–1:3) to provide the title compound (1.37 g, 19%) as colorless (anhydrous) powder. $^1$H-NMR (CDCl$_3$) δ5.76(2H, s), 7.21–7.85(8H,m), 8.33(1H,s).

IR (KBr): 1655, 1600, 1580, 1530, 1400, 1270, 1230, 1170, 1090, 990, 925, 750 cm$^{-1}$.

REFERENCE EXAMPLE 5

7-(4-(4-Chlorobenzoyl)benzyl)-2,6-diethoxypurine

To a solution of 7-(4-(4-chlorobenzoyl)benzyl)-2,6-dichloropurine (1.12 g) in ethanol (30 ml) was added sodium ethoxide (1.83 g) and the mixture was stirred at room temperature for 96 hours. This reaction mixture was diluted with water and extracted with ethyl acetate. The extract was washed with saturated aqueous NaCl solution and dried over anhydrous sodium sulfate and the solvent was distilled off. The residue was washed with ether and hexane to provide the title compound (0.78 g, 67%) as colorless powder. $^1$H-NMR (CDCl$_3$) δ: 1.34(3H,t,J=7.0Hz), 1.50(3H,t,J= 7.0Hz), 4.50(2H,q,J=7.0Hz), 4.55(2H,q,J=7.0Hz), 5.53 (2H,s), 7.25–7.80(8H,m), 7.98(1H,s).

IR (KBr): 2980, 1660, 1620, 1570, 1490, 1450, 1380, 1345, 1300, 1190, 1140, 1120, 1090, 1065, 930 cm$^{-1}$.

REFERENCE EXAMPLE 6

1-[4-(4-Chlorobenzoyl)benzyl]-4,5-dimethoxycarbonyl-imidazole

Under argon gas, sodium hydride (816 mg) was washed with hexane (10 ml) and dissolved in DMF (30 ml). This solution was cooled to 0° C. and dimethyl 1H-imidazole-4,5-dicarboxylate (3.17 g) was added. The mixture was stirred at 0° C. for 15 minutes and at room temperature for 1.5 hours and, then, recooled to 0° C. To this reaction mixture was added 4-(4-chlorobenzoyl)benzyl bromide (5.14 g) and the mixture was stirred at room temperature for 1 hour. After addition of ice, the reaction mixture was diluted with ethyl acetate (150 ml) and the organic layer was washed with water (100 ml) 4 times and dried over anhydrous magnesium sulfate. After the desiccant was filtered off, the solvent was distilled off and the residue was purified by silica gel column chromatography (stationary phase 100 g; dichloromethane: ether=10:2→2:1) to provide 4.06 g (59%) of the title compound. $^1$H-NMR (CDCl$_3$) δ: 3.86(3H,s), 3.94(3H,s), 5.52 (2H,s), 7.26(2H,d,J=7.2Hz), 7.47(2H,d,J=8.6Hz), 7.64–7.80 (5H,m).

REFERENCE EXAMPLE 7

1-[4-(4-Chlorobenzoyl)benzyl]imidazo[4,5-d]-pyridazine-4(5H),7(6H)-dione

To a solution of 1-[4-(4-chlorobenzoyl)benzyl]-4,5-dimethoxycarbonylimidazole (3.31 g) in methanol (20 ml) was added hydrazine monohydrate (1.68 g) and the mixture was refluxed for 5 hours. The resulting crystals were harvested by filtration and suspended in water (100 ml) and, after addition of concentrated HCl (10 ml), the suspension was stirred at 80° C. for 30 minutes. The resulting crystals were collected by filtration and dried in vacuo to provide 2.67 g (yield 88%) of the title compound. $^1$H-NMR (DMSO) δ: 5.78(2H,s), 7.45–7.77(8H,m), 8.49(1H,s).

REFERENCE EXAMPLE 8

1-[4-(4-Chlorobenzoyl)benzyl]-4,7-dichloroimidazo-[4,5-d]pyridazine

In phosphorus oxychloride (33.2 g) was dissolved 1-[4-(4-chlorobenzoyl)benzyl]-imidazo[4,5-d]pyridazine-4(5H), 7(6H)-dione (2.57 g) and the mixture was refluxed for 2 hours. After the phosphorus oxychloride was distilled off under reduced pressure, saturated aqueous solution of NaHCO$_3$ was added to the residue and the resulting crystals were collected by filtration. The crystals were rinsed with water, dried in vacuo, and purified by silica gel column chromatography (stationary phase 30 g; dichloromethane: ethyl acetate=1:0–4:1) to provide 2.17 g (yield 77%) of the title compound. $^1$H-NMR (CDCl$_3$) δ:5.85(2H,s), 7.26(2H, d,J=8.6Hz), 7.46(2H,d,J=8.4Hz), 7.72(2H,d,J=8.6Hz), 7.80 (2H,d,J=8.4Hz), 8.24(1H,s).

IR (KBr): 1654, 754 cm$^{-1}$.

REFERENCE EXAMPLE 9

3-[4-(4-Chlorobenzoyl)benzylamino]-1-propanol

To a solution of 3-amino-1-propanol (3.00 g) in ethanol (40 ml) was added 4-(4-chlorobenzoyl)benzyl bromide (3.10 g) and the mixture was refluxed for 4.5 hours. After cooling to room temperature, the solvent was distilled off under reduced pressure and the residue was extracted with ethyl acetate. The extract was dried over anhydrous magnesium sulfate and the solvent was distilled off under reduced pressure. The residue was purified by silica gel column chromatography (developed with chloroform: methanol= 9:1) to provide the title compound as white powder (1.36 g; yield 45%). $^1$H-NMR (CDCl$_3$) δ: 1.76(2H,q,J=5.6Hz), 2.29 (2H,m), 2.93(2H,t,J=5.6Hz), 3.83(2H,t,J=5.6Hz), 3.90(2H, s), 7.41–7.50(4H,m), 7.71–7.78(4H,m).

IR (KBr): 3255, 3140, 2840, 1660, 1600 cm$^{-1}$.

REFERENCE EXAMPLE 10

2-Tert-butyl-4-chloro-5-[N-(3-hydroxypropyl)-N-(4-(4-chlorobenzoyl)benzyl)amino]-3(2H)-pyridazinone In a solvent mixture of dioxane (5 ml) and water (5 ml) were dissolved 2-tert-butyl-4,5-dichloro-3(2H)-pyridazinone (473 mg) and 3-[4-(4-chlorobenzoyl)benzyl-amino]-1-propanol (1.30 g) and the mixture was stirred at 100° C. for 64 hours. After cooling to room temperature, the reaction mixture was diluted with water and extracted with ethyl acetate. The extract was washed with saturated aqueous NaCl solution and dried over anhydrous magnesium sulfate. The solvent was then distilled off under reduced pressure and the residue was purified by silica gel column chromatography (developer; n-hexane: ethyl acetate=4:1-2:1) to provide the title compound as white powder (120 mg; yield 12%). $^1$H-NMR (CDCl$_3$) δ: 1.63(9H,s), 1.83–1.98(3H, m), 3.51(2H,t,J=7.2Hz), 3.70(2H,m), 4.71(2H,m), 7.40(2H, d,J=8.4Hz), 7.46(2H,d,J=8.4Hz), 7.60(1H,s), 7.75(2H,d,J= 8.4Hz), 7.77(2H,d,J=8.4Hz).

REFERENCE EXAMPLE 11

2,3-Dichloro-5-methyl-1H-pyrrolo[2,3-d]pyridazin-4 (5H)-one

A solution of methylhydrazine (4.72 g) and 3-carbethoxy-4,5-dichloro-2-formylpyrrole (4.72 g) in ethanol (50 ml) was refluxed for 2 hours. After cooling to room temperature, concentrated sulfuric acid (0.5 ml) was added and the mixture was refluxed for another 21 hours. The reaction mixture was cooled to room temperature and the resulting crystals were collected by filtration. The crystals were rinsed with ethanol and ether and dried in vacuo to provide the title compound as brown powder (3.29 g; yield 81%). H-NMR (DMSO-d$_6$) δ: 3.66(3H,s), 8.11(1H,s).

IR (KBr): 3080, 2980, 1630, 1570 cm$^{-1}$.

REFERENCE EXAMPLE 12

Ethyl 1-[4-(4-chlorobenzoyl)benzyl]-5-(diethoxymethyl)imidazole-4-carboxylate (A) and Ethyl 1-[4-(4-chlorobenzoyl)benzyl]-4-(diethoxymethyl)imidazole-5-carboxylate (B)

To a suspension of 60% sodium hydride-oil (363 g) in DMF (15 ml) on an ice-water bath was added a solution of ethyl 5-(diethoxymethyl)imidazole-4-carboxylate (2.00 g) in DMF (25 ml) dropwise and the mixture was stirred at room temperature for 45 minutes. Then, a solution of 4-(4-chlorobenzoyl)benzyl bromide (2.81 g) in DMF (15 ml) was added and the mixture was further stirred at 60° C. for 3 hours. The reaction was stopped by adding a saturated aqueous solution of ammonium chloride and the mixture was extracted with ethyl acetate. The extract was dried over anhydrous magnesium sulfate and the solvent was distilled off under reduced pressure. The residue was purified by silica gel column chromatography (developer: n-hexane-ethyl acetate=1:2) to provide the title compound (A) as white powder (2.18 g; yield 56%) and the title compound (B) as brown oil (1.13 g; yield 29%). (A): $^1$H-NMR (CDCl$_3$) δ: 1.13(6H,t,J=7.0Hz), 1.42(3H,t,J=7.0Hz), 3.43–3.59(2H, m), 3.70–3.87(2H,m), 4.39(2H,q,J=7.0Hz), 5.53(2H,s), 6.41 (1H,s), 7.28(2H,d,J=8.4Hz), 7.41(1H,s), 7.46(2H,d,J=8.4Hz), 7.72(2H,d,J=8.4Hz), 7.74(2H,d,J=8.6Hz).

IR (KBr): 3120, 3050, 2980, 2950, 2900, 1700, 1660 cm$^{-1}$. (B): $^1$H-NMR (CDCl$_3$) δ: 1.25(6H,t,J=7.2Hz), 1.32 (3H,t,J=7.0Hz), 3.61–3.85(4H,m), 4.30(2H,q,J=7.2Hz), 5.57(2H,s), 6.08(1H,s), 7.24(2H,d,J=8.4Hz), 7.46(2H,d,J=8.4Hz), 7.68–7.77(5H,m).

REFERENCE EXAMPLE 13

Ethyl 1-[4-(4-chlorobenzoyl)benzyl]-5-formyl-imidazole-4-carboxylate

In 20% aqueous acetic acid (15 ml) was dissolved ethyl 1-[4-(4-chlorobenzoyl)benzyl]-5-(diethoxymethyl)-imidazole-4-carboxylate (1.70 g) and the solution was stirred at room temperature for 23 hours. This solution was diluted with water and extracted with ethyl acetate. The extract was washed serially with water, saturated aqueous NaHCO$_3$ solution, and water and dried over anhydrous magnesium sulfate. The solvent was distilled off under reduced pressure to provide the title compound as white powder (1.37g; yield 95%). $^1$H-NMR (CDCl$_3$) δ: 1.45(3H,t,J=7.2Hz), 4.47(2H,q,J=7.2Hz), 5.65(2H,s), 7.28(2H,d,J=8.4Hz), 7.46(2H,d,J=8.4Hz), 7.69–7.77(5H,m), 10.51(1H, s).

IR (KBr): 3100, 2980, 1740, 1710, 1675, 1610, 1590 cm$^{-1}$.

REFERENCE EXAMPLE 14

Ethyl 1-[4-(4-chlorobenzoyl)benzyl]-4-formyl-imidazole-5-carboxylate

In 20% aqeuous acetic acid (10 ml) was dissolved ethyl 1-[4-(4-chlorobenzoyl)benzyl]-4-(diethoxymethyl)-imidazole-5-carboxylate (1.20 g) and the mixture was stirred at room temperature for 8 hours. This reaction mixture was diluted with water and extracted with ethyl acetate. The extract was washed serially with water, saturated aqueous NaHCO$_3$ solution, and water, and dried over anhydrous magnesium sulfate. The solvent was then distilled off under reduced pressure and the residue was purified by silica gel column chromatography (developer; n-hexane: ethyl acetate=1:1) to provide the title compound as white powder (671 mg; yield 67%). $^1$H-NMR (CDCl$_3$) δ: 1.38(3H,t,J=7.0Hz), 4.41(2H,q,J=7.0Hz), 5.66(2H,s), 7.26(2H,d,J=8.8Hz), 7.46(2H,d,J=8.8Hz), 7.70–7.79(5H,m), 10.42(1H, s).

IR (KBr): 3000, 1720, 1685, 1655, 1610, 1580 cm$^{-1}$.

REFERENCE EXAMPLE 15

2-Hydroxy-3-methylpyrido[1,2-a]pyrimidin-4-one

To a mixture of 2-aminopyridine (9.71 g) and di-methyl 2-methylmalonate (19.70 g) was added concentrated hydrochloric acid (10 drops) and the mixture was stirred at 150° C. for 1 hour, after which it was allowed to cool to room temperature. To this reaction mixture was added hexane-ethyl acetate and the resulting light-yellow precipitate was collected by filtration. Yield 0.403 g (2.2%) $^1$H-NMR (CDCl$_3$–CD$_3$OD) δ: 2.09(3H,s), 7.31–7.50(2H,m), 9.12(1H, m).

IR (KBr): 3358, 3167, 1666, 1622, 1126, 769, 621 cm$^{-1}$.

REFERENCE EXAMPLE 16

2-Mercapto-6,7-dimethoxy-3-methylquinazolin-4-one

A solution of 2-amino-4,5-dimethoxybenzoic acid (20.0 g) and methyl isothiocyanate (7.23 g) in ethanol was refluxed for 30 minutes. The precipitate was collected by filtration to provide the title compound as colorless needles. Yield 11.77 g (47%) $^1$H-NMR (CDCl$_3$) δ: 3.67(3H,s), 3.85 (3H,s), 3.89(3H,s), 6.93(1H,s), 7.31(1H,s).

IR (KBr): 1648, 1622, 1402, 1273, 1209, 1092, 1028 cm$^{-1}$.

REFERENCE EXAMPLE 17

2-Amino-6-methylbenzoic acid

To a methanolic solution (150 ml) of 6-methyl-2-nitrobenzoic acid (14.25 g) was added palladium-on-carbon (1.40 g) and the hydrogenation reaction was conducted at atmospheric temperature and pressure (hydrogen consumption 5.3 l). The catalyst was filtered off and the filtrate was concentrated under reduced pressure to provide the title compound as light-yellow solid (15.12 g; yield 100%). $^1$H-NMR (CDCl$_3$) δ: 2.47(3H,s), 6.50(2H,t,J=8.1Hz), 7.00–7.07(4H,m).

IR (KBr): 2927, 2645, 1645, 1599, 1545, 1470, 1394, 1334, 1288, 1236, 813, 775, 580, 419 cm$^{-1}$.

REFERENCE EXAMPLE 18

2-Mercapto-3,5-dimethylquinazolin-4-one

A solution of the 2-amino-6-methylbenzoic acid obtained in Reference Example 17 (14.12 g) and methyl isothiocyanate (7.22 g) in ethanol was refluxed for 1 hour. The title compound was collected by filtration as colorless needles. Yield 7.72 g (40.0%) $^1$H-NMR (CDCl$_3$) δ: 2.47(3H,s), 6.50(2H,t,J=8.1Hz), 7.00–7.07 (4H,m).

IR (KBr): 3286, 1660, 1614, 1537, 1474, 1431, 1385, 1271, 1109, 1049, 991, 795, 691, 665, 420 cm$^{-1}$.

REFERENCE EXAMPLE 19

N,N-Dimethylphenylacetamide

Phenylacetyl chloride (25 ml) was added dropwise to a 50% aqueous solution of dimethylamine with ice-cooling.

After the solvent was removed under reduced pressure, the residue was dissolved in ethyl acetate. The organic layer was washed with saturated aqueous $NaHCO_3$ solution, dried over $MgSO_4$, and concentrated under reduced pressure to provide the title compound as colorless oil. Yield 28.90 g (95%) $^1$H-NMR ($CDCl_3$) δ: 2.95(3H,s), 2.98(3H,s), 3.71 (2H,s), 7.26–7.30(5H,m).

IR (Neat) : 3466, 2937, 1643, 1495, 1450, 1398, 1266, 1132, 1068, 733, 700, 598 $cm^{-1}$.

REFERENCE EXAMPLE 20

7-[4-(4-Chlorobenzoyl)benzyl]-4-methoxy-5-methyl-2-methylthio-7H-pyrrolo[2,3-d]pyrimidine In an argon gas stream, 60% sodium hydride-oil (220 mg) was suspended in anhydrous DMF (5 ml) and a powder of 4-methoxy-5-methyl-2-methylthio-7H-pyrrolo[2,3-d]pyrimidine (1.05 g) was added in small portions with ice-cooling and stirring. After completion of addition, the mixture was stirred for 30 minutes and then a solution of 4-(4-chlorobenzoyl)benzyl bromide (1.63 g) in DMF (5 ml) was added. Then, at room temperature, the mixture was stirred for 2 hours. To this reaction mixture was added water (50 ml) and the resulting precipitate was collected by filtration, rinsed with water, dried, and purified by flash column chromatography (silica gel; hexane: ethyl acetate= 9:1) to provide the title compound (1.19 g). $^1$H-NMR ($CDCl_3$) δ: 2.33(3H,d,J=1.2Hz), 2.60(3H,s), 4.08(3H,s), 5.36(2H,s), 6.57(1H,d,J=1.2Hz), 7.28(2H,d,J=8.6Hz), 7.44 (2H,d,J=8.6Hz), 7.70(2H,d,J=8.6Hz), 7.72(2H,d,J=8.6Hz).

IR (KBr): 3430, 3100, 2920, 1650, 1600, 1590, 1560, 1530, 1480, 1455, 1430, 1395, 1335, 1300, 1280, 1240, 1190, 1170, 1145, 1100, 1090 $cm^{-1}$.

REFERENCE EXAMPLE 21

7-[4-(4-Chlorobenzoyl)benzyl]-4-methoxy-2-methyl-thio-7H-pyrrolo[2,3-d]pyrimidine Under argon gas, 4-methoxy-2-methylthio-7H-pyrrolo[2,3-d]pyrimidine (0.54 g) was dissolved in anhydrous 1,2-dimethoxyethane (hereinafter referred to as DME) (10 ml) and 60% sodium hydride-oil (132 mg) was added in 2 installments with ice-cooling and stirring. After completion of addition, the mixture was further stirred for 30 minutes and a solution of 4-(4-chlorobenzoyl)benzyl bromide (1.11 g) in DME (5 ml) was added. Then, at room temperature, the mixture was stirred overnight. This reaction mixture was diluted with ethyl acetate, washed with saturated aqueous NaCl solution, and dried over anhydrous sodium sulfate. The solvent was distilled off under reduced pressure and the residue was purified by flash column chromatography (silica gel; hexane:ethyl acetate=9:1) to provide the title compound (0.941 g). $^1$H-NMR ($CDCl_3$) δ: 2.61(3H,s), 4.10(3H,s), 5.44(2H,s), 6.49(1H,d,J=3.6Hz), 6.87(1H,d,J=3.6Hz), 7.29 (2H,d,J=8.6Hz), 7.44(2H,d,J=8.6Hz), 7.72(4H,d,J=8.6Hz).

IR (KBr): 3450, 3120, 3000, 2960, 2930, 1660, 1610, 1590, 1560, 1510, 1460, 1390, 1380, 1335, 1280, 1260, 1240, 1170, 1155, 1090, 1065 $cm^{-1}$.

REFERENCE EXAMPLE 22

6-t-Butylpyrido[2,3-d]pyridazin-5(6H)-one

In acetic acid-water (1:1) (5 ml) was dissolved ethyl 2-formyl-3-pyridinecarboxylate (1.3 g) followed by addition of t-butylhydrazine hydrochloride (1.8 g), and the mixture was refluxed with stirring for 1 hour. This reaction mixture was cooled to room temperature, adjusted to pH 5.0 with saturated aqueous $NaHCO_3$ solution, and extracted with dichloromethane. The organic layer was washed with saturated aqueous NaCl solution, dried over anhydrous magnesium sulfate, and concentrated. The residue was dissolved in acetic acid (2 ml) and refluxed for 1 hour. This reaction mixture was cooled, adjusted to pH 5.0 with saturated aqueous $NaHCO_3$ solution, and extracted with dichloromethane. The organic layer was washed with saturated aqueous NaCl solution, dried over anhydrous magnesium sulfate, and concentrated. The residue was purified by silica gel chromatography (n-hexane: ethyl acetate =1:1). White powder, 1.2 g. $^1$H-NMR ($CDCl_3$) δ: 1.73(9H,s), 7.64(1H, dd,J=8.2&4.4Hz), 8.38(1H,s), 8.69(1H,d,J=8.2Hz), 9.03 (1H,d,J=4.4Hz).

REFERENCE EXAMPLE 23

6-Tert-butyl-1,2,3,4-tetrahydropyrido[2,3-d]-pyridazin-5(6H)-one

In acetic acid (20 ml) was dissolved 6-t-butyl-pyrido[2,3-d]pyridazin-5(6H)-one (955 mg) followed by addition of platinum oxide (94 mg), and the mixture was stirred under hydrogen at room temperature for 7 hours. The catalyst was then filtered off, the filtrate was concentrated to dryness, and the residue was washed with diethyl ether and dried. White powder, 911 mg. $^1$H-NMR ($CDCl_3$) δ: 1.63(9H,s), 1.8–2.0 (2H,m), 2.54(2H,t,J=6.2Hz), 3.28(2H,t,J=5.4Hz), 4.24(1H, brs), 7.19(1H,s).

REFERENCE EXAMPLE 24

6-Methylpyrido[2,3-d]pyridazin-5(6H)-one

In ethanol (3 ml) was dissolved ethyl 2-formyl-3-pyridinecarboxylate (519 mg) followed by addition of methylhydrazine (267 mg), and the mixture was refluxed with stirring for 2 hours. This reaction mixtrue was concentrated to dryness and the residue was washed with diethyl ether-acetone and dried. Yellow powder, 391 mg. $^1$H-NMR (DMSO-$d_6$) δ: 3.75(3H,s), 7.86(1H,dd,J=8.4&4.4Hz), 8.48 (1H,s), 8.62(1H,d,J=8.4Hz), 9.14(1H,d,J=4.4Hz).

REFERENCE EXAMPLE 25

6-Tert-butyl-1,2,3,4-tetrahydropyrido[2,3-d]-pyridazin-5(6H)-one

In acetic acid (15 ml) was dissolved 6-methyl-pyrido[2,3-d]pyridazin-5(6H)-one (402 mg) followed by addition of platinum oxide (50 mg) and the mixture was stirred under hydrogen at room temperature for 15 hours. After the catalyst was filtered off, the filtrate was concentrated to dryness and the residue was washed with acetone and dried. White powder, 250 mg. $^1$H-NMR ($CDCl_3$) δ: 1.8–2.0(2H, m), 2.58(2H,t,J=6.4Hz), 3.29(2H,t,J=5.6Hz), 3.69(3H,s), 4.30(1H,brs), 7.23(1H,s).

REFERENCE EXAMPLE 26

2-Tert-butyl-4-chloro-5-dimethylamino-3(2H)-pyridazinone

In ethanol-water (2:1) (45 ml)was dissolved 2-t-butyl-4, 5-dichloro-3(2H)-pyridazinone (4.4 g) followed by addition of 50% dimethylamine (7.2 g), and the mixture was stirred at room temperature for 15 hours. After removal of ethanol, the residue was extracted with diethyl ether and the organic layer was washed with saturated aqueous NaCl solution, dried over anhydrous magnesium sulfate, and concentrated to dryness. This residue was washed with n-hexane and dried. White powder, 4.4 g. $^1$H-NMR (CDCl$_3$) δ: 1.63(9H,s), 3.10(6H,s), 7.57(1H,s).

REFERENCE EXAMPLE 27

2-Tert-butyl-5-dimethylamino-3(2H)-pyridazinone

In methanol (40 ml) was dissolved 2-t-butyl-4-chloro-5-dimethylamino-3(2H)-pyridazinone (4.3 g) followed by addition of 10% palladium-on-carbon (water content 50%) (430 mg), and the mixture was stirred under hydrogen at room temperature for 48 hours. The catalyst was then filtered off and the filtrate was concentrated. To the residue was added saturated aqueous NaHCO$_3$ solution and the mixture was extracted with ethyl acetate. The organic layer was washed with saturated aqueous NaCl solution, dried over anhydrous magnesium sulfate, and concentrated to dryness. The residue was washed with n-hexane and dried. White powder, 3.4 g. $^1$H-NMR (CDCl$_3$) δ: 1.63(9H,s), 2.98(6H,s), 5.65(1H,d,J=3.0Hz), 7.55(1H,d,J=3.0Hz).

REFERENCE EXAMPLE 28

2-Tert-butyl-5-dimethylamino-4-formyl-3(2H)-pyridazinone

Phosphorus oxychloride (6.5 g) was added dropwise to DMF (15 ml) with ice-cooling and the mixture was stirred at room temperature for 30 minutes. Then, 2-t-butyl-5-dimethylamino-3(2H)-pyridazinone (3.3 g)/DMF (40 ml) was added dropwise with ice-cooling and the mixture was stirred at 70° C. for 1 hour. This reaction mixture was poured gradually into ice-NaHCO$_3$/water and extracted with ethyl acetate. The organic layer was washed with saturated aqueous NaCl solution, dried over anhydrous magnesium sulfate, and concentrated to dryness. The residue was washed with n-hexane and dried. Yellow powder, 3.7 g. $^1$H-NMR (CDCl$_3$) δ: 1.63(9H,s), 3.10(6H,s), 7.71(1H,s), 10.27(1H,s).

REFERENCE EXAMPLE 29

5-Tert-butyl-1H-pyrazolo[3,4-d]pyridazin-4(5H)-one

2-Tert-butyl-5-dimethylamino-4-formyl-3(2H)-pyridazinone (3.5 g) was added to hydrazine (5.1 g)/ethanol (30 ml) and the mixture was refluxed for 40 hours. The solvent ethanol-hydrazine was then distilled off and the residue was extracted with ethyl acetate. The organic layer was washed with saturated aqueous NaCl solution, dried over anhydrous magnesium sulfate, and concentrated to dryness. The residue was washed with n-hexane-diethyl ether and dried. White powder, 1.9 g. $^1$H-NMR (CDCl$_3$) δ: 1.71(9H,s), 8.19(1H,s), 8.32(1H,s).

REFERENCE EXAMPLE 30

5-Methyl-1H-triazolo[4,5-d]pyridazin-4(5H)-one

In water (10 ml) was dissolved 4,5-diamino-2-methyl-3(2H)-pyridazinone (280 mg) followed by addition of concentrated hydrochloric acid (0.5 ml) with ice-cooling. Then, sodium nitrite (290 mg)/water (5 ml) was added dropwise at a temperature not exceeding 10° C. and the mixture was stirred at that temperature for 1 hour and then at 100° C. for 1 hour. This reaction mixture was allowed to stand in the refrigerator for 16 hours and the resulting precipitate was collected by filtration, rinsed with water, and dried. White powder, 262 mg. $^1$H-NMR (DMSO-d$_6$) δ: 3.76(3H,s), 8.71 (1H,s).

REFERENCE EXAMPLE 31

5-Methyl-1H-pyrrolo[2,3-d]pyridazin-4(5H)-one

A solution of methylhydrazine (4.84 g) and 3-ethoxycarbonyl-2-formylpyrrole (3.34 g) in ethanol (30 ml) was refluxed for 2 hours. After cooling to room temperature, concentrated sulfuric acid (0.7 ml) was added and the mixture was further refluxed for 19 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; dichloromethane: methanol=19:1) to provide the title compound as white powder (1.81 g; yield 61%). $^1$H-NMR (DMSO-d$_6$) δ: 3.68(3H,s), 6.65(1H,d,J=2.8Hz), 7.42(1H,t, J=2.8Hz), 8.17(1H,s), 12.02(1H,m).

IR (KBr): 3200, 3100, 1640 cm$^{-1}$.

REFERENCE EXAMPLE 32

2,3,5-Trimethyl-1H-pyrrolo[2,3-d]pyridazin-4(5H)-one

A solution of methylhydrazine (1.82 g) and 3-ethoxycarbonyl-4,5-dimethyl-2-formylpyrrole (3.85 g) in ethanol (40 ml) was refluxed for 2 hours. After cooling to room temperature, concentrated sulfuric acid (0.7 ml) was added and the mixture was further refluxed for 13 hours. The mixture was cooled to room temperature and the resulting precipitate was collected by filtration, washed with ethanol and ether, and dried under reduced pressure to provide the title compound as light-yellow powder (3.64 g; yield 100%). $^1$H-NMR (DMSO-d$_6$) δ: 2.26(6H,s), 3.62(3H,s), 7.98(1H,s), 11.6–11.7(1H,m).

REFERENCE EXAMPLE 33

2-Tert-butyl-5-dimethylamino-4-(1-hydroxy)ethyl-3(2H)-pyridazinone

In THF (45 ml) was dissolved 2-t-butyl-5-dimethylamino-4-formyl-3(2H)-pyridazinone (3.2 g) followed by dropwise addition of 3.0M methylmagnesium bromide/diethyl ether (7.1 ml) with ice-cooling. The mixture was stirred at 50° C. for 30 minutes. To this reaction mixture was added 1N-hydrochloric acid (22 ml) with ice-cooling and, then, saturated aqueous NaHCO$_3$ solution was added. This mixture was extracted with ethyl acetate and the organic layer was washed with saturated aqueous NaCl solution, dried over anhydrous magnesium sulfate, and concentrated to dryness. Yellow oil, 3.5 g. $^1$H-NMR (CDCl$_3$) δ: 1.63(9H, s), 1.63(3H,d,J=6.6Hz), 2.91(6H,s), 4.93(1H,dq,J= 6.6&11.0Hz), 5.55(1H,d,J=11.0Hz), 7.65(1H,s).

REFERENCE EXAMPLE 34

4-Acetyl-2-t-butyl-5-dimethylamino-3(2H)-pyridazinone

In toluene was dissolved 2-t-butyl-5-dimethylamino-4-(1-hydroxy)ethyl-3(2H)-pyridazinone (3.4 g) followed by addition of active manganese dioxide (17.0 g), and the mixture was stirred at 80° C. for 24 hours. The oxidizing agent was filtered off and the filtrate was concentrated. The residue was washed with n-hexane and diethyl ether and dried. Yellow powder, 2.5 g. $^1$H-NMR (CDCl$_3$) δ: 1.62(9H,s), 2.63(3H,s), 2.92(6H,s), 7.62(1H,s).

REFERENCE EXAMPLE 35

5-Tert-butyl-3-methyl-1H-pyrazolo[3,4-d]pyridazin-4(5H)-one

4-Acetyl-2-t-butyl-5-dimethylamino-3(2H)-pyridazinone (2.5 g) was added to hydrazine (3.2 g)/ethanol (30 ml) and the mixture was refluxed for 6 hours. After the ethanol-hydrazine was distilled off, the residue was extracted with ethyl acetate. The organic layer was washed with saturated aqueous NaCl solution, dried over anhydrous magnesium sulfate, and concentrated to dryness. The residue was washed with n-hexane and diethyl ether and dried. White powder, 1.7 g. $^1$H-NMR (CDCl$_3$) δ: 1.70(9H,s), 2.74(3H,s), 8.10(1H,s).

REFERENCE EXAMPLE 36

5-Dimethylamino-4-(1-hydroxy)ethyl-2-methyl-3(2H)-pyridazinone

In THF (10 ml) was dissolved 5-dimethylamino-4-formyl-2-methyl-3(2H)-pyridazinone (362 mg) followed by dropwise addition of 3.0M methylmagnesium bromide/diethyl ether (1.0 ml) with ice-cooling, and the mixture was stirred at 50° C. for 30 minutes. To this reaction mixtrue was added 1N-hydrochloric acid (3 ml) with ice-cooling. Then, saturated aqueous NaHCO$_3$ solution was added and the mixture was extracted with ethyl acetate. The organic layer was washed with saturated aqueous NaCl solution, dried over anhydrous magnesium sulfate, and concentrated to dryness. Yellow oil, 371 mg. $^1$H-NMR (CDCl$_3$) δ: 1.64(3H, d,J=6.6Hz), 2.94(6H,s), 3.72(3H,s), 4.93(1H,dq,J=6.6&11.4Hz), 5.31(1H,d,J=11.4Hz), 7.66(1H,s).

REFERENCE EXAMPLE 37

4-Acetyl-5-dimethylamino-2-methyl-3(2H)-pyridazinone

In chloroform was dissolved 5-dimethylamino-4-(1-hydroxy)ethyl-2-methyl-3(2H)-pyridazinone (355 mg) followed by addition of active manganese dioxide (2.0 g), and the mixture was stirred at 50° C. for 24 hours. After the oxidizing agent was filtered off, the filtrate was concentrated and the residue was washed with n-hexane and diethyl ether and dried. Yellow powder, 178 mg. $^1$H-NMR (CDCl$_3$) E: 2.6.7(3H,s), 2.94(6H,s), 3.69(3H,s), 7.66(1H,s).

REFERENCE EXAMPLE 38

3,5-Dimethyl-1H-pyrazolo[3,4-d]pyridazin-4(5H)-one

4-Acetyl-5-dimethylamino-2-methyl-3(2H)-pyridazinone (137 mg) was added to hydrazine (224 mg)/ethanol (5 ml) and the mixture was refluxed with stirring for 6 hours. After the ethanol-hydrazine was distilled off, the residue was washed with diethyl ether and dried. White powder, 114 g. $^1$H-NMR (CDCl$_3$) δ: 2.57(3H,s), 3.64(3H,s), 8.30(1H,s).

REFERENCE EXAMPLE 39

1-Methyl-2-mercapto-7H-pyrrolo[2,3-d]pyrimidin-4-one

Sodium metal (1.21 g) was dissolved in anhydrous ethanol (50 ml) followed by addition of N-methylthiourea (4.96 g), and the mixture was stirred for dissolution at 50° C. for 30 minutes. Then, a solution of ethyl 2-cyano-4,4-diethoxybutyrate (11.47 g) in ethanol (10 ml) was added and the mixture was refluxed at 100° C. for 5 hours. The solvent was then distilled off under reduced pressure and the residue was-dissolved by adding water (20 ml). Then, 10% hydrochloric acid (75 ml) was added and the mixture was stirred overnight. The resulting precipitate was collected by filtration, washed serially with water, ethanol and ether, and dried to provide the title compound (6.8 g). $^1$H-NMR (DMSO-d$_6$) δ: 3.82(3H,s), 6.41–6.44(1H,m), 6.92–6.95(1H, s), 12.02(1H,s), 12.06(1H,s).

REFERENCE EXAMPLE 40

1-[4-(4-Chlorobenzoyl)benzyl]-2,3-diethoxycarbonyl-pyrrole

Under argon gas, diethyl 1H-pyrrole-2,3-dicarboxylate (4.79 g) was dissolved in DME (100 ml) and the solution was cooled to 0° C. Then, sodium hydride (990 mg) was added and the mixture was stirred at room temperature for 0.5 hour, after which it was cooled to 0° C. again. To this reaction mixtrue was added 4-(4-chlorobenzoyl)benzyl bromide (8.53 g) and the mixture was stirred at room temperature for 14 hours. This reaction mixture was diluted with water and extracted with ethyl acetate (500 ml) and the organic layer was washed with NaHCO$_3$/H$_2$O (300 ml) twice and saturated aqueous NaCl solution (100 ml) once, and dried over anhydrous magnesium sulfate. The desiccant was filtered off and the filtrate was concentrated under reduced pressure to remove the solvent. The residue was purified by silica gel column chromatography (stationary phase 250 g; hexane: ethyl acetate=6:1→1:1) to provide 9.56 g (yield 96%) of the title compound. $^1$H-NMR (CDCl$_3$) δ: 1.26(3H,t,J=7.1Hz), 1.35(3H,t,J=7.0Hz), 4.26(2H,q,J=7.1Hz), 4.30(2H,q,J=7.1 Hz),5.49(2H,s), 6.57(1H,d,J=3.0Hz), 6.88(1H,d,J=3.2Hz), 7.19(2H,d,J=8.4Hz), 7.45(2H, d,J=8.6Hz), 7.72(4H,d,J=8.8Hz).

REFERENCE EXAMPLE 41

3-Ethyl-5-methyl-2-mercaptoquinazolin-4-one

An ethanolic solution (200 ml) of 6-methyl-anthranylic acid (14.97 g, 0.099 mol) and ethyl isothiocyanate (15.00 ml, 0.171 mol) was refluxed for 5 hours. The reaction mixture was allowed to cool and the resulting colorless needles were harvested by filtration. 9.63 g (43.0%). $^1$H-NMR (CDCl$_3$) δ: 1.37(3H,t,J=7.0Hz), 2.80(3H,s), 4.57 (2H,q,J=7.0Hz), 6.96(1H,d,J=8.0Hz), 7.08(1H,d,J=8.0Hz), 7.49(1H,t,J=8.0Hz).

IR (KBr): 3188, 3130, 2981, 1693, 1618, 1549, 1468, 1338, 1232, 1117, 775 cm$^{-1}$.

REFERENCE EXAMPLE 42

7-[4-(4-Fluorobenzoyl)benzyl]-4-methoxy-5-methyl-2-methylthio-7H-pyrrolo[2,3-d]pyrimidine Under argon gas, 4-methoxy-5-methyl-2-methylthio-7H-pyrrolo[2,3-d]pyrimidine (4.18 g) was dissolved in anhydrous DME (120 ml). Then, with ice-cooling and stirring, 60% sodium hydride-oil (0.88 g) was added in 3 installments. After completion of addition, the mixture was stirred for 30 minutes, at the end of which time a solution of 4-(4-fluorobenzoyl)benzyl bromide (6.74 g) in anhydrous DME (20 ml) was added. Then, at room temperature, the mixture was stirred for 2 hours. The solvent was distilled off under reduced pressure and the residue was dissolved in ethyl acetate, washed with saturated aqueous NaCl solution, and dried over anhydrous sodium sulfate. The solvent was then distilled off under reduced pressure, whereupon colorless needles separated out. These crystals were collected by filtration, rinsed with ethyl acetate, and dried to provide the title compound (7.07 g). $^1$H-NMR (CDCl$_3$) δ: 2.33(3H,d,J=1.2Hz), 2.61(3H,s), 4.09(3H,s), 5.37(2H,s), 6.58(1H,d,J=1.2Hz), 7.15(2H,t,J=8.6Hz), 7.29(2H,d,J=8.4Hz), 7.71(2H, d,J=8.4Hz), 7.82(2H,dd,J=5.4&8.8Hz).

REFERENCE EXAMPLE 43

7H-Pyrrolo[2,3-d]pyrimidin-4(3H)-one

In methanol (714 ml) was suspended 2-mercapto-7H-pyrrolo[2,3-d]pyrimidin-4(3H)-one (15.06 g) followed by addition of 28% sodium methoxide/methanol (18.4 ml). While this solution was stirred at 50° C., Raney nickel was added until disappearance of the starting compound had been verified by TLC. The catalyst was then filtered off and the filtrate was neutralized with 1N-HCl (90 ml). The solvent was then distilled off under reduced pressure and the resulting precipitate was collected by filtration, rinsed serially with water, methanol and ether, and dried to provide the title compound (8.1 g). $^1$H-NMR (DMSO-$d_6$) δ: 6.44(1H,d, J=3.0Hz), 7.03(1H,d,J=3.0Hz), 7.83(1H,s), 11.80(1H,brs).

REFERENCE EXAMPLE 44

5-Methyl-7H-pyrrolo[2,3-d]pyrimidin-4(3H)-one

In methanol (714 ml) was suspended 2-mercapto-5-methyl-7H-pyrrolo[2,3-d]pyrimidin-4(3H)-one (15.06 g) followed by addition of 28% sodium methoxide/methanol (18.4 ml). While this solution was stirred at 50° C., Raney nickel was added until disappearance of the starting compound had been verified by TLC. The catalyst was then filtered off and the filtrate was neutralized with 1N-HCl (90 ml). The solvent was distilled off under reduced pressure and the resulting precipitate was collected by filtration, rinsed serially with water, methanol and ether, and dried to provide the title compound (8.1 g). $^1$H-NMR (DMSO-$d_6$) δ: 6.44 (1H,d,J=3.0Hz), 7.03(1H,d,J=3.0 Hz), 7.83(1H,s), 11.80 (1H,brs).

REFERENCE EXAMPLE 45

3-Isopropyl-7H-pyrrolo[2,3-d]pyrimidin-4(3H)-one

Under argon gas, 7H-pyrrolo[2,3-d]pyrimidin-4(3H)-one (1.0 g) was dissolved in DMF (35 ml) with warming. Then, anhydrous potassium carbonate (1.02 g) and isopropyl iodide (1.1 ml) were added and the mixture was stirred at 55° C. for 13 hours. The insoluble matter was filtered off and the solvent was distilled off under reduced pressure. The residue was purified by flash column chromatography (silica gel; hexane: ethyl acetate=4:1→1:1) to provide the title compound (110 mg). $^1$H-NMR (CDCl$_3$) δ: 1.48(6H,d,J=7.0Hz), 5.31(1H,m), 6.74(1H,dd,J=2.2&3.4Hz), 6.96(1H,dd,J=2.2&3.4Hz), 7.95(1H,s), 9.20(1H,brs).

REFERENCE EXAMPLE 46

3-Propyl-7H-pyrrolo[2,3-d]pyrimidin-4(3H)-one

Under argon gas, 7H-pyrrolo[2,3-d]pyrimidin-4(3H)-one (1.0 g) was dissolved in DMF (35 ml) with warming. Then, anhydrous potassium carbonate (1.02 g) and propyl iodide (1.08 ml) were added and the mixture was stirred at 55° C. for 20 hours. The insoluble matter was filtered off and the solvent was distilled off under reduced pressure. The residue was purified by flash column chromatography (silica gel; hexane: ethyl acetate=4:1–1:1) to provide the title compound (521 mg). $^1$H-NMR (CDCl$_3$) δ: 0.96(3H,t,J=7.4Hz), 1.73-1.92(2H,m), 4.01(2H,t,J=7.4Hz), 6.71(1H,dd,J=2.2&3.4Hz), 7.01(1H,dd,J=2.2&3.4Hz), 7.94(1H,s).

REFERENCE EXAMPLE 47

N-t-Butoxycarbonyl-4-piperidone

In THF (100 ml) was suspended 4-piperidone monohydrochloride (5.22 g) followed by addition of N,N-dimethylaminopyridine (208 mg). Then, triethylamine (18.9 ml) was added under ice-cooling. The mixture was stirred at room temperature for 1.5 hours, at the end of which time di-tert-butyl dicarbonate (14.84 g) was added. After 20 hours of stirring at room temperature, triethylamine (9.4 ml) and di-tert-butyl dicarbonate (14.84 g) were further added. The mixture was stirred for 4 days and after the THF was distilled off, the residue was diluted with ethyl acetate, washed serially with 10% citric acid, water, aqueous NaHCO$_3$ solution, water, and aqueous NaCl solution, dried over MgSO$_4$, and concentrated. The residue was purified by silica gel column chromatography (hexane: ethyl acetate= 2:1) to provide the title compound as yellow powder (4.24 g). $^1$H-NMR (CDCl$_3$) δ: 1.50(9H,s), 2.45(4H,t,J=6.2Hz), 3.73(4H,t,J=6.2Hz).

REFERENCE EXAMPLE 48

Ethyl N-t-Butoxycarbonyl-4-piperidideneacetate

In THF (5 ml) was suspended sodium hydride (412 mg) followed by dropwise addition of ethyl diethylphosphonoacetate (2.18 ml) under ice-cooling. The mixture was then stirred at room teAperature for 30 minutes, after which a solution of N-tert-butoxycarbonyl-4-piperidone (1.00 g) in THF (5 ml) was added. After 1 hour of stirring at room temperature, water was added under ice-cooling. The mixture was diluted with ethyl acetate, washed with aqueous NaHCO$_3$ solution and aqueous NaCl solution, dried over MgSO$_4$, and concentrated. The residue was purified by silica gel column chromatography (hexane: ethyl acetate=4:1) to provide the title compound as white powder (1.40 g). 10 m.p. 79°–80° C. $^1$H-NMR (CDCl$_3$) δ: 1.28(3H,t,J=7.0Hz), 1.47(9H,s), 2.28(2H,t,J=5.6Hz), 3.48(2H,t,J=5.8Hz), 3.51 (2H,t,J=5.6Hz), 4.15(2H,q,J=7.0Hz), 5.71(1H,s).

IR (KBr): 2924, 1709, 1680, 1429, 1166 cm$^{-1}$.

REFERENCE EXAMPLE 49

Ethyl N-t-Butoxycarbonyl-4-piperidylacetate

In methanol (10 ml) was dissolved ethyl N-tert-butoxycarbonyl-4-piperidylideneacetate (1.20 g) followed by addition of palladium-on-carbon (180 mg). After nitrogen purging, hydrogen gas was introduced and the mixture was stirred at room temperature for 2 hours. The catalyst was then filtered off and the filtrate was concentrated to provide the title compound as white powder (1.18 g). $^1$H-NMR (CDCl$_3$) δ: 1.1–1.3(2H,m), 1.26(3H,t,J=7.2Hz),1.45(9H,s), 1.6–2.0(3H,m), 2.23(2H,d,J=7.0Hz), 2.72(2H,t,J=12.0Hz), 4.0–4.1(2H,m), 4.13(2H,q,J=7.2Hz).

IR (Neat) : 1736, 1695, 1421, 1286, 1159 cm$^{-1}$.

REFERENCE EXAMPLE 50

N-t-Butoxycarbonyl-4-(1-hydroxyethyl)piperidine

In diethyl ether (20 ml) was dissolved ethyl N-tert-butoxycarbonyl-4-piperidineacetate (1.18 g) followed by addition of methanol (0.19 ml). Then, lithium borohydride (123 mg) was added under ice-cooling. The mixture was stirred at room temperature for 15 hours, after which time water was added under ice-cooling. The mixture was diluted with ethyl acetate, washed with aqueous NaCl solution, dried over MgSO$_4$, and concentrated to provide the title compound as colorless oil (0.96 g). $^1$H-NMR (CDCl$_3$) δ: 1.0–1.4(4H,m), 1.45(9H,s), 1.5–1.8(4H,m), 2.69(2H,t,J= 13.3Hz), 3.6–3.8(2H,brm), 4.0–4.2(2H,brm).

IR (Neat) : 3350, 2927, 1697, 1672, 1429, 1169 cm$^{-1}$.

REFERENCE EXAMPLE 51

N-t-Butoxycarbonyl-4-(1-bromoethyl)piperidine

In dichloromethane (20 ml) was dissolved N-tert-butoxycarbonyl-4-(1-hydroxyethyl)piperidine (0.92 g). After addition of carbon tetrabromide, (1.62 g), triphenylphosphine (1.58 g) was slowly added under ice-cooling. The mixture was stirred at room temperature for 2 hours, at the end of which time the dichloromethane was distilled off. The residue was diluted with ethyl acetate and an aqueous solution of NaHCO$_3$ and the insoluble matter was filtered off. The filtrate was extracted with ethyl acetate, washed with aqueous NaCl solution, dried over MgSO$_4$, and concentrated. The residue was purified by silica gel column chromatography (hexane: ethyl acetate =8:1) to provide the title compound as colorless oil (1.34 g). $^1$H-NMR (CDCl$_3$) δ: 1.0–1.3(3H,m), 1.4;5(9H,s), 1.6–1.9(4H,m), 2.6–2.8(2H, brm), 3.45(2H,t,J=6.8Hz), 4.0–4.2(2H,brm).

IR (Neat) : 2926, 1691, 1425, 1242, 1167 cm$^{-1}$.

EXAMPLE 1

2-[4-(4-Chlorobenzoyl)benzyl]thio-3-methyl-4(3H)-quinazolinone

2-Mercapto-3-methyl-4(3H)-quinazolinone (1.0 g) as synthesized by the method described in Chemical Pharmaceutical Bulletin 17, 2357, 1969 and sodium hydroxide (250 mg) were dissolved in 50% ethanol (15 ml)-DMF (15 ml). To this solution was added 4-(4-chlorobenzoyl)benzyl bromide (1.8 g) and the mixtrue was stirred at room temperature for 1 hour. This-reaction mixture was poured in water and the resulting crystals were collected by filtration, rinsed with water and methanol, and recrystallized from ethyl acetate-methanol to provide the title compound as colorless solid (1.29 g). $^1$H-NMR (CDCl$_3$) δ: 3.61(3H,s), 4.62(2H,s), 7.35–7.50(3H,m), 7.55–7.80(8H,m), 8.24(1H,d,J=8.0Hz).

IR (KBr): 1670, 1645, 1550 cm$^{-1}$.

EXAMPLE 2

2-[4-(4-Fluorobenzoyl)benzyl]thio-3-methyl-4(3H)-quinazolinone

To a solution of 2-mercapto-3-methyl-4(3H)-quinazolinone (1.0 g) and sodium hydroxide (250 mg) in 50% ethanol (15 ml)-DMF (15 ml) was added 4-(4-fluorobenzoyl)benzyl bromide (1.55 g) and the mixture was stirred at room temperature for 1 hour. This reaction mixtrue was poured in water and the resulting crystals were collected by filtration, rinsed with water and methanol, and recrystallized from methanol to provide the title compound as colorless solid (1.85 g). $^1$H-NMR (CDCl$_3$) δ: 3.61(3H,s), 4.62(2H,s), 7.15(2H,t,J=8.6Hz), 7.40(1H,dt,J=8.2&1.4Hz), 7.58–7.90(8H,m), 8.23(1H,dd,J=8.0&1.4Hz).

IR (KBr): 1670, 1645, 1550 cm$^{-1}$

EXAMPLE 3

2-[3-(4-Chlorobenzoyl)benzyl]thio-3-methyl-4(3H)-quinazolinone

To a solution of 2-mercapto-3-methyl-4(3H)-quinazolinone (1.0 g) and sodium hydroxide (250 mg) in 50% ethanol (15 ml)-DMF (15 ml) was added 3-(4-chlorobenzoyl)benzyl bromide (1.88 g) and the mixture was stirred at room temperature for 1 hour. This reaction mixtrue was poured in water and the resulting crystals were collected by filtration, rinsed with water and methanol, and recrystallized from methanol to provide the title compound as colorless solid (2.22 g). $^1$H-NMR (CDCl$_3$) δ: 3.59(3H,s), 4.59(2H,s), 7.34–7.52(5H,m), 7.61–7.80(5H,m), 7.96(1H,d,J=2.0Hz), 8.22(1H,dd,J=8.0,1.4Hz).

IR (KBr): 1660, 1650, 1525 cm$^{-1}$.

EXAMPLE 4

2-[4-(2,4-Dichlorobenzoyl)benzyl]thio-3-methyl-4(3H)-quinazolinone

To a solution of 2-mercapto-3-methyl-4(3H)-quinazolinone (1.0 g) and sodium hydroxide (250 mg) in 50% ethanol (15 ml)-DMF (15 ml) was added 4-(2,4-dichlorobenzoyl)benzyl bromide (1.88 g) and the mixture was stirred at room temperature for 1 hour. This reaction mixtrue was poured in water and the resulting crystals were collected by filtration, rinsed with water and methanol, and recrystallized from methanol to provide the title compound as colorless solid (2.16 g). IH-NMR (CDCl$_3$) δ: 3.59(3H,s), 4.59(2H,s), 7.25–7.80(10H,m), 8.22(1H,dd,J=8.2,1.4Hz).

IR (KBr): 1670, 1650, 1550 cm$^{-1}$.

EXAMPLE 5

2-[4-(4-Chlorobenzoyl)benzyl]thio-3-methyl-6,7-dihydro-5H-cyclopenta[d]pyrimidin-4(3H)-one 2-Mercapto-3-methyl-6,7-dihydro-5H-cyclopenta[d]-pyrimidin-4(3H)-one (1.0 g) as obtained in Reference Example 1 and sodium hydroxide (220 mg) were dissolved in 50% ethanol (15 ml)-DMF (8 ml). To this solution was added 4-(4-chlorobenzoyl)benzyl bromide (1.75 g) and the mixtrue was stirred at room temperature for 1 hour. This reaction mixture was poured in water and the resulting crystals were collected by filtration. The crystals were rinsed with water and methanol and recrystallized from methanol to provide the title compound as colorless solid (1.15 g). $^1$H-NMR (CDCl$_3$) δ: 2.06(2H,q,J=7.4Hz), 2.79(2H,t,J=7.4Hz), 2.84(2H,t,J=7.4Hz), 3.49(3H,s), 4.50(2H,s), 7.46 (2H,d,J=8.6Hz), 7.54(2H,d,J=8.6Hz), 7.74(4H,d,J=8.6Hz).

IR (KBr): 1670, 1645, 1495 cm$^{-1}$.

EXAMPLE 6

2-[4-(4-Chlorobenzoyl)benzyl]thio-1,7-dimethyl-6-oxopurine 1,7-Dimethyl-2-mercapto-6-oxopurine (286 mg) as obtained in Reference Example 2 and sodium hydroxide (60 mg) were dissolved in 50% ethanol (10 ml)-DMF (15 ml). To this solution was added 4-(4-chlorobenzoyl)benzyl bromide (480 mg) and the mixture was stirred at room temperature for 1 hour. This reaction mixture was poured in water and the resulting crystals were collected by filtration, rinsed with water and methanol, and recrystallized from methanol to provide the title compound as colorless solid (535 mg). $^1$H-NMR (CDCl$_3$) δ: 3.57(3H,s), 4.05(3H,s), 4.63(2H,s), 7.45(2H,d,J=8.4Hz), 7.61(2H,d,J=8.4Hz), 7.73 (1H,s), 7.74(4H,d,J=8.4Hz).

IR (KBr): 1680, 1650, 1490 cm$^{-1}$.

EXAMPLE 7

2-[4-(4-Chlorobenzoyl)benzyl]thio-3-methylthieno-[3,2-d]pyrimidin-4(3H)-one

To a solution of 2-mercapto-3-methylthieno[3,2-d]pyrimidin-4-(3H)-one (1.0 g) and sodium hydroxide (205 mg) in 50% ethanol (12 ml)-DMF (20 ml) was added 4-(4-chlorobenzoyl)benzyl bromide (1.56 g) and the mixture was stirred at room temperature for 1 hour. This reaction mixture was poured in water and the resulting crystals were collected by filtration, rinsed with water and methanol, and recrystallized from methanol to provide the title compound as colorless solid (1.497 g) . $^1$H-NMR (CDCl$_3$) δ: 3.61(3H, s), 4.58(2H,s), 7.23(1H,d,J=5.2Hz), 7.45(2H,d,J=8.6Hz), 7.59(2H,d,J=8.2Hz), 7.70–7.80(5H,m).

IR (KBr): 1665, 1645, 1510 cm$^{-1}$.

EXAMPLE 8

2-[4-(4-Chlorobenzoyl)benzyl]thio-3-methyl-5,6,7,8-tetrahydrobenzo[b]thieno[2,3-d]pyrimidin-4(3H)-one To a solution of 2-mercapto-3-methyl-5,6,7,8-tetrahydrobenzo[b]thieno[2,3-d]pyrimidin-4(3H)-one (500 mg) and sodium hydroxide (75 mg) in 50% ethanol (5 ml)-DMF (5 ml) was added 4-(4-chlorobenzoyl)benzyl bromide (565 mg) and the mixture was stirred at room temperature for 1 hour. This reaction mixture was poured in water and the resulting crystals were collected by filtration, rinsed with water and methanol, and recrystallized from methanol to provide the title compound as colorless solid (497 mg). $^1$H-NMR (CDCl$_3$) δ: 1.72–1.94(4H,m), 2.75(2H, m), 2.98(2H,m), 3.53(3H,s), 4.53(2H,s), 7.45(2H,d,J= 8.6Hz), 7.56(2H,d,J=8.4Hz), 7.74(4H,d,J=8.6Hz).

IR (KBr): 1670, 1660, 1510 cm$^{-1}$.

EXAMPLE 9

6-[4-(4-Chlorobenzoyl)benzyl]thio-5-methyl-1H-pyrazolo[3,4-d]pyrimidin-4(5H)-one To a solution of 6-mercapto-5-methyl-1H-pyrazolo-[3,4-d]pyrimidin-4(5H)-one potassium (1.0 g) in DMF (10 ml) was added 4-(4-chlorobenzoyl)benzyl bromide (1.393 g) and the mixture was stirred at room temperature for 1 hour. This reaction mixture was poured in water and the resulting crystals were collected by filtration, rinsed with water and methanol, and recrystallized from methanol to provide the title compound as colorless solid (1.647 g). $^1$H-NMR (DMSO-d$_6$) δ: 3.53(3H,s), 4.58(2H,s), 7.50(2H,t,J=8.6Hz), ,7.65(2H,d,J=8.6Hz), 7.73(2H,d,J=8.6Hz), 7.74(2H,d,J= 8.6Hz), 7.79(1H,s).

IR (KBr): 3200, 1660, 1640, 1575, 1280 cm$^{-1}$.

EXAMPLE 10

6-[4-(4-Chlorobenzoyl)benzyl]thio-1,5-dimethyl-1H-pyrazolo[3,4-d]pyrimidin-4(5H)-one and 6-[4-(4-chlorobenzoyl)benzyl]thio-2,5-dimethyl-2H-pyrazolo[3,4-d]-pyrimidin-4(5H)-one To a suspension of 6-[4-(4-chlorobenzoyl)benzyl]-thio-5-methyl-1H-pyrazolo[3,4-d]pyrimidin-4(5H)-one (1.0 g) in DMF (20 ml) was added 60% sodium hydride (197 mg) and the mixture was stirred at room temperature for 10 minutes. After a clear solution had been obtained, methyl iodide (515 mg) was added and the mixture was stirred at room temperature for 1 hour. This reaction mixture was concentrated and the residue was purified by silica gel column chromatography (hexane-ethyl acetate =3:2) to provide 6-[4-(4-chlorobenzoyl)benzyl]thio-1,5-dimethyl-1H-pyrazolo[3,4-d]pyrimidin-4(5H)-one as colorless solid (120 mg) and 6-[4-(4-chlorobenzoyl)benzyl]thio-2,5-dimethyl-2H-pyrazolo[3,4-d]pyrimidin-4(5H)-one as colorless solid (570 mg).

6-[4-(4-Chlorobenzoyl)benzyl]thio-1,5-dimethyl-1H-pyrazolo[3,4-d]pyrimidin-4(5H)-one $^1$H-NMR (CDCl$_3$) δ: 3.54(3H,s), 4.06(3H,s), 4.60(2H,s), 7.46(2H,d,J=8.6Hz), 7.61(2H,d,J=8.4Hz), 7.75(4H,d,J=8.6Hz), 7.99(1H,s).

IR (KBr): 1680, 1645, 1570 cm$^{-1}$.

6-[4-(4-Chlorobenzoyl)benzyl]thio-2,5-dimethyl-2H-pyrazolo[3,4-d]pyrimidin-4(5H)-one $^1$H-NMR (CDCl$_3$) δ: 3.57(3H,s), 3.97(3H,s), 4.57(2H,s), 7.47(2H,d,J=8.6Hz), 7.59(2H,d,J=8.4Hz), 7.75(2H,d,J=8.6 Hz), 7.78(2H,d,J= 8.4Hz), 8.00(1H,s).

IR (KBr): 1700, 1660, 1550 cm$^{-1}$.

EXAMPLE 11

6-[4-(4-Chlorobenzoyl)benzyl]thio-3,5-dimethyl-1H-pyrazolo[3,4-d]pyrimidin-4(5H)-one To a solution of 6-mercapto-3,5-dimethyl-1H-pyrazolo[3,4-d]pyrimidin-4(5H)-one potassium (800 mg) in DMF (12 ml) was added 4-(4-chlorobenzoyl)benzyl bromide (1.05 g) and the mixture was stirred at room temperature for 1 hour. This reaction mixture was poured in water and the resulting crystals were collected by filtration, rinsed with water and methanol, and recrystallized from methanol to provide the title compound as colorless solid (1.086 g). $^1$H-NMR (DMSO-d$_6$) δ: 2.44(3H,s), 3.42(3H,s), 4.60(2H,s), 7.63(2H, d,J=8.6Hz), 7.71(4H,s), 7.75(2H,d,J=8.6Hz), 13.29(1H,brs).

IR (KBr): 3210, 1660, 1575, 1550, 1280 cm$^{-1}$.

EXAMPLE 12

6-[4-(4-Chlorobenzoyl)benzyl]thio-1,3,5-trimethyl-1H-pyrazolo[3,4-d]pyrimidin-4(5H)-one and 6-[4-(4-chlorobenzoyl)benzyl]thio-2,3,5-trimethyl-2H-pyrazolo[3,4-d]pyrimidin-4(5H)-one To a suspension of 6-[4-(4-chlorobenzoyl)benzyl]-thio-3,5-dimethyl-1H-pyrazolo[3,4-d]pyrimidin-4(5H)-one (500 mg) in DMF (15 ml) was added 60% sodium hydride (55 mg) and the mixture was stirred at room temperature for 10 minutes. After a clear solution formed, methyl iodide (235 mg) was added and the mixture was stirred at room temperature for 1 hour. This reaction mixture was concentrated and the residue was purified by silica gel column chromatography (hexane: ethyl acetate=3:2) to provide 6-[4-(4-chlorobenzoyl)benzyl]thio-1,3,5-trimethyl-1H-pyrazolo[3,4-d]pyrimidin-4(5H)-one as colorless solid (90 mg) and 6-[4-(4-chlorobenzoyl)benzyl]thio-2,3,5-trimethyl-2H-pyrazolo[3,4-d]pyrimidin-4(5H)-one as colorless solid (170 mg).

6-[4-(4-Chlorobenzoyl)benzyl]thio-1,3,5-trimethyl-1H-pyrazolo[3,4-d]pyrimidin-4(5H)-one H-NMR (CDCl$_3$) δ: 2.66(3H,s), 3.51(3H,s), 3.91(3H,s), 4.59(2H,s), 7.46(2H,d, J=8.8Hz), 7.60(2H,d,J=8.4Hz), 7.70–7.80(4H,m).

IR (KBr): 1680, 1645, 1585, 1520 cm$^{-1}$.

6-[4-(4-Chlorobenzoyl)benzyl]thio-2,3,5-trimethyl-2H-pyrazolo[3,4-d]pyrimidin-4(5H)-one $^1$H-NMR (CDCl$_3$) δ: 2.55(3H,s), 3.54(3H,s), 3.88(3H,s), 4.55(2H,s), 7.47(2H,d, J=8.6Hz), 7.58(2H,d,J=8.2Hz), 7.75(2H,d,J=8.6Hz), 7.77 (2H,d,J=8.2Hz).

IR (KBr): 1695, 1660, 1550 cm$^{-1}$.

EXAMPLE 13

6-[4-(4-Chlorobenzoyl)benzyl]thio-3,5-dimethylisoxazolo[5,4-d]pyrimidin-4(5H)-one To a solution of 6-mercapto-3,5-dimethylisoxazolo-[5,4-d]pyrimidin-4(5H)-one (800 mg) and sodium hydroxide (165 mg) in 50% ethanol (10 ml)-DMF (10 ml) was added 4-(4-chlorobenzoyl)benzyl bromide (1.25 g) and the mixture was stirred at room temperature for 1 hour. This reaction mixture was concentrated and the residue was purified by silica gel column chromatography (hexane:ethyl acetate= 2:1) to provide the title compound as colorless solid (470 mg). $^1$H-NMR (CDCl$_3$) δ: 2.57(3H,s), 3.55(3H,s), 4.59(2H, s), 7.46(2H,d,J=8.6Hz), 7.58(2H,d,J=8.4Hz), 7.74(2H,d,J= 8.4Hz), 7.76(2H,d,J=8.6Hz).

IR (KBr): 1715, 1690, 1650, 1590, 1525 cm$^{-1}$.

EXAMPLE 14

9-[4-(4-Chlorobenzoyl)benzyloxy]-2,3-dimethyl-4H-pyrido[1,2-a]pyrimidin-4-one

9-Hydroxy-2,3-dimethyl-4H-pyrido[1,2-a]pyrimidin-4-one (500 mg) as obtained in Reference Example 3 and potassium carbonate (375 mg) were dissolved in acetone (15 ml). To this solution was added 4-(4-chlorobenzoyl)benzyl bromide (896 mg) and the mixture was stirred at room temperature overnight. This reaction mixture was concentrated and the residue was washed serially with water and ethyl acetate and recrystallized from methanol to provide the title compound as colorless solid (415 mg). $^1$H-NMR (DMSO-d$_6$) δ: 2.14(3H,s), 2.43(3H,s), 7.16(1H,t,J=7.2Hz), 7.31(1H,d,J=7.4Hz), 7.63(2H,d,J=8.0Hz), 7.68(2H,d,J= 8.0Hz), 7.77(2H,d,J=8.0Hz), 7.80(2H,d,J=8.0Hz), 8.50(1H, d,J=7.0Hz).

IR (KBr): 1630, 1480, 1280 cm$^{-1}$.

EXAMPLE 15

7-[4-(4-Chlorobenzoyl)benzyl]-1,3-dimethylxanthine

To a solution of theophylline (1.80 g) in DMF (20 ml) were added potassium carbonate (1.66 g) and 4-(4-chlorobenzoyl)benzyl bromide (3.10 g) and the mixture was stirred at room temperature for 14 hours. The reaction mixture was then diluted with water and extracted with ethyl acetate. The extract was washed with saturated aqueous NaCl solution and dried over anhydrous sodium sulfate. The solvent was then distilled off and the residue was purified by silica gel column chromatography (hexane: ethyl acetate= 1:4) to provide the title compound as colorless powder (2.79 g, 68%). $^1$H-NMR (CDCl$_3$) δ: 3.41(3H,s), 3.63(3H,s), 5.59 (2H,s), 7.38–7.50(4H,m), 7.65(1H,s), 7.68–7.81(4H,m).

IR (KBr): 3110, 1690, 1650, 1400, 1280, 1230 cm$^{-1}$.

EXAMPLE 16

7-[4-(4-Chlorobenzoyl)benzyl]-1,3-dimethylxanthine hydrochloride

To a solution of 7-[4-(4-chlorobenzoyl)benzyl]-1,3-dimethylxanthine (100 mg) in methanol (4 ml) was added 4N-hydrochloric acid (1 ml) and the mixture was stirred at room temperature for 10 minutes. To this reaction mixture was added ether and the resulting precipitate was collected by filtration to provide the title compound as white powder (84 mg, 77%). $^1$H-NMR (CDCl$_3$) δ: 3.45(3H,s), 3.70(3H,s), 5.70(2H,s), 7.42–7.83(8H,m), 8.47(1H,s).

IR (KBr): 3010, 2950, 1710, 1675, 1660 cm$^{-1}$.

EXAMPLE 17

7-[4-(4-Chlorobenzoyl)benzyl]-3-methylxanthine

To a solution of 3-methylxanthine (1.06 g) in DMF (26 ml) were added potassium carbonate (1.06 g) and 4-(4-chlorobenzoyl)benzyl bromide (1.98 g) and the mixture was stirred at room temperature for 24 hours. To this reaction mixture were added water and ethyl acetate and the floating matter was filtered off and the filtrate aqueous solution was diluted with 1N-hydrochloric acid and extracted with chloroform. The extract was washed with saturated aqueous NaCl solution and dried over anhydrous sodium sulfate. The solvent was then distilled off and the residue was washed with ethyl acetate to provide the title compound as colorless powder (239 mg, 10%). $^1$H-NMR (CDCl$_3$) δ: 3.54(3H,s), 3.57(3H,s), 7.41–7.52(4H,m), 7.68–7.81(5H,m).

IR (KBr): 3450, 3160, 3040, 2820, 1685, 1585, 1540, 1375, 1280, 1230, 1190, 925, 750 cm$^{-1}$.

EXAMPLE 18

1-[4-(4-Chlorobenzoyl)benzyl]-3,7-dimethylxanthine

To a mixture of theobromine (0.90 g) and DMF (20 ml) was added sodium hydride (240 ml) as well as 4-(4-chlorobenzoyl)benzyl bromide (1.55 g) and the mixture was stirred at room temperature for 18 hours. This reaction mixture was diluted with water and extracted with ethyl acetate. The extract was washed with saturated aqueous NaCl solution and dried over anhydrous sodium sulfate. The solvent was then distilled off and the residue was washed with ether to provide the title compound as colorless powder (1.37 g, 67%). $^1$H-NMR (CDCl$_3$) δ: 3.60(3H,s), 4.00(3H,s), 5.27(2H,s), 7.38–7.79(8H,m)

IR (KBr): 3310, 2940, 1710, 1655, 1645, 1600, 1580, 1545, 1280, 930 cm$^{-1}$

EXAMPLE 19

8-Chloro-7-[4-(4-chlorobenzoyl)benzyl]-1,3-dimethylxanthine

To a solution of 8-chlorotheophylline (2.15 g) in DMF (20 ml) was added potassium carbonate (1.66 g) as well as 4-(4-chlorobenzoyl)benzyl bromide (3.10 g) and the mixture was stirred at room temperature for 20 hours. This reaction mixture was diluted with water and extracted with ethyl acetate. The extract was washed with saturated aqueous NaCl solution and dried over anhydrous sodium sulfate. The solvent was then distilled off and the residue was washed with ether to provide the title compound as white powder (3.34 g, 75%). $^1$H-NMR (CDCl$_3$) δ: 3.41(3H,s), 3.57(3H,s), 5.64(2H,s), 7.41–7.52(4H,m), 7.68–7.80(4H,m).

IR (KBr): 2940, 1710, 1660, 1580, 1530, 1445, 1400, 1370, 1280, 740 cm$^{-1}$.

EXAMPLE 20

7-[4-(4-Chlorobenzoyl)benzyl]-1,3-dimethyl-8-methoxyxanthine

To a solution of 8-chloro-7-[4-(4-chlorobenzoyl)-benzyl]-1,3-dimethylxanthine (866 mg) in DMF (40 ml) was added sodium methoxide (10 ml, 28% in methanol) and the mixture was stirred at room temperature for 30 minutes. This reaction mixture was diluted with water and extracted with ethyl acetate, washed with saturated aqueous NaCl solution, and dried over anhydrous sodium sulfate. The solvent was then distilled off and the residue was washed with ether to provide the title compound as colorless powder (470 mg, 54%). $^1$H-NMR (CDCl$_3$) δ: 3.40(3H,s), 3.54(3H,s), 4.17 (3H,s), 5.36(2H,s), 7.38–7.78(8H,m).

IR (KBr): 2950, 1705, 1670, 1655, 1610, 1525, 1460, 1410, 1285 cm$^{-1}$.

EXAMPLE 21

7-[4-(4-Chlorobenzoyl)benzyl]-1,3-dimethyluric acid

To 7-[4-(4-chlorobenzoyl)benzyl]-1,3-dimethyl-8-methoxyxanthine (400 mg) was added concentrated hydrochloric acid (8 ml) at room temperature and the mixture was stirred at 130° C. for 1 hour. After cooling, the resulting precipitate was collected by filtration and rinsed with water and ether to provide the title compound as colorless powder (333 mg, 86%). $^1$H-NMR (CDCl$_3$+5% CD$_3$OD) E: 3.36(3H, s), 3.45(3H,s), 5.23(2H,s), 7.40–7.80(8H,m).

IR (KBr): 3450, 2950, 2710, 1680, 1550, 1280, 1185, 740 cm$^{-1}$.

EXAMPLE 22

1-[4-(4-Chlorobenzoyl)benzyl]-4,6-dimethyltriazolo[4,5-d]pyrimidine-5,7-dione To a solution of N,N-dimethylazidophosgeniminium chloride (1.70 g) in methylene chloride (40 ml) was added 4-amino-1,3-dimethyluracil (1.55 g) and the mixture was refluxed for 3 hours. This reaction mixture was concentrated and the residue was dissolved in DMF (30 ml), followed by addition of potassium carbonate (6.91 g) and 4-(4-chlorobenzoyl)benzyl bromide (3.10 g), and the mixture was stirred at room temperature for 18 hours. This reaction mixture was diluted with water and extracted with ethyl acetate. The extract was washed with saturated aqueous NaCl solution and dried over anhydrous sodium sulfate. The solvent was then distilled off and the residue was purified by silica gel column chromatography (hexane: ethyl acetate= 2:1→1:1) to provide the title compound as colorless powder (0.92 g, 22%). $^1$H-NMR (CDCl$_3$) δ: 3.41(3H,s), 3.66(3H,s), 5.93(2H,s), 7.39–7.80(8H,m).

IR (KBr): 1710, 1680, 1560, 1270, 925, 745 cm$^{-1}$.

EXAMPLE 23

7-[3-(4-Chlorobenzoyl)benzyl]-1,3-dimethylxanthine

To a solution of theophylline (1.80 g) in DMF (50 ml) were added potassium carbonate (1.66 g) and 3-(4-chlorobenzoyl)benzyl bromide (3.10 g) and the mixture was stirred at room temperature for 24 hours. This reaction mixture was diluted with water and extracted with ethyl acetate. The extract was washed with saturated aqueous NaCl solution and dried over anhydrous sodium sulfate. The solvent was distilled off and the residue was recrystallized (acetone-hexane) to provide the title compound as white powder (1.64 g, 40%). $^1$H-NMR (CDCl$_3$) δ: 3.40(3H,s), 3.60(3H,s), 5.57(2H,s), 7.42–7.79(9H,m).

IR (KBr): 1700, 1660, 1550, 1290, 750 cm$^{-1}$.

EXAMPLE 24

7-[4-(2,4-Dichlorobenzoyl)benzyl]-1,3-dimethylxanthine

To a solution of theophylline (1.80 g) in DMF (20 ml) were added potassium carbonate (1.66 g) and 4-(2,4-dichlorobenzoyl)benzyl bromide (3.33 g) and the mixture was stirred at room temperature for 24 hours. This reaction mixture was diluted with water and extracted with ethyl acetate. The extract was washed with saturated aqueous NaCl solution and dried over anhydrous sodium sulfate. The solvent was then distilled off and the residue was recrystallized (ethyl acetate) to provide the title compound as white powder (3.38 g, 76%). $^1$H-NMR (CDCl$_3$) δ: 3.39(3H,s), 3.60(3H,s), 5.58(2H,s), 7.25–7.84(8H,m).

IR (KBr): 1700, 1660, 1290, 930, 745 cm$^{-1}$.

EXAMPLE 25

7-[4-(4-Fluorobenzoyl)benzyl]-1,3-dimethylxanthine

To a solution of theophylline (1.80 g) in DMF (20 ml) were added potassium carbonate (1.66 g) and 4-(4-fluorobenzoyl)benzyl bromide (2.93 g) and the mixture was stirred at room temperature for 24 hours. This reaction mixture was diluted with water and extracted with ethyl acetate. The extract was washed with saturated aqueous NaCl solution and dried over anhydrous sodium sulfate. The solvent was then distilled off and the residue was washed with ether to provide the title compound as white powder (2.79 g, 74%). $^1$H-NMR (CDCl$_3$) δ: 3.41(3H,s), 3.60(3H,s), 5.59(2H,s), 7.08–7.86(9H,m).

IR (KBr): 1700, 1660, 1640, 1590, 1545, 1270, 1230 cm$^{-1}$.

EXAMPLE 26

7-[4-(2-Chlorobenzoyl)benzyl]-1,3-dimethylxanthine

To a solution of theophylline (0.90 g) in DMF (20 ml) were added potassium carbonate (0.83 g) and 4-(2-chlorobenzoyl)benzyl bromide (1.55 g) and the mixture was stirred at room temperature for 13 hours. This reaction mixture was diluted with water and extracted with ethyl acetate and the extract was washed with saturated aqueous NaCl solution and dried over anhydrous sodium sulfate. The solvent was then distilled off and the residue was washed with ether to provide the title compound as needles (1.70 g, 83%). $^1$H-NMR (CDCl$_3$) δ: 3.39(3H,s), 3.60(3H,s), 5.58 (2H,s), 7.30–7.48(6H,m), 7.63(1H,s), 7.76–7.85(2H,m).

IR (KBr): 3100, 1700, 1660, 1540, 1430, 1285, 740 cm$^{-1}$.

EXAMPLE 27

7-[4-(4-Chlorobenzoyl)benzyl]xanthine hydrochloride

To 1,3-diethoxy-7-(4-(4-chlorobenzoyl)benzyl)purine (100 mg) was added concentrated hydrochloric acid (10 ml) at room temperature and the mixture was stirred at 130° C. for 2 hours. After this reaction mixture was allowed to cool, the precipitate was collected by filtration and washed with water and ether to provide the title compound as colorless powder (73 mg, 73%). $^1$H-NMR (CDCl$_3$+5% CD$_3$OD) δ: 5.59(2H,s), 7.45–7.55(4H,m), 7.70–7.90(4H,m), 8.05(1H,s).

IR (KBr): 2950, 2760, 1710, 1650, 1575, 1270 cm$^{-1}$.

EXAMPLE 28

7-[4-(4-Chlorobenzoyl)benzyl]-1,3,8-trimethylxanthine

To a solution of 1,3,8-trimethylxanthine (0.97 g) in DMF (20 ml) were added potassium carbonate (0.83 g) and 4-(4-chlorobenzoyl)benzyl bromide (1.55 g) and the mixture was stirred at room temperature for 2 hours. The reaction mixture was diluted with water and extracted with ethyl acetate. The extract was washed with saturated aqueous NaCl solution and dried over anhydrous sodium sulfate. The solvent was then distilled off and the residue was washed with acetone to provide the title compound as white powder (1.34 g, 61%). $^1$H-NMR (CDCl$_3$) δ: 2.46(3H,s), 3.41(3H,s), 3.60(3H,s), 5.63(2H,s), 7.25–7.80(8H,m).

IR (KBr): 2950, 1705, 1660, 1610, 1590, 1545, 1490, 1410, 1395, 1290, 1270, 1090, 925, 755, 745 cm$^{-1}$.

EXAMPLE 29

7-[4-(4-Chlorobenzoyl)benzyl]-1,3-dimethyl-8-ethylxanthine

To a solution of 1,3-dimethyl-8-ethylxanthine (416 mg) in DMF (10 ml) were added potassium carbonate (332 mg) and 4-(4-chlorobenzoyl)benzyl bromide (619 mg) and the mixture was stirred at room temperature for 21 hours. This reaction mixture was diluted with water and extracted with ethyl acetate. The extract was washed with saturated aqueous NaCl solution and dried over anhydrous sodium sulfate. The solvent was distilled off and the residue was recrystallized (ethyl acetate-ether) to provide the title compound as white powder (584 mg, 67%). $^1$H-NMR (CDCl$_3$) δ: 1.30 (3H,t,J=7.6Hz), 2.72(2H,q,J=7.6Hz), 3.40(3H,s), 3.61(3H, s), 5.64(2H,s), 7.21–7.80(8H,m).

IR (KBr): 1700, 1600, 1650, 1410, 1280 cm$^{-1}$.

EXAMPLE 30

2-[4-(4-Chlorobenzoyl)benzylthio]-3-methylpyrido-[2,3-d]pyrimidin-4-one

To a solution of 3-methylpyrido[2,3-d]pyrimidin-4-one-2-thione (193 mg) in DMF (5 ml) were added sodium hydride (60 mg) and 4-(4-chlorobenzoyl)benzyl bromide (310 mg) and the mixture was stirred at room temperature for 30 minutes. The reaction mixtrue was then diluted with saturated aqueous NaHCO$_3$ solution and extracted with ethyl acetate. The extract was washed with saturated aqueous NaCl solution and dried over anhydrous sodium sulfate and the solvent was then distilled off. The residue was recrystallized (ethyl acetate-ether-hexane) to provide the title compound as white powder (162 mg, 38%). $^1$H-NMR (CDCl$_3$) δ: 3.62(3H,s), 4.73(2H,s), 7.26–7.79(9H,m), 8.54–8.61(1H,m), 8.90–8.95(1H,m).

IR (KBr): 1680, 1645, 1580, 1550, 1425, 1285, 1270, 1080, 725 cm$^{-1}$.

EXAMPLE 31

1-[4-(4-Chlorobenzoyl)benzyl]-4-chloroimidazo[4,5-d]pyridazin-7(6H)-one and 1-[4-(4-chlorobenzoyl)benzyl]-7-chloroimidazo[4,5-d]pyridazin-4(5H)-one In dioxane (20 ml) was dissolved 1-[4-(4-chloro-benzoyl)benzyl]-4,7-dichloroimidazo[4,5-d]pyridazine (2.006 g) followed by addition of aqueous sodium hydroxide solution (3.78 g NaOH/30 ml water), and the mixtrue was refluxed for 15 hours. Then, water (100 ml) and acetic acid (5 ml) were added and the resulting crystals were collected by filtration. The crystals were purified by silica gel column chromatography (stationary phase 50 g; dichloromethane: ethyl acetate=10:1–1:1) to provide 1.32 g (yield 69%) of the title compound 1-[4-(4-chlorobenzoyl)benzyl]-4-chloroimidazo[4,5-d]pyridazin-7(6H)-one and 441 mg (yield 23%) of the title compound 1-[4-(4-chlorobenzoyl)benzyl]-7-chloroimidazo[4,5-d]pyridazin-4(5H)-one.

1-[4-(4-Chlorobenzoyl)benzyl]-4-chloroimidazo[4,5-d]pyridazin-7(6H)-one $^1$H-NMR (CDCl$_3$) δ: 5.80(2H,s), 7.51 (2H,d,J=8.4Hz), 7.60(2H,d,J=8.8Hz), 7.73(4H,d,J=8.8Hz), 8.69(1H,s).

IR (KBr): 3101, 2933, 1672, 1533, 742 cm$^1$.

1-[4-(4-Chlorobenzoyl)benzyl]-7-chloroimidazo[4,5-d]pyridazin-4(5H)-one $^1$H-NMR (CDCl$_3$) δ: 5.86(2H,s), 7.31 (2H,d,J=8.4Hz), 7.61(2H,d,J=8.8Hz), 7.74(4H,d,J=8.6Hz), 8.62(1H,s).

IR (KBr): 3116, 2926, 1676, 1533, 739 cm$^{-1}$.

EXAMPLE 32

1-[4-(4-Chlorobenzoyl)benzyl]-4-chloro-6-methyl-imidazo[4,5-d]pyridazin-7(6H)-one In DMF (15 ml) was dissolved 1-[4-(4-chlorobenzoyl)benzyl]-4-chloroimidazo[4,5-d]pyridazin-7(6H)-one (963 mg) followed by addition of potassium carbonate (985 mg). Then, methyl iodide (0.45 ml) was added and the mixture was stirred at room temperature for 65 hours. To this reaction mixture was added water (50 ml) and the resulting crystals were harvested by filtration. This crystal crop was purified by silica gel column chromatography (stationary phase 30 g; dichloromethane: ether=1:0–3:1) to provide 655 mg (66%) of the title compound. $^1$H-NMR (CDCl$_3$) δ: 3.86(3H,s), 5.81(2H,s), 7.45(2H,d,J=7.8Hz), 7.46(2H,d,J=8.6Hz), 7.73(2H,d,J=8.6Hz), 7.78(2H,d,J=8.2Hz), 8.01(1H, s).

IR (neat): 2949, 1666, 1537, 741 cm$^{-1}$.

EXAMPLE 33

1-[4-(4-Chlorobenzoyl)benzyl]-5-methyl-7-chloro-imidazo[4,5-d]pyridazin-4(5H)-one The procedure of Example 32 was repeated except that 1-[4-(4-chlorobenzoyl)benzyl]-7-chloroimidazo[4,5-d]pyridazin-4(5H)-one was used as the starting compound. Thus, this starting compound (424 mg) was dissolved in DMF (7 ml) followed by addition of potassium carbonate (465 mg). Then, methyl iodide (0.2 ml) was added and the mixture was stirred at room temperature for 65 hours. To this reaction mixture was added water (50 ml) and the resulting crystals were harvested by filtration. This crystal crop was purified by silica gel column chromatography (stationary phase 30 g; ethyl acetate: methanol=1:0–20:1) to provide 218 mg (50%) of the title compound. $^1$H-NMR (CDCl$_3$) δ: 3.87(3H,s), 5.74(2H,s), 7.23(2H,d,J=8.4Hz), 7.46(2H,d,J=8.4Hz), 7.72(2H,d,J=8.6Hz), 7.78(2H,d,J=8.2Hz), 8.01(1H, s).

IR (neat): 2951, 1672, 1529, 739 cm$^{-1}$.

EXAMPLE 34

1-[4-(4-Chlorobenzoyl)benzyl]-4-methoxy-6-methyl-imidazo[4,5-d]pyridazin-7(6H)-one In methanol (5 ml) was dissolved 1-[4-(4-chloro-benzoyl)benzyl]-4-chloro-6-methylimidazo[4,5-d]pyridazin-7(6H)-one (72 mg) followed by addition of 28% sodium methoxide/methanol (1.0 ml), and the mixture was refluxed for 5 hours. To this reaction mixture was added a large quantity of water and the resulting crystals were rinsed with water and dried under reduced pressure to provide 50 mg (yield 70%) of the title compound. $^1$H-NMR (CD$_3$OD) δ: 3.7,1(3H,s), 4.00(3H,s), 5.85(2H,s), 7.50(2H,d,J=8.6Hz), 7.52(2H,d,J=8.8Hz), 7.74(2H,d,J=8.8Hz), 7.75(2H,d,J=8.6Hz), 8.42(1H,s).

IR (neat): 2945, 1660, 1561, 1269, 1234, 739 cm$^{-1}$.

EXAMPLE 35

1-[4-(4-Chlorobenzoyl)benzyl]-5-methyl-7-methoxy-imidazo[4,5-d]pyridazin-4(5H)-one The procedure of Example 34 was repeated except that 1-[4-(4-chlorobenzoyl)benzyl]-5-methyl-7-chloroimidazo

[4,5-d]pyridazin-4(5H)-one was used as the starting compound. Thus, this starting compound (52 mg) was dissolved in methanol (5 ml) followed by addition of 28% sodium methoxide/methanol (0.5 ml), and the mixture was refluxed for 3 hours. To this reaction mixture was added a large quantity of water and the resulting crystals were rinsed with water and dried under reduced pressure to provide 20 mg (yield 39%) of the title compound. $^1$H-NMR (CD$_3$OD) δ: 3.73(3H,s), 3.97(3H,s), 5.70(2H,s), 7.41(2H,d,J=8.4Hz), 7.51(2H,d,J=8.8Hz), 7.73(2H,d,J=8.6Hz), 7.76(2H,d,J=8.2Hz), 8.36(1H,s).

IR (neat): 2947, 1660, 1568, 1272, 737 cm$^{-1}$.

EXAMPLE 36

8-Tert-butyl-5-[4-(4-chlorobenzoyl)benzyl]-2,3,4,5-tetrahydropyridazino[4,5-b]-1,4-oxazepin-9(8H)-one To a solution of sodium ethoxide in ethanol as prepared by dissolving sodium metal (6.5 mg) in ethanol (1 ml) was added a solution of 2-tert-butyl-4-chloro-5-[N-(4-(4-chlorobenzoyl)benzyl)-N-(3-hydroxypropyl)-amino]-3-(2H)-pyridazinone (91 mg) in ethanol (5 ml) and the mixture was refluxed for 46 hours. After cooling to room temperature, the reaction mixture was diluted with water and extracted with ethyl acetate. The extract was washed with water and saturated aqueous NaCl solution in that order and dried over anhydrous magnesium sulfate. The solvent was then distilled off under reduced pressure and the residue was purified by silica gel column chromatography (developer; n-hexane: ethyl acetate=1:1→1:2) to provide the title compound as white powder (120 mg, yield 12%). $^1$H-NMR (CDCl$_3$) δ: 1.62(9H,s), 2.06(2H,q,J=6.2Hz), 3.55(2H,t,J=6.2Hz), 4.42(2H,t,J=6.2Hz), 4.55(2H,m), 7.32(1H,s), 7.41(2H,d,J=8.4Hz), 7.48(2H,d,J=8.4Hz), 7.76(2H,d,J=8.4Hz), 7.81(2H,d,J=8.4Hz).

EXAMPLE 37

1-[4-(4-Chlorobenzoyl)benzyl]-2,3-dichloro-5-methyl-1H-pyrrolo[2,3-d]pyridazin-4(5H)-one A solution of 2,3-dichloro-5-methyl-1H-pyrrolo[2,3-d]pyridazin-4(5H)-one (404 mg) in DMF (70 ml) was dripped into a suspension of 60% sodium hydride-oil (96 mg) in DMF (10 ml) on an ice-water bath. After 3 hours of stirring at room temperature, a solution of 4-(4-chlorobenzoyl)benzyl bromide (681 mg) in DMF (15 ml) was added and the mixture was further stirred at room temperature for 18 hours. The reaction was stopped by adding water and the reaction mixture was extracted with ethyl acetate. The extract was dried over anhydrous magnesium sulfate and the solvent was distilled off under reduced pressure. The residue was then purified by silica gel column chromatography (developer; n-hexane: ethyl acetate=2:1→1:1) to provide the title compound as white powder (351 mg, yield 39%). $^1$H-NMR (DMSO-d$_6$) δ: 3.68(3H,s), 5.73(2H,s), 7.30(2H,d,J=8.6Hz), 7.61(2H,d,J=8.6Hz), 7.72(2H,d,J=8.6Hz), 7.73(2H,d,J=8.6Hz), 8.71(1H,s).

IR (KBr): 3055, 3040, 2990, 2960, 1660, 1640, 1605 cm$^{-1}$.

EXAMPLE 38

1-[4-(4-Chlorobenzoyl)benzyl]-5-methyl-1H-imidazo[4,5-d]pyridazin-4(5H)-one

A solution of methylhydrazine (472 mg) and ethyl 1-[4-(4-chlorobenzoyl)benzyl]-5-formylimidazole-4-carboxylate (1.03 g) in ethanol (20 ml) was refluxed for 3 hours. After cooling to room temperature, concentrated sulfuric acid (0.2 ml) was added and the mixture was further refluxed for 21 hours. This reaction mixture was diluted with water and extracted with ethyl acetate. The extract was dried over anhydrous magnesium sulfate, the solvent was distilled off under reduced pressure, and the residue was purified by silica gel column chromatography (developer; chloroform:methanol=19:1) to provide the title compound as white powder (66 mg, yield 7%). $^1$H-NMR (CDCl$_3$) δ: 3.90(3H,s), 5.47(2H,s), 7.31(2H,d,J=8.4Hz), 7.48(2H,d,J=8.4Hz), 7.73(2H,d,J=8.4Hz), 7.81(2H,d,J=8.4Hz), 7.92(1H,s), 8.00(1H,s).

EXAMPLE 39

3-[4-(4-Chlorobenzoyl)benzyl]-5-methyl-3H-imidazo-[4,5-d]pyridazin-4(5H)-one

A solution of methylhydrazine (209 mg) and ethyl 1-[4-(4-chlorobenzoyl)benzyl]-4-formylimidazole-5-carboxylate (6.01 g) in ethanol (10 ml) was refluxed for 2.5 hours. After cooling to room temperature, concentrated sulfuric acid (0.1 ml) was added and the mixture was further refluxed for 15 hours. This reaction mixture was diluted with water and extracted with ethyl acetate. The extract was dried over anhydrous magnesium sulfate, the solvent was distilled off under reduced pressure, and the residue was purified by silica gel column chromatography (developer; n-hexane: ethyl acetate=2:1) to provide the title compound as white powder (115 mg, yield 20%). H-NMR (CDCl$_3$) δ: 3.88(3H, s), 5.81(2H,s), 7.46(4H,d,J=8.6Hz), 7.73(2H,d,J=8.6Hz), 7.77(2H,d,J=8.6Hz), 7.97(1H,s), 8.33(1H,s).

IR (KBr): 3100, 2950, 1650, 1600, 1580, 1540 cm$^{-1}$.

EXAMPLE 40

2-[4-(4-Chlorobenzoyl)benzyloxy]-3-methylpyrido[1,2-a]pyrimidin-4-one

2-Hydroxy-3-methylpyrido[1,2-a]pyrimidin-4-one (0.31 g) as obtained in Reference Example 15 and 4-(4-chlorobenzoyl)benzyl bromide (0.56 g) were dissolved in DMF (10.0 ml). To this solution was added potassium carbonate (0.25 g) and the mixture was stirred at 80° C. for 30 minutes. This reaction mixture was diluted with ethyl acetate and washed with saturated aqueous NaCl solution and the organic layer was dried over anhydrous magnesium sulfate and concentrated under reduced pressure. The residue was recrystallized from methanol to provide the title compound as colorless needles (0.224 g, yield 31%). $^1$H-NMR (CDCl$_3$) δ: 2.23(3H,s), 5.62(2H,s), 7.10(1H,t,J=7.4Hz), 7.45–7.82(10H,m), 9.08(1H,d,J=7.4Hz).

IR (KBr) : 1689, 1657, 1581, 1431, 1284, 1174, 1088, 930, 748 cm$^{-1}$.

EXAMPLE 41

2-[4-(4-Chlorobenzoyl)benzylthio]-6,7-dimethoxy-3-methylquinazolin-4-one

To a solution of 2-mercapto-6,7-dimethoxy-3-methylquinazolin-4-one (0.998 g) as obtained in Reference Example 16 and 4-(4-chlorobenzoyl)benzyl bromide (1.26 g) in ethanol (15.0 ml)-THF (5.0 ml) was added iN-sodium hydroxide (3.90 ml) and the mixture was stirred at 70° C overnight. This reaction mixture was diluted with ethyl acetate and washed with saturated aqueous NaCl solution. The organic layer was dried over anhydrous magnesium sulfate and concentrated under reduced pressure, and the residue was recrystallized from ethyl acetate to provide the title compound as colorless needles (1.06 g, yield 56%).
$^1$H-NMR (CDCl$_3$) δ: 3.60(3H,s), 3.99(3H,s), 4.02(3H,s), 4.61(2H,s), 7.00(1Hrs), 7.46(2H,d,J=8.6Hz), 7.56(1H,s), 7.60(2H,d,J=8.0Hz), 7.73–7.78(4H,m).

IR (KBr) : 1660, 1610, 1549, 1497, 1271, 1076, 1022, 928, 781, 743 cm$^{-1}$.

EXAMPLE 42

2-[4-(4-Chlorobenzoyl)benzylthio]-3,5-dimethyl-quinazolin-4-one

To a solution of 2-mercapto-3,5-dimethylquinazolin-4-one (1.05 g) as obtained in Reference Example 18 and 4-(4-chlorobenzoyl)benzyl bromide (1.60 g) in ethanol (15.0 ml)-THF (15.0 ml)-DMF (5.0 ml) was added 1N-sodium hydroxide (5.10 ml) and the mixture was stirred at 70° C. for 30 minutes. This reaction mixture was diluted with ethyl acetate and washed with saturated aqueous NaCl solution and the organic layer was dried over anhydrous magnesium sulfate and then concentrated under reduced pressure. The residue was recrystallized from ethyl acetate to provide the title compound as colorless needles (1.54 g, yield 70%).
$^1$H-NMR (CDCl$_3$) δ: 2.85(3H,s), 3.55(3H,s), 4.60(2H,s), 7.16(1H,d,J=7.0Hz), 7.42–7.47(2H,m), 7.53(2H,d,J= 8.2Hz), 7.61(2H,d,J=8.6Hz), 7.72–7.77(4H,m)-IR (KBr) : 1666, 1554, 1466, 1408, 1306, 1277, 1090, 928 cm$^{-1}$.

EXAMPLE 43

2-[4-(2,4-Dichlorobenzoyl)benzylthio]-3,5-dimethylquinazolin-4-one

To a solution of 2-mercapto-3,5-dimethylquinazolin-4-one (0.511 g) as obtained in Reference Example 18 in ethanol (10.0 ml)-THF (10.0 ml) was added 1N-sodium hydroxide (2.60 ml). Then, 4-(2,4-dichlorobenzoyl)benzyl bromide (0.872 g) was added and the mixture was stirred at 60° C. for 3.5 hours. This reaction mixture was diluted with ethyl acetate and washed with saturated aqueous NaCl solution and the organic layer was dried over anhydrous magnesium sulfate and then concentrated under reduced pressure. The residue was recrystallized from ethyl acetate to provide the title compound as colorless needles (0.825 g, yield 69%). $^1$H-NMR (CDCl$_3$) δ: 2.84(3H,s), 3.53(3H,s), 4.57(2H,s), 7.15(1H,d,J=6.8Hz), 7.32–7.54(5H,m), 7.59 (2H,d,J=8.2Hz), 7.75(2H,d,J=8.2Hz).

IR (KBr) : 1672, 1581, 1554, 1464, 1417, 1306, 1282, 1092, 930 cm$^{-1}$.

EXAMPLE 44

2-[3-(4-Chlorobenzoyl)benzylthio]-3,5-dimethyl-quinazolin-4-one

To a solution of 2-mercapto-3,5-dimethylquinazolin-4-one (0.522 g) as obtained in Reference Example 18 in ethanol (10.0 ml)-THF (10.0 ml) was added 1N-sodium hydroxide (2.50 ml). Then, 3-(4-chlorobenzoyl)benzyl bromide (0.770 g) was added and the mixture was stirred at 60° C. for 3.5 hours. This reaction mixture was diluted with ethyl acetate and washed with saturated aqueous NaCl solution and the organic layer was dried over anhydrous magnesium sulfate and then concentrated under reduced pressure. The residue was recrystallized from ethyl acetate to provide the title compound as colorless needles (0.877 g, yield 81%).
$^1$H-NMR (CDCl$_3$) δ: 2.84(3H,s), 3.53(3H,s), 4.57(2H,s), 7.15(IH,d,J=7.2Hz), 7.30–7.55(5H,m), 7.65–7.74(4H,m), 7.96(1H,bs).

IR (KBr): 1666, 1581, 1554, 1466, 1306, 1090, 733 cm$^{-1}$.

EXAMPLE 45

2-[4-(4-Fluorobenzoyl)benzylthio]-3,5-dimethyl-quinazolin-4-one

To a solution of 2-mercapto-3,5-dimethylquinazolin-4-one (0.492 g) as obtained in Reference Example 18-in ethanol (10.0 ml)-THF (10.0 ml) was added 1N-sodium hydroxide (2.50 ml). Then, 4-(4-fluorobenzoyl)benzyl bromide (0.700 g) was added and the mixture was stirred at 60° C. for 3.5 hours. This reaction mixture was diluted with ethyl acetate and washed with saturated aqueous NaCl solution and the organic layer was dried over anhydrous magnesium sulfate and then concentrated under reduced pressure. The residue was recrystallized from ethyl acetate to provide the title compound as colorless needles (0.717 g, yield 72%).
$^1$H-NMR (CDCl$_3$) δ: 2.85(3H,s), 3.55(3H,s), 4.60(2H,s), 7.10–7.20(3H,m), 7.46–7.63(4H,m), 7.72–7.87(4H,m).

IR (KBr) : 1666, 1601, 1554, 1464, 1414, 1304, 1277, 1234, 1153, 1092 cm$^{-1}$.

EXAMPLE 46

7-[4-(4-Chlorobenzoyl)benzyl]-5-methyl-2-methylthio-7H-pyrrolo[2,3-d]pyrimidin-4(3H)-one Under argon gas, 7-[4-(4-chlorobenzoyl)benzyl]-4-methoxy-5-methyl-2-methylthio-7H-pyrrolo[2,3-d] pyrimidine (0.671 g) was dissolved in dioxane (8 ml) followed by addition of 4,4'-thiobis(6-t-butyl-m-cresol) (7.2 mg). Then, 0.5N-hydrochloric acid (1.12 ml) was added and the mixture was stirred at 105° C. for 36 hours. Thereafter, 0.5 N-hydrochloric acid (1.12 ml) was added again and the mixture was further stirred at the same temperature as above for 24 hours. To this reaction mixture was added water (30 ml) and the resulting precipitate was collected by filtration and dried. The dried precipitate was purified by flash column chromatography (chloroform) to provide the title compound (0.312 g). $^1$H-NMR (DMSO-d$_6$) δ: 2.24(3H,s), 2.51(3H,d, J=1.0Hz), 5.33(2H,s), 6.83(1H,d,J=1.0Hz), 7.43(2H,d,J= 8.2Hz), 7.60(2H,d,J=8.6Hz), 7.71(2H,d,J=8.2Hz), 7.73(2H, d,J=8.6Hz), 12.01(1H,s).

IR (KBr): 3430, 3220, 3030, 2920, 2830, 1660, 1605, 1570, 1545, 1520, 1460, 1410, 1305, 1280, 1205, 1180, 1170, 1135, 1035, 1085, 1010 cm$^{-1}$.

EXAMPLE 47

7-[4-(4-Chlorobenzoyl)benzyl]-2-methylthio-7H-pyrrolo[2,3-d]pyrimidin-4(3H)-one Under argon gas, 7-[4-(4-chlorobenzoyl)benzyl]-4-methoxy-2-methylthio-7H-pyrrolo[2,3-d]pyrimidine (0.615 g) was dissolved in dioxane (6 ml) followed by addition of 4,41-thiobis(6-t-butyl-m-cresol) (7 mg). Then, 0.5N-HCl (1.2 ml) was added and the mixture was stirred at 105° C. for 36 hours. Thereafter, 0.5N-HCl (1.2 ml) was added again and the mixture was further stirred at the same temperature as above for 24 hours. After cooling to room temperature, the precipitate was collected by filtration, washed with methanol and ether, and dried to provide the title compound (0.405 g) $^1$H-NMR (DMSO-d$_6$) δ: 2.53(3H,s), 5.42(2H,s), 6.44(1H,d,J=3.4Hz), 7.15(1H,d,J=3.4Hz), 7.45(2H,d,J= 8.0Hz), 7.60(2H,d,J=8.4Hz), 7.72(2H,d,J=8.0Hz), 7.73 (2H,d,J=8.4Hz), 12.18(1H,s).

IR (KBr): 3450, 2920, 2840, 1670, 1640, 1605, 1550, 1405, 1310, 1280, 1230, 1205, 1140, 1085 cm$^{-1}$.

EXAMPLE 48

7-[4-(4-Chlorobenzoyl)benzyl]-3,5-dimethyl-2-methylthio-7H-pyrrolo[2,3-d]pyrimidin-4(3H)-one Under argon gas, 7-[4-(4-chlorobenzoyl)benzyl]-5-methyl-2-methylthio-7H-pyrrolo[2, 3-d]pyrimidin-4(3H)-one (254 mg) was dissolved in anhydrous DME (10 ml)-anhydrous DMF (6 ml). Then, 60% sodium hydride-oil (26.4 mg) was added with ice-cooling and, after 30 minutes of agitation, methyl iodide (98 mg) was added. Then, at room temperature, the mixture was stirred for 2.5 hours. This reaction mixture was diluted with ethyl acetate, washed with saturated aqueous NaCl solution, and dried over anhydrous sodium sulfate. The solvent was then distilled off under reduced pressure and the residue was purified by flash column chromatography (chloroform) to provide the title compound (176 mg). $^1$H-NMR (CDCl$_3$) δ: 2.39(3H,s), 2.56 (3H,s), 3.56(3H,s), 5.29(2H,s), 6.47(1H,d,J=1.0Hz), 7.29 (2H,d,J=8.4Hz), 7.45(2H,d,J=8.4Hz), 7.73(4H,d,J=8.4Hz).

IR (KBr): 3450, 3050, 3030, 1665, 1650, 1605, 1590, 1570, 1535, 1515, 1485, 1410, 1340, 1310, 1280, 1270, 1230, 1180, 1150, 1080 cm$^{-1}$.

EXAMPLE 49

7-[4-(4-Chlorobenzoyl)benzyl]-3-methyl-2-methylthio-7H-pyrrolo[2,3-d]pyrimidin-4(3H)-one Under argon gas, 7-[4-(4-chlorobenzoyl)benzyl]-2-methylthio-7H-pyrrolo[2,3-d]pyrimidin-4(3H)-one (82 mg) was dissolved in anhydrous DME (10 ml)-anhydrous DMF (4 ml). Then, 60% sodium hydride-oil (9.6 mg) was added with ice-cooling and, after 30 minutes of agitation, methyl iodide (34 mg) was added. Then, at room temperature, the mixture was stirred for 2.5 hours. This reaction mixture was diluted with ethyl acetate, washed with saturated aqueous NaCl solution, and dried over anhydrous sodium sulfate. The solvent was distilled off under reduced pressure and the residue was purified by flash column chromatography (hexane: ethyl acetate=4:1) to provide the title compound (30 mg). $^1$H-NMR (CDCl$_3$) δ: 2.58(3H,s), 3.60(3H,s), 5.37 (2H,s), 6.67(1H,d,J=3.4Hz), 6.75(1H,d,J=3.4Hz), 7.30(2H, d,J=8.0Hz), 7.45(2H,d,J=8.6Hz), 7.73(2H,d,J=8.6Hz), 7.74 (2H,d,J=8.0Hz).

IR (KBr): 3430, 3100, 3050, 3000, 2920, 1670, 1650, 1606, 1580, 1540, 1495, 1465, 1410, 1350, 1295, 1275, 1215, 1170, 1085 cm$^{-1}$.

EXAMPLE 50

2-[4-(4-Chlorobenzoyl)benzyl]thio-5-methyl-7H-pyrrolo[2,3-d]pyrimidin-4(3H)-one

In dimethylformamide (30 ml) was dissolved 5-methyl-2-mercapto-7H-pyrrolo[2,3-d]pyrimidin-4(3H)-one (1.36 g) followed by addition of 1N-sodium hydroxide (7.5 ml). Then, under ice-cooling, a solution of 4-(4-chlorobenzoyl)benzyl bromide (2.48 g) in DMF (10 ml) was added dropwise. The mixture was then stirred at room temperature for 4 hours, at the end of which time it was poured in ice-water (250 ml). The resulting precipitate was collected by filtration, rinsed with water, and dried. The dried precipitate was purified by flash column chromatography (3–5% ethanol-containing chloroform) to provide the title compound (1.57 g). IH-NMR (DMSO-d$_6$) δ: 2.23(3H,s), 4.50 (2H,s), 6.65(1H,s), 7.60(2H,d,J=8.6Hz), 7.64(2H,d,J= 8.6Hz), 7.69(2H,d,J=8.6Hz), 7.74(2H,d,J=8.6Hz), 11.42 (1H,s), 11.95(1H,s).

IR (KBr): 3420, 3180, 3100, 3020, 2920, 2830, 1660, 1600, 1580, 1545, 1515, 1480, 1430, 1400, 1360, 1300, 1280, 1235, 1170, 1085, 1065, 1010 cm$^{-1}$.

EXAMPLE 51

2-[4-(4-Chlorobenzoyl)benzyl]thio-7H-pyrrolo[2,3-d]pyrimidin-4(3H)-one

In DMF (20 ml) was dissolved 2-mercapto-7H-pyrrolo[2, 3-d]pyrimidin-4(3H)-one (836 ml) followed by addition of 1N-sodium hydroxide (5 ml). Then, under ice-cooling, a solution of 4-(4-chlorobenzoyl)benzyl bromide (1.63 g) in DMF (5 ml) was added dropwise. The mixture was stirred at room temperature for 4 hours, at the end of which time it was poured in ice-water (200 ml). The resulting precipitate was collected by filtration, rinsed with water, and dried. This precipitate was purified by flash column chromatography (3–5% ethanol-containing chloroform) to provide the title compound (1.33 g). $^1$H-NMR (DMSO-d$_6$) δ: 4.52(2H,s), 6.34–6.37(1H,m), 6.91–6.95(1H,m), 7.61(2H,d,J=8.4Hz), 7.65(2H,d,J=8.4Hz), 7.70(2H,d,J=8.4Hz), 7.74(2H,d,J= 8.4Hz), 11.42(1H,s), 11.95(1H,s).

IR (KBr): 3430, 3220, 3100, 3030, 2960, 2900, 2840, 1650, 1605, 1565, 1410, 1350, 1300, 1280, 1270, 1215, 1170, 1140, 1090, 1015 cm$^{-1}$.

EXAMPLE 52

2-[4-(4-Fluorobenzoyl)benzyl]thio-5-methyl-7H-pyrrolo[2,3-d]pyrimidin-4(3H)-one

In methanol (25 ml) was suspended 5-methyl-2-mercapto-7H-pyrrolo[2,3-d]pyrimidin-4(3H)-one (1.82 g) followed by addition of 1N-sodium hydroxide (10.5 ml) for dissolution. Then, under ice-cooling, a solution of 4-(4-fluorobenzoyl)benzyl bromide (3.51 g) in DME (10 ml) was added dropwise. The mixture was stirred at room temperature for 4 hours and the resulting crystalline precipitate was collected by filtration and rinsed with water. The crystals were further rinsed with 50% ethanol/water, methanol and ether serially, dried, and recrystallized from DME (1,2-dimethoxyethane) to provide the title compound (2.71 g). $^1$H-NMR (DMSO-d$_6$) δ: 2.24(3H,s), 4.51(2H,s), 6.65(1H,s), 7.37(2H,t,J=8.8Hz), 7.64(2H,d,J=8.8Hz), 7.70(2H,d,J= 8.8Hz), 7.81(2H,dd,J=5.6,8.8Hz), 11.43(1H,s), 11.97(1H,s).

IR (KBr): 3430, 3180, 3120, 3060, 2980, 2920, 2830, 1650, 1600, 1580, 1545, 1500, 1455, 1435, 1410, 1300, 1280, 1235, 1180, 1155, 1120, 1065 cm$^{-1}$.

EXAMPLE 53

2-[4-(2,4-Dichlorobenzoyl)benzyl]thio-5-methyl-7H-pyrrolo[2,3-d]pyrimidin-4(3H)-one In methanol (18.7 ml) was suspended 5-methyl-2-mercapto-7H-pyrrolo[2,3-d]pyrimidin-4(3H)-one (1.36 g) followed by addition of 1N-sodium hydroxide (7.88 ml) for dissolution. Then, under ice-cooling, a solution of 4-(2,4-dichlorobenzoyl)benzyl bromide (3.09 g) in DME (8 ml) was added dropwise. The mixture was stirred at room temperature for 4 hours and the resulting crystalline precipitate was collected by filtration and rinsed with water. The crystals were further rinsed with 50% ethanol/water, methanol and ether, dried, and recrystallized from DME (1,2-dimethoxyethane) to provide the title compound (2.03 g). $^1$H-NMR (DMSO-d$_6$) δ: 2.23(3H,s), 4.48(2H,s), 6.65(1H,s), 7.53(1H,d,J=8.2Hz), 7.59(1H,dd,J=1.6,8.8Hz), 7.64(2H,d, J=8.4Hz), 7.69(2H,d,J=8.4Hz), 7.80(1H,d,J=1.6Hz), 11.40 (1H,s), 11.96(1H,s).

IR (KBr): 3430, 3270, 3130, 3080, 2920, 2820, 1670, 1650, 1600, 1580, 1550, 1515, 1455, 1430, 1410, 1370, 1280, 1240, 1190, 1180, 1150, 1100, 1085, 1050 cm$^{-1}$.

EXAMPLE 54

2-[3-(4-Chlorobenzoyl)benzyl]thio-5-methyl-7H-pyrrolo[2,3-d]pyrimidin-4(3H)-one

In methanol (18.7 ml) was suspended 5-methyl-2-mercapto-7H-pyrrolo[2,3-d]pyrimidin-4(3H)-one (1.36 g) followed by addition of 1N-sodium hydroxide (7.88 ml) for dissolution. Then, under ice-cooling, a solution of 3-(4-chlorobenzoyl)benzyl bromide (2.79 g) in DME-DMF (6:5; 22 ml) was added dropwise. The mixture was stirred at room temperature for 20 hours, at the end of which time it was poured in ice-water (200ml). The resulting precipitate was collected by filtration and rinsed with water. Then, it was further washed with 50% ethanol/water, methanol and ether in that order, dried, and purified by flash column chromatography (chloroform, containing 1% methanol) to provide the title compound (1.94 g). $^1$H-NMR (DMSO-d$_6$) δ: 2.25 (3H,s), 4.50(2H,s), 6.65(1H,s), 7.50(2H,d,J=8.0Hz), 7.69 (2H,d,J=8.6Hz), 7.51–7.82(4H,m), 11.38(1H,s), 11.95(1H, s).

IR (KBr): 3430, 3180, 3120, 3060, 2920, 2830, 1650, 1580, 1545, 1515, 1480, 1455, 1430, 1400, 1360, 1300, 1280, 1235, 1200, 1190, 1170, 1120, 1090, 1065, 1010 cm$^{-1}$.

EXAMPLE 55

2-[4-(4-Chlorobenzoyl)benzyl]thio-3,5,7-trimethyl-7H-pyrrolo[2,3-d]pyrimidin-4(3H)-one Under argon gas, 2-[4-(4-chlorobenzoyl)benzyl]thio-5-methyl-7H-pyrrolo[2,3-d-]pyrimidin-4(3H)-one (640 mg) was suspended in anhydrous DME (15.6 ml) and, under ice-cooling and stirring, 60% sodium hydride-oil (144 mg) was added in two installments. Thereafter, methyl iodide (509 mg) was added and the mixture was stirred at room temperature overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (hexane: ethyl acetate=4:1) to provide the title compound (542 mg). $^1$H-NMR (CDCl$_3$) δ: 2.38(3H,s), 3.55(3H,s), 3.66(3H,s), 4.54(2H,s), 6.44(1H,d,J=1.0Hz), 7.46(2H,d,J=8.4Hz), 7.59(2H,d,J=8.4Hz), 7.75(4H,d,J=8.4Hz).

IR (KBr): 3430, 3110, 3060, 2920, 1680, 1660, 1605, 1580, 1540, 1515, 1460, 1400, 1300, 1275, 1225, 1200, 1170, 1090, 1050, 1010 cm$^{-1}$.

EXAMPLE 56

2-[4-(4-Chlorobenzoyl)benzyl]thio-3,7-dimethyl-7H-pyrrolo[2,3-d]pyrimidin-4(3H)-one (A)

2-[1-[4-(4-Chlorobenzoyl)phenyl]ethyl]thio-3,7-dimethyl-7H-pyrrolo[2,3-d]pyrimidin-4(3H)-one (B)

Under argon gas, 2-[4-(4-chlorobenzoyl)benzyl]thio-7H-pyrrolo[2,3-d]pyrimidin-4(3H)-one (1.2 g) was dissolved in anhydrous DME (15 ml) and, under ice-cooling and stirring, 60% sodium hydride-oil (288 mg), was added in two installments. Then, methyl iodide (1.11 g) was added and the mixture was stirred at room temperature overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (hexane: ethyl acetate= 6:1→4:1→2.5:1) to provide the title compound (A 470 mg, B 92 mg). Compound (A) $^1$H-NMR (CDCl$_3$) δ: 3.59(3H,s), 3.74(3H,s), 4.56(2H,s), 6.60(1H,d,J=3.4Hz), 6.71(1H,d,J= 3.4Hz), 7.46(2H,d,J=8.6Hz), 7.59(2H,d,J=8.4Hz), 7.75(2H, d,J=8.6Hz), 7.76(2H,d,J=8.4Hz).

IR (KBr): 3450, 3120, 2980, 2930, 1700, 1660, 1605, 1585, 1540, 1510, 1460, 1400, 1300, 1270, 1220, 1170, 1105, 1090, 1050, 1010 cm$^{-1}$. Compound (B) $^1$H-NMR (CDCl$_3$) δ: 1.83(3H,d,J=7.2Hz), 3.55(3H,s), 3.71(3H,s), 5.20(1H,q,J=7.2Hz), 6.57(1H,d,J=3.4Hz), 6.68(1H,d,J= 3.4Hz), 7.45(2H,d,J=8.4Hz), 7.62(2H,d,J=8.4Hz), 7.74(2H, d,J=8.6Hz), 7.76(2H,d,J=8.6Hz).

IR (KBr): 3430, 2970, 2930, 1680, 1660, 1600, 1580, 1540, 1505, 1460, 1400, 1300, 1280, 1210, 1170, 1100, 1085, 1040, 1010 cm$^{-1}$.

EXAMPLE 57

2-[4-(4-Fluorobenzoyl)benzyl]thio-3,5,7-trimethyl-7H-pyrrolo[2,3-d]pyrimidin-4(3H)-one (A)

2-[1-[4-(4-Fluorobenzoyl)phenyl]ethyl]thio-3,5,7-trimethyl-7H-pyrrolo[2,3-d]pyrimidin-4(3H)-one (B)

Under argon gas, 2-[4-(4-fluorobenzoyl)benzyl]thio-5-methyl-7H-pyrrolo[2,3-d]pyrimidin-4(3H)-one (1.97 g) was suspended in anhydrous DME (50 ml) and, under ice-cooling and stirring, 60% sodium hydride-oil (420 mg) was added in two installments. The mixture was stirred at room temperature for 15 minutes, after which methyl iodide (1.85 g) was added. Then, the mixture was stirred at room temperature overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (hexane: ethyl acetate=4:1–2.5:1) to provide the title compound (A 1.29 g, B 7 mg).

Compound (A)

$^1$H-NMR (CDCl$_3$) δ: 2.38(3H,d,J=1.2 Hz), 3.54(3H,s), 3.66(3H,s), 4.54(2H,s), 6.43(1H,d,J=1.2 Hz), 7.15(2H,t,J= 8.8 Hz), 7.58(2H,d,J=8.4 Hz), 7.74(2H,d,J=8.4 Hz), 7.83 (1H,dd,J=5.4,8.8 Hz).

IR (KBr): 3450, 3110, 3060, 2920, 1680, 1660, 1600, 1575, 1540, 1520, 1500, 1455, 1405, 1300, 1280, 1225, 1195, 1150, 1090, 1050 cm$^{-1}$.

Compound (B)

$^1$H-NMR (CDCl$_3$) δ: 1.82(3H,d,J=7.2 Hz), 2.37(3H,d,J= 1.2 Hz), 3.51(3H,s), 3.65(3H,s), 5.19(2H,q,J=7.2 Hz), 6.42 (1H,d,J=1.2 Hz), 7.16(2H,t,J=8.8 Hz), 7.62(2H,d,J=8.4 Hz), 7.76(2H,d,J=8.4 Hz), 7.84(2H,dd,J=5.6,8.8 Hz).

IR (KBr): 3430, 3100, 3060, 2920, 1680, 1650, 1595, 1570, 1540, 1510, 1445, 1405, 1305, 1275, 1225, 1195, 1150, 1090, 1045 cm$^{-1}$.

EXAMPLE 58

2-[4-(2,4-Dichlorobenzoyl)benzyl]thio-3,5,7-trimethyl-7H-pyrrolo[2,3-d]pyrimidin-4(3H)-one (A)

2-[1-[4-(2,4-Dichlorobenzoyl)phenyl]ethyl]thio-3,5,7-trimethyl-7H-pyrrolo[2,3-d]pyrimidin-4(3H)-one (B)

Under argon gas, 2-[4-(2,4-dichlorobenzoyl) benzyl]thio-5-methyl-7H-pyrrolo[2,3-d]pyrimidin-4(3H)-one (1.78 g)

was suspended in anhydrous DME (50 ml) followed by addition of 60% sodium hydride-oil (336 mg) in two installments. The mixture was stirred at room temperature for 15 minutes, after which methyl iodide (1.48 g) was added. Then, the mixture was stirred at room temperature overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (hexane: ethyl acetate= 4:1–2.5:1) to provide the title compound (A 1.28 g, B 24 mg).

Compound (A)

$^1$H-NMR (CDCl$_3$) δ: 2.37(3H,d,J=1.2 Hz), 3.53(3H,s), 3.63(3H,s), 4.52(2H,s), 6.43(1H,d,J=1.2 Hz), 7.31,(1H,d,J= 8.2 Hz), 7.37(1H,dd,J=1.8,8.2 Hz), 7.49(1H,d,J=1.8 Hz), 7.57(2H,d,J=8.6 Hz), 7.75(2H,d,J=8.6 Hz).

IR (KBr): 3430, 3100, 3050, 2920, 1680, 1670, 1605, 1580, 1540, 1515, 1460, 1400, 1365, 1285, 1255, 1225, 1220, 1180, 1150, 1095, 1055 cm$^{-1}$.

Compound (B)

$^1$H-NMR (CDCl$_3$) δ: 1.79(3H,d,J=7.2 Hz), 2.35(3H,d,J= 1.0 Hz), 3.50(3H,s), 3.61(3H,s), 5.16(2H,q,J=7.2 Hz), 6.41 (1H,d,J=1.0 Hz), 7.30(1H,d,J=8.2 Hz), 7.36(1H,dd,J=1.8, 8.2 Hz), 7.49(1H,d,J=1.8 Hz), 7.60(2H,d,J=8.6 Hz), 7.76 (2H,d,J=8.6 Hz).

IR (KBr): 3430, 2920, 1675, 1600, 1580, 1570, 1540, 1520, 1450, 1405, 1370, 1310, 1280, 1240, 1220, 1195, 1150, 1100, 1090, 1050 cm$^{-1}$.

EXAMPLE 59

2-[3-(4-Chlorobenzoyl)benzyl]thio-3,5,7-trimethyl-7H-pyrrolo[2,3-d]pyrimidin-4(3H)-one Under argon gas, 2-[3-(4-chlorobenzoyl) benzyl]thio-5-methyl-7H-pyrrolo[2,3-d]pyrimidin-4(3H)-one (1.31 g) was suspended in anhydrous DME (32 ml) and, under ice-cooling and stirring, 60% sodium hydride-oil (269 mg) was added in two installments. The mixture was stirred for 15 minutes, after which methyl iodide (1.18 g) was added. Then, the mixture was further stirred at room temperature overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (hexane: ethyl acetate=4:1–2.5:1) to provide the title compound (950 mg). 1H-NMR (CDCl$_3$) δ: 2.39(3H,d,J=1.0 Hz), 3.53(3H,s), 3.54 (3H,s), 4.52(2H,s), 6.42(1H,d,J=1.0 Hz), 7.36(2H,d,J=8.6 Hz), 7.35–7.50(1H,m), 7.65–7.72(2H,m), 7.69(2H,d,J=8.6 Hz), 7.97(1H,d,J=1.6 Hz).

IR (KBr): 3450, 3100, 2920, 1680, 1640, 1600, 1580, 1540, 1515, 1455, 1430, 1405, 1290, 1280, 1245, 1225, 1200, 1170, 1130, 1105, 1090, 1040, 1010 cm$^{-1}$.

EXAMPLE 60

6-Tert-butyl-1-[4-(4-chlorobenzoyl)benzyl]-1,2,3,4-tetrahydropyrido[2,3-d]pyridazin-5(6H)-one In DMF (5 ml) was dissolved 6-t-butyl-1,2,3,4-tetrahydropyrido[2,3-d]pyridazin-5(6H)-one (207 mg) followed by addition of sodium hydride (60%) (80 mg), and the mixture was stirred at room temperature for 30 minutes. Then, 4-(4-chlorobenzoyl)benzyl bromide (464 mg) was added and the mixture was further stirred at room temperature for 1 hour. This reaction mixture was diluted with water and extracted with ethyl acetate. The organic layer was serially washed with water and saturated aqueous NaCl solution, dried over anhydrous magnesium sulfate, and concentrated. The residue was purified by silica gel chromatography (dichloromethane: ethyl acetate=4:1) to provide 139 mg of white powder.

$^2$H-NMR (CDCl$_3$) δ: 1.63(9H,s), 1.9–2.1(2H,m), 2.64 (2H,t,J=6.2 Hz), 3.35(2H,t,J=5.6 Hz), 4.61(2H,s), 7.34(2H, d,J=8.6 Hz), 7.39(1H,s), 7.47(2H,d,J=8.6 Hz), 7.76(2H,d,J= 8.6 Hz), 7.79(2H,d,J=8.6 Hz).

IR (KBr): 1605, 1655 cm$^{-1}$.

EXAMPLE 61

1-[4-(4-Chlorobenzoyl)benzyl]-6-methyl-1,2,3,4-tetrahydropyrido[2,3-d]pyridazin-5(6H)-one In DMF (5 ml) was dissolved 6-methyl-1,2,3,4-tetrahydropyrido[2,3-d]pyridazin-5(6H)-one (116 mg) followed by addition of sodium hydride (60%) (56 mg), and the mixture was stirred at room temperature for 30 minutes. Then, 4-(4-chlorobenzoyl)benzyl bromide (341 mg) was added and the mixture was further stirred at room temperature for 1 hour. This reaction mixture was diluted with water and extracted with ethyl acetate-THF. The organic layer was serially washed with water and saturated aqueous NaCl solution, dried over anhydrous magnesium sulfate, and concentrated. The residue was purified by silica gel chromatography (ethyl acetate) to provide 165 mg of the title compound as yellow amorphous solid.

$^1$H-NMR (CDCl$_3$) δ: 1.9–2.1(2H,m), 2.67(2H,t,J=6.4 Hz), 3.37(2H,t,J=5.6 Hz), 3.70(3H,s), 4.63(2H,s), 7.32(2H, d,J=8.4 Hz), 7.43(2H,d,J=8.4 Hz), 7.49(1H,s), 7.75(2H,d,J= 8.4 Hz), 7.78(2H,d,J=8.4 Hz).

EXAMPLE 62

5-Tert-butyl-1-[4-(4-chlorobenzoyl)benzyl]-1H-pyrazolo[3,4-d]pyridazin-4(5H)-one (A)

5-Tert-butyl-2-[4-(4-chlorobenzoyl)benzyl]-2H-pyrazolo[3,4-d]pyridazin-4(5H)-one (B)

In DMF (5 ml) was dissolved 5-t-butyl-1H-pyrazolo-[3, 4-d]pyridazin-4(5H)-one (288 mg) followed by addition of 4-(4-chlorobenzoyl)benzyl bromide (712 mg) and potassium carbonate (318 mg), and the mixture was stirred at room temperature for 15 hours. This reaction mixture was extracted with diethyl ether and the organic layer was serially washed with water and saturated aqueous NaCl solution, dried over anhydrous magnesium sulfate, and concentrated. The residue was purified by silica gel chromatography (n-hexane: ethyl acetate=1:1), washed with a solvent, and dried. The washing solvent used was n-hexane-diethyl ether for 5-t-butyl-1-[4-(4-chlorobenzoyl)benzyl]-1H-pyrazolo [3,4-d]pyridazin-4(5H)-one or diethyl ether for 5-t-butyl-2-[4-(4-chlorobenzoyl)benzyl]-2H-pyrazolo [3,4-d]pyridazin-4(5H)-one.

Compound (A): write powder, 159 mg $^1$H-NMR (CDCl$_3$) δ: 1.69(9H,s), 5.61(2H,s), 7.33(2H,d, J=8.0 Hz), 7.46(2H,d,J=8.4 Hz), 7.73(2H,d,J=8.0 Hz), 7.77 (2H,d,J=8.4 Hz), 7.95(1H,s), 8.23(1H,s).

IR (KBr): 1650, 1660 cm$^{-1}$.

Anal. Calcd.: C, 65.63%; H, 5.03%; N, 13.31% Found : C, 65.61%; H, 5.03%; N, 12.99%

Compound (B): white powder, 245 mg

¹H-NMR (CDCl₃) δ: 1.68(9H,s), 5.59(2H,s), 7.38(2H,d, J=8.0 Hz), 7.46(2H,d,J=8.4 Hz), 7.73(2H,d,J=8.0 Hz), 7.78 (2H,d,J=8.4 Hz), 8.20(1H,s), 8.22(1H,s).

IR (KBr): 1585, 1650, 1660 cm⁻¹.

EXAMPLE 63

5-Tert-butyl-1-[4-(4-fluorobenzoyl)benzyl]-1H-pyrazolo[3,4-d]pyridazin-4(5H)-one (A)

5-Tert-butyl-2-[4-(4-fluorobenzoyl)benzyl]-2H-pyrazolo[3,4-d]pyridazin-4(5H)-one (B)

In DMF (5 ml) was dissolved 5-t-butyl-1H-pyrazolo-[3,4-d]pyridazin-4(5H)-one (288 mg) followed by addition of 4-(4-fluorobenzoyl)benzyl bromide (674 mg) and potassium carbonate (318 mg), and the mixture was stirred at room temperature for 15 hours. This reaction mixture was extracted with ethyl acetate and the organic layer was serially washed with water and saturated aqueous NaCl solution, dried over anhydrous magnesium sulfate, and concentrated. The residue was purified by silica gel chromatography (n-hexane: ethyl acetate=1:1), washed with a solvent, and dried. As the washing solvent, n-hexane-diethyl ether was used for 5-t-butyl-1-[4-(4-fluorobenzoyl)benzyl]-1H-pyrazolo[3,4-d]pyridazin-4(5H)-one and diethyl ether was used for 5-t-butyl-2-[4-(4-fluorobenzoyl)benzyl]-2H-pyrazolo [3, 4-d]pyridazin-4(5H)-one.

Compound (A): white powder, 115 mg

¹H-NMR (DMSO-d₆) δ: 1.63(9H,s), 5.81(2H,s); 7.3–7.5 (4H,m), 7.7–7.9(4H,m), 8.27(1H,s), 8.66(1H,s).

IR (KBr): 1650, 1665 cm⁻¹.

Compound (B): white powder, 235 mg

¹H-NMR (DMSO-d₆) δ: 1.61(9H,s), 5.74(2H,s), 7.3–7.5 (4H,m), 7.7–7.8(4H,m), 8.33(1H,s), 8.89(1H,s).

IR (KBr): 1600, 1650, 1655 cm⁻¹.

EXAMPLE 64

1-[4-(4-Chlorobenzoyl)benzyl]-5-methyl-1H-pyrazolo [3,4-d]pyridazin-4(5H)-one (A)

2-[4-(4-Chlorobenzoyl)benzyl]-5-methyl-2H-pyrazolo [3,4-d]pyridazin-4(5H)-one (B)

In DMF (2 ml) was dissolved 5-methyl-1H-pyrazolo-[3,4-d]pyridazin-4(5H)-one (101 mg) followed by addition of 4-(4-chlorobenzoyl)benzyl bromide (310 mg) and potassium carbonate (138 mg), and the mixture was stirred at room temperature for 15 hours. The reaction mixture was extracted with ethyl acetate-THF, and the organic layer was dried over anhydrous magnesium sulfate and concentrated. The residue was purified by silica gel column chromatography (n-hexane: ethyl acetate=1:4), washed with the following solvent, and dried. As the washing solvent, diethyl ether-ethyl acetate was used for 1-[4-(4-chlorobenzoyl) benzyl]-5-methyl-1H-pyrazolo [3,4-d]pyridazin-4(5H)-one and ethyl acetate was used for 2-[4-(4-chlorobenzoyl) benzyl]-5-methyl-2H-pyrazolo [3,4-d]pyridazin-4(5H)-one.

Compound (A): white powder, 20 mg

¹H-NMR (DMSO-d₆) δ: 3.70(3H,s), 5.84(2H,s), 7.42(2H, d,J=8.4 Hz), 7.60(2H,d,J=8.6 Hz), 7.72(2H,d,J=8.4 Hz), 7.73(2H,d,J=8.6 Hz), 8.33(1H,s), 8.73(1H,s).

IR (KBr): 1655 cm⁻¹.

Compound (B): white powder, 137 mg

¹H-NMR (DMSO-d₆) δ: 3.64(3H,s), 5.75(2H,s), 7.49(2H, d,J=7.6 Hz), 7.61(2H,d,J=8.4 Hz), 7.74(4H,br,d), 8.38(1H, s), 8.94(1H,s).

IR (KBr): 1585, 1650 cm⁻¹.

EXAMPLE 65

1-[4-(4-Chlorobenzoyl)benzyl]-5-methyl-1H-triazolo [4,5-d]pyridazin-4(5H)-one

In DMF (5 ml) was dissolved 5-methyl-1H-triazolo-[4,5-d]pyridazin-4(5H)-one (227 mg) followed by addition of 4-(4-chlorobenzoyl)benzyl bromide (712 mg) and potassium carbonate (318 mg), and the mixture was stirred at room temperature for 2 hours. The reaction mixture was then extracted with ethyl acetate and the organic layer was serially washed with water and saturated aqueous NaCl solution, dried over anhydrous magnesium sulfate, and concentrated. The residue was purified by silica gel column chromatography (n-hexane: ethyl acetate=1:1), washed with diethyl ether, and dried. White powder, 110 mg.

¹H-NMR (CDCl₃) δ: 3.89(3H,s), 5.90(2H,s), 7.42(2H,d, J=8.4 Hz), 7.47(2H,d,J=8.8 Hz), 7.73(2H,d,J=8.8 Hz), 7.81 (2H,d,J=8.4 Hz), 7.96(1H,s).

IR (KBr): 1655, 1670 cm⁻¹.

EXAMPLE 66

1-[4-(4-Fluorobenzoyl)benzyl]-2,3-dichloro-5-methyl-1H-pyrrolo [2,3-d]pyridazin-4(5H)-one A solution of 2,3-dichloro-5-methyl-1H-pyrrolo [2,3-d] pyridazin-4(5H)-one (404 mg) in DMF (70 ml) was dripped into a suspension of 60% sodium hydride-oil (96 mg) in DMF (10 ml) on an ice-water bath. The mixture was stirred at room temperature for 2 hours, after which a solution of 4-(4-fluorobenzoyl) benzyl bromide (645 mg) in DMF (15 ml) was added and the mixture was further stirred at room temperature for 16 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:1) to provide the title compound as white powder (371 mg, yield 43%).

¹H-NMR (DMSO-d₆) δ: 3.35(3H,s), 5.74(2H,s), 7.30(2H, t,J=8.0 Hz), 7.38(2H,d,8.8 Hz), 7.73(2H,d,J=8.0 Hz), 7.81 (2H,dd,J=5.4,8.8 Hz), 8.59(1H,s).

IR (KBr): 3050, 2950, 1650, 1640, 1600 cm⁻¹.

EXAMPLE 67

2,3-Dichloro-1-[4-(2,4-dichlorobenzoyl)benzyl]-5-methyl-1H-pyrrolo [2,3-d]pyridazin-4(5H)-one A solution of 2,3-dichloro-5-methyl-1H-pyrrolo [2,3-d] pyridazin-4(5H)-one (404 mg) in DMF (70 ml) was dripped into a suspension of 60% sodium hydride-oil (96 mg) in DMF (10 ml) on an ice-water bath. The mixture was stirred at room temperature for 2 hours, after which a solution of 4-(2,4-dichlorobenzoyl)benzyl bromide (757 mg) in DMF (15 ml) was added and the mixture was further stirred at room temperature for 16 hours. The reaction was stopped by adding water and the reaction mixture was extracted with ethyl acetate. The extract was dried over anhydrous magnesium sulfate and the solvent was distilled off under reduced pressure. The residue was washed with ether to provide the title compound as yellowish brown powder (471 mg, yield 49%).

¹H-NMR (DMSO-d₆) δ: 3.67(3H,s), 5.73(2H,s), 7.27(2H, d,J=8.4 Hz), 7.54(1H,d,J=8.2 Hz), 7.60(1H,dd,J=2.2,8.2 Hz), 7.73(2H,d,J=8.4 Hz), 7.82(1H,d,J=2.2 Hz), 8.55(1H,s).

EXAMPLE 68

1-[3-(4-Chlorobenzoyl)benzyl]-2,3-dichloro-5-methyl-1H-pyrrolo [2,3-d]pyridazin-4(5H)-one A solution of 2,3-dichloro-5-methyl-1H-pyrrolo [2,3-d]pyridazin-4(5H)-one (303 mg) in DMF (50 ml) was dripped into a suspension of 60% sodium hydride-oil (72 mg) in DMF (10 ml) on an ice-water bath. The mixture was stirred at room temperature for 2.5 hours, after which a solution of 3-(4-chlorobenzoyl) benzyl bromide (511 mg) in DMF (10 ml) was added and the mixture was further stirred at room temperature for 17 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:1) to provide the title compound as white powder (104 mg, yield 16%).

$^1$H-NMR (DMSO-d$_6$) δ: 3.68(3H,s), 5.71(2H,s), 7.42(1H, dm,J=7.8 Hz), 7.56(1H,t,J=7.8 Hz), 7.61(2H,d,J=8.6 Hz), 7.55–7.65(1H,m), 7.65–7.77(1H,m), 7.71(2H,d,J=8.6 Hz), 8.59(1H,s).

IR (KBr): 3050, 2950, 1660, 1630, 1580 cm$^{-1}$.

EXAMPLE 69

2,3-Dichloro-5-methyl-1-[4-(4-trifluoromethylbenzoyl) benzyl]-1H-pyrrolo[2,3-d]pyridazin-4(5H)-one A solution of 2,3-dichloro-5-methyl-1H-pyrrolo [2,3-d]pyridazin-4(5H)-one (404 mg) in DMF (70 ml) was dripped into a suspension of 60% sodium hydride-oil (96 mg) in DMF (10 ml) on an ice-water bath. The mixture was stirred at room temperature for 2 hours, after which a solution of 4-(4-trifluoromethylbenzoyl)benzyl bromide (754 mg) in DMF (15 ml) was added and the mixture was further stirred at room temperature for 15 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:1) to provide the title compound as white powder (448 mg, yield 47%).

$^1$H-NMR (DMSO-d$_6$) δ: 3.68(3H,s), 5.75(2H,s), 7.31(2H, d,J=8.2 Hz), 7.78(2H,d,J=8.2 Hz), 7.91(4H,s), 8.58(1H,s).

IR (KBr): 3040, 2930, 1660, 1650, 1605 cm$^{-1}$.

EXAMPLE 70

1-[4-(4-Chlorobenzoyl)benzyl]-5-methyl-1H-pyrrolo-[2,3-d]pyridazin-4(5H)-one

A solution of 5-methyl-1H-pyrrolo[2,3-d]pyridazin-4 (5H)-one (298 mg) in DMF (10 ml) was dripped into a suspension of 60% sodium hydride-oil (96 mg) in DMF (8 ml) on an ice-water bath. The mixture was stirred at room temperature for 30 minutes, after which a solution of 4-(4-chlorobenzoyl)benzyl bromide (712 mg) in DMF (15 ml) was added and the mixture was further stirred at room temperature for 1.5 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:2) to provide the title compound as white powder (505 mg, yield 57%).

$^1$H-NMR (DMSO-d$_6$) δ: 3.68(3H,s), 5.65(2H,s), 6.74(1H, d,J=3.0 Hz), 7.39(2H,d,J=8.4 Hz), 7.61(2H,d,J=8.4 Hz), 7.63(1H,d,J=3.0 Hz), 7.73(4H,d,J=8.4 Hz), 8.45(1H,s)

IR (KBr): 3050, 2940, 1650, 1600, 1580, 1540 cm$^{-1}$.

EXAMPLE 71

1-[4-(4-Fluorobenzoyl)benzyl]-5-methyl-1H-pyrrolo-[2,3-d]pyridazin-4(5H)-one

A solution of 5-methyl-1H-pyrrolo[2,3-d]pyridazin-4 (5H)-one (373 mg) in DMF (10 ml) was dripped into a suspension of 60% sodium hydride-oil (120 mg) in DMF (10 ml) on an ice-water bath. The mixture was stirred at room temperature for 1 hour, after which a solution of 4-(4-fluorobenzoyl)benzyl bromide (806 mg) in DMF (20 ml) was added and the mixture was further stirred at room temperature for 13 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; dichloromethane: methanol=99:1) to provide the title compound as white powder (615 mg, yield 68%).

$^1$H-NMR (DMSO-d$_6$) δ: 3.68(3H,s), 5.64(2H,s), 6.74(1H, d,J=3.0 Hz), 7.37(2H,t,J=9.0 Hz), 7.39(2H,d,J=8.0 Hz), 7.62 (1H,d,J=3.0 Hz), 7.72(2H,d,J=8.0 Hz), 7.80(2H,dd,J=5.4, 9.0 Hz), 8.45(1H,s).

IR (KBr): 3040, 2990, 2940, 1650, 1600, 1540 cm$^{-1}$.

EXAMPLE 72

1-[4-(2,4-Dichlorobenzoyl)benzyl]-5-methyl-1H-pyrrolo [2,3-d]pyridazin-4(5H)-one A solution of 5-methyl-1H-pyrrolo[2,3-d]pyridazin-4 (5H)-one (298 mg) in DMF (10 ml) was dripped into a suspension of 60% sodium hydride-oil (96 mg) in DMF (8 ml) on an ice-water bath. The mixture was stirred at room temperature for 1 hour, after which a solution of 4-(2,4-dichlorobenzoyl)benzyl bromide (757 mg) in DMF (15 ml) was added and the mixture was further stirred at room temperature for 1.5 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:3) to provide the title compound as white powder (511 mg, yield 62%).

$^1$H-NMR (DMSO-d$_6$) δ: 3.67(3H,s), 5.64(2H,s), 6.73(1H, d,J=3.0 Hz), 7.36(2H,d,J=8.2 Hz), 7.53(1H,d,J=8.2 Hz), 7.60(1H,d,J=3.0 Hz), 7.60(1H,dd,J=7.8,8.2 Hz), 7.72(2H,d, J=8.2 Hz), 7.81(2H,d,J=1.8 Hz), 8.40(1H,s).

IR (KBr): 3050, 2940, 1660, 1640, 1600, 1540 cm$^{-1}$.

EXAMPLE 73

1-[3-(4-Chlorobenzoyl)benzyl]-5-methyl-1H-pyrrolo-[2,3-d]pyridazin-4(5H)-one

A solution of 5-methyl-1H-pyrrolo[2,3-d]pyridazin-4 (5H)-one (298 mg) in DMF (10 ml) was dripped into a suspension of 60% sodium hydride-oil (96 mg) in DMF (8 ml) on an ice-water bath. The mixture was stirred at room temperature for 1 hour, after which a solution of 3-(4-chlorobenzoyl)benzyl bromide (681 mg) in DMF (15 ml) was added and the mixture was further stirred at room temperature for 2 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl-acetate=1:3) to provide the title compound as white powder (630 mg, yield 83%).

$^1$H-NMR (DMSO-d$_6$) δ: 3.68(3H,s), 5.62(2H,s), 6.71(1H, d,J=3.0 Hz), 7.53–7.73(9H,m), 8.47(1H,s).

IR (KBr): 3100, 3040, 2960, 2850, 1650, 1580, 1540 cm$^{-1}$.

EXAMPLE 74

5-Methyl-1-[4-(4-trifluoromethylbenzoyl)benzyl]-1H-pyrrolo [2,3-d]pyridazin-4(5H)-one A solution of 5-methyl-1H-pyrrolo[2,3-d]pyridazin-4(5H)-one (298 mg) in DMF (10 ml) was dripped into a suspension of 60% sodium hydride-oil (96 mg) in DMF (8 ml) on an ice-water bath. The mixture was stirred at room temperature for 1 hour, after which a solution of 4-(4-trifluoromethylbenzoyl)benzyl bromide (755 mg) in DMF (15 ml) was added and the mixture was further stirred at room temperature for 3 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:2) to provide the title compound as light-brown powder (436 mg, yield 53%).

$^1$H-NMR (CDCl$_3$) δ: 3.86(3H,s), 5.43(2H,s), 6.95(1H,d, J=3.0 Hz), 7.13(1H,d,J=3.0 Hz), 7.22(2H,d,J=8.8 Hz), 7.76 (2H,d,J=8.8 Hz), 7.80(2H,d,J=8.2 Hz), 7.87(2H,d,J=8.2 Hz), 7.93(1H,s).

IR (KBr): 3100, 3050, 2950, 1660, 1640, 1605 cm$^{-1}$.

EXAMPLE 75

1-[4-(4-Chlorobenzoyl)benzyl]-2,3,5-trimethyl-1H-pyrrolo [2,3-d]pyridazin-4(5H)-one A solution of 2,3,5-trimethyl-1H-pyrrolo[2,3-d]-pyridazin-4(5H)-one (532 mg) in DMF (45 ml) was dripped into a suspension of 60% sodium hydride-oil (144 mg) in DMF (12 ml) on an ice-water bath. The mixture was stirred at room temperature for 30 minutes, after which a solution of 4-(4-chlorobenzoyl)benzyl bromide (1.02 g) in DMF (15 ml) was added and the mixture was further stirred at room temperature for 1.5 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:2) to provide the title compound as light-yellow powder (711 mg, yield 58%).

$^1$H-NMR (CDCl$_3$) δ: 2.23(3H,s), 2.48(3H,s), 3.83(3H,s), 5.35(2H,s), 7.04(2H,d,J=8.2 Hz), 7.46(2H,d,J=8.6 Hz), 7.73 (2H,d,J=8.6 Hz), 7.74(2H,d,J=8.2 Hz), 7.85(1H,s).

IR (KBr): 3050, 2930, 1660, 1630, 1605, 1520 cm$^{-1}$.

EXAMPLE 76

1-[4-(4-Fluorobenzoyl)benzyl]-2,3,5-trimethyl-1H-pyrrolo [2,3-d]pyridazin-4(5H)-one A solution of 2,3,5-trimethyl-1H-pyrrolo[2,3-d]-pyridazin-4(5H)-one (354 mg) in DMF (30 ml) was dripped into a suspension of 60% sodium hydride-oil (96 mg) in DMF (8 ml) on an ice-water bath. The mixture was stirred at room temperature for 1 hour, after which a solution of 4-(4-fluorobenzoyl)benzyl bromide (645 mg) in DMF (15 ml) was added and the mixture was further stirred at room temperature for 2 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:1) to provide the title compound as white powder (628 mg, yield 81%).

$^1$H-NMR (CDCl$_3$) E: 2.23(3H,s), 2.48(3H,s), 3.83(3H,s), 5.35(2H,s), 7.04(2H,d,J=8.4 Hz), 7.16(2H,t,J=8.6 Hz), 7.74 (2H,d,J=8.4 Hz), 7.78(2H,dd,J=3.0,8.6 Hz), 7.86(1H,s).

IR (KBr): 3055, 2940, 1650, 1610, 1595, 1510 cm$^{-1}$.

EXAMPLE 77

1-[4-(2,4-Dichlorobenzoyl)benzyl]-2,3,5-trimethyl-1H-pyrrolo [2,3-d]pyridazin-4(5H)-one A solution of 2,3,5-trimethyl-1H-pyrrolo[2,3-d]-pyridazin-4(5H)-one (354 mg) in DMF (30 ml) was dripped into a suspension of 60% sodium hydride-oil (96 mg) in DMF (8 ml) on an ice-water bath. The mixture was stirred at room temperature for 1 hour, after which a solution of 4-(2,4-dichlorobenzoyl)benzyl bromide (757 mg) in DMF (15 ml) was added and the mixture was further stirred at room temperature for 1.5 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer: n-hexane-ethyl acetate 1:1) to provide the title compound as light-yellow powder (612 mg, yield 70%).

$^1$H-NMR (CDCl$_3$) δ: 2.20(3H,s), 2.46(3H,s), 3.82(3H,s), 5.33(2H,s), 7.01(2H,d,J=8.6 Hz), 7.30(1H,d,J=8.0 Hz), 7.36 (1H,dd,J=1.8,8.0 Hz), 7.48(1H,d,J=1.8 Hz), 7.75(2H,d,J= 8.6 Hz), 7.82(1H,s).

IR (KBr): 3100, 2910, 1660, 1600, 1580, 1520 cm$^1$.

EXAMPLE 78

1-[4-(4-Trifluoromethylbenzoyl)benzyl.]-2,3,5-trimethyl-1H-pyrrolo [2,3-d]pyridazin-4(5H)-one A solution of 2,3,5-trimethyl-1H-pyrrolo[2,3-d]-pyridazin-4(5H)-one (354 mg) in DMF (30 ml) was dripped into a suspension of 60% sodium hydride-oil (96 mg) in DMF (8 ml) on an ice-water bath. The mixture was stirred at room temperature for 1 hour, after which a solution of 4-(4-trifluoromethylbenzoyl)benzyl bromide (755 mg) in DMF (15 ml) was added and the mixture was further stirred at room temperature for 1.5 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:1) to provide the title compound as light-yellow powder (566 mg, yield 64%).

$^1$H-NMR (CDCl$_3$) δ: 2.23(3H,s), 2.48(3H,s), 3.82(3H,s), 5.36(2H,s), 7.05(2H,d,J=8.4 Hz), 7.74(2H,d,J=8.4 Hz), 7.77 (2H,d,J=8.0 Hz), 7.84(1H,s), 7.86(2H,d,J=8.0 Hz).

IR (KBr): 3050, 2910, 1660, 1600, 1570, 1520 cm$^{-1}$.

EXAMPLE 79

1-[4-(4-Methoxybenzoyl)benzyl]-2,3,5-trimethyl-1H-pyrrolo [2,3-d]pyridazin-4(5H)-one A solution of 2,3,5-trimethyl-1H-pyrrolo[2,3-d]-pyridazin-4(5H)-one (1.06 g) in DMF (90 ml) was dripped into a suspension of 60% sodium hydride-oil (288 mg) in DMF (24 ml) on an ice-water bath. The mixture was stirred at room temperature for 1 hour, after which a solution of 4-(4-methoxybenzoyl)benzyl bromide (2.40 g) in DMF (30 ml) was added and the mixture was further stirred at room temperature for 2 hours. The reaction was stopped by adding water and the reaction mixture was extracted with ethyl acetate. The extract was dried over anhydrous magnesium sulfate and the solvent was distilled off under reduced pressure. The residue was purified by silica gel column chromatography (developer; n-hexane: ethyl acetate=1:1–1:2) to provide the title compound as light-yellow powder (1.70 g, yield 71%).

$^1$H-NMR (CDCl$_3$) δ: 2.23(3H,s), 2.48(3H,s), 3.83(3H,s), 3.89(3H,s), 5.34(2H,s), 6.96(2H,d,J=8.6 Hz), 7.03(2H,d,J= 8.0 Hz), 7.72(2H,d,J=8.0 Hz), 7.80(2H,d,J=8.6 Hz), 7.83 (1H,s).

IR (KBr): 3050, 2910, 1660, 1635, 1600, 1570, 1520 cm$^{-1}$.

EXAMPLE 80

5-Tert-butyl-1-[3-(4-chlorobenzoyl)benzyl]-1H-pyrazolo [3,4-d]pyridazin-4(5H)-one (A)

5-Tert-butyl-2-[3-(4-chlorobenzoyl)benzyl]-2H-pyrazolo [3,4-d]pyridazin-4(5H)-one (B)

In DMF (5 ml) was dissolved 5-t-butyl-1H-pyrazolo-[3,4-d]pyridazin-4(5H)-one (288 mg) followed by addition of 3-(4-chlorobenzoyl)benzyl bromide (712 mg) and potassium carbonate (318 mg), and the mixture was stirred at room temperature for 15 hours. This reaction mixture was extracted with ethyl acetate and the organic layer was serially washed with water and saturated aqueous NaCl solution, dried over anhydrous magnesium sulfate, and concentrated. The residue was purified by silica gel column chromatography (n-hexane: ethyl acetate=1:1), washed with the following solvent, and dried. As the washing solvent, diethyl ether was used for 5-t-butyl-1-[3-(4-chlorobenzoyl)benzyl]-1H-pyrazolo[3,4-d]pyridazin-4(5H)-one and n-hexane-diethyl ester was used for 5-t-butyl-2-[3-(4-chlorobenzoyl)benzyl]-2H-pyrazolo [3,4-d]pyridazin-4(5H)-one.

Compound (A): white powder, 172 mg $^1$H-NMR (DMSO-d$_6$) δ: 1.62(9H,s), 5.78(2H,s), 7.5–7.7 (8H,m), 8.25(1H,s), 8.66(1H,s).

Anal. Calcd.: C, 65.63%; H, 5.03%; N, 13.31% Found : C, 65.88%; H, 4.97%; N, 13.47%

Compound (B): white powder, 42 mg $^1$H-NMR (DMSO-d$_6$) δ: 1.61(9H,s), 5.72(2H,s), 7.5–7.8 (8H,m), 8.33(1H,s), 8.88(1H,s).

Anal. Calcd.: C, 65.63%; H, 5.03%; N, 13.31% Found : C, 65.75%; H, 4.90%; N, 13.41%

EXAMPLE 81

5-Tert-butyl-1-[4-(2,4-dichlorobenzoyl)benzyl]-1H-pyrazolo [3,4-d]pyridazin-4(5H)-one (A)

5-Tert-butyl-2-[4-(2,4-dichlorobenzoyl)benzyl]-2H-pyrazolo [3,4-d]pyridazin-4(5H)-one (B)

In DMF (5 ml) was dissolved 5-t-butyl-1H-pyrazolo [3,4-d]pyridazin-4(5H)-one (288 mg) followed by addition of 4-(2,4-dichlorobenzoyl)benzyl bromide (791 mg) and potassium carbonate (318 mg), and the mixture was stirred at room temperature for 15 hours. This reaction mixture was extracted with ethyl acetate and the organic layer was serially washed with water and saturated aqueous NaCl solution, dried over anhydrous magnesium sulfate, and concentrated. The residue was purified by silica gel column chromatography (n-hexaneethyl acetate=1:1). Then, 5-t-butyl-2-[4-(2,4-dichlorobenzoyl)benzyl]-2H-pyrazolo [3,4-d]pyridazin-4(5H)-one was washed with n-hexane-diethyl ether and dried.

Compound (A): white powder, 208 mg $^1$H-NMR (DMSO-d$_6$) δ: 1.62(9H,s), 5.81(2H,s), 7.44(2H, d,J=8.4 Hz), 7.53(1H,d,J=8.2 Hz), 7.60(1H,d,J=8.2 Hz), 7.73(2H,d,J=8.4 Hz), 7.81(1H,s), 8.26(1H,s), 8.63(1H,s).

Compound (B): white powder, 220 mg $^1$H-NMR (DMSO-d$_6$) δ: 1.60(9H,s), 5.73(2H,s), 7.47(2H, d,J=8.4 Hz), 7.73(2H,d,J=8.4 Hz), 7.53(1H,d,Hz), 7.60(1H, d,J=8.2 Hz), 7.81(1H,s), 8.32(1H,s), 8.88(1H,s).

EXAMPLE 82

5-Tert-butyl-1-[4-(4-chlorobenzoyl)benzyl]-3-methyl-1H-pyrazolo [3,4-d]pyridazin-4(5H)-one In DMF (10 ml) was dissolved 5-t-butyl-3-methyl-1H-pyrazolo [3,4-d]pyridazin-4(5H)-one (516 mg) followed by addition of 4-(4-chlorobenzoyl)benzyl bromide (1.2 g) and potassium carbonate (525 mg), and the mixture was stirred at room temperature for 15 hours. This reaction mixture was extracted with ethyl acetate-THF and the organic layer was serially washed with water and saturated aqueous NaCl solution, dried over anhydrous magnesium sulfate, and concentrated. The residue was purified by silica gel column chromatography (n-hexane: ethyl acetate=1:1), washed with n-hexane-diethyl ether, and dried. White powder, 527 g.

$^1$H-NMR (DMSO-d$_6$) δ: 1.62(9H,s), 2.52(3H,s), 5.70(2H, s), 7.44(2H,d,J=8.4 Hz), 7.61(2H,d,J=8.4 Hz), 7.73(2H,d,J= 8.4 Hz), 7.74(2H,d,J=8.4 Hz), 8.56(1H,s).

EXAMPLE 83

5-Tert-butyl-1-[4-(4-fluorobenzoyl)benzyl]-3-methyl-1H-pyrazolo [3,4-d]pyridazin-4(5H)-one (A)

5-Tert-butyl-2-[4-(4-fluorobenzoyl)benzyl]-3-methyl-2H-pyrazolo [3,4-d]pyridazin-4(5H)-one (B)

In DMF (10 ml) was dissolved 5-t-butyl-3-methyl-1H-pyrazolo [3,4-d]pyridazin-4(5H)-one (516 mg) followed by addition of 4-(4-fluorobenzoyl)benzyl bromide (1.1 g) and potassium carbonate (525 mg), and the mixture was stirred at room temperature for 15 hours. This reaction mixture was extracted with diethyl ether and the organic layer was serially washed with water and saturated aqueous NaCl solution, dried over anhydrous magnesium sulfate, and concentrated. The residue was purified by silica gel column chromatography (n-hexane:ethyl acetate=1:1), washed with the following solvent, and dried. As the washing solvent, n-hexane:diethyl ether was used for 5-t-butyl-1-[4-(4-fluorobenzoyl) benzyl]-3-methyl-1H-pyrazolo[3,4-d]-pyridazin-4(5H)-one and diethyl ether-ethyl acetate for 5-t-butyl-2-[4-(4-fluorobenzoyl)benzyl]-3-methyl-2H-pyrazolo [3,4-d]pyridazin-4(5H)-one.

Compound (A): white powder, 513 mg $^1$H-NMR (DMSO-d$_6$) δ: 1.62(9H,s), 2.52(3H,s), 5.70(2H, s), 7.36(2H,dd,J=8.8,8.4 Hz), 7.44(2H,d,J=8.4 Hz), 7.72 (2H,d,J=8.4 Hz), 7.81(2H,dd,J=5.8,8.8 Hz), 8.55(1H,s).

Anal. Calcd.: C, 68.89%; H, 5.54%; N, 13.39%

Found : C, 68.82%; H, 5.52%; N, 13.37%

Compound (B): white powder, 262 mg $^1$H-NMR (DMSO-d$_6$) δ: 1.61(9H,s), 2.68(3H,s), 5.70(2H, s), 7.35(2H,d,J=8.4 Hz), 7.37(2H,dd,J=8.8,9.2 Hz), 7.71 (2H,d,J=8.4 Hz), 7.81(2H,dd,J=5.4,9.2 Hz), 8.27(1H,s).

Anal. Calcd.: C, 68.89%; H, 5.54%; N, 13.39% Found : C, 68.99%; H, 5.41%; N, 13.42%

EXAMPLE 84

1-[4-(4-Chlorobenzoyl)benzyl]-3,5-dimethyl-1H-pyrazolo [3,4-d]pyridazin-4(5H)-one (A)

2-[4-(4-Chlorobenzoyl)benzyl]-3,5-dimethyl-2H-pyrazolo [3,4-d]pyridazin-4(5H)-one (B)

In DMF (2 ml) was dissolved 3,5-dimethyl-1H-pyrazolo [3,4-d]pyridazin-4(5H)-one (94 mg) followed by addition of 4-(4-chlorobenzoyl)benzyl bromide (279 mg) and potassium carbonate (124 mg), and the mixture was stirred at room temperature for 15 hours. This reaction mixture was extracted with ethyl acetate and the organic layer was serially washed with water and saturated aqueous NaCl solution, dried over anhydrous magnesium sulfate, and concentrated. The residue was purified by silica gel column chromatography (n-hexane: ethyl acetate=1:4), washed with the following solvent, and dried. As the washing solvent, n-hexane:diethyl ether was used for 1-[4-(4-chlorobenzoyl) benzyl]-3,5-dimethyl-1H-pyrazolo[3,4-d]pyridazin-4(5H)-one and diethyl ether for 2-[4-(4-chlorobenzoyl)benzyl]-3, 5-dimethyl-2H-pyrazolo [3,4-d]pyridazin-4(5H)-one.

Compound (A): white powder, 92 mg $^1$H-NMR (DMSO-d$_6$) δ: 2.52(3H,s), 3.67(3H,s), 5.73(2H, s), 7.41(2H,d,J=8.2 Hz), 7.61(2H,d,J=8.8 Hz), 7.72(2H,d,J= 8.2 Hz), 7.73(2H,d,J=8.8 Hz), 8.65(1H,s).

Compound (B): white powder, 54 mg $^1$H-NMR (DMSO-d$_6$) δ: 2..69(3H,s), 3.62(3H,s), 5.72 (2H,s), 7.35(2H,d,J=8.2 Hz), 7.61(2H,d,J=8.8 Hz), 7.73(2H, d,J=8.2 Hz), 7.74(2H,d,J=8.8 Hz), 8.33(1H,s).

EXAMPLE 85

2-[4-(4-Chlorobenzoyl)benzylthio]-3-methylpteridin-4-one

To a solution of 3-methylpteridin-4-one-2-thione, (194 mg) in ethanol (5 ml) were added 1N-aqueous sodium hydroxide solution (1.2 ml) and 4-(4-chlorobenzoyl) benzyl bromide (310 mg) and the mixture was stirred at room temperature for 24 hours. The reaction mixture was diluted with water and extracted with ethyl acetate. The extract was washed with saturated aqueous NaCl solution and dried over anhydrous sodium sulfate. The solvent was then distilled off and the residue was purified by silica gel column chromatography (ethyl acetate) to provide the title compound as white powder (118 mg, 28%).

$^1$H-NMR (CDCl$_3$) δ: 3.69(3H,s), 4.73(2H,s), 7.42–7.82 (8H,m), 8.77(1H,d,J=2.2 Hz), 8.91(1H,d,J=2.2 Hz).

IR (KBr): 1700, 1650, 1545, 1530, 1410, 1400, 1280, 1170 cm$^{-1}$.

EXAMPLE 86

7-[4-[4-(Trifluoromethyl)benzoyl]benzyl]-1,3-dimethylxanthine

To a solution of theophylline (1.80 g) in DMF (20 ml) were added potassium carbonate (1.66 g) and 4-[4-(trifluoromethyl)benzoyl]benzyl bromide (3.43 g) and the mixture was stirred at room temperature for 20 hours. This reaction mixture was diluted with water and extracted with ethyl acetate. The extract was washed with saturated aqueous NaCl solution and dried over anhydrous sodium sulfate and the solvent was distilled off. To the residue was added 4N-hydrogen chloride/ethyl acetate and the resulting precipitate was harvested by filtration. To this precipitate was added a saturated aqueous solution of NaHCO$_3$ and the mixture was extracted with ethyl acetate. The extract was washed with saturated aqueous NaCl solution and dried over anhydrous sodium sulfate and the solvent was distilled off to provide the title compound as colorless powder (1.57 g, 36%).

$^1$H-NMR (CDCl$_3$) δ: 3.41(3H,s), 3.61(3H,s), 5.61(2H,s), 7.40–7.90(9H,m).

IR (KBr): 1705, 1660, 1605, 1550, 1410, 1325, 1275, 1130, 1060 cm$^{-1}$.

EXAMPLE 87

7-[4-(1-Indolylcarbonyl)benzyl]-1,3-dimethylxanthine

To a solution of theophylline (1.80 g) in DMF (20 ml) were added potassium carbonate (1.66 g) and 4-[(1-indolyl) carbonyl]benzyl chloride (2.70 g) and the mixture was stirred at room temperature for 22 hours. This reaction mixture was diluted with water and extracted with ethyl acetate. The extract was washed with saturated aqueous NaCl solution and dried over anhydrous sodium sulfate and the solvent was distilled off to provide the title compound as colorless powder (2.25 g, 54%).

$^1$H-NMR (CDCl$_3$) δ: 3.42(3H,s), 3.62(3H,s), 5.17(2H,s), 6.62(1H,d,J=3.0 Hz), 7.22–7.80(9H,m), 8.36–8.45(1H,m).

IR (KBr): 1700, 1650, 1540, 1450, 1380, 1340 cm$^{-1}$.

EXAMPLE 88

6-Chloro-2-[3-(4-chlorobenzoyl)benzylthio-3,5,7-trimethyl-7H-pyrrolo [2,3-d]pyrimidin-4(3H)-one In anhydrous dichloromethane (8 ml) was dissolved 2-[3-(4-chlorobenzoyl)benzyl]thio-3,5,7-trimethyl-7H-pyrrolo [2,3-d]pyrimidin-4(3H)-one (0.351 g) and, under ice-cooling and stirring, N-chlorosuccinimide (0.113 g) was added. After 2 hours of stirring, the solvent was distilled off under reduced pressure and the residue was purified by flash column chromatography (silica gel; chloroform) to provide the title compound (0.104 g)

$^1$H-NMR (CDCl$_3$) δ: 2.36(3H,s), 3.53(3H,s), 3.56(3H,s), 4.51(2H,s), 7.40(2H,d,J=8.4 Hz), 7.40–7.50(1H,m), 7.62–7.73(2H,m), 7.71(2H,d,J=8.4 Hz), 7.97(1H,s).

EXAMPLE 89

6-Chloro-7-[4-(4-chlorobenzoyl)benzyl]-3,5-dimethyl-2-methylthio-7H-pyrrolo [2,3-d]pyrimidin-4(3H)-one In anhydrous dichloromethane (3 ml) was dissolved 7-[4-(4-chlorobenzoyl)benzyl]-3,5-dimethyl-2-methylthio-7H-pyrrolo[2,3-d]pyrimidin-4(3H)-one (88 mg) and, under ice-cooling and stirring, N-chlorosuccinimide (28 mg) was added. After 2 hours of stirring, the solvent was distilled off under reduced pressure and the residue was purified by flash column chromatography (silica gel; chloroform) to provide the title compound (55 mg).

$^1$H-NMR (CDCl$_3$) δ: 2.38(3H,s), 2.56(3H,s), 3.56(3H,s), 5.39(2H,s), 7.33(2H,d,J=8.2 Hz), 7.45(2H,d,J=8.2 Hz), 7.73 (4H,d,J=8.6 Hz).

EXAMPLE 90

7-[4-(4-Chlorobenzoyl)benzyl]-3-ethyl-5-methyl-2-methylthio-7H-pyrrolo[2,3-d]pyrimidin-4(3H)-one Under argon gas, 7-[4-(4-chlorobenzoyl)benzyl]-5-methyl-2-methylthio-7H-pyrrolo[2,3-d]pyrimidin-4(3H)-one (2.46 g) was dissolved in anhydrous DME (72.5 ml)anhydrous DMF (72.5 ml) and, under ice-cooling, 60% sodium hydride-oil (255 mg) was added in two installments. The mixture was stirred for 30 minutes sand ethyl iodide (1.09 g) was added. Then, the mixture was further stirred at room temperature overnight. The reaction mixture was diluted with ethyl acetate, washed with saturated aqueous NaCl solution, and dried over anhydrous sodium sulfate. The solvent was then distilled off under reduced pressure and the residue was purified by flash column chromatography [silica gel; dichloromethane→methanol: dichloromethane (1:49)] to provide the title compound (1.04 g).

$^1$H-NMR (CDCl$_3$) δ: 1.36(3H,t,J=7.0 Hz), 2.39(3H,s), 2.56(3H,s), 4.19(2H,q,J=7.0 Hz), 5.28(2H,s), 6.46(1H,s), 7.31(2H,d,J=8.4 Hz), 7.46(2H,d,J=8.4 Hz), 7.74(4H,d,J=8.6 Hz).

EXAMPLE 91

7-[4-(4-Fluorobenzoyl)benzyl]-5-methyl-2-methylthio-7H-pyrrolo[2,3-d]pyrimidin-4(3H)-one Under argon gas, 7-[4-(4-fluorobenzoyl)benzyl]-4-methoxy-5-methyl-2-methylthio-7H-pyrrolo[2,3-d]pyrimidine (6.75 g) was dissolved in dioxane (45 ml) followed by addition of 4,4'-thiobis(6-t-butyl-m-cresol) (75 mg). Then, 0.5N-hydrochloric acid (12 ml) was added and the mixture was stirred at 105° C for 23 hours. Thereafter, 0.5N-hydrochloric acid (12 ml) was further added and the mixture was stirred at the same temperature as above for 22 hours. Then, 1N-hydrochloric acid (3 ml) and dioxane (6 ml) were added and the mixture was further stirred at the same temperature for 24 hours. This reaction mixture was allowed to stand at room temperature and the resulting crystals were collected by filtration, rinsed with methanol, DME, and ether, and finally dried to provide the title compound (5.35 g).

$^1$H-NMR (DMSO-d$_6$) δ: 2.24(3H,s), 2.52(3H,s), 5.34(2H, s), 6.84(1H,s), 7.37(2H,t,J=8.2 Hz), 7.43(2H,d,J=8.2 Hz), 7.71(2H,d,J=8.2 Hz), 7.81(2H,dd,J=5.6,8.6 Hz), 12.06(1H, s).

EXAMPLE 92

3,5-Dimethyl-7-[4-(4-fluorobenzoyl)benzyl]-2-methylthio-7H-pyrrolo[2,3-d]pyrimidin-4(3H)-one Under argon gas, 7-[4-(4-fluorobenzoyl)benzyl]-5-methyl-2-methylthio-7H-pyrrolo[2,3-d]pyrimidin-4(3H)-one (1.85 g) was dissolved in anhydrous DME (50 ml)anhydrous DMF (50 ml) and, under ice-cooling, 60% sodium hydride-oil (176 mg) was added in two installments. After 30 minutes of stirring, methyl iodide (681 mg) was added. Then, at room temperature, the mixture was stirred overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (silica gel; ethyl acetate: hexane=1:5.6–1:2.3) to provide the title compound (1.31 g).

$^1$H-NMR (CDCl$_3$) δ: 2.40(3H,d,J=1.0 Hz), 2.57(3H,s), 3.57(3H,s), 5.29(2H,s), 6.47(1H,d,J=1.0 Hz), 7.16(2H,t,J= 8.8 Hz), 7.30(2H,d,J=8.2 Hz), 7.74(2H,d,J=8.2 Hz), 7.83 (2H,dd,J=5.4,8.8 Hz).

EXAMPLE 93

3-Ethyl-7-[4-(fluorobenzoyl)benzyl]-5-methyl-2-methylthio-7H-pyrrolo[2,3-d]pyrimidin-4(3H)-one Under argon gas, 7-[4-(4-fluorobenzoyl)benzyl]-5-methyl-2-methylthio-7H-pyrrolo[2,3-d]pyrimidin-4(3H)-one (1.85 g) was dissolved in anhydrous DME (50 ml)anhydrous DMF (50 ml) and, under ice-cooling, 60% sodium hydride-oil (176 mg) was added in two installments. The mixture was stirred for 30 minutes and, then, ethyl iodide (749 mg) was added. Thereafter, the mixture was further stirred at room temperature overnight. The reaction mixture was then diluted with ethyl acetate, washed with saturated aqueous NaCl solution, and dried over anhydrous sodium sulfate. The solvent was then distilled off under reduced pressure and the residue was purified by flash column chromatography (silica gel; ethyl acetate: hexane= 1:5.6–1:2.3) to provide the title compound (867 mg).

$^1$H-NMR (CDCl$_3$) δ: 1.36(3H,t,J=7.2 Hz), 2.40(3H,d,J= 1.0 Hz),2.56(3H,s), 4.19(2H,q,J=7.2 Hz), 5.29(2H,s), 6.47 (1H,d,J=1.0 Hz), 7.16(2H,t,J=8.6 Hz), 7.31(2H,d,J=8.2 Hz), 7.74(2H,d,J=8.2 Hz), 7.83(2H,dd,J=5.4,8.6 Hz).

EXAMPLE 94

7-[4-(4-Chlorobenzoyl)benzyl]-3,5-dimethyl-7H-pyrrolo [2,3-d]pyrimidin-4(3H)-one In a mixture of DME (120 ml) and ethanol (12 ml) was dissolved 7-[4-(4-chlorobenzoyl)benzyl]-3,5-dimethyl-2-methylthio-7H-pyrrolo[2,3-d]pyrimidin-4(3H)-one (800 mg) followed by addition of acetic acid (672 mg), and the mixture was warmed to 40° C. Then, Raney nickel was added until disappearance of the starting compound had been verified by TLC. The catalyst was then filtered off and the solvent was distilled off under reduced pressure. The residue was dissolved in ethyl acetate, washed with saturated aqueous NaHCO$_3$ solution and saturated aqueous NaCl solution in that order, and dried over anhydrous magnesium sulfate. The solvent was then distilled off under reduced pressure and the residue was allowed to stand, whereupon crystals separated out. This crystal crop was harvested by filtration, rinsed with ethanol and hexane, and dried to provide the title compound (608 mg).

$^1$H-NMR (CDCl$_3$) δ: 2.43(3H,d,J=1.0 Hz), 3.57(3H,s), 5.34(2H,s), 6.60(1H,d,J=1.0 Hz), 7.26(2H,d,J=8.4 Hz), 7.45 (2H,d,J=8.4 Hz), 7.73(4H,d,J=8.4 Hz), 7.84(1H,s).

EXAMPLE 95

3,5-Dimethyl-7-[4-(4-fluorobenzoyl)benzyl]-7H-pyrrolo [2,3-d]pyrimidin-4(3H)-one In a mixture of DME (100 ml) and ethanol (10 ml) was dissolved 3,5-dimethyl-7-[4-(4-fluorobenzoyl) benzyl]-2- methylthio-7H-pyrrolo[2,3-d]pyrimidin-4(3H)-one (755 mg) followed by addition of acetic acid (560 mg), and the mixture was warmed to 40° C. Then, Raney nickel was added until disappearance of the starting compound had been verified by TLC. The catalyst was then filtered off and the solvent was distilled off under reduced pressure. The residue was dissolved in ethyl acetate, washed with saturated aqueous NaHCO₃ solution and saturated aqueous NaCl solution in that order, and dried over anhydrous magnesium sulfate. The solvent was then distilled off under reduced pressure and the residue was allowed to stand, whereupon crystals separated out. This crystal crop was harvested by filtration, rinsed with ethanol and hexane, and dried to provide the title compound (512 mg).

¹H-NMR (CDCl₃) δ: 2.43(3H,d,J=1.0 Hz), 3.57(3H,s), 5.34(2H,s), 6.60(1H,d,J=1.0 Hz), 7.15(2H,d,J=8.8 Hz), 7.26 (2H,d,J=8.0 Hz), 7.73(2H,d,J=8.0 Hz), 7.82(2H,dd,J=5.6, 8.8 Hz), 7.84(1H,s).

EXAMPLE 96

7-[4-(4-Chlorobenzoyl)benzyl]-3-ethyl-5-methyl-7H-pyrrolo [2,3-d]pyrimidin-4(3H)-one In a mixture of DME (65 ml) and ethanol (6 ml) was dissolved 7-[4-(4-chlorobenzoyl)benzyl]-3-ethyl-5-methyl-2-methylthio-7H-pyrrolo[2,3-d]pyrimidin-4(3H)-one (500 mg) followed by addition of acetic acid (336 mg), and the mixture was warmed to 40° C. Then, Raney nickel was added until disappearance of the starting compound had been verified by TLC. The catalyst was then filtered off and the solvent was distilled off under reduced pressure. The residue was dissolved in ethyl acetate, washed with saturated aqueous NaHCO₃ solution and saturated aqueous NaCl solution in that order, and dried over anhydrous magnesium sulfate. The solvent was then distilled off under reduced pressure and the residue was allowed to stand, whereupon crystals separated out. This crystal crop was harvested by filtration, rinsed with ethanol and hexane, and dried to provide the title compound (370 mg).

¹H-NMR (CDCl₃) δ: 1.41(3H,t,J=7.2 Hz), 2.43(3H,d,J= 1.0 Hz), 4.06(2H,q,J=7.2 Hz), 5.34(2H,S), 6.59(1H,d,J=1.0 Hz), 7.27(2H,d,J=8.6 Hz), 7.45(2H,d,J=8.6 Hz), 7.73(4H,d, J=8.6 Hz).

EXAMPLE 97

3-Ethyl-7-[4-(4-fluorobenzoyl)benzyl]-5-methyl-7H-pyrrolo [2,3-d]pyrimidin-4(3H)-one In a mixture of DME (50 ml) and ethanol (2 ml) was dissolved 3-ethyl-7-[4-(4-fluorobenzoyl)benzyl]-5-methyl-2-methylthio-7H-pyrrolo[2,3-d]pyrimidin-4(3H)-one (344 mg) followed by addition of acetic acid (224 mg), and the mixture was warmed to 40° C. Then, Raney nickel was added until disappearance of the starting compound had been verified by TLC. The catalyst was then filtered off and the solvent was distilled off under reduced pressure. The residue was dissolved in ethyl acetate, washed with saturated aqueous NaHCO₃ solution and saturated aqueous NaCl solution in that order, and dried over anhydrous magnesium sulfate. The solvent was then distilled off under reduced pressure and the residue was allowed to stand, whereupon crystals separated out. This crystal crop was harvested by filtration, rinsed with ethanol and hexane, and dried to provide the title compound (230 mg).

¹H-NMR (CDCl₃) δ: 1.41(3H,t,J=7.2 Hz), 2.44(3H,d,J= 1.2 Hz), 4.06(2H,q,J=7.2 Hz), 5.34(2H,s), 6.59(1H,d,J=1.2 Hz), 7.15(2H,t,J=8.8 Hz), 7.27(2H,d,J=8.2 Hz), 7.73(2H,d, J=8.2 Hz), 7.82(2H,dd,J=5.6,8.8 Hz), 7.84(1H,s).

EXAMPLE 98

2-[4-(4-Fluorobenzoyl)benzyl]thio-7H-pyrrolo[2,3-d]pyrimidin-4(3H)-one

In methanol (65.7 ml) was suspended 2-mercapto-7H-pyrrolo [2,3-d]pyrimidin-4(3H)-one (2.51 g) followed by addition of 1N-sodium hydroxide (15.75 ml) for dissolution. Then, a solution of 4-(4-fluorobenzoyl)benzyl bromide (5.06 g) in DME (15 ml) was added dropwise with ice-cooling. Then, the mixture was stirred at room temperature overnight. The solvent was then distilled off under reduced pressure and the residue was purified by flash column chromatography (silica gel; ethyl acetate: hexane=1:4–1:1-ethyl acetate) to provide the title compound (2.43 g).

¹H-NMR (DMSO-d₆) δ: 4.53(2H,s), 6.38(1H,brs), 6.94 (1H,brs), 7.42(2H,t,J=8.8 Hz), 7.68(4H,s), 7.82(2H,dd,J= 5.6,8.8 Hz), 11.81(1H,s), 12.13(1H,s).

EXAMPLE 99

3,7-Dimethyl-2-[4-(4-fluorobenzoyl)benzyl]thio-7H-pyrrolo [2,3-d]pyrimidin-4(3H)-one Under argon gas, 2-[4-(4-fluorobenzoyl) benzyl]thio-7H-pyrrolo[2,3-d]pyrimidin-4(3H)-one (818 mg) was dissolved in anhydrous DME (21.5 ml) and, under ice-cooling and stirring, 60% sodium hydride-oil (181 mg) was added in two installments. Then, methyl iodide (794 mg) was added and the mixture was stirred at room temperature overnight. This reaction mixture was diluted with ethyl acetate, washed with saturated aqueous NaCl solution, and dried over anhydrous sodium sulfate. The solvent was then distilled off under reduced pressure and the residue was purified by flash column chromatography (hexaneethyl acetate=4:1–3:2) to provide the title compound (640 mg).

¹H-NMR (CDCl₃) δ: 3.59(3H,s), 3.74(3H,s), 4.56(2H,s), 6.61(1H,d,J=3.4 Hz), 6.72(1H,d,J=3.4 Hz), 7.17(2H,t,J=8.9 Hz), 7.60(2H,d,J=8.4 Hz), 7.76(2H,d,J=8.4 Hz), 7.84(2H,, dd,J=5.4,8.9 Hz).

EXAMPLE 100

5,6-Dichloro-3,7-dimethyl-2-[4-(4-fluorobenzoyl) benzyl]thio-7H-pyrrole[2,3-d]pyrimidin-4(3H)-one In anhydrous dichloromethane (7.5 ml) was dissolved 3,7-dimethyl-2-[4-(4-fluorobenzoyl) benzyl]thio-7H-pyrrolo[2,3-d]pyrimidin-4(3H)-one (204 mg) and, under ice-cooling and stirring, N-chlorosuccinimide (141 mg) was added. After 2 hours of stirring, the solvent was distilled off under reduced pressure and the residue was purified by flash column chromatography (silica gel; dichloromethane) to provide the title compound (125 mg).

¹H-NMR (CDCl₃) :δ: 3.56(3H,s), 3.69(3H,s), 4.53(2H,s), 7.17(2H,t,J=8.6 Hz), 7.57(2H,d,J=8.4 Hz), 7.76(2H,d,J=8.4 Hz), 7.84(2H,dd,J=5.4,8.6 Hz).

EXAMPLE 101

5-Dimethylaminomethyl-2-[4-(4-fluorobenzoyl) benzyl]thio-7H-pyrrolo[2,3-d]pyrimidin-4(3H)-one (A)

6-Dimethylaminomethyl-2-[4-(4-fluorobenzoyl) benzyl]thio-7H-pyrrolo[2,3-d]pyrimidin-4(3H)-one (B)

In 80% acetic acid/water (15 ml) was dissolved 2-[4-(4-fluorobenzoyl)benzyl]thio-7H-pyrrolo[2,3-d]-pyrimidin-4

(3H)-one (570 mg) followed by addition of 37% formalin (244 mg) and, then, 50% dimethylamine-water (270 mg). The mixture was stirred at 60° C. for 13 hours. The solvent was then distilled off under reduced pressure and the residue was dissolved in water (15 ml), made basic with concentrated aqueous ammonia, and extracted with chloroform. The extract was washed with saturated aqueous NaCl solution and dried over anhydrous sodium sulfate. The solvent was then distilled off under reduced pressure and the residue was purified by flash column chromatography (silica gel; ethanol-chloroform: 1:49-ethanol (containing 7% ammonia) -chloroform=1:19–1:9) to provide the title compound (36 mg of compound A and 233 mg of compound B).

Compound A $^1$H-NMR (DMSO-d$_6$) δ: 2.36(6H,brs), 3.76(2H,s), 4.47 (2H,s), 6.84(1H,s), 7.37(2H,t,J=8.8 Hz), 7.65(4H,s), 7.81 (2H,dd,J=5.6,8.8 Hz), 11.47(1H,s).

Compound B $^1$H-NMR (DMSO-d$_6$) δ: 2.14(6H,brs), 3.39(2H,s), 4.50 (2H,s), 6.19(1H,s), 7.37(2H,t,J=8.8 Hz), 7.68(4H,s), 7.81 (2H,dd,J=5.6,8.8 Hz), 11.77(1H,s), 12.06(1H,s).

EXAMPLE 102

2-[4-(4-Chlorobenzoyl)benzyl]thio-1,7-dimethyl-7H-pyrrolo [2,3-d]pyrimidin-4-one Under argon gas, 2-[4-(4-chlorobenzoyl) benzyl]thio-1-methyl-7H-pyrrolo(2,3-d]pyrimidin-4-one (103 mg) was dissolved in anhydrous DMSO (20 ml) with warming. Then, at room temperature, 60% sodium hydride-oil (11 mg) was added and the mixture was stirred for 20 minutes. Then, methyl iodide (42.6 mg) was added and the mixture was further stirred overnight. The reaction mixture was diluted with water (200 ml) and the resulting precipitate was collected by filtration, dried, and purified by flash column chromatography (silica gel; chloroform-ethanol: chloroform=1:49) to provide the title compound (47 mg).

$^1$H-NMR (CDCl$_3$) δ: 3.94(6H,s), 4.65(2H,s), 6.48(1H,d, J=3.4 Hz), 6.62(1H,d,J=3.4 Hz), 7.46(2H,d,J=8.8 Hz), 7.58 (2H,d,J=8.4 Hz), 7.73(2H,d,J=8.4 Hz), 7.74(2H,d,J=8.8 Hz).

EXAMPLE 103

1-[4-(4-Chlorobenzoyl)benzyl]-pyrrolo[2,3-d]-pyridazine-4(5H),7(6H)-dione

In ethanol (70 ml) was dissolved 1-[4-(4-chlorobenzoyl) benzyl]-2,3-diethoxycarbonylpyrrole (3.31 g) followed by addition of anhydrous hydrazine (10.54 g) and the mixture was refluxed for 3 hours. The solvent was then distilled off under reduced pressure and the resulting crystals were suspended in water (150 ml) and, after addition of concentrated hydrochloric acid (30 ml), stirred at 85° C. for 30 minutes. The crystals were rinsed with water, methanol and ether serially and dried under reduced pressure to provide 1.46 g (yield 81%) of the title compound.

$^1$H-NMR (DMSO-d$_6$) δ: 5.83(2H,s), 6.54(1H,d,J=3.0 Hz), 7.20–7.75(9H,m), 11.2(2H,brs).

EXAMPLE 104

1-[4-(4-Chlorobenzoyl)benzyl]-4,7-dichloropyrrolo-[2,3-d]pyridazine

In phosphorus oxychloride (44.7 g) was dissolved 1-[4-(4-chlorobenzoyl)benzyl]-pyrrolo[2,3-d]pyridazine-4(5H),7(6H)-dione (1.46 g) and the solution was refluxed for 2 hours. The phosphorus oxychloride was distilled off under reduced pressure and the residue was washed with saturated aqueous NaHCO$_3$ solution. The resulting crystals were collected by filtration, dissolved in ethyl acetate, and dried over anhydrous magnesium sulfate. The solvent was then distilled off under reduced pressure and the residue was purified by silica gel column chromatography (stationary phase 40 g; dichloromethane: ether=1:0–9:1) and recrystallized from ethyl acetate-ether to provide 1.23 g (yield 76%) of the title compound.

$^1$H-NMR (CDCl$_3$) δ: 5.89(2H,s), 6.87(1H,d,J=3.0 Hz), 7.15(2H,d,J=8.0 Hz), 7.45(1H,d,J=3.0 Hz), 7.46(2H,d,J=8.6 Hz), 7.73(2H,d,J=8.6 Hz), 7.77(2H,d,J=8.6 Hz).

EXAMPLE 105

1-[4-(4-Chlorobenzoyl)benzyl]-4-chloropyrrolo[2,3-d]pyridazin-7(6H)-one (A)

1-[4-(4-Chlorobenzoyl)benzyl]-7-chloropyrrolo[2,3-d]pyridazin-4(5H)-one (B)

In dioxane (15 ml) was dissolved 1-[4-(4-chlorobenzoyl) benzyl]-4,7-dichloropyrrolo [2,3-d]pyridazine (1.08 g). Then, sodium hydroxide (4.42 g) and water (5 ml) were added and the mixture was refluxed for 69 hours. This reaction mixture was diluted with water (120 ml) and the resulting crystals were collected by filtration. The crystals were purified by silica gel column chromatography (stationary phase 50 g; dichloromethane: ether=1:0–9:1; ethyl acetate: methanol=1:9) to provide 416 mg (yield 40%) of the title compound 1-[4-(4-chlorobenzoyl)benzyl]-4-chloropyrrolo [2,3-d]pyridazin-7(6H)-one(A) and 196 mg (yield 19%) of the title compound 1-[4-(4-chlorobenzoyl) benzyl]-7-chloropyrrolo [2,3-d]pyridazin-4(5H)-one(B).

Compound A $^1$H-NMR (CDCl$_3$) δ: 5.87(2H,s), 6.59(1H,d,J=2.9 Hz), 7.23(1H,d,J=3.0 Hz), 7.37(2H,d,J=8.3 Hz), 7.45(2H,d,J=8.7 Hz), 7.73(2H,d,J=8.7 Hz), 7.75(2H,d,J=8.3 Hz), 10.02(1H, brs).

Compound B $^1$H-NMR (CDCl$_3$) δ: 5.80(2H,s), 7.04(1H,d,J=3.0 Hz), 7.13(2H,d,J=8.6 Hz), 7.19(1H,d,J=3.0 Hz), 7.46(2H,d,J=8.8 Hz), 7.73(2H,d,J=8.8 Hz), 7.77(2H,d,J=8.4 Hz), 10.18(1H, brs).

EXAMPLE 106

1-[4-(4-Chlorobenzoyl)benzyl]-4-chloro-6-methylpyrrolo [2,3-d]pyridazin-7(6H)-one In DMF (200 ml) was dissolved 1-[4-(4-chlorobenzoyl) benzyl]-4-chloropyrrolo [2,3-d]pyridazin-7(6H)-one (830 mg) followed by addition of potassium carbonate (2.11 g). Then, methyl iodide (0.13 ml) was added and the mixture was stirred at room temperature for 95 hours. This reaction mixture was diluted with water (50 ml) and extracted with ethyl acetate (200 ml). The organic layer was washed with water (100 ml) 3 times and further with saturated aqueous NaCl solution (100 ml) and dried over anhydrous magnesium sulfate. After the desiccant was filtered off, the solvent was distilled off under reduced pressure and the resulting crystals were rinsed with ethyl acetate to provide 742 mg (yield 84%) of the title compound.

$^1$H-NMR (CDCl$_3$) δ: 3.82(3H,s), 5.89(2H,s), 6.54(1H,d, J=3.0 Hz), 7.19(1H,d,J=3.0 Hz), 7.34(2H,d,J=8.2 Hz), 7.45 (2H,d,J=8.4 Hz), 7.73(2H,d,J=8.4 Hz), 7.74(2H,d,J=8.2 Hz).

EXAMPLE 107

1-[4-(4-Chlorobenzoyl)benzyl]-5-methyl-7-chloropyrrolo [2,3-d]pyridazin-4(5H)-one In DMF (15 ml) was dissolved 1-[4-(4-chlorobenzoyl) benzyl]-7-chloropyrrolo [2,3-d]pyridazin-4(5H)-one (352 mg) followed by addition of potassium carbonate (858 mg). Then, methyl iodide (0.06 ml) was added and the mixture was stirred at room temperature for 16 hours. The reaction mixture was diluted with water (30 ml) and extracted with ethyl acetate (200 ml). The organic layer was washed with water (100 ml) 3 times and saturated aqueous NaCl solution once and dried over anhydrous magnesium sulfate. After removal of the desiccant by filtration, the solvent was distilled off under reduced pressure and the resulting crystals were rinsed with hexane to provide 290 mg (yield 80%) of the title compound.

$^1$H-NMR (CDCl$_3$) δ: 3.83(3H,s), 5.77(2H,s), 7.01(1H,d, J=3.0 Hz), 7.13(2H,d,J=8.2 Hz), 7.16(1H,d,J=3.0 Hz), 7.46 (2H,d,J=8.6 Hz), 7.73(2H,d,J=8.6 Hz), 7.76(2H,d,J=8.2 Hz).

EXAMPLE 108

1,3-Dimethyl-7-[4-(4-methoxybenzoyl) benzyl] xanthine

In DMF (20 ml) was dissolved theophylline (1.84 g). To this solution were added potassium carbonate (1.42 g) and p-methoxybenzoylbenzyl bromide (3.78 g) and the mixture was stirred at room temperature for 14 hours. After addition of water and dilution with ethyl acetate (1200 ml), the organic layer was washed with water (500 ml) twice and saturated aqueous NaCl solution (500 ml) once and dried over anhydrous magnesium sulfate. After removal of the desiccant by filtration, the solvent was distilled off under reduced pressure and the resulting crystals were rinsed with ethyl acetate to provide 2.83 g (yield 69%) of the title compound.

$^1$H-NMR (CDCl$_3$) δ: 2.44(3H,s), 3.89(3H,s), 6.96(2H,d, J=9.0 Hz), 7.28(2H,d,J=8.0 Hz), 7.68(2H,d,J=8.2 Hz), 7.82 (2H,d,J=8.8 Hz).

EXAMPLE 109

7-[4-(4-Chlorobenzoyl)benzyloxy]-6-methyl-5H-thiazolo [3,2-a]pyrimidin-5-one

To a solution of 6-methyl-2-hydroxy-5H-thiazolo [3,2-a] pyrimidin-5-one (365 mg) and potassium carbonate (526 mg) in DMF (10 ml) was added 4-(4-chlorobenzoyl)benzyl bromide (664 mg) and the mixture was stirred at 80° C. for 2 hours. This reaction mixture was concentrated and the residue was diluted with water-ethyl acetate and extracted with ethyl acetate. The extract was purified by silica gel column chromatography (hexane: ethyl acetate: chloroform=2:1:1) and recrystallized from ethyl acetate to provide the title compound as colorless solid (400 mg).

$^1$H-NMR (CDCl$_3$) δ: 2.11(3H,s), 5.53(2H,s), 6.92(1H,d, J=4.9 Hz), 7.47(2H,d,J=8.5 Hz), 7.55(2H,d,J=8.2 Hz), 7.76 (2H,d,J=8.2 Hz), 7.80(2H,d,J=8.5 Hz), 7.98(1H,d,J=4.9 Hz).

IR (KBr): 1670, 1640, 1565, 1490 cm$^{-1}$.

EXAMPLE 110

7-[4-(4-Chlorobenzoyl)benzyloxy]-2,3,6-trimethyl-5H-thiazolo [3,2-a]pyrimidin-5-one To a solution of 2,3,6-trimethyl-2-hydroxy-5H-thiazolo [3,2-a]pyrimidin-5-one (382 mg) and potassium carbonate (357 mg) in DMF (10 ml) was added 4-(4-chlorobenzoyl) benzyl bromide (581 mg) and the mixture was stirred at 80° C. for 2 hours. This reaction mixture was concentrated and the residue was diluted with water-ethyl acetate and extracted with ethyl acetate. Recrystallization from ethyl acetate gave the title compound as colorless solid (266 mg).

$^1$H-NMR (CDCl$_3$) δ: 2.04(3H,s), 2.27(3H,s), 2.73(3H,s), 5.48(2H,s), 7.46(2H,d,J=8.4 Hz), 7.53(2H,d,J=8.2 Hz), 7.76 (2H,d,J=8.4 Hz), 7.79(2H,d,J=8.2 Hz).

IR (KBr): 1665, 1580, 1500 cm$^{-1}$.

EXAMPLE 111

5-[4-(4-Chlorobenzoyl)benzyl]-1,3-dimethylpyrrolo [3,2-d]pyrimidine-2,4-dione

To a solution of 1,3-dimethylpyrrolo[3,2-d]-pyrimidine-2,4-dione (0.402 g, 2.24 mmol) and 4-(4-chlorobenzoyl) benzyl bromide (1.20 g, 3.88 mmol) in DMF (5 ml) was added potassium carbonate (0.73 g, 5.28 mmol) and the mixture was stirred at 60° C. for 2 hours. The solvent was then distilled off under reduced pressure and the residue was diluted with water and extracted with ethyl acetate. The organic layer was washed with saturated aqueous NaCl solution, dried over MgSO$_4$, and concentrated under reduced pressure. The residue was purified by silica gel column chromatography (developer: isopropyl ether: ethyl acetate: methylene chloride=2:1:1) and recrystallized from ethyl acetate to provide colorless needles. 0.360 g (39%)

$^1$H-NMR (CDCl$_3$) δ: 3.40(3H,s), 3.49(3H,s), 5.66(2H,s), 6.00(1H,d,J=3.0 Hz), 7.01(1H,d,J=3.0 Hz), 7.29(2H,d,J=8.6 Hz), 7.45(2H,d,J=8.6 Hz), 7.72(2H,d,J=8.6 Hz),.7.73(2H,d, J=8.6 Hz).

IR (KBr): 1693, 1653, 1549, 1466, 1434, 1406, 1267, 1065, 1016, 962, 922, 856, 744, 669, 503 cm$^{-1}$.

EXAMPLE 112

1,3-Dimethyl-5-[4-(4-trifluoromethylbenzoyl) benzyl]-pyrrolo[3,2-d]pyrimidine-2,4-dione To a solution of 1,3-dimethylpyrrolo[3,2-d]-pyrimidine-2,4-dione (0.405 g, 2.26 mmol) and 4-(4-trifluoromethylbenzoyl) benzyl bromide (2.01 g) in DMF (5 ml) was added potassium carbonate (0.82 g, 5.93 mmol) and the mixture was stirred at 60° C. for 2 hours. The solvent was then distilled off under reduced pressure and the residue was diluted with water and extracted with ethyl acetate. The organic layer was washed with saturated aqueous NaCl solution, dried over MgSO$_4$, and concentrated under reduced pressure. The residue was purified by silica gel column chromatography (developer; isopropyl ether: ethyl acetate: methylene chloride=2:1:1) and recrystallized from ethyl acetate to provide colorless needles.

0.398 g (40%)

IR (KBr): 1695, 1651, 1468, 1408, 1319, 1277, 1164, 1063, 10146, 926, 759 cm$^{-1}$.

EXAMPLE 113

3,5-Dimethyl-2-[4-(3-indolylcarbonyl)benzylthio]-quinazolin-4-one

To a solution of 3,5-dimethyl-2-mercaptoquinazolin-4-one (0.497 g, 2.41 mmol) in EtOH (10.0 ml)-THF (10.0 ml) was added 1N-sodium hydroxide/water (2.5ml) followed by addition of 4-(3-indolylcarbonyl)benzyl bromide (0.650 g, 2.41 mmol) and the mixture was stirred at room temperature for 2.5 hours. This reaction mixture was diluted with ethyl acetate and washed with saturated aqueous NaCl solution. The organic layer was dried over MgSO$_4$ and concentrated under reduced pressure and the residue was purified by silica gel column chromatography (developer; ethyl acetate:THF= 1:1) to provide 0.178 g (17%) of light-red-solid.

¹H-NMR (CDCl₃) δ: 2.76(3H,s), 4.65(2H,s), 7.18–7.28 (4H,m), 7.48(2H,d,J=7.6 Hz), 7.58–7.83(4H,m), 7.93(1H, dd,J=6.2,3.0 Hz), 8.27(1H,m).

IR (KBr): 3149, 1670, 1602, 1556, 1431, 1309, 1213, 1092, 750 cm⁻¹.

EXAMPLE 114

3,5-Dimethyl-2-[4-(3,4,5-trimethoxybenzoyl)benzylthio]quinazolin-4-one

To a solution of 3,5-dimethyl-2-mercaptoquinazolin-4-one (0.497 g, 2.41 mmol) in EtOH (10.0 ml)-THF (10.0 ml) was added 1N-sodium hydroxide/water (2.5 ml). Then, 4-(3,4,5-trimethoxybenzoyl) benzyl bromide (0.970 g, 2.52 mmol) was added and the mixture was stirred at room temperature overnight. This reaction mixture was diluted with ethyl acetate and washed with saturated aqueous NaCl solution and the organic layer was dried over MgSO₄ and concentrated under reduced pressure. The residue was recrystallized from ethyl acetate to provide 0.983 g (83%) of colorless needles.

¹H-NMR (CDCl₃) δ: 2.85(3H,s), 3.55(3H,s), 3.86(6H,s), 3.94(3H,s), 4.60(2H,s), 7.04(2H,s), 7.15(1H,d,J=7.2 Hz), 7.44(1H,d,J=7.2 Hz), 7.51(1H,t,J=7.2 Hz), 7.61(2H,d,J=8.0 Hz), 7.78(2H,d,J=8.0 Hz).

IR (KBr): 1672, 1581, 1556, 1500, 1462, 1414, 1333, 1234, 1126, 1093, 1001, 806, 773, 696 cm⁻¹.

EXAMPLE 115

3,5-Dimethyl-2-[4-(4-methoxybenzoyl)benzylthio]-quinazolin-4-one

To a solution of 3,5-dimethyl-2-mercaptoquinazolin-4-one (0.495 g, 2.41 mmol) in EtOH (10.0 ml)-THF (10.0 ml) was added 1N-sodium hydroxide/water (2.5 ml). Then, 4-(4-methoxybenzoyl) benzyl bromide (purity 84%, 0.960 g, 2.52 mmol) was added and the mixture was stirred at room temperature for 1.5 hours. This reaction mixture was diluted with ethyl acetate and washed with saturated aqueous NaCl solution. The organic layer was dried over MgSO₄ and concentrated under reduced pressure. The residue was recrystallized from ethyl acetate to provide 0.736 g (71%) of colorless needles.

¹H-NMR (CDCl₃) δ: 2.85(3H,s), 3.55(3H,s), 3.89(3H,s), 4.60(2H,s), 6.95(2H,d,J=6.8 Hz), 7.15(1H,d,J=6.2 Hz), 7.44(1H,d,J=6.2 Hz), 7.55(1H,t,J=6.2 Hz), 7.59(2H,d,J=6.8 Hz), 7.72(2H,d,J=8.0 Hz), 7.82(2H,d,J=8.0 Hz).

IR (KBr): 1672, 1601, 1554, 1462, 1417, 1308, 1255, 1173, 1090, 1030, 928 cm⁻¹.

EXAMPLE 116

3,5-Dimethyl-2-[4-(4-trifluoromethylbenzoyl)benzylthio]quinazolin-4-one

To a solution of 3,5-dimethyl-2-mercaptoquinazolin-4-one (0.495 g, 2.41 mmol) in EtOH (10.0 ml)-THF (10.0 ml) was added 1N-sodium hydroxide/water (2.5 ml). Then, 4-(4-trifluoromethylbenzoyl) benzyl bromide (purity 63.4%, 1.37 g, 2.52 mmol) was added and the mixture was stirred at room temperature overnight. This reaction mixture was diluted with ethyl acetate and washed with saturated aqueous NaCl solution, and the organic layer was dried over MgSO₄ and concentrated under reduced pressure. The residue was recrystallized from methanol to provide 1.218 g of colorless needles.

¹H-NMR (CDCl₃) δ: 2.85(3H,s), 3.55(3H,s), 4.60(2H,s), 7.16(1H,d,J=7.2 Hz), 7.32(2H,d,J=8.2 Hz), 7.43(1H,d,J=7.2 Hz), 7.55(1H,t,J=7.2 Hz), 7.63(2H,d,J=8.0 Hz), 7.88(2H,d, J=8.0 Hz).

IR (KBr): 1671, 1556, 1410, 1325, 1297, 1171, 1130, 1066, 930, 860, 690 cm⁻¹.

EXAMPLE 117

2-[4-(4-Chlorobenzoyl)benzylthio]-3-ethyl-5-methylquinazolin-4-one

To a solution of 3-ethyl-5-methyl-2-mercaptoquinazolin-4-one (0.506 g, 2.30 mmol) in EtOH (10.0 ml)-THF (10.0 ml) was added 1N-sodium hydroxide/water (2.7 ml). Then, 4-(4-chlorobenzoyl)benzyl bromide (0.720 g, 2.33 mmol) was added and the mixture was stirred at room temperature for 5 hours. This reaction mixture was diluted with ethyl acetate and washed with saturated aqueous NaCl solution, and the organic layer was dried over MgSO₄ and concentrated under reduced pressure. The residue was then recrystallized from ethyl acetate to provide 0.695 g (67%) of colorless needles.

¹H-NMR (CDCl₃) δ: 1.35(3H,t,J=7.2 Hz), 2.84(3H,s), 4.13(2H,q,J=7.2 Hz), 4.59(2H,s), 7.14(1H,d,J=8.0 Hz), 7.41–7.54(4H,m), 7.60(2H,d,J=8.0 Hz), 7.73(2H,d,J=6.8 Hz), 7.74(2H,d,J=8.0 Hz).

IR (KBr): 1668, 1551, 1276, 1221, 1097, 926, 731 cm⁻¹.

EXAMPLE 118

2-[4-(4-Fluorobenzoyl)benzylthio]-3-ethyl-5-methylquinazolin-4-one

To a solution of 3-ethyl-5-methyl-2-mercaptoquinazolin-4-one (0.506 g, 2.30 mmol) in EtOH (10.0 ml)-THF (10.0 ml) was added 1N-aqueous sodium hydroxide solution (2.7 ml). Then, 4-(4-fluorobenzoyl)benzyl bromide (0.715 g, 2.44 mmol) was added and the mixture was stirred at room temperature for 5 hours. This reaction mixture was diluted with ethyl acetate and washed with saturated aqueous NaCl solution, and the organic layer was dried over MgSO₄ and concentrated under reduced pressure. The residue was recrystallized from methanol to provide 0.803 g (81%) of colorless needles.

¹H-NMR (CDCl₃) δ: 1.35(3H,t,J=7.2 Hz), 2.85(3H,s), 4.13(2H,q,J=7.2 Hz), 4.59(2H,s), 7.10–7.20(3H,m), 7.42 (1H,d,J=7.0 Hz), 7.54(1H,t,J=7.0 Hz), 7.74(2H,d,J=8.4 Hz), 7.76–7.87(2H,m).

IR (KBr): 1666, 1599, 1552, 1450, 1412, 1371, 1277, 1225, 1153, 1103, 856, 808, 777, 734, 698 cm¹.

EXAMPLE 119

3-Ethyl-5-methyl-2-[4-(4-trifluoromethylbenzoyl)benzylthio]quinazolin-4-one

To a solution of 3-ethyl-5-methyl-2-mercaptoquinazolin-4-one (0.507 g, 2.30 mmol) in EtOH (10.0 ml)-THF (10.0 ml) was added 1N-aqueous sodium hydroxide solution (2.7 ml). Then, 4-(4-trifluoromethylbenzoyl)benzyl bromide (purity 63%, 1.28 g, 2.35 mmol) was added and the mixture was stirred at room temperature for 5 hours. This reaction mixture was diluted with ethyl acetate and washed with saturated aqueous NaCl solution, and the organic layer was dried over MgSO₄ and concentrated under reduced pressure. The residue was then recrystallized from methanol to provide 0.811 g (73%) of colorless needles.

¹H-NMR (CDCl₃) δ: 1.35(3H,t,J=7.2 Hz), 2.85(3H,s), 4.12(2H,q,J=7.2 Hz), 4.60(2H,s), 7.14(1H,d,J=7.0 Hz), 7.42 (1H,t,J=7.0 Hz), 7.54(1H,t,J=7.0 Hz), 7.63(2H,d,J=8.0 Hz), 7.74(2H,d,J=8.0 Hz), 7.78(2H,d,J=8.0 Hz), 7.88(2H,d,J=8.0 Hz).

IR (KBr): 1670, 1552, 1321, 1171, 1130, 1065, 930 cm⁻¹.

EXAMPLE 120

3-Ethyl-2-[4-(4-methoxybenzoyl)benzylthio]-5-methylquinazolin-4-one

To a solution of 3-ethyl-5-methyl-2-mercaptoquinazolin-4-one (0.507 g, 2.30 mmol) in EtOH (10.0 ml)-THF (10.0 ml) was added 1N-aqueous NaOH solution (2.7 ml). Then, 4-(4-methoxybenzoyl)benzyl bromide (purity 84%, 0.840 g, 2.31 mmol) was added and the mixture was stirred at room temperature for 5 hours. This reaction mixture was diluted with ethyl acetate and washed with saturated aqueous NaCl solution, and the organic layer was dried over MgSO₄ and concentrated under reduced pressure. The residue was recrystallized from methanol to provide 0.826 g (81%) of colorless needles.

¹H-NMR (CDCl₃) δ: 1.35(3H,t,J=7.0 Hz), 2.85(3H,s), 3.89(3H,s), 4.14(2H,q,J=7.0 Hz), 4.59(2H,s), 6.96(2H,d,J= 8.8 Hz), 7.15(1H,d,J=7.2 Hz), 7.43(1H,d,J=7.2 Hz), 7.54 (1H,t,J=7.2 Hz), 7.58(2H,d,J=8.1 Hz), 7.73(2H,d,J=8.1 Hz), 7.82(2H,d,J=8.8 Hz).

IR (KBr): 1674, 1601, 1552, 1257, 1173, 1103, 1028, 930, 851, 811, 781 cm⁻¹.

EXAMPLE 121

2-[4-(4-Fluorobenzoyl)benzyloxy]-3-methylpyrido [1,2-a]pyrimidin-4-one

To a solution of 2-hydroxy-3-methylpyrido[1,2-a]-pyrimidin-4-one (0.480 g, 2.72 mmol) and 4-(4-fluorobenzoyl) benzyl bromide (0.900 g, 3.07 mmol) in DMF (10.0 ml)-DMSO (10.0 ml) was added potassium carbonate (0.800 g, 5.78 mmol) and the mixture was stirred at room temperature for 2.5 hours. This reaction mixture was diluted with ethyl acetate and washed with saturated aqueous NaCl solution, and the organic layer was dried over MgSO₄ and concentrated under reduced pressure. The residue was recrystallized from ethyl acetate to provide 0.425 g (40.2%) of colorless needles.

¹H-NMR (CDCl₃) δ: 2.23(3H,s), 5.63(2H,s), 7.11–7.21 (2H,m), 7.45–7.61(4H,m), 7.64–7.89(5H,m), 9.09(1H,d,J= 7.2 Hz).

IR (KBr): 1670, 1578, 1531, 1477, 1279, 1165, 926, 854, 762 cm⁻¹.

EXAMPLE 122

2-[4-(2-Ethoxycarbonylbenzoyl)benzyloxy]-3-methylpyrido [1,2-a]pyrimidin-4-one

To a solution of 2-hydroxy-3-methylpyrido[1,2-a]-pyrimidin-4-one (0.277 g, 1.57 mmol) and 4-(2-ethoxycarbonylbenzoyl) benzyl bromide (0.565 g, 1.63 mmol) in DMF (10.0 ml)-DMSO (10.0 ml) was added potassium carbonate (0.360 g, 2.60 mmol) and the mixture was stirred at room temperature overnight. This reaction mixture was diluted with ethyl acetate and washed with saturated aqueous NaCl solution. The organic layer was dried over MgSO₄ and concentrated under reduced pressure. The residue was purified by silica gel column chromatography (developer: ethyl acetate-hexane =2:1) to provide 0.345 g (54.0%) of colorless, amorphous solid.

¹H-NMR (CDCl₃) δ: 1.05(3H,t,J=7.2 Hz), 2.20(3H,s), 4.08(2H,q,J=7.2 Hz), 5.59(2H,s), 7.10(1H,dt,J=7.2,1.4 Hz), 7.41(1H,dt,J=6.6,2.0 Hz), 7.51–7.81(8H,m), 8.07(1H,dd,J= 6.8,1.6 Hz), 9.07(1H,dd,J=6.8,1.6 Hz).

IR (KBr): 1716, 1674, 1635, 1576, 1531, 1479, 1281, 1165, 769 cm⁻¹.

EXAMPLE 123

2-[4-(1-Indolylcarbonyl)benzyloxy]-3-methylpyrido-[1,2-a]pyrimidin-4-one

To a solution of 2-hydroxy-3-methylpyrido[1,2-a]-pyrimidin-4-one (0.258 g, 1.46 mmol) and 4-(1-indolylcarbonyl) benzyl chloride (0.430 g, 1.59 mmol) in DMF (10.0 ml)-DMSO (5.0 ml) was added potassium carbonate (0.330 g, 2.39 mmol) and the mixture was stirred at room temperature overnight. This reaction mixture was diluted with ethyl acetate and washed with saturated aqueous NaCl solution, and the organic layer was dried over MgSO₄ and concentrated under reduced pressure. The residue was recrystallized from ethyl acetate to provide 0.19 g (33.0%) of colorless needles.

¹H-NMR (CDCl₃-DMSO-d₆) δ: 2.24(3H,s), 5.64(2H,s), 6.62(1H,m), 7.12(1H,t,J=7.7 Hz), 7.27–7.40(4H,m), 7.49–7.80(6H,m), 8.42(1H,d,J=7.7 Hz), 9.09(2H,d,J=7.7 Hz).

IR (KBr): 1676, 1578, 1533, 1450, 1336, 1282, 1169, 754 cm⁻¹.

EXAMPLE 124

3-Methyl-2-[4-(4-trifluoromethylbenzoyl) benzyloxy]pyrido[1,2-a]pyrimidin-4-one

To a solution of 2-hydroxy-3-methylpyrido[1,2-a]-pyrimidin-4-one (0.250 g, 1.42 mmol) and 4-(4-trifluoromethylbenzoyl) benzyl bromide (purity: 63.4%, 0.852 g, 2.48 mmol) in DMF (10.0 ml)-DMSO (5.0 ml) was added potassium carbonate (0.360 g, 2.60 mmol) and the mixture was stirred at room temperature overnight. This reaction mixture was diluted with ethyl acetate and washed with saturated aqueous NaCl solution, and the organic layer was dried over MgSO₄ and concentrated under reduced pressure. The residue was recrystallized from ethyl acetate to provide 0.21 g (34.0%) of colorless needles.

¹H-NMR (CDCl₃) δ: 2.23(3H,s), 5.63(2H,s), 7.12(1H,t, J=6.8 Hz), 7.50(1H,d,J=8.8 Hz), 7.61(2H,d,J=8.3 Hz), 7.68 (1H,m), 7.76(2H,d,J=8.1 Hz), 7.84(2H,d,J=8.1 Hz), 7.91 (2H,d,J=8.3 Hz), 9.09(1H,d,J=7.2 Hz).

IR (KBr): 1672, 1578, 1531, 1479, 1325, 1279, 1167, 1128, 1065, 914, 744 cm⁻¹.

EXAMPLE 125

2-[4-(4-Fluorobenzoyl)benzyl]thio-3-methylthieno-[3,2-d]pyrimidin-4(3H)-one

To a solution of 2-mercapto-3-methylthieno[3,2-d]-pyrimidin-4(3H)-one (1.0 g) and sodium hydroxide (205 mg) in 50% ethanol (12 ml)-DMF (20 ml) was added 4-(4-fluorobenzoyl)benzyl bromide (1.48 g) and the mixture was stirred at room temperature for 1 hour. This reaction mixture was poured in water and the resulting crystals were collected by filtration, rinsed with water and methanol, and recrystallized from methanol to provide the title compound as colorless solid (1.44 g).

¹H-NMR (CDCl₃) δ: 3.62(3H,s), 4.58(2H,s), 7.16(2H,t, J=8.6 Hz), 7.24(1H,d,J=5.2 Hz), 7.59(2H,d,J=8.4 Hz), 7.70–7.90(5H,m).

IR (KBr): 1670, 1640, 1500 cm⁻¹.

EXAMPLE 126

2-[4-(4-Fluorobenzoyl)benzyl]thio-3-methyl-6,7-dihydro-5H-cyclopenta[d]pyrimidin-4(3H)-one To a solution of 2-mercapto-3-methyl-6,7-dihydro-5H-cyclopenta[d]pyrimidin-4(3H)-one (1.0 g) as obtained in Reference Example 1 and sodium hydroxide (220 mg) in 50% ethanol (15 ml)-DMF (8 ml) was added 4-(4-fluorobenzoyl)benzyl bromide (2.11 g) and the mixture was stirred at room temperature for 1 hour. This reaction mixture was poured in water and the resulting crystals were collected by filtration, rinsed with water and methanol, and recrystallized from methanol to provide the title compound as colorless solid (1.235 g).

¹H-NMR (CDCl₃) δ: 2.07(2H,q,J=7.4 Hz), 2.80(2H,t,J= 7.8 Hz), 2.84(2H,t,J=7.8 Hz), 3.50(3H,s), 4.50(2H,s), 7.17 (2H,t,J=8.4 Hz), 7.54(2H,d,J=8.0 Hz), 7.74(2H,d,J=8.0 Hz), 7.85(2H,dd,J=8.4,5.6 Hz).

IR (KBr): 1660, 1650, 1595, 1495 cm⁻¹.

EXAMPLE 127

6-[4-(4-Fluorobenzoyl)benzyl]thio-5-methyl-1H-pyrazolo[3,4-d]pyrimidin-4(5H)-one To a solution of 6-mercapto-5-methyl-1H-pyrazolo-[3,4-d]pyrimidin-4(5H)-one potassium (1.0 g) in DMF (20 ml) was added 4-(4-fluorobenzoyl)benzyl bromide (1.745 g) and the mixture was stirred at room temperature for 1 hour. This reaction mixture was poured in water and the resulting crystals were collected by filtration, rinsed with water and methanol to provide the title compound as colorless solid (1.467 g).

¹H-NMR (DMSO-d₆) δ: 3.45(3H,s), 4.63(2H,s), 7.39(2H, t,J=8.8 Hz), 7.72(4H,s), 7.83(2H,dd,J=8.8,5.4 Hz), 8.03(1H, s), 13.67(1H,brs).

IR (KBr): 3200, 1670, 1640, 1575 cm⁻¹.

EXAMPLE 128

6-[4-(4-Chlorobenzoyl)benzyl]thio-5-ethyl-1H-pyrazolo[3,4-d]pyrimidin-4(5H)-one

To a solution of 6-mercapto-5-ethyl-1H-pyrazolo[3,4-d] pyrimidin-4(5H)-one potassium (1.0 g) in DMF (25 ml) was added 4-(4-fluorobenzoyl)benzyl bromide (1.31 g) and the mixture was stirred at room temperature for 1 hour. This reaction mixture was poured in water and the resulting crystals were collected by filtration and rinsed with water and methanol to provide the title compound as colorless solid (1.714 g).

¹H-NMR (DMSO-d₆) δ: 1.24(3H,t,J=7.0 Hz), 4.07(2H,q, J=7.0 Hz), 4.62(2H,s), 7.60(2H,d,J=8.0 Hz), 7.70–7.80(7H, m).

IR (KBr): 3100, 1660, 1580, 1540 cm⁻¹.

EXAMPLE 129

1-[4-(4-Chlorobenzoyl)benzyl]thio-5-ethyl-6-methylthio-1H-pyrazolo[3,4-d]pyrimidin-4(5H)-one (A)

2-[4-(4-Chlorobenzoyl)benzyl]thio-5-ethyl-6-methylthio-2H-pyrazolo[3,4-d]pyrimidin-4(5H)-one (B)

To a solution of 5-ethyl-6-mercapto-1H-pyrazolo[3,4-d] pyrimidin-4(5H)-one potassium (5.0 g) in DMF (40 ml) was added methyl iodide (3.65 g) and the mixture was stirred for 1 hour. This reaction mixture was concentrated and the residue was diluted with water. The resulting crystals were collected by filtration and rinsed with water to provide 5-ethyl-6-methylthio-1H-pyrazolo[3,4-d]pyrimidin-4(5H)-one as colorless solid (2.908 g).

¹H-NMR (DMSO-d₆) δ: 1.24(3H,t,J=7.0 Hz), 2.61(3H,s), 4.08(2H,q,J=7.0 Hz), 8.09(1H,brs).

In a solution of 5-ethyl-6-methylthio-1H-pyrazolo-[3,4-d]pyrimidin-4(5H)-one (1.0 g) in DMF (20 ml) was added 60% sodium hydride (230 mg) and the mixture was stirred at room temperature for 10 minutes. Then, 4-(4-chlorobenzoyl)benzyl bromide (1.46 g) was added and the mixture was further stirred at room temperature for 1 hour. This reaction mixture was concentrated and the residue was dissolved in ethyl acetate, washed with water and saturated aqueous NaCl solution, and dried. The solvent was then distilled off and hexane-ethyl acetate (3:1) was added to the residue. The resulting crystals were collected by filtration to provide 2-[4-(4-chlorobenzoyl)benzyl]thio-5-ethyl-6-methylthio-2H-pyrazolo[3,4-d]pyrimidin-4-(5H)-one (B) as colorless solid (530 mg).

¹H-NMR (CDCl₃) δ: 1.34(3H,t,J=7.0 Hz), 2.65(3H,s), 4.17(2H,q,J=7.0 Hz), 5.48(2H,s), 7.41(2H,d,J=8.4 Hz), 7.46 (2H,d,J=8.6 Hz), 7.73(2H,d,J=8.6 Hz), 7.76(2H,d,J=8.4 Hz), 8.06(1H,s).

IR (KBr): 1695, 1650, 1570 cm⁻¹.

The filtrate obtained above was concentrated, and the residue was purified by silica gel column chromatography (hexane-ethyl acetate-chloroform=3:2:1) and crystallized from methanol to provide 1-[4-(4-chlorobenzoyl)benzyl] thio-5-ethyl-6-methylthio-1H-pyrazolo[3,4-d]pyrimidin-4 (5H)-one (A) as colorless solid (160 mg).

¹H-NMR (CDCl₃) δ: 1.35(3H,t,J=7.0 Hz), 2.63(3H,s), 4.20(2H,q,J=7.0 Hz), 5.54(2H,s), 7.43(2H,d,J=8.0 Hz), 7.45 (2H,d,J=8.6 Hz), 7.73(2H,d,J=8.6 Hz), 7.75(2H,d,J=8.0 Hz), 8.05(1H,s).

IR (KBr): 1695, 1645, 1540 cm⁻¹.

EXAMPLE 130

7-[4-(4-Chlorobenzoyl)benzyloxy]-6-methyl-2,3-dihydro-5H-thiazolo[3,2-a]pyrimidin-5-one To a solution of 7-hydroxy-6-methyl-2,3-dihydro-5H-thiazolo[3,2-a]-5-one (1.0 g) and potassium carbonate (750 mg) in DMF (15 ml) was added 4-(4-chlorobenzoyl)benzyl bromide (2.0 g) and the mixture was stirred at 60° C. for 2 hours. This reaction mixture was concentrated and the residue was purified by silica gel column chromatography (hexane: ethyl acetate=1:1) and recrystallized from isopropyl ether to provide the title compound as colorless solid (200 mg).

¹H-NMR (CDCl₃) δ: 1.97(3H,s), 3.47(2H,t,J=7.8 Hz), 4.46(2H,t,J=7.8 Hz), 5.43(2H,s), 7.46(2H,d,J=8.0 Hz), 7.50 (2H,d,J=8.0 Hz), 7.76(2H,d,J=8.0 Hz), 7.78(2H,d,J=8.0 Hz).

IR (KBr): 1650, 1515, 1390 cm⁻¹.

EXAMPLE 131

1-[4-(4-Chlorobenzoyl)benzyl]-6-(3-dimethylaminopropylthio)-5-ethyl-1,5-dihydro-4H-pyrazolo[3,4-d]-pyrimidin-4-one hydrochloride (A)

2-[4-(4-Chlorobenzoyl)benzyl]-6-(3-dimethylaminopropylthio)-5-ethyl-2,3-dihydro-4H-pyrazolo[3,4-d]-pyrimidin-4-one hydrochloride (B)

To a solution of 5-ethyl-6-mercapto-1,5-dihydro-4H-pyrazolo[3,4-d]pyrimidin-4-one potassium (2.0 g) in DMF (25 ml) was added 28% sodium methoxide (1.75 ml). Then, 3-dimethylaminopropyl chloride hydrochloride (1.62 g) was added and the mixture was stirred at 60° C. for 1 day. To this reaction mixture was added 60% sodium hydride (232 mg) and the mixture was stirred at room temperature for 10 minutes. Thereafter, 4-(4-chlorobenzoyl)benzyl bromide (1.778 g) was added and the reaction mixture was stirred at room temperature for 30 minutes. This reaction mixture was concentrated and the residue was dissolved in ethyl acetate, washed with water, dried, and concentrated. The residue was purified by silica gel column chromatography (chloroform: methanol: concentrated aqueous ammonia=50:1:0.1) and treated with hydrogen chloride/ethyl acetate to provide the title compound (A) (518 mg) and (B) (262 mg) both as colorless solid.

Compound (A)

$^1$H-NMR (CDCl$_3$) δ: 1.34(3H,t,J=7.0 Hz), 2.31(2H,m), 2.73(6H,d,J=4.6 Hz), 3.03(2H,m), 3.41(2H,t,J=7.0 Hz), 4.17 (2H,q,J=7.0 Hz), 5.61(2H,s), 7.35(2H,d,J=8.2 Hz), 7.46(2H, d,J=8.6 Hz), 7.73(4H,d,J=8.6 Hz), 8.07(1H,s).

IR (KBr): 1710, 1650, 1545 cm$^{-1}$.

Compound (B)

$^1$H-NMR (CDCl$_3$) δ: 1.33(3H,t,J=7.0 Hz), 2.30–2.50(2H, m), 2.83(6H,d,J=4.4 Hz), 3.19(2H,m), 3.41(2H,t,J=7.0 Hz), 4.15(2H,q,J=7.0 Hz), 5.48(2H,s), 7.40(2H,d,J=8.2 Hz), 7.47 (2H,d,J=8.6 Hz), 7.74(2H,d,J=8.6 Hz), 7.78(2H,d,J=8.2 Hz), 8.07(1H,s).

IR (KBr): 1695, 1655, 1580 cm$^{-1}$.

EXAMPLE 132

5-Ethyl-1-[4-(4-methoxybenzoyl)benzyl]-6-methylthio-1,5-dihydro-4H-pyrazolo[3,4-d]pyrimidin-4-one (A)

5-Ethyl-2-[4-(4-methoxybenzoyl)benzyl]-6-methylthio-2,5-dihydro-4H-pyrazolo[3,4-d]pyrimidin-4-one (B)

To a solution of 5-ethyl-6-methylthio-1,5-dihydro-4H-pyrazolo[3,4-d]pyrimidin-4-one (900 mg) in DMF (20 ml) was added 60% sodium hydride (207 mg) and the mixture was stirred at room temperature for 10 minutes. Then, 4-(4-methoxybenzoyl)benzyl bromide (1.31 g) was added and the mixture was further stirred at room temperature for 30 minutes. This reaction mixture was concentrated and the residue was dissolved in ethyl acetate, washed with water, dried, and concentrated. The residue was purified by silica gel column chromatography (hexane: ethyl acetate-chloroform=3:2:1) to provide the title compounds (A) (400 mg) and (B) (366 mg) both as white solid.

Compound (A)

$^1$H-NMR (CDCl$_3$) δ: 1.35(3H,t,J=7.2 Hz), 2.63(3H,s), 3.89(3H,s), 4.19(2H,q,J=7.2 Hz), 5.54(2H,s), 6.95(2H,d,J= 8.8 Hz), 7.41(2H,d,J=8.0 Hz), 7.73(2H,d,J=8.0 Hz), 7.80 (2H,d,J=8.8 Hz), 8.05(1H,s).

IR (KBr): 1695, 1645, 1595, 1550, 1495, 1315, 1260, 1170 cm$^{-1}$.

Compound (B)

$^1$H-NMR (CDCl$_3$) δ: 1.34(3H,t,J=7.0 Hz), 2.65(3H,s), 3.89(3H,s), 4.17(2H,q,J=7.0 Hz), 5.47(2H,s), 6.96(2H,d,J= 8.8 Hz), 7.40(2H,d,J=8.0 Hz), 7.75(2H,d,J=8.0 Hz), 7.81 (2H,d,J=8.8 Hz), 8.06(1H,s).

IR (KBr): 1695, 1650, 1600, 1575, 1515, 1315, 1280, 1170 cm$^1$.

EXAMPLE 133

7-[4-(4-Chlorobenzoyl)benzyl]-1-ethyl-3-methylxanthine

In DMF (10 ml) was dissolved 1-ethyl-3-methylxanthine (385 mg), a production process for which is described in Journal of American Chemical Society 75, 114, 1953. To this solution were added potassium carbonate (415 mg) and 4-(4-chlorobenzoyl)benzyl bromide (619 mg) and the mixture was stirred at room temperature for 14 hours. This reaction mixture was diluted with water and extracted with ethyl acetate. The extract was washed with saturated aqueous NaCl solution and dried over anhydrous sodium sulfate and the solvent was distilled off. The residue was purified by silica gel column chromatography (hexane: ethyl acetate= 1:4) and recrystallized (ethyl acetate-ether-hexane) to provide the title compound as white powder (207 mg, 25%).

$^1$H-NMR (CDCl$_3$) δ: 1.25(3H,t,J=7.0 Hz), 3.60(3H,s), 4.08(2H,q,J=7.0 Hz), 5.60(2H,s), 7.40–7.53(4H,m), 7.64 (1H,s), 7.70–7.85(4H,m).

IR (KBr): 1695, 1660, 1650, 1600, 1580, 1545, 1455, 1380, 1270, 1230, 1090, 930, 740 cm$^1$.

EXAMPLE 134

2-[4-(4-Chlorobenzoyl)benzyloxy]-3,5-dimethyl-4 (3H)-quinazolinone.

To a solution of 4-(4-chlorobenzoyl)benzyl alcohol (1.0 g) in DMF (20 ml) was added 60% sodium hydride (210 mg) and the mixture was stirred at room temperature for 10 minutes. Then, 2-chloro-3,5-dimethyl-4(3H)-quinazolinone (850 mg) was added and the mixture was stirred at room temperature for 1 hour and at 80° C. for 10 minutes. This reaction mixture was concentrated and the residue was dissolved in ethyl acetate, washed with water, dried, and concentrated. The residue was purified by silica gel column chromatography (hexane: ethyl acetate: chloroform=4:1:1) to provide the title compound as colorless solid (350 mg).

$^1$H-NMR (CDCl$_3$) δ: 2.85(3H,s), 3.53(3H,s), 5.61(2H,s), 7.09(1H,d,J=8.0 Hz), 7.34(1H,d,J=8.0 Hz), 7.42–7.53(3H, m), 7.60(2H,d,J=8.2 Hz), 7.76(2H,d,J=8.6 Hz), 7.82(2H,d, J=8.2 Hz).

IR (KBr): 1680, 1665, 1630, 1600 cm$^{-1}$.

EXAMPLE 135

3,5-Dimethyl-2-[4-(4-fluorobenzoyl)benzyloxy]-4 (3H)-quinazolinone

To a solution of 4-(4-fluorobenzoyl)benzyl alcohol (1.0 g) in DMF (20 ml) was added 60% sodium hydride (210 mg) and the mixture was stirred at room temperature for 10 minutes. Then, 2-chloro-3,5-dimethyl-4(3H)-quinazolinone (907 mg) was added and the mixture was stirred at room temperature for 1 hour. This reaction mixture was concentrated and the residue was dissolved in ethyl acetate, washed with water, dried, and concentrated. The residue was purified by silica gel column chromatography (hexane: ethyl acetate =3:1) to provide the title compound as colorless solid (560 mg).

$^1$H-NMR (CDCl$_3$) δ: 2.85(3H,s), 3.53(3H,s), 5.61(2H,s), 7.09(1H,d,J=8.2 Hz), 7.17(2H,t,J=8.6 Hz), 7.35(1H,d,J=8.2 Hz), 7.50(1H,t,J=8.2 Hz), 7.61(2H,d,J=8.2 Hz), 7.82(2H,d, J=8.2 Hz), 7.86(2H,dd,J=8.6,5.4 Hz).

IR (KBr): 1675, 1660, 1630, 1595 cm$^{-1}$.

EXAMPLE 136

2-[4-(4-Chlorobenzoyl)benzyl]thio-3,5,6-trimethylthieno[2,3-d]pyrimidin-4(3H)-one To a solution of 2-mercapto-3,5,6-trimethylthieno-[2,3-d] pyrimidin-4(3H)-one (1.13 g) and sodium hydroxide (205 mg) in 50% methanol (16 ml)-DMF (4 ml) was added 4-(4-chlorobenzoyl)benzyl bromide (1.69 g) and the mixture was stirred at room temperature for 1 hour. This reaction mixture was poured in water and the resulting crystals were collected by filtration, rinsed with water, and recrystallized from ethyl acetate to provide the title compound as colorless solid (1.425 g).

¹H-NMR (CDCl₃) δ: 2.37(3H,s), 2.45(3H,s), 3.54(3H,s), 4.53(2H,s), 7.46(2H,d,J=8.2 Hz), 7.56(2H,d,J=8.2 Hz), 7.74 (4H,d,J=8.2 Hz).

IR (KBr): 1680, 1655, 1525, 1275, 1090 cm⁻¹.

EXAMPLE 137

2-[4-(4-Chlorobenzoyl)benzyl]thio-3,5-dimethylthieno[2,3-d]pyrimidin-4(3H)-one

To a solution of 3,5-dimethyl-2-mercaptothieno[2,3-d]pyrimidin-4(3H)-one (1.06 g) and sodium hydroxide (205 mg) in 50% methanol (16 ml)-DMF (4 ml) was added 4-(4-chlorobenzoyl)benzyl bromide (1.69 g) and the mixture was stirred at room temperature for 1 hour. This reaction mixture was poured in water and the resulting crystals were collected by filtration, rinsed with water, and recrystallized from ethyl acetate to provide the title compound as colorless solid (878 mg).

¹H-NMR (CDCl₃) δ: 2.55(3H,s), 3.55(3H,s), 4.55(2H,s), 6.67(1H,s), 7.46(2H,d,J=7.8 Hz), 7.57(2H,d,J=8.2 Hz), 7.74 (4H,d,J=8.2 Hz).

IR (KBr): 1680, 1645, 1515, 1285, 1090 cm⁻¹.

EXAMPLE 138

3,5-Dimethyl-2-[4-[4-[[1-(2-dimethylaminoethyl)-1H-tetrazol-5-yl]thiomethyl]benzoyl]benzylthio]-4(3H)-quinazolinone.

In DMF (20 ml) were dissolved 3,5-dimethyl-2-mercapto-4(3H)-quinazolinone (1.03 g), 4,4'-bis(bromomethyl) benzophenone (1.75 g), 1-(2-dimethylaminoethyl)-5-mercapto-1H-tetrazole (865 mg), and 1N-sodium hydroxide/water (11 ml) and the solution was stirred at room temperature for 30 minutes. This reaction mixture was concentrated and the residue was dissolved in ethyl acetate, washed with water, dried, and concentrated. The residue was purified by silica gel column chromatography (chloroform: methanol: aqueous ammonia=50:1:0.1) and crystallized from methanol to provide the title compound as colorless solid (337 mg).

¹H-NMR (CDCl₃) δ: 2.22(6H,s), 2.69(2H,t,J=6.4 Hz), 2.84(3H,s), 3.54(3H,s), 4.24(2H,t,J=6.4 Hz), 4.58(2H,s), 4.59(2H,s), 7.15(1H,d,J=7.2 Hz), 7.40–7.63(6H,m), 7.70–7.80(4H,m).

IR (KBr): 1670, 1650, 1605, 1580, 1555, 1305, 1280 cm⁻¹.

EXAMPLE 139

3,5-Dimethyl-2-[4-[4-[(3,5,6-trimethyl-3H-pyrimidin-4-one-2-yl) thiomethyl]benzoyl]benzylthio]-4-(3H)-quinazoline A solution of 3,5-dimethyl-2-mercapto-4(3H)-quinazolinone (1.03 g), 4,4'-bis (bromomethyl) benzophenone (1.75 g), 3,5,6-trimethyl-2-mercapto-3H-pyrimidin-4-one (960 mg), and 1N-sodium hydroxide/water (11 ml) in DMF (20 ml) was stirred at room temperature for 30 minutes. This reaction mixture was concentrated and the residue was dissolved in ethyl acetate, washed with water, dried, and concentrated. The residue was purified by silica gel column chromatography (hexane: ethyl acetate: chloroform=3:1:1) and crystallized from methanol to provide the title compound as colorless solid (662 mg).

¹H-NMR (CDCl₃) δ: 2.03(3H,s), 2.28(3H,s), 2.85(3H,s), 3.47(3H,s), 3.54(3H,s), 4.47(2H,s), 4.59(2H,s), 7.15(1H,d, J=7.2 Hz), 7.40–7.63(6H,m), 7.75(2H,d,J=8.0 Hz), 7.76(2H, d,J=8.2 Hz).

IR (KBr): 1660, 1555, 1520 cm⁻¹.

EXAMPLE 140

3,5-Dimetyl-2-[4-(4-toluoyl)benzylthio)-4(3H)-quinazolinone

A solution of 3,5-dimethyl-2-mercapto-4(3H)-quinazolinone (197 mg), 4-(4-toluoyl)benzyl bromide (336 mg) and 1N-sodium hydroxide/water (1 ml) in DMF (10 ml) was stirred at room temperature for 30 minutes. This reaction mixture was concentrated and the residue was dissolved in ethyl acetate, washed with water, dried, and concentrated. The residue was purified by silica gel column chromatography (hexane: ethyl acetate: chloroform=5:1:1) and crystallized from methanol to provide the title compound as colorless solid (140 mg).

¹H-NMR (CDCl₃) δ: 2.44(3H,s), 2.85(3H,s), 3.55(3H,s), 4.59(2H,s), 7.15(1H,d,J=8.2 Hz), 7.27(2H,d,J=8.0 Hz), 7.40–7.63(4H,m), 7.70(2H,d,J=8.2 Hz), 7.75(2H,d,J=8.2 Hz).

IR (KBr): 1665, 1650, 1605, 1580, 1555, 1310, 1280 cm⁻¹.

EXAMPLE 141

3,5-Dimethyl-2-[4-[4-[(thiazolidin-2-yl)thiomethyl] benzoyl]benzylthio]-4(3H)-quinazolinone A solution of 3,5-dimethyl-2-mercapto-4(3H)-quinazolinone (1.03 g), 4,4'-bis (bromomethyl) benzophenone (1.75 g), 2-mercaptothiazoline (600 mg), and 1N-sodium hydroxide/water (11 ml) in DMF (20 ml) was stirred at room temperature for 30 minutes. This reaction mixture was concentrated and the residue was dissolved in ethyl acetate, washed with water, dried, and concentrated. The residue was purified by silica gel column chromatography (hexane: ethyl acetate: chloroform=3:1:1) and crystallized from methanol to provide the title compound as colorless solid (489 mg).

¹H-NMR (CDCl₃) δ: 2.84(3H,s), 3.43(2H,t,J=8.2 Hz), 3.55(3H,s), 4.23(2H,t,J=8.2 Hz), 4.41(2H,s), 4.59(2H,s), 7.15(1H,d,J=7.0 Hz), 7.40–7.63(6H,m), 7.74(2H,d,J=8.0 Hz), 7.76(2H,d,J=8.2 Hz).

IR (KBr): 1660, 1605, 1580, 1555, 1305, 1280 cm⁻¹.

EXAMPLE 142

3,5-Dimethyl-2-[4-[4-[(1-methyl-1H-tetrazol-5-yl) thiomethyl]benzoyl]benzylthio]-4(3H)-quinazolinone A solution of 3,5-dimethyl-2-mercapto-4(3H)-quinazolinone (1.03 g), 4,4'-bis (bromomethyl) benzophenone (1.75 g), 1-methyl-5-mercapto-1H-tetrazole (700 mg), and 1N-aqeuous sodium hydroxide solution (5.5 ml) in DMF (20 ml) was stirred at room temperature for 30 minutes. This reaction mixture was concentrated and the residue was dissolved in ethyl acetate, washed with water, dried, and concentrated. The residue was purified by silica gel column chromatography (chloroform: methanol: aqueous ammonia=50:1:0.1) and crystallized from methanol to provide the title compound as colorless solid (603 mg).

$^1$H-NMR (CDCl$_3$) δ: 2.85(3H,s), 3.55(3H,s), 3.86(3H,s), 4.60(2H,s), 4.61(2H,s), 7.16(1H,d,J=6.6 Hz), 7.40–7.63(6H, m), 7.75(4H,d,J=8.0 Hz).

IR (KBr): 1665, 1605, 1580, 1555, 1305, 1280 cm$^{-1}$.

EXAMPLE 143

2-[4-(4-Chlorobenzoyl)benzylthio]-4(3H)-quinazolinone

A solution of 2-mercapto-4(3H)-quinazolinone (1.78 g), 4-(4-chlorobenzoyl)benzyl bromide (3.07 g) and 1N-sodium hydroxide/water (10.5 ml) in ethanol (20 ml) was stirred at room temperature for 30 minutes. To the reaction mixture was added water and the resulting precipitate was collected by filtration, washed with water, methanol and ethyl acetate, dried, and recrystallized from ethyl acetate to provide the title compound as colorless solid (3.24 g).

$^1$H-NMR (CDCl$_3$) δ: 4.58(2H,s), 7.33–7.80(11H,m), 8.14 (1H,d,J=8.0 Hz), 12.30(1H,brs).

IR (KBr): 1690, 1660, 1580, 1560 cm$^{-1}$.

EXAMPLE 144

3,5-Dimethyl-2-[4-[4-(4-methylpiperazinylmethyl) benzoyl]benzylthio]-4(3H)-quinazolinone A solution of 3,5-dimethyl-2-mercapto-4(3H) quinazolinone (1.03 g), 4,4'-bis (bromomethyl) benzophenone (1.75 g), N-methylpiperazine (500 ml) and 1N-sodium hydroxide/water (5.5 ml) in DMF (35 ml) was stirred at room temperature for 30 minutes. This reaction mixture was concentrated and the residue was dissolved in ethyl acetate, washed with water, dried, and concentrated. The residue was purified by silica gel column chromatography (chloroform: methanol: aqueous ammonia=40:1:0.1) to provide the title compound as colorless amorphous solid (180 mg).

$^1$H-NMR (CDCl$_3$) δ: 2.31(3H,s), 2.35–2.60(8H,m), 2.85 (3H,s), 3.55(3H,s), 3.58(2H,s), 4.60(2H,s), 7.16(1H,d,J=7.0 Hz), 7.40–7.63(6H,m), 7.75(2H,d,J=8.0 Hz), 7.77(2H,d,J= 8.2 Hz).

IR (KBr): 1670, 1605, 1580, 1555, 1305, 1280 cm$^{-1}$.

EXAMPLE 145

3,5-Dimethyl-2-[4-[4-(4-phenylpiperazinylmethyl) benzoyl]benzylthio]-4-(3H)-quinazolinone A solution of 3,5-dimethyl-2-mercapto-4(3H) quinazolinone (1.03 g), 4,4'-bis (bromomethyl) benzophenone (1.75 g), phenylpiperazine (810 mg), and 1N-sodium hydroxide/water (5.5 ml) in DMF (35 ml) was stirred at 60° C. for 1 hour. This reaction mixture was concentrated and the residue was dissolved in ethyl acetate, washed with water, dried, and concentrated. The residue was purified by silica gel column chromatography (hexane: ethyl acetate: chloroform=4:1:1) and crystallized from isopropyl ether to provide the title compound as colorless solid (372 mg).

$^1$H-NMR (CDCl$_3$) δ: 2.64(4H,t,J=5.0 Hz), 2.85(3H,s), 3.22(4H,t,J=5.0 Hz), 3.55(3H,s), 3.64(2H,S), 4.60(2H,s), 6.80–7.00(3H,m), 7.15(1H,d,J=7.0 Hz), 7.20–7.32(2H,m), 7.40–7.65(6H,m), 7.76(2H,d,J=8.2 Hz), 7.78(2H,d,J=8.2 Hz).

IR (KBr): 1685, 1655, 1600, 1550, 1305, 1260, 1190 cm$^{-1}$.

EXAMPLE 146

2-[4-(4-Acetoxybenzoyl)benzylthio]-3,5-dimethylthieno[2,3-d]pyrimidin-4(3H)-one

To a solution of 3,5-dimethyl-2-mercaptothieno[2,3-d] pyrimidin-4(3H)-one (1.40 g) and 1N-sodium hydroxide/water (6.7 ml) in ethanol (13 ml)-DMF (25 ml) was added 4-(4-acetoxybenzoyl)benzyl bromide (2.68 g) and the mixture was stirred at room temperature at 60° C. for 1 hour. This reaction mixture was poured in water and extracted with ethyl acetate. The extract was washed with water, dried, and concentrated, and the residue was recrystallized from methanol to provide the title compound as colorless solid (887 mg).

$^1$H-NMR (CDCl$_3$) δ: 2.44(3H,s), 2.55(3H,s), 3.55(3H,s), 4.54(2H,s), 6.67(1H,s), 7.21(2H,d,J=8.6 Hz), 7.56(2H,d,J= 8.2 Hz), 7.77(2H,d,J=8.2 Hz), 7.84(2H,d,J=8.6 Hz).

IR (KBr): 1750, 1680, 1650, 1600, 1520, 1195 cm$^{-1}$.

EXAMPLE 147

3,5-Dimethyl-2-[4-(4-hydroxybenzoyl)benzylthio]-thieno[2,3-d]pyrimidin-4(3H)-one A solution of 2-[4-(4-acetoxybenzoyl)benzylthio]-3,5-dimethylthieno [2,3-d]pyrimidin-4(3H)-one (1.40 g) and 1N-sodium hydroxide/water (6.7 ml) in tetrahydrofuran (20 ml) was stirred at room temperature for 10 minutes. This reaction mixture was concentrated and the residue was dissolved in water and acidified with 1N-HCl. The resulting precipitate was extracted with ethyl acetate, washed with water, dried, and concentrated. The residue was recrystallized from methanol-ethyl acetate to provide the title compound as colorless solid (775 mg).

$^1$H-NMR (CDCl$_3$) δ: 2.55(3H,d,J=1.2 Hz), 3.55(3H,s), 4.55(2H,s), 5.59(1H,s), 6.67(1H,d,J=1.2 Hz), 6.91(2H,d,J= 8.6 Hz), 7.55(2H,d,J=8.2 Hz), 7.73(2H,d,J=8.2 Hz), 7.78 (2H,d,J=8.6 Hz).

IR (KBr): 3320, 1645, 1600, 1580, 1520, 1310, 1280 cm$^{-1}$.

EXAMPLE 148

3,5-Dimethyl-2-[4-[4-(2-morpholinoethoxy)benzoyl] -benzylthio]thieno[2,3-d]pyrimidin-4(3H)-one A solution of 3,5-dimethyl-2-[4-(4-hydroxybenzoyl) benzylthio]thieno[2,3-d]pyrimidin-4(3H)-one (422 g), 1-(2-chloroethyl)morpholine hydrochloride (205 mg), and potassium carbonate (414 mg) in DMF (10 ml) was stirred at 60° C. for 24 hours. This reaction mixture was concentrated and the residue was dissolved in water and extracted with ethyl acetate. The extract was washed with water, dried, and concentrated, and the residue was crystallized from hexane-isopropyl ether to provide the title compound as light-yellow solid (495 mg).

$^1$H-NMR (CDCl$_3$) δ: 2.55(3H,d,J=1.2 Hz), 2.59(4H,t,J= 4.6 Hz), 2.84(2H,t,J=5.8 Hz), 3.55(3H,s), 3.75(4H,t,J=4.6 Hz), 4.19(2H,t,J=5.8 Hz), 4.55(2H,s), 6.67(1H,d,J=1.2 Hz), 6.96(2H,d,J=9.0 Hz), 7.55(2H,d,J=8.4 Hz), 7.73(2H,d,J=8.4 Hz), 7.81(2H,d,J=9.0 Hz).

IR (KBr): 1680, 1650, 1600, 1530, 1310, 1265, 1170, 1120 cm$^{-1}$.

EXAMPLE 149

2-[4-(4-Chlorobenzoyl)benzylthio]-3-methyl-5,6,7,8-tetrahydro-4(3H)-quinazolinone A solution of 2-mercapto-3-methyl-5,6,7,8-tetrahydro-4 (3H)-quinazolinone (980 mg), 4-(4-chlorobenzoyl) benzyl bromide (1.53 g), and 1N-sodium hydroxide/water (5.5 ml) in ethanol (10 ml)-DMF (5 ml) was stirred at room temperature for 30 minutes. This reaction mixture was concentrated and the residue was dissolved in ethyl acetate, washed with water, dried, and concentrated. The residue was recrystallized from methanol-ethyl acetate to provide the title compound as colorless solid (1.27 g).

$^1$H-NMR (CDCl$_3$) δ: 1.65–1.85(4H,m), 2.40–2.65(4H, m), 3.47(3H,s), 4.47(2H,s), 7.46(2H,d,J=8.2 Hz), 7.55(2H, d,J=8.2 Hz), 7.74(2H,d,J=8.2 Hz), 7.75(2H,d,J=8.2 Hz).

IR (KBr): 1655, 1520, 1410, 1280, 1270 cm$^{-1}$.

EXAMPLE 150

2-[4-(4-Chlorobenzoyl)benzylthio]-3-fluoromethyl-4 (3H)-quinazolinone

To a suspension of 2-[4-(chlorobenzoyl) benzylthio]-4 (3H)-quinazolinone (1.0 g) in DMF (30 ml) was added 60% sodium hydride (100 mg). When the solution had become transparent, fluoromethyl bromide (500 mg) was added and the mixture was stirred at room temperature for 30 minutes. The solvent was then distilled off and the residue was dissolved in ethyl acetate and washed with water. The organic layer was dried, purified by silica gel column chromatography (hexane: ethyl acetate: chloroform=5:1:1), and recrystallized from methanol to provide the title compound as colorless solid (500 mg).

$^1$H-NMR (CDCl$_3$) δ: 4.63(2H,s), 6.21(2H,d,J=51.2 Hz), 7.38–7.80(11H,m), 8.24(1H,d,J=7.8 Hz).

IR (KBr): 1695, 1650, 1605, 1580, 1555 cm$^{-1}$.

EXAMPLE 151

3,5-Dimethyl-2-[4-[4-[(1,3-dimethylxanthin-7-yl) methyl]benzoyl]benzylthio]-4(3H)-quinazolinone A solution of 4,4'-bis(bromomethyl)benzophenone (1.75 g), theophylline (900 mg) and potassium carbonate (828 mg) in DMF (40 ml) was stirred at 40° C. for 1 hour. Then, 3,5-dimethyl-2-mercapto-4(3H)-quinazolinone (1.03 g) was added and the mixture was stirred at 60° C. for 1 hour. This reaction mixture was concentrated, the residue was dissolved in ethyl acetate, and the solution was washed with water, dried, and concentrated. The residue was purified by silica gel column chromatography (ethyl acetate) to provide the title compound as colorless solid (787 mg).

$^1$H-NMR (CDCl$_3$) δ: 2.84(3H,s), 3.40(3H,s), 3.54(3H,s), 3.60(3H,s), 4.58(2H,s), 5.58(2H,s), 7.15(1H,d,J=7.2 Hz), 7.35–7.80(11H,m).

IR (KBr): 1700, 1660, 1605, 1555 cm$^{-1}$.

EXAMPLE 152

3-Methyl-2-[4-(4-trifluoromethylbenzoyl) benzylthio]-thieno[3,2-d]pyrimidin-4(3H)-one To a solution of 2-mercapto-3-methylthieno[3,2-d]-pyrimidin-4(3H)-one (1.0 g) and 1N-sodium hydroxide/water (5.1 mg) in ethanol (10 ml) was added 4-(4-trifluoromethylbenzoyl)benzyl bromide (1.73 g) and the mixture was stirred at 60° C. for 1 hour. This reaction mixture was poured in water and the resulting crystals were collected by filtration, rinsed with water, and recrystallized from ethyl acetate-hexane to provide the title compound as colorless solid (1.11 g).

$^1$H-NMR (CDCl$_3$) δ: 3.61(3H,s), 4.58(2H,s), 7.23(1H,d, J=5.2 Hz), 7.61(2H,d,J=8.0 Hz), 7.70–7.81(5H,m), 7.88(2H, d,J=8.0 Hz).

IR (KBr): 1670, 1655, 1510, 1330, 1120 cm.

EXAMPLE 153

2-[4-(4-Acetoxybenzoyl)benzylthio]-3-methylthieno-[3,2-d]pyrimidin-4(3H)-one

To a solution of 2-mercapto-3-methylthieno[3,2-d]-pyrimidin-4(3H)-one (1.98 g) and 1N-sodium hydroxide/water (10 ml) in ethanol (30 ml) was added 4-(4-acetoxybenzoyl)benzyl bromide (3.95 g) and the mixture was stirred at 60° C. for 1 hour. This reaction mixture was poured in water and the resulting crystals were collected by filtration, rinsed with water, and recrystallized from ethyl acetate to provide the title compound as colorless solid (3.87 g).

$^1$H-NMR (CDCl$_3$) δ: 2.35(3H,s), 3.62(3H,s), 4.58(2H,s), 7.21(2H,d,J=8.6 Hz), 7.25(1H,d,J=5.2 Hz), 7.59(2H,d,J=8.2 Hz), 7.72–7.90(5H,m).

IR (KBr): 1760, 1670, 1655, 1505, 1225 cm$^{-1}$.

EXAMPLE 154

2-[4-(4-Hydroxybenzoyl)benzylthio]-3-methylthieno-[3,2-d]pyrimidin-4(3H)-one

To a solution of 2-[4-(4-acetoxybenzoyl) benzylthio]-3-methylthieno[3,2-d]pyrimidin-4(3H)-one (3.51 g) in THF (20 ml) was added 1N-sodium hydroxide/water (10 ml) and the mixture was stirred at room temperature for 30 minutes. This reaction mixture was concentrated, the residue was dissolved in water, and 1N-hydrochloric acid was added. The resulting crystals were collected by filtration, rinsed with water, and dried to provide the title compound as colorless solid (3.22 g).

$^1$H-NMR (CDCl$_3$) δ: 3.61(3H,s), 4.58(2H,s), 6.91(2H,d, J=8.6 Hz), 7.25(1H,d,J=5.6 Hz), 7.56(2H,d,J=8.2 Hz), 7.68–7.80(5H,m).

IR (KBr): 3200 (br), 1660, 1630, 1605, 1505, 1280 cm$^{-1}$.

EXAMPLE 155

3-Methyl-2-[4-[4-(4-phenylpiperazinylmethyl) benzoyl]benzylthio]thieno[3,2-d]pyrimidin-4(3H)-one A solution of 2-mercapto-3-methylthieno[3,2-d]-pyrimidin-4(3H)-one (990 mg), 4,4'-bis (bromomethyl) benzophenone (1.75 g), phenylpiperazine (810 mg) and potassium carbonate (828 mg) in DMF (30 ml) was stirred at 60° C. for 2 hours. This reaction mixture was concentrated and the residue was dissolved in ethyl acetate. The solution was washed with water, dried, and concentrated, and the residue was purified by silica gel column chromatography (chloroform: methanol: aqueous ammonia=250:1:0.1) to provide the title compound as light-yellow syrup (428 mg).

$^1$H-NMR (CDCl$_3$) δ: 2.64(4H,t,J=4.8 Hz), 3.22(4H,t,J= 4.8 Hz), 3.61(3H,s), 3.64(2H,s), 4.58(2H,s), 6.80–6.96(3H, m), 7.20–7.31(3H,m), 7.48(2H,d,J=8.2 Hz), 7.58(2H,d,J= 8.4 Hz), 7.70–7.82(5H,m).

IR (Neat): 1670, 1600, 1535, 1505, 1275 cm$^{-1}$.

EXAMPLE 156

3-Methyl-2-[4-[4-(2-morpholinoethoxy) benzoyl] benzylthio]thieno[3,2-d]pyrimidin-4(3H)-one A solution of 2-[4-(4-hydroxybenzoyl)benzylthio]-3-methylthieno[3,2-d]pyrimidin-4(3H)-one (408 mg), 1-(2- chloroethyl)morpholine hydrochloride (205 mg) and potassium carbonate (414 mg) in DMF (10 ml) was stirred at 60° C. for 15 hours. This reaction mixture was concentrated and poured in water-ethyl acetate and the resulting crystals were collected by filtration, rinsed with water, and dried to provide the title compound as colorless solid (410 mg).

$^1$H-NMR (CDCl$_3$) δ: 2.59(4H,t,J=4.6 Hz), 2.84(2H,t,J=5.7 Hz), 3.61(3H,s), 3.74(4H,t,J=4.6 Hz), 4.19(2H,t,J=5.7 Hz), 4.58(2H,s), 6.96(2H,d,J=8.8 Hz), 7.24(1H,d,J=5.2 Hz), 7.56(2H,d,J=8.4 Hz), 7.69–7.85(5H,m).

IR (KBr): 1670, 1645, 1595, 1505, 1260 cm$^{-1}$.

EXAMPLE 157

2-[4-(6-Chloronicotinoyl)benzylthio]-3-methylthieno [3,2-d]pyrimidin-4(3H)-one

To a solution of 2-mercapto-3-methylthieno[3,2-d]-pyrimidin-4(3H)-one (1.98 g) and 1N-sodium hydroxide/water (10.5 ml) in ethanol (30 ml) was added 4-(6-chloronicotinoyl)benzyl bromide (3.35 g) and the mixture was stirred at 60° C. fro 1 hour. This reaction mixture was poured in water and the resulting crystals were collected by filtration, rinsed with water, and recrystallized from ethyl acetate to provide the title compound as light-yellow solid (3.194 g).

$^1$H-NMR (CDCl$_3$) δ: 3.62(3H,s), 4.59(2H,s), 7.24(1H,d, J=5.2 Hz), 7.48(1H,d,J=8.0 Hz), 7.63(2H,d,J=8.4 Hz), 7.75 (1H,d,J=5.2 Hz), 7.77(2H,d,J=8.4 Hz), 8.09(1H,dd,J=2.6, Hz), 8.76(1H,d,J=2.6 Hz).

IR (KBr): 1670, 1655, 1510, 1290 cm$^{-1}$.

EXAMPLE 158

3-Methyl-2-[4-[6-(4-piperidinopiperidinyl) nicotinoyl]benzylthio]thieno[3,2-d]pyrimidin-4(3H)-one hydrochloride A solution of 2-[4-(6-chloronicotinoyl]benzylthio]-3-methylthieno[3,2-d]pyrimidin-4(3H)-one (427 mg) and 4-piperidinopiperidine (202 mg) in pyridine (10 ml) was stirred at 80° C. for 10 hours. This reaction mixture was concentrated, the residue was dissolved in chloroform, and the solution was washed with water, dried, and concentrated. The residue was purified by silica gel column chromatography (chloroform: methanol: aqueous ammonia=50:1:0.1) and treated with HCl/ethyl acetate for conversion to hydrochloride to provide the title compound as colorless solid (373 mg).

$^1$H-NMR (CDCl$_3$) δ: 1.80–2.41(6H,m), 2.50–2.92(4H, m), 3.30–3.60(7H,m), 3.62(3H,s), 4.59(2H,s), 4.88(2H,m), 7.20–7.30(2H,m), 7.60–7.80(5H,m), 8.38(1H,br d,J=8.8 Hz), 8.47(1H,br s).

IR (KBr): 1660, 1640, 1600, 1535, 1505 cm$^{-1}$.

EXAMPLE 159

2-[4-(2,4-Dichlorobenzoyl)benzylthio]-3-methylthieno[3,2-d]pyrimidin-4(3H)-one

To a solution of 2-mercapto-3-methylthieno[3,2-d]-pyrimidin-4(3H)-one (1.0 g) and 1N-sodium hydroxide/water (5.5 ml) in ethanol (20 ml) was added 4-(2,4-dichlorobenzoyl)benzyl bromide (1.91 g) and the mixture was stirred at 60° C. for 1 hour. This reaction mixture was poured in water and the resulting crystals were collected by filtration, rinsed with water, and recrystallized from ethyl acetate to provide the title compound as colorless solid (1.69 g).

$^1$H-NMR (CDCl$_3$) δ: 3.60(3H,s), 4.56(2H,s), 7.22(1H,d, J=5.4 Hz), 7.27–7.40(2H,m), 7.49(1H,d,J=2.0 Hz), 7.57(2H, d,J=8.2 Hz), 7.74(1H,d,J=5.4 Hz), 7.76(2H,d,J=8.2 Hz).

IR (KBr): 1665, 1650, 1600, 1535, 1510, 1290 cm$^{-1}$.

EXAMPLE 160

2-[4.-(1-Indolylcarbonyl)benzylthio]-3-methylthieno [3,2-d]pyrimidin-4(3H)-one

To a solution of 2-mercapto-3-methylthieno[3,2-d]-pyrimidin-4(3H)-one (1.0 g) and 1N-sodium hydroxide/water (5.5 ml) in ethanol (20 ml) was added 4-(1-indolylcarbonyl)benzyl chloride (1.5 g) and the mixture was stirred at 60° C. for 1 hour. This reaction mixture was poured in water and the resulting crystals were collected by filtration, rinsed with water, and recrystallized from ethyl acetate to provide the title compound as colorless solid (808 mg).

$^1$H-NMR (CDCl$_3$) δ: 3.62(3H,s), 4.60(2H,s), 6.61(1H,d, J=3.8 Hz), 7.20–7.42(4H,m), 7.56–7.80(6H,m), 8.39(1H,d, J=8.4 Hz).

IR (KBr): 1680, 1665, 1530, 1510, 1450, 1335 cm$^{-1}$.

EXAMPLE 161

3,5-Dimethyl-2-[4-[4-(2-piperidinoethoxy)benzoyl]-benzylthio]thieno[2,3-d]pyrimidin-4(3H)-one hydrochloride A solution of 3,5-dimethyl-2-[4-(4-hydroxybenzoyl) benzylthio]thieno[2,3-d]pyrimidin-4(3H)-one (255 mg), 1-(2-chloroethyl)piperidine hydrochloride (122 mg) and potassium carbonate (250 mg) in DMF (8 ml) was stirred at 60° C. for 15 hours. This reaction mixture was concentrated, the residue was dissolved in ethyl acetate, and the solution was washed with water and dried. Then, HCl/ethyl acetate was added and the precipitated hydrochloride was collected by filtration and dried to provide the title compound as colorless solid (268 mg).

$^1$H-NMR (CDCl$_3$) δ: 1.35–2.00(6H,m), 2.15–2.40(2H, m), 2.55(3H,d,J=1.2 Hz), 2.82(2H,m), 3.43(2H,m), 3.55(3H, s), 3.67(2H,m), 4.55(2H,s), 4.69(2H,t,J=4.4 Hz), 6.67(1H, d,J=1.2 Hz), 6.97(2H,d,J=8.8 Hz), 7.56(2H,d,J=8.2 Hz), 7.73(2H,d,J=8.2 Hz), 7.81(2H,d,J=8.8 Hz), 12.64(1H,br s).

IR (KBr): 1680, 1640, 1595, 1515, 1310, 1250 cm$^{-1}$.

EXAMPLE 162

3-Methyl-2-[4-[4-(2-piperidinoethoxy) benzoyl] benzylthio]thieno[3,2-d]pyrimidin-4(3H)-one A solution of 2-[4-(4-hydroxybenzoyl)benzylthio]-3-methylthieno[3,2-d]pyrimidin-4(3H)-one (408 mg), 1-(2-chloroethyl) piperidine hydrochloride (202 mg) and potassium carbonate (414 mg) in DMF (10 ml) was stirred at 60° C. for 15 hours. This reaction mixture was concentrated and the residue was dissolved in ethyl acetate, washed with water, and dried. Then, hydrogen chloride/ethyl acetate was added and the precipitated hydrochloride was collected by filtration and dried to provide the title compound as colorless solid (471 mg).

$^1$H-NMR (CDCl$_3$) δ: 1.35–2.00(6H,m), 2.15–2.40(2H, m), 2.81(2H,m), 3.42(2H,m), 3.62(3H,s), 3.67(2H,m), 4.58 (2H,s), 4.69(2H,t,J=4.4 Hz), 6.97(2H,d,J=8.8 Hz), 7.24(1H, d,J=5.2 Hz), 7.58(2H,d,J=8.2 Hz), 7.73(2H,d,J=8.2 Hz), 7.75(1H,d,J=5.2 Hz), 7.81(2H,d,J=8.8 Hz), 12.65(1H,br s).

IR (KBr): 1680, 1635, 1600, 1535, 1505, 1300, 1280, 1250 cm$^{-1}$.

EXAMPLE 163

1-[4-(4-Chlorobenzoyl)benzyl]-6,7-dimethylimidazo[1,2-a]pyrimidin-5(1H)-one

To a solution of 6,7-dimethylimidazo[1,2-a]-pyrimidin-5-one (1.10 g, 6.75 mmol) and 4-(4-chlorobenzoyl) benzyl bromide (1.60 g, 5.20 mmol) in DMSO (20.0 ml) was added potassium carbonate (1.16 g, 8.39 mmol) and the mixture was stirred at room temperature overnight. This reaction mixture was diluted with ethyl acetate and washed with saturated aqueous NaCl solution. The organic layer was dried over $MgSO_4$ and concentrated under reduced pressure. The residue was purified by silica gel column chromatography (developer: ethyl acetate) to provide a colorless amorphous solid. This solid was recrystallized from ethyl acetate to provide colorless needles. 1.16 g (57%)

$^1$H-NMR (CDCl$_3$) δ: 2.15(3H,s), 2.41(3H,s), 5.33(2H,s), 6.86(1H,d,J=2.8 Hz), 7.48–7.41(4H,m), 7.54(1H,d,J=2.8 Hz), 7.72(2H,d,J=7.8 Hz), 7.77(2H,d,J=7.8 Hz).

IR (KBr): 1655, 1583, 1522, 1279, 1223, 1090, 926, 733 cm$^{-1}$.

EXAMPLE 164

1-[4-(2,4-Dichlorobenzoyl)benzyl]-6,7-dimethylimidazo[1,2-a]pyrimidin-5(1H)-one

To a solution of 6,7-dimethylimidazo[1,2-a]-pyrimidin-5-one (0.401 g, 2.46 mmol) and 4-(2,4-dichlorobenzoyl) benzyl bromide (0.86 g, 2.50 mmol) in DMSO (10.0 ml) was added potassium carbonate (0.376 g, 2.72 mmol) and the mixture was stirred at room temperature overnight. This reaction mixture was diluted with ethyl acetate and washed with saturated aqueous NaCl solution. The organic layer was dried over $MgSO_4$ and concentrated under reduced pressure. The residue was recrystallized from methanol to provide colorless needles.

0.578 g (55%)

$^1$H-NMR (CDCl$_3$) δ: 2.14(3H,s), 2.88(3H,s), 5.32(2H,s), 6.83(1H,d,J=2.8 Hz), 7.32–7.39(4H,m), 7.48–7.54(2H,m), 7.78(2H,d,J=8.4 Hz).

IR (KBr): 1659, 1581, 1521, 1284, 1223, 930, 733 cm$^{-1}$.

EXAMPLE 165

1-[3-(4-Chlorobenzoyl)benzyl]-6,1-dimethylimidazo-[1,2-a]pyrimidin-5(1H)-one

To a solution of 6,7-dimethylimidazo[1,2-a]-pyrimidin-5-one (0.402 g, 2.47 mmol) and 3-(4-chlorobenzoyl) benzyl bromide. (0.76 g, 2.45 mmol) in DMSO (10.0 ml) was added potassium carbonate (0.360 g, 2.60 mmol) and the mixture was stirred at room temperature overnight. This reaction mixture was diluted with ethyl acetate and washed with saturated aqueous NaCl solution. The organic layer was dried over $MgSO_4$ and concentrated under reduced pressure. The residue was recrystallized from ethyl acetate to provide colorless needles. 0.373 g (39%)

$^1$H-NMR (CDCl$_3$) δ: 2.15(3H,s), 2.38(3H,s), 5.31(2H,s), 6.85(1H,d,J=2.6 Hz), 7.43–7.55(4H,m), 7.69–7.79(4H,m).

IR (KBr): 1657, 1583, 1522, 1281, 1221, 727 cm$^{-1}$.

EXAMPLE 166

7-[4-(4-Chlorobenzoyl)benzyl]-1,3-diethylxanthine

To a solution of 1,3-diethylxanthine (190 mg), a synthetic process for which is described in Journal of American Chemical Society, 75, 114 (1953), in DMF (5 ml) were added potassium carbonate (189 mg) and 4-(4-chlorobenzoyl)benzyl bromide (282 mg) and the mixture was stirred at room temperature for 17 hours. This reaction mixture was diluted with water and extracted with ethyl acetate. The extract was washed with saturated aqueous NaCl solution and dried over anhydrous sodium sulfate and the solvent was distilled off. The residue was purified by silica gel column chromatography (hexane: ethyl acetate= 1:1) and recrystallized (ether-hexane) to provide the title compound as colorless powder (217 mg, 54%).

$^1$H-NMR (CDCl$_3$) δ: 1.25(3H,t,J=7.0 Hz), 1.36(3H,t,J=7.0 Hz), 4.07(2H,q,J=7.0 Hz), 4.18(2H,q,J=7.0 Hz), 5.59 (1H,s), 7.41–7.52(4H,m), 7.63(1H,s), 7.69–7.83(4H,m).

IR (KBr): 1700, 1660, 1650, 1455, 1270 cm$^{-1}$.

EXAMPLE 167

6-Chloro-2-[4-(4-chlorobenzoyl)benzyl]thio-3-methyl-4(3H)-quinazolinone

To a solution of 6-chloro-3-methyl-2-mercaptoquinazolin-4-one (0.500 g, 2.21 mmol) in EtOH (10.0 ml)-THF (10.0 ml) was added 1N-aqueous sodium hydroxide solution (2.50 ml). Then, 4-(4-chlorobenzoyl) benzyl bromide (0.261, 0.843 mmol) was added and the mixture was stirred at room temperature overnight. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate-methanol to provide colorless needles. 0.230 g (68%)

$^1$H-NMR (CDCl$_3$) δ: 3.60(3H,s), 4.59(2H,s), 7.45(2H,d, J=8.4 Hz), 7.53(1H,d,J=8.6 Hz), 7.59(2H,d,J=8.4 Hz), 7.63 (1H,dd,J=8.6&2.2 Hz), 7.75(2H,d,J=8.4 Hz), 8.19(1H,d,J= 2.2 Hz).

IR (KBr): 1741, 1672, 1549, 1470, 1410, 1308, 1297, 1082, 930, 832, 733 cm$^{-1}$.

EXAMPLE 168

2-[4-(4-Chlorobenzoyl)benzyl]thio-3,6-dimethyl-4(3H)-quinazolinone

To a solution of 3,6-dimethyl-2-mercaptoquinazolin-4-one (0.160 g, 0.776 mmol) in EtOH (5.0 ml)-THF (5.0 ml) was added 1N-aqueous sodium hydroxide solution (1.0 ml). Then, 4-(4-chlorobenzoyl) benzyl bromide (0.261 g, 0.843 mmol) was added and the mixture was stirred at room temperature for 2 hours. The solvent was then distilled off and the residue was dissolved in ethyl acetate and washed with saturated aqueous NaCl solution. The organic. layer was dried over $MgSO_4$ and concentrated under reduced pressure. The residue was recrystallized from ethyl acetate to provide colorless needles.

0.230 g (68%)

$^1$H-NMR (CDCl$_3$) δ: 2.47(3H,s), 3.60(3H,s), 4.60(2H,s), 7.43–7.52(4H,m), 7.60–7.63(2H,m), 7.72–7.77(4H,m), 8.03 (1H,bs).

IR (KBr): 1678, 1549, 1489, 1406, 1311, 1286, 1136, 1072, 928, 829, 771, 730, 629, 534, 470 cm$^{-1}$.

EXAMPLE 169

1-[4-(4-Chlorobenzoyl)benzyl]-6-ethyl-7-methylimidazo[1,2-a]pyrimidin-5(1H)-one

To a solution of 6-ethyl-7-methylimidazo[1,2-a]-pyrimidin-5-one (0.710 g, 4.00 mmol) and 4-(4- chlorobenzoyl)benzyl bromide (1.12 g, 3.6 mmol) in DMF (15.0 ml) was added potassium carbonate (0.600 g, 4.3 mmol) and the mixture was stirred at room temperature overnight. The solvent was then distilled off under reduced pressure and the residue was purified by silica gel column chromatography (developer; methylene chloride: acetone= 5:1). The colorless solid obtained was recrystallized from ethyl acetate-hexane to provide needles.

0.243 g (16%)

$^1$H-NMR (CDCl$_3$) δ: 1.45(3H,t,J=7.4 Hz), 2.43(3H,s), 2.66(2H,q,J=7.4 Hz), 5.33(2H,s), 6.85(1H,d,J=2.7 Hz), 7.40 (2H,d,J=8.4 Hz)i 7.46(2H,d,J=8.4 Hz), 7.54(1H,d,J=2.7 Hz), 7.75(2H,d,J=8.4 Hz), 7.78(2H,d,J=8.4 Hz).

IR (KBr): 2968, 1659, 1585, 1522, 1417, 1367, 1279, 1213, 1173, 1088, 928, 689 cm$^{-1}$.

EXAMPLE 170

4,4'-Bis[[3,5-dimethyl-4(3H)-quinazolinon-2-yl]-thiomethyl]benzophenone

To a solution of 3,5-dimethyl-2-mercaptoquinazolin-4-one (1.98 g, 9.60 mmol) in EtOH (15.0 ml)-THF (15.0 ml) was added 1N-aqueous sodium hydroxide solution (10.0 ml). Then, a solution of 4,4'-bis(bromomethyl) benzophenone (3.50 g) in THF (20 ml) was added over 1 hour and the mixture was stirred at room temperature for 20 minutes. The solvent was then distilled off. To the residue was added ethyl acetate and the resulting colorless crystalline solid was harvested by filtration. This crystal crop was rinsed with water and ethanol and dried in vacuo to provide a colorless solid.

1.10 g (40%)

$^1$H-NMR (CDCl$_3$) δ: 2.58(6H,s), 3.54(6H,s), 4.58(4H,s), 7.15(2H,d,J=7.2 Hz), 7.44(2H,d,J=7.2 Hz), 7.54(2H,t,J=7.2 Hz), 7.59(4H,d,J=8.4 Hz), 7.75(4H,d,J=8.4 Hz).

IR (KBr): 1670, 1554, 1462, 1415, 1306, 1277, 1090, 930, 808, 694 cm$^{-1}$.

EXAMPLE 171

2-[4-[4-(Dimethylaminomethyl)benzoyl]benzyl]thio-3,5-dimethyl-4(3H)-quinazolinone hydrochloride To a solution of 3,5-dimethyl-2-mercaptoquinazolin-4-one (1.98 g, 9.60 mmol) in EtOH (15.0 ml)-THF (15.0 ml) was added 1N-aqueous sodium hydroxide solution (10.0 ml). Then, a solution of 4,4'-bis(bromomethyl) benzophenone (3.50 g) in THF (20 ml) was added over 1 hour and the mixture was stirred at room temperature for 20 minutes. Then, 50% aqueous dimethylamine solution was added and the mixture was further stirred at room temperature for 1 hour. The solvent was then distilled off, ethyl acetate was added to the residue, and the resulting colorless precipitate was filtered off. Then, hydrochloric acid was added to the filtrate and the colorless solid that separated out was collected by filtration, washed with water and ethanol, and dried in vacuo.

0.789 g (17%)

$^1$H-NMR (CDCl$_3$) δ: 2.82(6H,d,J=4.8 Hz), 2.84(3H,s), 3.60(3H,s), 4.26(2H,d,J=5.4 Hz), 4.91(2H,s), 7.22(1H,d,J= 7.4 Hz), 7.59(1H,d,J=8.0 Hz), 7.64(2H,d,J=8.0 Hz), 7.77 (2H,d,J=8.0 Hz), 7.81(1H,dd, J=8.0&7.4 Hz), 7.82(2H,d,J= 8.1 Hz), 7.86(2H,d,J=8.1 Hz).

IR (KBr): 3413, 2931, 2551, 2470, 1695, 1554, 1466, 1416, 1306, 1279, 1089, 927, 864, 804, 773, 696 cm$^{-1}$.

EXAMPLE 172

2-[4-(4-Chlorobenzoyl)benzyloxy]-3,7-dimethyl-4H-pyrido[1,2-a]pyrimidin-4-one

To a solution of 3,7-dimethylpyrido[1,2-a]-pyrimidine-2,4-dione (0.308 g, 1.62 mmol) and 4-(4-chlorobenzoyl) benzyl bromide (0.511 g, 1.65 mmol) in DMF (10.0 ml)-DMSO (10.0 ml) was added potassium carbonate (0.31 g, 2.24 mmol) and the mixture was stirred at room temperature overnight. This reaction mixture was diluted with ethyl acetate and washed with saturated aqueous NaCl solution and the organic layer was dried over MgSO$_4$ and concentrated under reduced pressure. The residue was recrystallized from ethyl acetate to provide colorless needles.

0.246 (36%)

$^1$H-NMR (CDCl$_3$) δ: 2.23(3H,s), 2.42(3H,s), 5.61(2H,s), 7.42(1H,d,J=8.8 Hz), 7.47(2H,d,J=7.3 Hz), 7.54–7.61(3H, m), 7.76(2H,d,J=7.3 Hz), 7.80(2H,d,J=7.3 Hz), 8.88(1H,s).

IR (KBr): 1726, 1657, 1604, 1554, 1464, 1409, 1308, 1279, 1184, 1089, 931, 864, 789, 694 cm$^{-1}$.

EXAMPLE 173

2-[4-(4-Chlorobenzoyl)benzyl]thio-6-hydroxy-3-methyl-4(3H)-quinazolinone

To a solution of 6-hydroxy-3-methyl-2-mercaptoquinazolin-4-one (0.518 g, 2.49 mmol) in EtOH (5.0 ml)-THF (5.0 ml) was added 1N-aqueous sodium hydroxide solution (2.50 ml). Then, 4-(4-chlorobenzoyl) benzyl bromide (0.261 g, 0.843 mmol) was added and the mixture was stirred at room temperature for 1 hour. The resulting crystals were harvested by filtration, rinsed with water and ethanol, and dried under reduced pressure to provide a light-yellow solid.

0.88 g (81%)

$^1$H-NMR (CDCl$_3$) δ: 3.48(3H,s), 4.62(2H,s), 7.24(1H,dd, J=8.8&2.8 Hz), 7.37(1H,d,J=2.8 Hz), 7.52(1H,d,J=8.8 Hz), 7.60(2H,d,J=8.6 Hz), 7.71(4H,s), 7.74(2H,d,J=8.6 Hz).

IR (KBr): 3383, 1663, 1560, 1495, 1408, 1363, 1309, 1282, 1234, 1089, 1064, 930, 833 cm$^{-1}$.

EXAMPLE 174

2-[4-(4-Chlorobenzoyl)benzyl]thio-6-methoxy-3-methyl-4(3H)-quinazolinone

To a solution of 2-[4-(4-chlorobenzoyl) benzyl]thio-6-hydroxy-3-methyl-4(3H)quinazolinone (0.306 g, 0.700 mmol) in DMF (5.0 ml) were added potassium carbonate (0.25 g, 1.45 mmol) and methyl iodide (0.100 ml, 1.61 mmol) and the mixture was stirred at room temperature for 3 hours. The solvent was then distilled off and the residue was dissolved in ethyl acetate and washed with saturated aqueous NaCl solution. The organic layer was dried over MgSO$_4$ and concentrated under reduced pressure. The residue was recrystallized from ethyl acetate-methanol to provide colorless needles.

0.202 g (64%)

$^1$H-NMR (CDCl$_3$) δ: 3.61(3H,s), 3.91(3H,s), 4.59(2H,s), 7.31(1H,dd,J=8.8&2.8 Hz), 7.44(1H,d,J=8.5 Hz), 7.53(1H, d,J=8.8 Hz), 7.59(1H,d,J=2.8 Hz), 7.60(2H,d,J=8.5 Hz), 7.33(2H,d,J=8.5 Hz), 7.74(2H,d,J=8.5 Hz).

IR (KBr): 1672, 1643, 1578, 1535, 1481, 1392, 1282, 1165, 1088, 928, 830 cm$^{-1}$.

EXAMPLE 175

2-[4-[4-Chlorobenzoyl)benzyl]thio-6-isopropoxy-3-methyl-4(3H)-quinazolinone

To a solution of 2-[4-(4-chlorobenzoyl) benzyl]thio-6-hydroxy-3-methyl-4(3H)-quinazolinone (0.300 g, 0.687 mmol) in DMF (5.0 ml) were added potassium carbonate (0.200 g, 1.45 mmol) and isopropyl iodide (0.200 ml, 2.00 mmol) and the mixture was stirred at 50° C. for 1 hour. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate-methanol to provide colorless needles.

0.232 g (71%)

$^1$H-NMR (CDCl$_3$) δ: 1.38(6H,d,J=6.0 Hz), 3.60(3H,s), 4.59(2H,s), 4.69(1H,m), 7.27(1H,dd,J=9.0&3.0 Hz), 7.43–7.50(3H,m), 7.55–7.62(3H,m), 7.73(2H,d,J=8.0 Hz), 7.74(2H,d,J=8.0 Hz).

IR (KBr): 1674, 1581, 1557, 1485, 1365, 1313, 1281, 1226, 1112, 1066, 928, 833 cm$^{-1}$.

EXAMPLE 176

6-Hydroxy-2-[4-(4-methoxybenzoyl)benzyl]thio-3-methyl-4(3H)-quinazolinone

To a solution of 6-hydroxy-3-methyl-2-mercaptoquinazolin-4-one (1.52 g, 7.30 mmol) in EtOH (15.0 ml)-THF (15.0 ml) was added 1N-aqueous sodium hydroxide solution (7.50 ml). Then, 4-(4-methoxybenzoyl) benzyl bromide (2.30 g, 7.50 mmol) was added and the mixture was stirred at room temperature for 4 hours. The resulting crystals were harvested by filtration, rinsed with water and ethanol, and dried in vacuo to provide a light-yellow solid.

1.830 g (58%)

$^1$H-NMR (CDCl$_3$) δ: 3.61(3H,s), 3.88(3H,s), 4.58(2H,s), 6.95(2H,d,J=9.0 Hz), 7.29(1H,dd,J=8.9&2.8 Hz), 7.54(1H,d,J=8.9 Hz), 7.58(2H,d,J=8.4 Hz), 7.73(2H,d,J=8.4 Hz), 7.78(1H,d,J=2.8 Hz), 7.81(2H,d,J=9.0 Hz).

IR (KBr): 3400, 1660, 1603, 1556, 1496, 1464, 1416, 1362, 1311, 1254, 1176, 1147, 1066, 1030, 930, 839, 775 cm$^1$.

EXAMPLE 177

2-[4-(4-Methoxybenzoyl)benzyl]thio-6-methoxy-3-methyl-4(3H)-quinazolinone

To a solution of 6-hydroxy-2-[4-(4-methoxybenzoyl) benzyl]thio-3-methyl-4(3H)-quinazolinone (0.400 g, 0.925 mmol) in DMF (10.0 ml) were added potassium carbonate (0.260 g, 1.88 mmol) and methyl iodide (0.200 ml, 3.21 mmol) and the mixture was stirred at room temperature for 2 hours. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate to provide colorless needles.

0.338 g (82%)

$^1$H-NMR (CDCl$_3$) δ: 3.61(3H,s), 3.88(3H,s), 3.91(3H,s), 4.59(2H,s), 6.95(2H,d,J=8.8 Hz), 7.31(1H,dd,J=8.8&3.2 Hz), 7.54(1H,d,J=8.8 Hz), 7.58(2H,d,J=8.0 Hz), 7.59(1H,d,J=3.2 Hz), 7.73(2H,d,J=8.0 Hz), 7.81(2H,d,J=8.8 Hz).

IR (KBr): 2931, 1682, 1649, 1606, 1551, 1489, 1412, 1360, 1319, 1266, 1173, 1066, 1022, 931, 833, 779, 750 cm$^{-1}$.

EXAMPLE 178

6-Isopropoxy-2-[4-(4-methoxybenzoyl)benzyl]thio-3-methyl-4(3H)-quinazolinone

To a solution of 6-hydroxy-2-[4-(4-methoxybenzoyl) benzyl]thio-3-methyl-4(3H)-quinazolinone (0.400 g, 0.925 mmol) in DMF (10.0 ml) were added potassium carbonate (0.260 g, 1.88 mmol) and isopropyl iodide (0.300 ml, 3.00 mmol) and the mixture was stirred at 50° C. for 8 hours. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate to provide colorless needles.

0.348 g (79%)

$^1$H-NMR (CDCl$_3$) δ: 1.37(6H,d,J=6.4 Hz), 3.60(3H,s), 3.88(3H,s), 4.59(2H,s), 6.59(2H,d,J=9.0 Hz), 7.27(1H,dd,J=7.8&3.0 Hz), 7.53(1H,d,J=7.8 Hz), 7.58(2H,d,J=8.1 Hz), 7.59(1H,d,J=3.0 Hz), 7.72(2H,d,J=8.1 Hz), 7.80(2H,d,J=9.0 Hz).

IR (KBr): 1673, 1674, 1605, 1554, 1487, 1311, 1254, 1174, 145, 1113, 1086, 841 cm$^1$.

EXAMPLE 179

2-[4-(4-Methoxybenzoyl)benzyl]thio-3,8-dimethyl-4(3H)-quinazolinone

To a solution of 3,8-dimethyl-2-mercaptoquinazolin-4-one (0.503 g, 2.44 mmol) in EtOH (5.0 ml)-THF (10.0 ml) was added 1N-aqueous sodium hydroxide solution (2.80 ml). Then, 4-(4-methoxybenzoyl)benzyl bromide (0.744 g, 2.44 mmol) was added and the mixture was stirred at room temperature overnight. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate to provide colorless needles.

0.696 g (66%)

$^1$H-NMR (CDCl$_3$) δ: 3.60(3H,s), 3.62(3H,s), 3.89(3H,s), 4.65(2H,s), 6.96(2H,d,J=8.8 Hz), 7.28(1H,t,J=8.0 Hz), 7.56 (1H,d,J=8.0 Hz), 7.59(2H,d,J=8.4 Hz), 7.74(2H,d,J=8.4 Hz), 7.82(2H,d,J=8.8 Hz), 8.09(1H,d,J=8.0 Hz).

IR (KBr): 1682, 1585, 1558, 1458, 1404, 1327, 1275, 1084, 930, 764 cm$^{-1}$.

EXAMPLE 180

2-[4-(4-Chlorobenzoyl)benzyl]thio-3,8-dimethyl-4(3H)-quinazolinone

To a solution of 3,8-dimethyl-2-mercaptoquinazolin-4-one (0.504 g, 2.44 mmol) in EtOH (5.0 ml)-THF (10.0 ml) was added 1N-aqueous sodium hydroxide solution (2.80 ml). Then, 4-(4-chlorobenzoyl) benzyl bromide (0.763 g, 2.46 mmol) was added and the mixture was stirred at room temperature overnight. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate to provide colorless needles.

0.768 g (72%)

$^1$H-NMR (CDCl$_3$) δ: 2.59(3H,s), 3.62(3H,s), 4.66(2H,s), 7.29(1H,t,J=7.6 Hz), 7.45(2H,d,J=8.4 Hz), 7.56(1H,d,J=7.6 Hz), 7.61(2H,d,J=8.4 Hz), 7.74(2H,d,J=8.4 Hz), 7.75(2H,d, J=8.4 Hz), 8.08(1H,d,J=7.6 Hz).

IR (KBr): 1682, 1663, 1585, 1458, 1404, 1327, 1275, 1084, 930, 764 cm$^{-1}$.

EXAMPLE 181

1-[4-(4-Chlorobenzoyl)benzyl]-6-isopropyl-7-methylimidazo[1,2-a]pyrimidin-5(1H)-one To a solution of 6-isopropyl-7-methylimidazo[1,2-a]pyrimidin-5-one (0.400 g, 2.23 mmol) and 4-(4- chlorobenzoyl) benzyl bromide (0.762 g, 2.46 mmol) in DMF (15.0 ml) was added potassium carbonate (0.600 g, 4.50 mmol) and the mixture was stirred at room temperature overnight. The solvent was then distilled off and the residue was purified by silica gel column chromatography (methylene chloride: acetone=20:1) to provide a colorless amorphous solid.

0.48 g (51%)

$^1$H-NMR (CDCl$_3$) δ: 1.39(6H,d,J=7.0 Hz), 2.45(3H,s), 3.17(1H,m), 5.31(2H,s), 6.83(1H,d,J=2.6 Hz), 7.40(2H,d,J=8.4 Hz), 7.46(2H,d,J=8.4 Hz), 7.53(1H,d,J=2.6 Hz), 7.73 (2H,d,J=8.4 Hz), 7.78(2H,d,J=8.4 Hz).

IR(KBr): 1659, 1585, 1512, 1408, 1367, 1279, 1088, 928, 735, 692 cm$^1$.

EXAMPLE 182

2-[4-(4-Chlorobenzoyl)benzyl]thio-5-methoxycarbonyl-3-methyl-4(3H)-quinazolinone To a solution of 5-carboxy-3-methyl-2-mercaptoquinazolin-4-one (0.520 g, 2.20 mmol) in EtOH (10.0 ml)-THF (10.0 ml) was added 1N-aqueous sodium hydroxide solution (4.40 ml). Then, 4-(4-chlorobenzoyl) benzyl bromide (0.638 g, 2.21 mmol) was added and the mixture was stirred at room temperature for 1 hour. This reaction mixture was acidified with hydrochloric acid and the precipitate which formed was collected by filtration, washed with water, and dissolved in DMF (20 ml)-water (5.0 ml). To this solution were added cesium carbonate (1.40 g, 4.30 mmol) and methyl iodide (1.00 ml) and the mixture was stirred at room temperature overnight. After removal of the solvent, the residue was diluted with ethyl acetate and washed with saturated aqueous NaCl solution. The organic layer was dried over MgSO$_4$ and concentrated under reduced pressure, and the residue was purified by silica gel column chromatography (methylene chloride) and recrystallized from ethyl acetate-ethanol to provide colorless needles.

$^1$H-NMR (CDCl$_3$) δ: 3.58(3H,s), 4.01(3H,s), 4.61(2H,s), 7.34(1H,dd,J=6.6&1.8 Hz), 7.46(2H,d,J=8.6 Hz), 7.60(2H, d,J=8.2 Hz), 7.68–7.77(6H,m).

IR (KBr): 1734, 1674, 1593, 1554, 1441, 1408, 1323, 1282, 1203, 1082, 926, 818, 762 cm$^1$.

EXAMPLE 183

2-[4-(4-Methoxycarbonylbenzoyl)benzyl]thio-3,5-dimethyl-4(3H)-quinazolinone

To a solution of 3,5-dimethyl-2-mercaptoquinazolin-4-one (5.00 g, 24.2 mmol) in EtOH (100.0 ml)-THF (100.0 ml) was added 1N-aqeuous sodium hydroxide solution (25.0 ml). Then, 4-(4-methoxycarbonylbenzoyl)benzyl bromide (8.06 g, 24.2 mmol) was added and the mixture was stirred at room temperature overnight. The resulting colorless solid was harvested by filtration, rinsed with water, dried in vacuo, and recrystallized from ethyl acetate to provide colorless needles.

10.89 g (98%)

$^1$H-NMR (CDCl$_3$) δ: 2.85(3H,s), 3.55(3H,s), 3.95(3H,s), 4.60(2H,s), 7.15(1H,d,J=7.4 Hz), 7.43(1H,d,J=7.4 Hz), 7.62 (2H,d,J=8.5 Hz), 7.77(2H,d,J=8.6 Hz), 7.79(1H,t,J=7.4 Hz), 7.82(2H,d,J=8.5 Hz), 8.14(2H,d,J=8.6 Hz).

IR (KBr): 1722, 1658, 1554, 1431, 1275, 1093, 1020, 966, 928, 962, 715 cm$^{-1}$.

EXAMPLE 184

3,5-Dimethyl-2-[4-[4-(4-methylpiperazinocarbonyl) benzoyl]benzyl]thio-4(3H)-quinazolinone To a solution of 2-[4-(4-carboxybenzoyl)benzyl]thio-3,5-dimethyl-4(3H)-quinazolinone (0.320 g, 0.720 mmol) in DMF (5.0 ml) were added DEPC (0.37 g, 2.27 mmol) and 1-methylpiperazine (0.200 ml, 1.80 mmol) and the mixture was stirred at room temperature overnight. The solvent was then distilled off and the residue was dissolved in ethyl acetate and washed with saturated aqueous NaCl solution. The organic layer was dried over MgSO$_4$ and concentrated under reduced pressure. The residue was purified by silica gel column chromatography (methylene chloride: methanol: ammonia=20:1:0.1). The resulting solid was recrystallized from ethanol to provide colorless needles.

0.201 g (18%)

$^1$H-NMR (CDCl$_3$) δ: 2.33(3H,s), 3.55(3H,s), 2.36(2H,m), 2.60(2H,m), 2.85(3H,s), 3.41(2H,m), 3.55(3H,s), 3.82(2H, m), 4.59(2H,s), 7.15(1H,d,J=6.6 Hz), 7.40(1H,d,J=6.6 Hz), 7.50(2H,d,J=8.0 Hz), 7.51(1H,t,J=6.6 Hz), 7.61(2H,d,J=8.0 Hz), 7.77(2H,d,J=8.0 Hz), 7.80(2H,d,J=8.0 Hz).

IR (KBr): 1674, 1628, 1552, 1462, 1433, 1299, 1276, 1144, 1092, 931 cm$^{-1}$.

EXAMPLE 185

2-[4-(2-Chlorobenzoyl)benzyl]thio-3,5-dimethyl-4 (3H)-quinazolinone

To a solution of 3,5-dimethyl-2-mercaptoquinazolin-4-one (0.513 g, 2.49 mmol) in EtOH (10.0 ml)-THF (10.0 ml) was added 1N-aqueous sodium hydroxide solution (2.70 ml). Then, 4-(2-chlorobenzoyl)benzyl bromide (0.800 g, 2.58 mmol) was added and the mixture was stirred at room temperature overnight. The solvent was then distilled off and the residue was dissolved in ethyl acetate and washed with saturated aqueous NaCl solution. The organic layer was dried over MgSO$_4$ and concentrated under reduced pressure. The residue was recrystallized from methanol to provide colorless needles.

0.704 g (65%)

$^1$H-NMR (CDCl$_3$) δ: 2.84(3H,s), 3.53(3H,s), 4.57(2H,s), 7.14(1H,d,J=7.0 Hz), 7.26–7.46(5H,m), 7.49(1H,t,J=7.0 Hz), 7.58(2H,d,J=8.6 Hz), 7.77(2H,d,J=8.6 Hz).

IR (KBr): 1678, 1659, 1599, 1552, 1286, 1240, 1089, 926, 860, 769, 692 cm$^{-1}$.

EXAMPLE 186

3,5-Dimethyl-2-[4-(4-nitrobenzoyl)benzyl]thio-4 (3H)-quinazolinone

To a solution of 3,5-dimethyl-2-mercaptoquinazolin-4-one (2.03 g, 9.74 mmol) in EtOH (30.0 ml)-THF (30.0 ml) was added 1N-aqueous sodium hydroxide solution (10.0 ml). Then, 4-(4-nitrobenzoyl)benzyl bromide (3.50 g, 10.9 mmol) was added and the mixture was stirred at room temperature overnight. The solvent was then distilled off and the residue was dissolved in ethyl acetate and washed with saturated aqueous NaCl solution. The organic layer was dried over MgSO$_4$ and concentrated under reduced pressure. The residue was recrystallized from methanol to provide light-yellow needles.

0.307 g (70%)

$^1$H-NMR (CDCl$_3$) δ: 2.85(3H,s), 3.55(3H,s), 4.60(2H,s), 7.15(1H,d,J=7.4 Hz), 7.43(1H,d,J=7.4 Hz), 7.54(1H,t,J=7.4 Hz), 7.64(2H,d,J=8.4 Hz), 7.77(2H,d,J=8.4 Hz), 7.91(2H,d, J=8.4 Hz), 8.33(2H,d,J=8.4 Hz).

IR (KBr): 1678, 1660, 1558, 1522, 1414, 1346, 1307, 1277, 1249, 1088, 929, 858, 810, 708 cm$^{-1}$.

EXAMPLE 187

7-[4-(4-Chlorobenzoyl)benzyl]-1-ethyl-3,8-dimethylxanthine

To a solution of 1-ethyl-3,8-dimethylxanthine (170 mg), a synthetic process for which is described in Journal of American Chemical Society, 75, 114 (1953), in DMF (8 ml) were added potassium carbonate (169 mg) and 4-(4-chlorobenzoyl)benzyl bromide (278 mg) and the mixture was stirred at room temperature for 20 hours. This reaction mixture was diluted with water and extracted with ethyl acetate, and the extract was washed with saturated aqueous NaCl solution and dried over anhydrous sodium sulfate. The solvent was then distilled off and the residue was recrystallized (ethyl acetate-hexane) to provide the title compound as colorless powder (87 mg, 24%).

$^1$H-NMR (CDCl$_3$) δ: 1.25(3H,t,J=7.0 Hz), 2.45(3H,s), 3.59(3H,s), 4.08(2H,q,J=7.0 Hz), 5.63(2H,s), 7.25–7.81(8H, m).

IR (KBr): 1700, 1660, 1610, 1400, 1280, 1270 cm$^{-1}$.

EXAMPLE 188

2-[4-(4-Aminobenzoyl)benzyl]thio-3,5-dimethyl-4(3H)-quinazolinone

To a solution of 3,5-dimethyl-2-[4-(4-nitrobenzoyl)benzyl]thio-4(3H)-quinazolinone (1.00 g, 2.24 mmol) in acetic acid (30.0 ml)-THF (15.0 ml) was added iron (2.00 g) and the mixture was stirred at room temperature overnight. After the solvent was distilled off, 1N-NaOH (20 ml) was added to the residue and the mixture was extracted with chloroform. The organic layer was dried over MgSO$_4$ and concentrated under reduced pressure and the residue was crystallized from ethyl acetate to provide a light-yellow solid. 0.380 g (41%)

$^1$H-NMR (DMSO-d$_6$) δ: 2.76(3H,s), 3.46(3H,s), 4.63(2H, s), 6.12(2H,s), 6.59(2H,d,J=8.8 Hz), 7.20(1H,d,J=7.4 Hz), 7.44–7.67(8H,m).

IR (KBr): 352, 1650, 1583, 1552, 1469, 1430, 1311, 1282, 1172, 1147, 1089, 928, 844 cm$^{-1}$.

EXAMPLE 189

1-[4-(4-Chlorobenzoyl)benzyl]-6,7,8,9-tetrahydroimidazo[2,1-b]quinazolin-5(1H)-one To a solution of 6,7,8,9-tetrahydroimidazo[2,1-b]-quinazolin-5(1H)-one (0.235 g, 1.24 mmol) and 4-(4-chlorobenzoyl)benzyl bromide (0.410 g, 1.32 mmol) in DMF (15.0 ml)-DMSO (5 ml) was added potassium carbonate (0.250 g, 1.81 mmol) and the mixture was stirred at room temperature overnight. The solvent was then distilled off and the residue was purified by preparative TLC (methylene chloride: methanol=20:1) to provide a colorless amorphous solid.

0.085 g (16%)

$^1$H-NMR (CDCl$_3$) δ: 1.82(4H,m), 2.64(2H,t,J=5.4 Hz), 2.73(2H,t,J=5.4 Hz), 5.32(2H,s), 6.84(1H,d,J=2.6 Hz), 7.40 (2H,d,J=8.1 Hz), 7.46(2H,d,J=8.1 Hz), 7.54(1H,d,J=2.6 Hz), 7.73(2H,d,J=8.1 Hz), 7.77(2H,d,J=8.1 Hz).

IR (KBr): 2933, 1659, 1585, 1528, 1419, 1306, 1277, 1209, 1170, 1088, 928, 733 cm$^{-1}$.

EXAMPLE 190

1-[4-(4-Chlorobenzoyl)benzyl]-1,6,7,8-tetrahydro-5H-cyclopent[d]imidazo[1,2-a]pyrimidin-5-one To a solution of 1,6,7,8-tetrahydro-5H-cyclopent[d]imidazo[1,2-a]pyrimidin-5-one (0.345 g, 1.967 mmol) and 4-(4-chlorobenzoyl)benzyl bromide (0.0650 g, 2.10 mmol) in DMF (15.0 ml)-DMSO (5 ml) was added potassium carbonate (0.30 g, 2.17 mmol) and the mixture was stirred at room temperature overnight. The solvent was then distilled off and the residue was purified by preparative TLC (methylene chloride: methanol=20:1) to provide a colorless amorphous solid.

0.260 g (33%)

$^1$H-NMR (CDCl$_3$) δ: 2.13(2H,quint,J=7.2 Hz), 2.89(4H, t,J=7.2 Hz), 5.36(2H,s), 6.89(1H,d,J=2.6 Hz), 7.39(2H,d,J= 8.4 Hz), 7.46(2H,d,J=8.4 Hz), 7.61(1H,d,2.6 Hz), 7.73(2H, d,J=8.4 Hz), 7.77(2H,d,J=8.4 Hz).

IR (Neat): 2954, 1675, 1660, 1579, 1522, 1417, 1279, 1240, 1173, 1089, 928, 849, 733 cm$^{-1}$.

EXAMPLE 191

3,5-Dimethyl-2-[4-[4-(t-butoxycarbonylmethyl)carbamoylbenzoyl]benzyl]thio-4(3H)-quinazolinone To a solution of 2-[4-(4-carboxybenzoyl)benzyl]thio-3,5-dimethyl-4(3H)-quinazolinone (0.495 g, 1.11 mmol) and t-butyl aminoacetate hydrochloride (0.236 g, 1.41 mmol) in DMF (10.0 ml) were added DEPC (0.364 g, 2.23 mmol) and triethylamine (0.60 ml) and the mixture was stirred at room temperature for 3.5 hours. The solvent was then distilled off and the residue was dissolved in ethyl acetate and washed with saturated aqueous NaCl solution. The organic layer was dried over MgSO$_4$ and concentrated under reduced pressure, and the residue was recrystallized from ethyl acetate to provide colorless needles.

0.351 g (55%)

$^1$H-NMR (CDCl$_3$) δ: 1.52(9H,s), 2.85(3H,s), 3.55(3H,s), 4.17(2H,d,J=5.0 Hz), 4.60(2H,s), 6.75(1H,t,J=5.0 Hz), 7.15 (1H,d,J=7.2 Hz), 7.44(1H,d,J=7.2 Hz), 7.55(1H,t,J=7.2 Hz), 7.62(2H,d,J=8.4 Hz), 7.77(2H,d,J=8.4 Hz), 7.83(2H,d,J=8.6 Hz), 7.92(2H,d,J=8.6 Hz).

IR (KBr): 3259, 2978, 1741, 1673, 1658, 1605, 1554, 1371, 1306, 1230, 1157, 1092, 931, 869, 808, 754 cm$^1$.

EXAMPLE 192

3,5-Dimethyl-2-[4-[4-(N-methoxycarbonylmethyl-N-methylcarbamoyl)benzoyl]benzyl]thio-4(3H)-quinazolinone To a solution of 2-[4-(4-carboxybenzoyl)benzyl]thio-3,5-dimethyl-4(3H)-quinazolinone (0.500 g, 1.12 mmol) and methyl N-methylaminoacetate hydrochloride (0.199 g, 1.43 mmol) in DMF (10.0 ml) were added DEPC (diethylphosphorocyamidate) (0.374 g, 2.29 mmol) and triethylamine (0.60 ml) and the mixture was stirred at room temperature for 3 hours. The solvent was then distilled off and the residue was dissolved in ethyl acetate and washed with saturated aqueous NaCl solution. The organic layer was dried over MgSO$_4$ and concentrated under reduced pressure. The residue was purified by silica gel column chromatography (hexane: ethyl acetate=1:3) and crystallized from ethanol to provide a colorless solid.

0.250 g (38%)

$^1$H-NMR (CDCl$_3$) δ: 2.84(3H,s), 3.05(⅓×3H,s), 3.15(⅓× 3H,s), 3.55(3H,s), 3.74(⅓×3H,s), 3.81(⅔×3H,s), 3.99(⅓× 2H,s), 4.31(⅔×2H,s), 4.59(2H,s), 7.15(1H,d,J=7.6 Hz), 7.40–7.66(6H,m), 7.67(2H,d,J=8.6 Hz), 7.82(2H,d,J=8.4 Hz).

IR (KBr): 2935, 1668, 1597, 1554, 1462, 1412, 1315, 1259, 1171, 1080, 1020, 930, 841, 769 cm$^{-1}$.

EXAMPLE 193

3,5-Dimethyl-2-[4-[4-(4-piperidinopiperidinocarbonyl)benzoyl]benzyl]thio-4(3H)-quinazolinone To a solution of 2-[4-(4-carboxybenzoyl) benzyl]thio-3,5-dimethyl-4(3H)-quinazolinone (0.495 g, 1.11 mmol) in DMF (10.0 ml) was added DEPC (0.370 g, 2.27 mmol) and the mixture was stirred at room temperature for 1 hour. Then, 4-piperidinopiperidine (0.277 g, 1.65 mmol) was added and the mixture was stirred overnight. The solvent was then removed and the residue was dissolved in ethyl acetate and washed with saturated aqueous NaCl solution. The organic layer was dried over $MgSO_4$ and concentrated under reduced pressure, and the residue was purified by silica gel column chromatography (isopropyl ether: methylene chloride: methanol: ammonia =5:5:1:0.1) to provide a colorless amorphous solid.

0.270 g (40%)

$^1$H-NMR (CDCl$_3$) δ: 1.40–2.56(15H,m), 2.75–2.80(1H, m), 2.85(3H,s), 2.90–3.10(1H,m), 3.55(3H,s), 3.70–3.85 (1H,m), 4.59(2H,s), 7.45–4.82(1H,m), 7.15(1H,d,J=7.8 Hz), 7.46(1H,t,J=7.8 Hz), 7.48(2H,d,J=8.0 Hz), 7.49(1H,d,J=7.8 Hz), 7.61(2H,d,J=8.0 Hz), 7.65(2H,d,J=8.0 Hz), 7.80(2H,d, J=8.0 Hz).

IR (KBr): 2931, 1664, 1631, 1608, 1554, 1508, 1448, 1306, 1277, 1092, 1016, 931, 864 cm$^{-1}$.

EXAMPLE 194

1-[4-(6-Chloronicotinoyl)benzyl]-6,7-dimethylimidazo[1,2-a]pyrimidin-5(1H)-one hydrochloride In a solution of 6,7-dimethylimidazo[1,2-a]-pyrimidin-5-one (0.900 g, 5.5 mmol) and 4-nicotinoylbenzyl bromide (1.92 g, 3.6 mmol) in DMF (20.0 ml)-DMSO (10.0 ml) was added potassium carbonate (2.10 g, 15.20 mmol) and the mixture was stirred at room temperature overnight. The solvent was then distilled off and the residue was purified by silica gel column chromatography (ethyl acetate) to give a light-yellow oil. To this ethyl acetate solution was added 4N-hydrogen chloride/ethyl acetate and the resulting crystals were harvested by filtration and dried in vacuo.

1.45 g (70%)

$^1$H-NMR (DMSO-d$_6$) δ: 2.02(3H,s), 2.39(3H,s), 5.59(2H, s), 7.41(1H,t,J=8.4 Hz), 7.56(2H,d,J=8.0 Hz), 7.67–7.73 (2H,m), 7.79(2H,d,J=8.0 Hz), 8.16(1H,dd,J=8.4&2.6 Hz), 8.69(1H,d,J=2.6 Hz).

IR (KBr): 2366, 1680, 1659, 1578, 1365, 1281, 1099, 926 cm$^1$.

EXAMPLE 195

3,5-Dimethyl-2-[4-[4-bis(t-butoxycarbonylmethyl) carbamoyl)benzoyl]benzyl]thio-4(3H)-quinazolinone To a solution of 3,5-dimethyl-2-[4-[4-(t-butoxycarbonylmethyl)carbamoylbenzoyl]benzyl]thio-4 (3H)-quinazolinone (0.511 g, 0.894 mmol) in DMF (15.0 ml) were added 60% sodium hydride (0.040 g, 1.00 mmol) and t-butyl bromoacetate (0.210 g, 1.08 mmol) and the mixture was stirred at room temperature overnight. The solvent was then distilled off and the residue was dissolved in ethyl acetate and washed with saturated aqueous NaCl solution. The organic layer was dried over $MgSO_4$ and, then, concentrated under reduced pressure, and the residue was purified by silica gel column chromatography (hexane: ethyl acetate=2:1) to provide a colorless amorphous solid.

0.270 g (40%)

$^1$H-NMR (CDCl$_3$) δ: 1.44(9H,s), 1.51(9H,s), 2.85(3H,s), 3.55(3H,s), 3.94(2H,s), 4.22(2H,s), 4.59(2H,s), 7.15(1H,d, J=7.0 Hz), 7.43(1H,d,J=8.6 Hz), 7.48–7.66(5H,m), 7.77(2H, d,J=8.6 Hz), 7.79(2H,d,J=8.0 Hz).

IR (KBr): 1741, 1662, 1556, 1153 cm$^{-1}$.

EXAMPLE 196

2-[4-(6-Chloronicotinoyl)benzyloxy]-3-methyl-4H-pyrido[1,2-a]pyrimidin-4-one

To a solution of 3-methylpyrido[1,2-a]pyrimidine-2,4-dione (1.520 g, 8.62 mmol) and 4-nicotinoylbenzyl bromide (3.00 g, 9.66 mmol) in DMF (25.0 ml)-DMSO (10.0 ml) was added potassium carbonate (3.50 g, 25.3 mmol) and the mixture was stirred at room temperature overnight. This reaction mixture was diluted with water and the resulting crystals were rinsed with ethanol and dried in vacuo to provide a light-yellow solid.

2.44 g (70%)

$^1$H-NMR (CDCl$_3$) δ: 2.28(3H,s), 5.63(2H,s), 7.12(1H,t, J=7.5 Hz), 7.49(2H,d,J=8.4 Hz), 7.62(2H,d,J=8.4 Hz), 7.71 (1H,t,J=8.4 Hz), 7.82(2H,d,J=8.4 Hz), 8.00(1H,dd,J= 8.4&2.4 Hz), 8.77(1H,d,J=2.4 Hz), 9.08(1H,d,J=7.5 Hz).

IR (KBr): 1670, 1576, 1477, 1280, 1165, 1103, 924, 764 cm$^{-1}$.

EXAMPLE 197

3-Methyl-2-[4-[6-(4-piperidinopiperidino)nicotinoyl] benzyloxy]-4H-pyrido[1,2-a]pyrimidin-4-one A solution of 2-[4-(6-chloronicotinoyl)benzyloxy]-3-methylpyrido[1,2-a]pyrimidin-4-one (0.49 g, 1.21 mmol) and 4-piperidinopiperidine (0.402 g, 2.39 mmol) in pyridine (15 ml) was stirred at 90° C. overnight. The solvent was then distilled off under reduced pressure and the residue was purified by silica gel column chromatography (isopropyl ether: methylene chloride: methanol: ammonia=5:5:1:0.1) to provide a light-yellow oil.

0.38 g (59%)

$^1$H-NMR (CDCl$_3$) δ: 1.42–1.76(8H,m), 1.92–1.99(2H, m), 2.23(3H,s), 2.48–2.58(5H,m), 2.87–3.01(2H,m), 4.49–4.60(2H,m), 5.61(2H,s), 6.68(1H,d,J=7.5 Hz), 7.10 (1H,t,J=7.5 Hz), 7.49(1H,d,J=8.9 Hz), 7.56(2H,d,J=8.1 Hz), 7.68(1H,d,J=8.1 Hz), 8.01(1H,dd,J=8.9&2.2 Hz), 8.59(1H, d,J=2.2 Hz), 9.08(1H,d,J=7.1 Hz).

IR (Neat): 2929, 2852, 1676, 1637, 1589, 1533, 1477, 1423, 1281, 1246, 1164, 1012, 922, 768 cm$^{-1}$.

EXAMPLE 198

2-[4-(2-Chloronicotinoyl)benzyl]thio-3,5-dimethyl-4 (3H)-quinazolinone

To a solution of 3,5-dimethyl-2-mercaptoquinazolin-4-one (0.516 g, 2.50 mmol) in EtOH (10.0 ml)-THF (10.0 ml) was added 1N-aqueous sodium hydroxide solution (2.60 ml). Then, 4-(2-chloronicotinoyl)benzyl bromide (0.807 g, 2.60 mmol) was added and the mixture was stirred at room temperature for 30 minutes. The solvent was then distilled off and the residue was dissolved in ethyl acetate and washed with saturated aqueous NaCl solution. The organic layer was dried over $MgSO_4$ and concentrated under reduced pressure. The residue was recrystallized from ethyl acetate to provide light-yellow needles.

0.810 g (74%)

$^1$H-NMR (CDCl$_3$) δ: 2.84(3H,s), 3.54(3H,s), 4.58(2H,s), 7.14(1H,d,J=7.6 Hz), 7.37(1H,dd,J=7.9&4.8 Hz), 7.41(1H, d,J=7.6 Hz), 7.51(1H,t,J=7.6 Hz), 7.61(2H,d,J=8.4 Hz), 7.71 (1H,dd,J=7.9&2.0 Hz), 7.76(2H,d,J=8.4 Hz), 8.54(1H,dd,J= 4.8&2.0 Hz).

IR (KBr): 1670, 1549, 1460, 1402, 1304, 1280, 1284, 1161, 1086, 1036, 924, 864, 746, 694, 656 cm$^{-1}$.

EXAMPLE 199

1-[4-(6-Chloronicotinoyl)benzyl]-6-ethyl-7-methylimidazo[1,2-a]pyrimidin-5(1H)-one To a solution of 6-ethyl-7-methylimidazo[1,2-a]pyrimidin-5-one (4.19 g, 23.60 mmol) and 4-(6-chloronicotinoyl)benzyl bromide (7.36 g, 23.70 mmol) in DMF (100.0 ml)-DMSO (20.0 ml) was added potassium carbonate (7.10 g, 50.70 mmol) and the mixture was stirred at room temperature overnight. The solvent was then distilled off under reduced pressure and the residue was purified by silica gel column chromatography (ethyl acetate). The resulting colorless oil was crystallized from ethyl acetate to provide colorless needles.

4.59 g (48%)

$^1$H-NMR (CDCl$_3$) δ: 1.15(3H,t,J=7.4 Hz), 2.43(3H,s), 2.66(2H,q,J=7.4 Hz), 5.35(2H,s), 6.86(1H,d,J=2.6 Hz), 7.44 (2H,d,J=8.0 Hz), 7.53(1H,d,J=8.0 Hz), 7.56(1H,d,J=2.6 Hz), 7.81(2H,d,J=8.0 Hz), 8.09(1H,dd,J=8.0&2.4 Hz), 8.75(1H, d,J=2.4 Hz)..

IR (KBr): 1655, 1581, 1520, 1414, 1282, 1217, 1103, 923 cm$^{-1}$.

EXAMPLE 200

6-Ethyl-1-[4-(4-methoxycarbonylbenzoyl)benzyl]-7-methylimidazo[1,2-a]pyrimidin-5(1H)-one To a solution of 6-ethyl-7-methylimidazo[1,2-a]pyrimidin-5-one (4.00 g, 22.6 mmol) and 4-(4-methoxycarbonylbenzoyl)benzyl bromide (11.00 g, 33.02 mmol) in DMF (100.0 ml)-DMSO (20.0 ml) was added potassium carbonate (7.14 g, 51.7 mmol) and the mixture was stirred at room temperature overnight. The solvent was then distilled off under reduced pressure and the residue was purified by silica gel column chromatography (ethyl acetate). The resulting colorless oil was crystallized from ethyl acetate to provide colorless needles.

4.59 g (48%)

$^1$H-NMR (CDCl$_3$) δ: 1.15(3H,t,J=6.6 Hz), 2.44(3H,s), 2.66(2H,q,J=6.6 Hz), 3.97(3H,s), 5.34(2H,s), 6.86(1H,d,J= 2.6 Hz), 7.42(2H,d,J=8.0 Hz), 7.56(1H,d,J=2.6 Hz), 7.81 (2H,d,J=8.0 Hz), 7.82(2H,d,J=8.0 Hz), 8.16(2H,d,J=8.0 Hz).

IR (KBr): 1724, 1657, 1581, 1520, 1277, 1109, 928, 721 cm$^{-1}$.

EXAMPLE 201

2-[4-(4-Methoxycarbonylbenzoyl)benzyloxy]-3-methyl-4H-pyrido[1,2-a]pyrimidin-4-one To a solution of 3-methylpyrido[1,2-a]pyrimidine-2,4-dione (2.20 g, 12.5 mmol) and 4-(4-methoxycarbonylbenzoyl)benzyl bromide (7.04 g, 12.7 mmol) in DMF (40.0 ml)-DMSO (20.0 ml) was added potassium carbonate (3.92 g, 28.4 mmol) and the mixture was stirred at room temperature overnight. This reaction mixture was diluted with water and the resulting crystals were collected by filtration, dissolved in ethyl acetate, and dried over MgSO$_4$. The solvent was then distilled off under reduced pressure and the residue was re-crystallized from ethyl acetate to provide colorless needles.

2.67 g (50%)

$^1$H-NMR (CDCl$_3$) δ: 2.23(3H,s), 3.97(3H,s), 5.63(2H,s), 7.11(1H,dt,J=6.7&1.5 Hz), 7.49(1H,dd,J=8.7&1.5 Hz), 7.60 (2H,d,J=8.4 Hz), 7.71(1H,ddd,J=8.7,6.7&1.5 Hz), 7.84(2H, d,J=8.4 Hz), 7.86(2H,d,J=8.4 Hz), 8.17(2H,d,J=8.4 Hz), 9.08(1H,dd,J=6.7&1.5 Hz).

IR (KBr): 1722, 1672, 1576, 1530, 1477, 1277, 1167, 1108 cm$^{-1}$.

EXAMPLE 202

6-Ethyl-1-[4-[6-(4-piperidinopiperidino)nicotinoyl] benzyl]-7-methylimidazo[1,2-a]pyrimidin-5(1H)-one tri-hydrochloride A solution of 1-[4-(6-chloronicotinoyl)benzyl]-6-ethyl-7-methylimidazo[1,2-a]pyrimidin-5(1H)-one (0.810 g, 1.99 mmol) and 4-piperidinopiperidine (0.372 g, 2.21 mmol) in pyridine (10.0 ml) was stirred at 90° C. overnight. The solvent was then distilled off under reduced pressure and the residue was purified by silica gel column chromatography (THF: methanol: ammonia=60:1:0.1) to give a light-yellow oil. This oil was dissolved in ethyl acetate, treated with 4N-hydrogen chloride/ethyl acetate and the resulting crystals were collected by filtration and dried in vacuo.

0.596 g (49%)

$^1$H-NMR (DMSO-d$_6$) δ: 1.04(3H,t,J=7.4 Hz), 1.72(2H, m), 1.82(2H,m), 2.23(2H,m), 2.38(3H,s), 2.51(2H,q,J=7.4 Hz), 2.94(2H,m), 3.02(2H,m), 3.40(2H,m), 4.20(3H,m), 4.65(4H,m), 5.49(2H,s), 7.07(1H,m), 7.49–7.54(2H,m), 7.63–7.95(4H,m), 7.98(1H,m), 8.42(1H,m).

IR (KBr): 3383, 2937, 2615, 2519, 1643, 1595, 1554, 1444, 1321, 1273, 1240, 1178, 1008, 762, 723 cm$^{-1}$.

EXAMPLE 203

6-Ethyl-7-methyl-1-[4-[6-(4-phenylpiperazino) nicotinoyl]benzyl]imidazo[1,2-a]pyrimidin-5(1H)-one trihydrochloride In ethyl acetate (10.0 ml) was dissolved 6-ethyl-7-methyl-1-[4-[6-(4-phenylpiperazino)nicotinoyl]benzyl]imidazo[1,2-a]pyrimidin-5(1H)-one (696 mg) followed by addition of 4N-hydrogen chloride/ethyl acetate and the resulting crystals were harvested by filtration and dried in vacuo to provide a light-yellow solid.

0.667 g (84%)

$^1$H-NMR (DMSO-d$_6$) δ: 1.04(3H,t,J=7.4 Hz), 2.39(3H,s), 2.51(2H,q,J=7.4 Hz), 3.41(4H,bs), 4.00(4H,br s), 5.50(2H, s), 7.00(1H,m), 7.11(1H,d,J=9.0 Hz), 7.22–7.38(4H,m), 7.51(2H,d,J=8.0 Hz), 7.62–7.73(4H,m), 8.00(1H,dd,J= 9.0&2.2 Hz), 8.46(1H,d,J=2.2 Hz).

IR (KBr): 3412, 2681, 1703, 1647, 1595, 1446, 1284, 1257, 756, 692 cm$^{-1}$.

EXAMPLE 204

6-Ethyl-7-methyl-1-[4-[6-(4-phenylpiperazino) nicotinoyl]benzyl]imidazo[1,2-a]pyrimidin-5(1H)-one A solution of 1-[4-(6-chloronicotinoyl)benzyl]-6-ethyl-7-methylimidazo[1,2-a]pyrimidin-5(1H)-one (0.810 g, 1.99 mmol) and 4-phenylpiperazine (0.350 g, 2.16 mmol) in pyridine (10.0 ml) was stirred at 90° C. overnight. The solvent was then distilled off under reduced pressure and the residue was purified by silica gel column chromatography (ethyl acetate) to provide a light-yellow amorphous solid.

0.907 g (85%)

$^1$H-NMR (CDCl$_3$) δ: 1.15(3H,t,J=7.6 Hz), 2.44(3H,s), 2.66(2H,q,J=7.6 Hz), 3.31(4H,t,J=4.8 Hz), 3.90(4H,t,J=4.8

Hz), 5.32(2H,s), 6.72(1H,d,J=9.0 Hz), 6.83(1H,d,J=2.6 Hz), 6.91(1H,t,J=8.4 Hz), 6.97(2H,d,J=8.4 Hz), 7.30(2H,t,J=8.4 Hz), 7.39(2H,d,J=8.2 Hz), 7.54(1H,d,J=2.6 Hz), 7.75(1H,d).

IR (KBr): 1657, 1589, 1518, 1417, 1282, 1225, 951, 824, 760 cm⁻¹.

EXAMPLE 205

3-Methyl-2-[4-[6-(4-phenylpiperazino)nicotinoyl]-benzyloxy]-4H-pyrido[1,2-a]pyrimidin-4-one A solution of 2-[4-(6-chloronicotinoyl)benzyloxy]-3-methylpyrido[1,2-a]pyrimidin-4-one (0.805 g, 1.98 mmol) and 4-phenylpiperazine (0.478 g, 2.95 mmol) in pyridine (10 ml) was stirred at 90°C overnight. The solvent was then distilled off under reduced pressure, the residue was diluted with water, and the resulting crystals were dried in vacuo to provide a light-yellow solid.

0.38 g (59%)

$^1$H-NMR (CDCl$_3$) δ: 2.22(3H,s), 3.32(4H,t,J=7.2 Hz), 3.90(4H,t,J=7.2 Hz), 5.62(2H,s), 6.73(1H,d,J=9.2 Hz), 6.86–7.02(3H,m), 7.10(1H,dt,J=7.0&1.2 Hz), 7.24–7.36 (2H,m), 7.45–7.82(6H,m), 8.08(1H,dd,J=9.2&2.6 Hz), 8.64 (1H,d,J=2.2 Hz), 9.08(1H,d,J=8.0 Hz).

IR (KBr): 1674, 1637, 1589, 1479, 1282, 1164 cm⁻¹.

EXAMPLE 206

3,5-Dimethyl-2-[4-[4-(4-phenylpiperazinocarbonyl)benzoyl]benzyl]thio-4(3H)-quinazolinone To a solution of 2-[4-(4-carboxybenzoyl)benzyl]thio-3,5-dimethyl-4(3H)-quinazolinone (0.472 g, 1.06 mmol) in DMF (10.0 ml) was added Diethylphosphorocyamidate (DEPC) (0.356 g, 2.18 mmol) and the mixture was stirred at room temperature for 15 minutes. Then, 4-phenylpiperazine (0.35 ml, 2.29 mmol) was added and the mixture was stirred at room temperature for 3 hours. The solvent was then distilled off and the residue was dissolved in ethyl acetate and washed with saturated aqueous NaCl solution. The organic layer was dried over MgSO$_4$ and concentrated under reduced pressure. The residue was recrystallized from THF to provide colorless needles.

0.366 g (59%)

$^1$H-NMR (CDCl$_3$) δ: 2.85(3H,s), 3.05–3.35(2H,m), 3.55 (3H,s), 3.59(1H,m), 3.95(1H,m), 4..60(2H,s), 6.88–6.98(3H, m), 7.15(1H,d,J=7.6 Hz), 7.25–7.35(2H,m), 7.43(1H,d,J= 7.4 Hz), 7.50–7.65(5H,m), 7.78(2H,d,J=8.4 Hz), 7.83(2H, d,J=8.2 Hz).

IR (KBr): 1666, 1635, 1554, 1432, 1277, 1090, 729 cm⁻¹.

EXAMPLE 207

3,5-Dimethyl-2-[4-[4-(4-hydroxypiperidinocarbonyl)benzoyl]benzyl]thio-4(3H)-quinazolinone To a solution of 2-[4-(4-carboxybenzoyl)benzyl]thio-3,5-dimethyl-4(3H)-quinazolinone (1.00 g, 2.26 mmol) in DMF (10.0 ml) was added DEPC (0.755 g, 4.63 mmol) and the mixture was stirred at room temperature for 10 minutes. Then, 4-hydroxypiperidine (0.522 g, 5.16 mmol) was added and the mixture was stirred at room temperature for 4 hours. The solvent was then distilled off and the residue was dissolved in ethyl acetate and washed with saturated aqueous NaCl solution. The organic layer was dried over MgSO$_4$ and then concentrated under reduced pressure, and the residue was recrystallized from THF to provide colorless needles.

0.735 g (62%)

$^1$H-NMR (CDCl$_3$) δ: 1.40–2.10(4H,m), 2.81(3H,s), 3.10–3.80(3H,m), 3.55(3H,s), 4.01(1H,m), 4.10–4.30(1H, m), 4.59(2H,s), 7.15(1H,d,J=6.6 Hz), 7.40–7.68(6H,m), 7.75–7.86(4H,m).

IR (KBr): 3425, 1664, 1608, 1554, 1448, 1305, 1277, 1088, 729 cm⁻¹.

EXAMPLE 208

2-[4-(4-Carboxybenzoyl)benzyloxy]-3-methyl-4H-pyrido[1,2-a]pyrimidin-4-one

A solution of 2-[4-(4-methoxycarbonyl)benzoyl) benzyloxy]-3-methyl-4H-pyrido[1,2-a]pyrimidin-4-one (1.48 g, 3.47 mmol)in DMF (30.0 ml) was heated at 90° C. To this solution was added 1N-aqueous sodium hydroxide solution (4.00 ml) and the mixture was stirred for 2 hours. The mixture was then adjusted to pH 6 with hydrochloric acid, whereupon colorless needles separated out. This crystal crop was harvested by filtration and dried in vacuo.

1.40 g (97%)

$^1$H-NMR (DMSO-d$_6$) δ: 2.09 3H,s), 5.63(2H,s), 7.32(1H, t,J=7.2 Hz), 7.57(1H,d,J=8.8 Hz), 7.67(2H,d,J=8.0 Hz), 7.80 (2H,d,J=8.0 Hz), 7.83(2H,d,J=8.0 Hz), 7.94(1H,dd,J= 8.8&7.2 Hz), 8.96(1H,d,J=7.2 Hz).

IR (KBr): 3421, 3050, 1716, 1691, 1579, 1527, 1408, 1282, 1257, 1178, 931, 788, 735 cm⁻¹.

EXAMPLE 209

1-[4-(4-Carboxybenzoyl)benzyl]-6-ethyl-7-methylimidazo[1,2-a]pyrimidin-5(1H)-one To a solution of 6-ethyl-1-[4-(4-methoxycarbonylbenzoyl)benzyl]-7-methylimidazo[1,2-a] pyrimidin-5(1H)-one (1.91 g, 4.45 mmol) in THF (30.0 ml)-methanol (10 ml) was added 1N-aqueous sodium hydroxide solution (5.00 ml) and the mixture was stirred at room temperature for 3 hours. This reaction mixture was adjusted to pH 4 with hydrochloric acid, whereupon colorless needles separated out. This crystal crop was harvested by filtration and dried in vacuo.

0.900 g (49%)

$^1$H-NMR (DMSO-d$_6$) δ: 1.03(3H,t,J=7.4 Hz), 2.33(3H,s), 3.33(2H,q,J=7.4 Hz), 5.40(2H,s), 7.49(2H,d,J=8.4 Hz), 7.58 (1H,d,J=2.6 Hz), 7.64(1H,d,J=2.6 Hz), 7.76(2H,d,J=8.4 Hz), 7.80(2H,d,J=8.4 Hz), 8.09(2H,d,J=8.4 Hz).

IR (KBr): 3396, 3134, 2968, 1713, 1645, 1562, 1523, 1414, 1275, 1225, 931, 787, 717 cm⁻¹.

EXAMPLE 210

3-Methyl-2-[4-[4-(4-phenylpiperazinocarbonyl)benzoyl]benzyloxy]-4H-pyrido[1,2-a]pyrimidin-4-one To a solution of 2-[4-(4-carboxybenzoyl)benzyloxy]-3-methyl-4H-pyrido[1,2-a]pyrimidin-4-one (0.495 g, 1.20 mmol) in DMF (15 ml) was added DEPC (0.75 ml, 4.91 mmol) and the mixture was stirred at room temperature for 30 minutes. Then, 4-phenylpiperazine (0.437 g, 2.68 mmol) was added and the mixture was further stirred overnight. This reaction mixture was diluted with ethyl acetate and washed with saturated aqueous NaCl solution. The organic layer was dried over MgSO$_4$ and concentrated under reduced pressure and the residue was recrystallized from ethyl acetate to provide colorless needles.

0.394 g (59%)

¹H-NMR (CDCl₃) δ: 2.23(3H,s), 3.13(2H,br s), 3.24(2H, br s), 3.59(2H,br s), 3.97(2H,br s), 5.63(2H,s), 6.93(1H,t,J=7.8 Hz), 6.95(2H,d,J=7.8 Hz), 7.11(1H,t,J=7.0 Hz), 7.31(2H, d,J=7.8 Hz), 7.50(1H,d,J=7.0 Hz), 7.56(2H,d,J=8.4 Hz), 7.60(2H,d,J=8.4 Hz), 7.71(1H,t,J=7.0 Hz), 7.85(2H,d,J=8.4 Hz), 7.87(2H,d,J=8.4 Hz), 9.07(1H,d,J=7.0 Hz).

IR (KBr): 1668, 1635, 1529, 1477, 1281, 1165, 1012, 928, 731 cm⁻¹.

EXAMPLE 211

6-Ethyl-7-methyl-1-[4-[4-(4-phenylpiperazinocarbonyl)benzoyl]benzyl]imidazo[1,2-a]pyrimidin-5(1H)-one To a solution of 1-[4-(4-carboxybenzoyl)benzyl]-6-ethyl-7-methylimidazo[1,2-a]pyrimidin-5(1H)-one (0.303 g, 0.729 mmol) in DMF (15 ml) was added DEPC (0.44 ml, 2.88 mmol) and the mixture was stirred at room temperature for 30 minutes. Then, 4-phenylpiperazine (0.407 g, 2.49 mmol) was added and the mixture was further stirred overnight. This reaction mixture was diluted with ethyl acetate and washed with saturated aqueous NaCl solution. The organic layer was dried over MgSO₄ and concentrated under reduced pressure and the residue was recrystallized from THF to provide colorless needles.

0.329 g (81%)

¹H-NMR (CDCl₃) δ: 1.15(3H,t,J=7.2 Hz), 2.43(3H,s), 2.66(2H,q), 5.33(2H,s), 6.85(1H,d,J=2.6 Hz), 6.92(1H,t,J=7.0 Hz), 6.94(2H,d,J=7.0 Hz), 7.30(2H,t,J=7.0 Hz), 7.42 (2H,d,J=8.4 Hz), 7.55(2H,d,J=8.4 Hz), 7.55(1H,d,J=2.6 Hz), 7.82(2H,d,J=8.4 Hz), 7.84(2H,d,J=8.4 Hz).

IR (KBr): 1653, 1587, 1520, 1435, 1277, 1221, 1011, 926, 729 cm⁻¹.

EXAMPLE 212

3-Methyl-2-[4-[4-(4-piperidinopiperidinocarbonyl)benzoyl]benzyloxy]-4H-pyrido[1,2-a]pyrimidin-4-one dihydrochloride To a solution of 2-[4-(4-carboxybenzoyl)benzyloxy]-3-methyl-4H-pyrido[1,2-a]pyrimidin-4-one (0.333 g, 0.804 mmol) in DMF (10 ml) was added DEPC (0.424 ml, 2.52 mmol) and the mixture was stirred at room temperature for 30 minutes. Then, 4-piperidinopiperidine (0.348 g, 2.13 mmol) was added and the mixture was further stirred for 2.5 hours. This reaction mixture was diluted with ethyl acetate and washed with saturated aqueous NaCl solution. The organic layer was dried over MgSO₄ and concentrated under reduced pressure. The residue was purified by silica gel column chromatography (THF: methanol: ammonia= 50:1:0.1) to give a colorless oil. This oil was treated with 4N-hydrogen chloride/ethyl acetate and the resulting hydrochloride was lyophilized from water to provide a colorless powder.

¹H-NMR (DMSO-d₆) δ: 1.30–1.60(2H,m), 1.60–2.00 (6H,m), 2.00–2.30(2H,m), 2.80–3.10(4H,m), 3.60–3.80(4H, m), 4.50–4.70(1H,m), 7.33(1H,t,J=8.2 Hz), 7.58(2H,d,J=8.0 Hz), 7.68(2H,d,J=8.0 Hz), 7.73(1H,d,J=8.2 Hz), 7.79(2H,d, J=8.0 Hz), 7.80(2H,d,J=8.0 Hz), 7.95(1H,t,J=8.2 Hz), 8.96 (1H,d,J=8.2 Hz).

IR (KBr): 3423, 2945, 1633, 1529, 1475, 1448, 1281, 1167, 1003, 930, 773 cm⁻¹.

EXAMPLE 213

6-Ethyl-7-methyl-1-[4-[4-(4-piperidinopiperidinocarbonyl)benzoyl]benzyl]imidazo[1,2-a]pyrimidin-5(1H)-one hydrochloride To a solution of 1-[4-(4-carboxybenzoyl)benzyl]-6-ethyl-7-methylimidazo[1,2-a]pyrimidin-5(1H)-one (0.302 g, 0.727 mmol) in DMF (10 ml) was added DEPC (0.318 mml, 1.95 mmol) and the mixture was stirred at room temperature for 30 minutes. Then, 4-piperidinopiperidine (0.336 g, 2.00 mmol) was added and the mixture was further stirred for 2.5 hours. This reaction mixture was diluted with ethyl acetate and washed with saturated aqueous NaCl solution. The organic layer was dried over MgSO₄ and concentrated under reduced pressure. The residue was purified by silica gel column chromatography (THF: methanol: ammonia= 50:1:0.1) to give a colorless oil. This oil was treated with 4N-HCl/ethyl acetate and the resulting hydrochloride was lyophilized from water to provide a colorless powder.

¹H-NMR (DMSO-d₆) δ: 1.19(3H,t,J=7.0 Hz), 1.35–1.55 (2H,m), 1.60–2.00(6H,m), 2.05–2.30(2H,m), 2.38(3H,s), 2.47(2H,q,J=7.0 Hz), 2.60–3.00(4H,m), 3.30–3.50(4H,m), 4.50–4.70(1H,m), 5.49(2H,s), 7.53(2H,d,J=8.2 Hz), 7.57 (2H,d,J=8.2 Hz), 7.64(1H,d,J=2.8 Hz), 7.68(1H,d,J=2.8 Hz), 7.77(2H,d,J=8.2 Hz), 7.78(2H,d,J=8.2 Hz).

IR (KBr): 3456, 2960, 2690, 1703, 1657, 1601, 1510, 1452, 1278, 1225, 1171, 1034, 1003 cm⁻¹.

EXAMPLE 214

2-[4-(4-Chlorobenzoyl)benzyl]thio-5-ethyl-3-methyl-4(3H)-quinazolinone

To a solution of 5-ethyl-3-methyl-2-mercaptoquinazolin-4-one (0.307 g, 1.39 mmol) in EtOH (5.0 ml)-THF (5.0 ml) was added 1N-aqueous sodium hydroxide solution (1.50 ml). Then, 4-(4-chlorobenzoyl)benzyl bromide (0.434 g, 1.40 mmol) was added and the mixture was stirred at room temperature for 1.5 hours. This reaction mixture was diluted with water (100 ml) and the resulting precipitate was collected by filtration, rinsed with water, and dried in vacuo. This solid product was recrystallized from ethyl acetate to provide light-yellow needles.

0.398 g (64%)

¹H-NMR (CDCl₃) δ: 1.27(3H,t,J=7.2 Hz), 2.29(2H,q,J=7.2 Hz), 4.59(2H,s), 7.18(1H,d,J=8.0 Hz), 7.44(1H,d,J=8.0 Hz), 7.45(2H,d,J=7.2 Hz), 7.58(1H,t,J=8.0 Hz), 7.60(2H,d, J=7.2 Hz), 7.72(2H,d,J=7.2), 7.73(2H,d,J=7.2 Hz).

IR (KBr): 1666, 1583, 1554, 1441, 1311, 1277, 1090, 928, 822 cm⁻¹.

EXAMPLE 215

5-Ethyl-2-[4-(4-methoxybenzoyl)benzyl]thio-3-methyl-4(3H)-quinazolinone

To a solution of 5-ethyl-3-methyl-2-mercaptoquinazolin-4-one (0.298 g, 1.35 mmol) in EtOH (5.0 ml)-THF (5.0 ml) was added 1N-aqueous sodium hydroxide solution (1.50 ml). Then, 4-(4-methoxybenzoyl)benzyl bromide (0.430 g, 1.41 mmol) was added and the mixture was stirred at room temperature for 40 minutes. This reaction mixture was diluted with water (100 ml) and the resulting precipitate was collected by filtration, rinsed with water, and dried in vacuo. This solid product was recrystallized from ethyl acetate to provide colorless needles.

0.572 g (95%)

¹H-NMR (CDCl₃) δ: 1.27(3H,t,J=8.0 Hz), 3.34(2H,q,J=8.0 Hz), 3.56(3H,s), 3.88(3H,s), 4.59(2H,s), 6.95(2H,d,J=9.0 Hz), 7.18(1H,d,J=8.8 Hz), 7.54(1H,d,J=8.8 Hz), 7.58 (2H,d,J=8.4 Hz), 7.59(1H,t,J=8.8 Hz), 7.72(2H,d,J=8.4 Hz), 7.81(2H,d,J=9.0 Hz).

IR (KBr): 1668, 1601, 1552, 1464, 1435, 1414, 1311, 1171, 1091, 1026, 928, 820 cm¹.

EXAMPLE 216

5-Ethyl-3-methyl-2-[4-(4-nitrobenzoyl)benzyl]thio-4 (3H)-quinazolinone

To a mixture of 5-ethyl-3-methyl-2-mercaptoquinazolin-4-one (0.295 g, 1.34 mmol) in EtOH (5.0 ml)-THF (5.0 ml) was added 1N-aqueous sodium hydroxide solution (1.50 ml). Then, 4-(4-nitrobenzoyl)benzyl bromide (0.434 g, 1.36 mmol) was added and the mixture was stirred at room temperature for 40 minutes. This reaction mixture was diluted with water (100 ml) and the resulting precipitate was collected by filtration, rinsed with water, and dried in vacuo. This solid was recrystallized from ethyl acetate to provide colorless needles.

0.408 g (70%)

$^1$H-NMR (CDCl$_3$) δ: 1.27(3H,t,J=7.6 Hz), 3.29(2H,q,J= 7.6 Hz), 3.56(3H,s), 4.60(2H,s), 7.19(1H,d,J=8.4 Hz), 7.44 (1H,d,J=8.4 Hz), 7.58(1H,t,J=8.4 Hz), 7.64(2H,d,J=8.4 Hz), 7.77(2H,d,J=8.4 Hz), 7.91(2H,d,J=8.8 Hz), 8.32(2H,d,J=8.8 Hz).

IR (KBr): 1666, 1601, 1552, 1524, 1466, 1437, 1412, 1346, 1311, 1092, 929 cm$^1$.

EXAMPLE 217

2-[4-(4-Diethylphosphonooxybenzoyl)benzylthio]-3, 5-dimethyl-4(3H)-quinazolinone 2-[4-(4-hydroxybenzoyl)benzylthio]-3,5-dimethyl-4(3H)-quinazolinone (268 mg), diethyl phosphorochloridate (0.16 mg), and triethylamine (0.28 ml) were dissolved in tetrahydrofuran (8 ml) and the solution was stirred at room temperature for 14 hours. This reaction mixture was concentrated and the residue was dissolved in ethyl acetate. The solution was then washed with water, dried, and concentrated, and the residue was crystallized from hexane to provide the title compound as colorless solid (270 mg).

$^1$H-NMR (CDCl$_3$) δ: 1.37(3H,t,J=7.1 Hz), 1.38(3H,t,J=7.0 Hz), 2.85(3H,s), 3.55(3H,s), 4.23(2H,q,J=7.1 Hz), 4.27 (2H,q,J=7.0 Hz), 4.60(2H,s), 7.16(1H,d,J=7.6 Hz), 7.32(2H, d,J=8.0 Hz), 7.44(1H,d,J=7.8 Hz), 7.53(1H,d,J=7.2 Hz), 7.61(2H,d,J=8.2 Hz), 7.75(2H,d,J=8.4 Hz), 7.81(7H,d,J=8.4 Hz).

IR (KBr): 1683, 1556, 1471, 1270, 1031 cm$^{-1}$.

EXAMPLE 218

3,5-Dimethyl-2-[4-[4-(2-dimethylaminoethoxy) benzoyl]benzylthio]-4(3H)-quinazolinone hydrochloride 2-[4-(4-Hydroxybenzoyl)benzylthio]-3,5-dimethyl-4(3H)-quinazolinone (306 mg), 2-dimethylaminoethyl chloride hydrochloride (218 mg), and potassium carbonate (316 mg) were dissolved in DMF (5 ml) and the solution was stirred at 80° C. for 20 hours. This reaction mixture was concentrated and the residue was dissolved in ethyl acetate, washed with water, and dried. Then, hydrogen chloride/ethyl acetate was added and the precipitated hydrochloride was collected by filtration to provide the title compound as colorless solid (193 mg).

$^1$H-NMR (DMSO-d$_6$) δ: 2.76(3H,s), 2.87(6H,s), 3.46(3H, s), 3.56(2H,m), 4.47(2H,m), 4.65(2H,s), 7.14(2H,d,J=8.8 Hz), 7.21(1H,d,J=7.6 Hz), 7.47(1H,d,J=8.2 Hz), 7.58–7.82 (7H,m).

IR (KBr): 1641, 1600, 1473, 1303, 1170, 808 cm$^{-1}$.

EXAMPLE 219

2-[4-(4-Acetoxybenzoyl)benzylthio]-3,5-dimethyl-4 (3H)-quinazolinone

A solution of 3,5-dimethyl-2-mercapto-4(3H)-quinazolinone (917 mg), 4-(4-acetoxybenzoyl)benzyl bromide (1.785 g) and 1N-aqueous sodium hydroxide solution (4.5 ml) in methanol (20 ml) was stirred at room temperature for 4 hours. This reaction mixture was concentrated and extracted with chloroform and the extract was washed with water, dried, and concentrated. The residue was purified by silica gel column chromatography (hexane: ethyl acetate= 6:1) to provide the title compound as colorless solid (4.26 mg).

$^1$H-NMR (CDCl$_3$) δ: 2.34(3H,s), 2.85(3H,s), 3.55(3H,s), 4.59(2H,s), 7.15(1H,d,J=7.6 Hz), 7.21(2H,d,J=8.4 Hz), 7.44 (1H,d,J=7.4 Hz), 7.50–7.64(3H,m), 7.77(2H,d,J=8.2 Hz), 7.83(2H,d,J=8.8 Hz).

IR (KBr): 1754, 1670, 1652, 1558, 1471, 1303, 1193 cm$^{-1}$.

EXAMPLE 220

3,5-Dimethyl-2-[4-(4-hydroxybenzoyl)benzylthio]-4 (3H)-quinazolinone

A solution of 3,5-dimethyl-2-mercapto-4(3H)-quinazolinone (952 mg), 4-(4-t-butyldimethylsilyloxybenzoyl)benzyl bromide (2.90 g) and 1N-aqueous sodium hydroxide solution (4.6 ml) in methanol (20 ml) was stirred at room temperature for 4 hours. This reaction mixture was concentrated and extracted with chloroform and the extract was washed with water, dried, and concentrated. The residue was purified by silica gel column chromatography (hexane: ethyl acetate=19:1). The resulting 2-[4-(4-t-butyldimethylsilyloxybenzoyl)benzylthio]-3,5-dimethyl-4(3H)-quinazolinone was dissolved in tetrahydrofuran (15 ml). To this solution was added 1M tetrabutylammonium fluoride/tetrahydrofuran (3.8 ml), and the mixture was stirred at room temperature for 1 hour. This reaction mixture was diluted with water and the resulting precipitate was collected by filtration, rinsed with water, and dried to provide the title compound as colorless solid (1.332 g).

$^1$H-NMR (DMSO-d$_6$) δ: 2.75(3H,s), 3.45(3H,s), 4.63(2H, s), 6.87(2H,d,J=8.7 Hz), 7.21(1H,d,J=7.3 Hz), 7.46(1H,d,J= 7.3 Hz), 7.57–7.72(7H,m).

IR (KBr): 1652, 1604, 1556, 1471, 1309, 1039 cm$^{-1}$.

EXAMPLE 221

2-[4-(4-Benzyloxybenzoyl)benzylthio]-3,5-dimethyl-4(3H)-quinazolinone

A solution of 2-[4-(4-hydroxybenzoyl)benzylthio]-3,5-dimethyl-4(3H)-quinazolinone (395 mg), benzyl bromide (0.13 ml) and potassium carbonate (408 mg) in DMF (5 ml) was stirred at 60° C. for 1 hour. This reaction mixture was concentrated and the residue was dissolved in ethyl acetate, washed with water, dried, and concentrated. The residue was recrystallized from ethyl acetate to provide the title compound as colorless solid (346 mg).

$^1$H-NMR (CDCl$_3$) δ: 2.85(3H,s), 3.55(3H,s), 4.60(2H,s), 5.15(2H,s), 7.03(2H,d,J=8.9 Hz), 7.16(1H,d,J=7.2 Hz), 7.34–7.64(9H,m), 7.73(2H,d,J=8.4 Hz), 7.81(2H,d,J=8.9 Hz).

IR (KBr): 1683, 1598, 1560, 1469, 1172, 1093 cm$^{-1}$.

EXAMPLE 222

3,5-Dimethyl-2-[4-[4-(2-pyrrolidinoethoxy)benzoyl] benzylthio]-4(3H)-quinazolinone hydrochloride A solution of 2-[4-(4-hydroxybenzoyl)benzylthio]-3,5-dimethyl-4(3H)-quinazolinone (384 mg), 1-(2-chloroethyl)

pyrrolidine hydrochloride (181 mg) and potassium carbonate (414 mg) in DMF (5 ml) was stirred at 60° C. for 62 hours. This reaction mixture was concentrated and the residue was dissolved in ethyl acetate, washed with water, and dried. Then, hydrogen chloride/ethyl acetate was added and the precipitated hydrochloride was collected by filtration to provide the title compound as colorless solid (227 mg).

$^1$H-NMR (DMSO-d$_6$) δ: 1.78–2.12(4H,m), 2.75(3H,s), 3.02–3.24(2H,m), 3.46(3H,s), 3.50–3.68(4H,m), 4.43(2H,t, J=5.0 Hz), 4.65(2H,s), 7.15(2H,d,J=8.8 Hz), 7.22(1H,d,J= 8.0 Hz), 7.47(1H,d,J=7.8 Hz), 7.58–7.82(7H,m).

IR (KBr): 1675, 1600, 1554, 1471, 1307, 1172, 1093 cm$^{-1}$.

EXAMPLE 223

3,5-Dimethyl-2-[4-[4-(2-piperidinoethoxy)benzoyl]-benzylthio]-4(3H)-quinazolinone hydrochloride A solution of 2-[4-(4-hydroxybenzoyl)benzylthio]-3,5-dimethyl-4(3H)-quinazolinone (399 mg), 1-(2-chloroethyl) piperidine hydrochloride (185 mg) and potassium carbonate (392 mg) in DMF (5 ml) was stirred at 60° C. for 62 hours. This reaction mixture was concentrated and the residue was dissolved in ethyl acetate, washed with water, and dried. Then, hydrogen chloride/ethyl acetate was added and the precipitated hydrochloride was recovered by filtration to provide the title compound as colorless solid (368 mg).

$^1$H-NMR (DMSO-d$_6$) δ: 1.76–1.96(6H,m), 2.75(3H,s), 2.90–3.16(2H,m), 3.64(3H,s), 3.20–3.70(4H,m), 4.49(2H,t, J=4.4 Hz), 4.65(2H,s), 7.14(2H,d,J=8.8 Hz), 7.21(1H,d,J= 6.8 Hz), 7.47(1H,d,J=7.4 Hz), 7.58–7.80(7H,m).

IR (KBr): 1675, 1598, 1554, 1309, 1147, 1093 cm$^{-1}$.

EXAMPLE 224

3,5-Dimethyl-2-[4-[4-(2-morpholinoethoxy)benzoyl]-benzylthio]-4(3H)-quinazolinone hydrochloride A solution of 2-[4-(4-hydroxybenzoyl)benzylthio]-3,5-dimethyl-4(3H)-quinazolinone (366 mg), 4-(2-chloroethyl) morpholine hydrochloride (192 mg) and potassium carbonate (356 mg) in DMF (5 ml) was stirred at 60° C. for 62 hours. This reaction mixture was concentrated and the residue was dissolved in ethyl acetate, washed with water, and dried. Then, hydrogen chloride/ethyl acetate was added and the precipitated hydrochloride was collected by filtration to provide the title compound as colorless solid (337 mg).

$^1$H-NMR (DMSO-d$_6$) δ: 2.75(3H,s), 3.08–3.68(9H,m), 3.70–4.08(4H,m), 4.53(2H,t,J=4.5 Hz), 4.65(2H,s), 7.15 (2H,d,J=9.0 Hz), 7.21(1H,d,J=7.2 Hz), 7.47(1H,d,J=8.0 Hz), 7.58–7.81(7H,m).

IR (KBr): 1683, 1600, 1558, 1471, 1305, 1172, 1095 cm$^{-1}$.

EXAMPLE 225

3,5-Dimethyl-2-[4-[4-(3-dimethylaminopropoxy)-benzoyl]benzylthio]-4(3H)-quinazolinone hydrochloride A solution of 2-[4-(4-hydroxybenzoyl)benzylthio]-3,5-dimethyl-4(3H)-quinazolinone (311 mg), 3-dimethylaminopropyl chloride hydrochloride (249 mg) and potassium carbonate (322 mg) in DMF (5 ml) was stirred at 60° C. for 18 hours. This reaction mixture was concentrated and the residue was dissolved in ethyl acetate, washed with water, and dried. Then, hydrogen chloride/ethyl acetate was added and the precipitated hydrochloride was collected by filtration to provide the title compound as colorless solid (185 mg).

$^1$H-NMR (DMSO-d$_6$) δ: 2.18(2H,m), 2.76(3H,s), 2.81 (6H,s), 3.24(2H,m), 3.46(3H,s), 4.17(2H,m), 4.65(2H,s), 7.08(2H,d,J=8.2 Hz), 7.23(1H,d,J=8.2 Hz), 7.48(1H,d,J=7.8 Hz), 7.58–7.82(7H,m).

IR (KBr): 1675, 1558, 1471, 1305, 1172 cm$^{-1}$.

EXAMPLE 226

2-[4-[4-(2-Acetoxyethoxy)benzoyl]benzylthio]-3,5-dimethyl-4(3H)-quinazolinone

A solution of 3,5-dimethyl-2-mercapto-4(3H)-quinazolinone (1.888 g), 4-(4-acetoxyethoxybenzoyl)benzyl bromide (3.895 g) and 1N-aqueous sodium hydroxide solution (14.3 ml) in methanol (30 ml) was stirred at room temperature for 30 minutes. This reaction mixture was concentrated and extracted with chloroform. The extract was washed with water, dried, and concentrated, and the residue was recrystallized from ethyl acetate to provide the title compound as colorless solid (2.597 g).

$^1$H-NMR (CDCl3) δ: 2.13(3H,s), 2.85(3H,s), 3.55(3H,s), 4.25(2H,m), 4.46(2H,m), 4.60(2H,s), 6.97(2H,d,J=9.0 Hz), 7.15(1H,d,J=6.6 Hz), 7.45(1H,d,J=6.8 Hz), 7.50–7.64(3H, m), 7.73(2H,d,J=8.2 Hz), 7.82(2H,d,J=8.8 Hz).

IR (KBr): 1737, 1668, 1600, 1554, 1174, 1085 cm$^{-1}$.

EXAMPLE 227

3,5-Dimethyl-2-[4-[4-(2-hydroxyethoxy)benzoyl]-benzylthio]-4(3H)-quinazolinone

A solution of 2-[4-[4-(2-acetoxyethoxy)benzoyl]-benzylthio]-3,5-dimethyl-4(3H)-quinazolinone (1.75 g) and 1N-aqueous sodium hydroxide solution (15 ml) in methanol (50 ml)-dichloromethane (25 ml) was stirred at room temperature for 3 hours. This reaction mixture was extracted with dichloromethane and the extract was dried and concentrated. The residue was recrystallized from ethyl acetate to provide the title compound as colorless solid (1.278 g).

$^1$H-NMR (CDCl$_3$) δ: 2.85(3H,s), 3.55(3H,s), 4.02(2H,m), 4.17(2H,t,J=4.4 Hz), 4.60(2H,s), 6.98(2H,d,J=8.8 Hz), 7.15 (1H,d,J=6.6 Hz), 7.45(1H,d,J=6.6 Hz), 7.52–7.63(3H,m), 7.73(2H,d,J=8.4 Hz), 7.82(2H,d,J=8.8 Hz).

IR (KBr): 1683, 1600, 1553, 1471, 1305, 1093 cm$^{-1}$.

EXAMPLE 228

3,5-Dimethyl-2-[4-[4-(N,N-dimethylcarbamoyloxy)-benzoyl]benzylthio]-4(3H)-quinazolinone A solution of 2-[4-(4-hydroxybenzoyl)benzylthio]-3,5-dimethyl-4(3H)-quinazolinone (478 mg), dimethylcarbamoyl chloride (0.15 ml) and potassium carbonate (315 mg) in DMF (7 ml) was stirred at 50° C. for 48 hours. This reaction mixture was concentrated and the residue was dissolved in ethyl acetate. The solution was washed with water, dried, and concentrated. The residue was recrystallized from ethyl acetate to provide the title compound as colorless solid (346 mg).

$^1$H-NMR (CDCl$_3$) δ: 2.85(3H,s), 3.04(3H,s), 3.13(3H,s), 3.55(3H,s), 4.59(2H,s), 7.15(1H,d,J=7.0 Hz), 7.23(2H,d,J= 8.8 Hz), 7.44(1H,d,J=8.2 Hz), 7.50–7.64(3H,m), 7.77(2H, d,J=8.2 Hz), 7.81(2H,d,J=8.8 Hz).

IR (KBr): 1733, 1670, 1602, 1562, 1471, 1160, 1091 cm$^{-1}$.

EXAMPLE 229

3,5-Dimethyl-2-[4-[4-[4-(4-formylpiperazinylcarbonyl)benzyloxy]benzoyl]benzylthio]-4(3H)-quinazolinone A solution of 2-[4-(4-hydroxybenzoyl)benzylthio]-3,5-dimethyl-4(3H)-quinazolinone (402 mg), 1-(4-chloromethylbenzoyl)-4-formylpiperazine (354 mg) and potassium carbonate (261 mg) in DMF (5 ml) was stirred at room temperature for 24 hours. This reaction mixture was concentrated and the residue was dissolved in ethyl acetate. The solution was washed with water, dried, and concentrated. The residue was purified by silica gel column chromatography (ethyl acetate) to provide the title compound as colorless solid (310 mg).

$^1$H-NMR (CDCl$_3$) δ: 2.85(3H,s), 3.35–3.80(8H,m), 3.55 (3H,s), 4.60(2H,s), 5.19(2H,s), 7.02(2H,d,J=8.9 Hz), 7.15 (1H,d,J=7.2 Hz), 7.49–7.61(8H,m), 7.73(2H,d,J=8.3 Hz), 7.82(2H,d,J=8.9 Hz), 8.12(1H,s).

IR (KBr): 1670, 1600, 1558, 1456, 1307, 1172 cm$^{-1}$.

EXAMPLE 230

2-[4-[4-(4-Benzyloxybenzyloxy]benzoyl]benzylthio]-3,5-dimethyl-4(3H)-quinazolinone A solution of 2-[4-(4-hydroxybenzoyl)benzylthio]-3,5-dimethyl-4(3H)-quinazolinone (309 mg), 4-benzyloxybenzyl chloride (224 mg) and potassium carbonate (295 mg) in DMF (5 ml) was stirred at room temperature for 14 hours. This reaction mixture was concentrated and the residue was dissolved in chloroform. The solution was washed with water, dried, and concentrated. The residue was recrystallized from chloroform-ethyl acetate to provide the title compound as colorless solid (355 mg).

$^1$H-NMR (CDCl$_3$) δ: 2.85(3H,s), 3.55(3H,s), 4.59(2H,s), 5.07(2H,s), 5.09(2H,s), 7.00(2H,d,J=8.6 Hz), 7.01(2H,d,J=8.8 Hz), 7.15(1H,d,J=7.2 Hz), 7.32–7.62(11H,m), 7.73(2H,d,J=8.3 Hz), 7.81(2H,d,J=8.8 Hz).

IR (KBr): 1683, 160, 1552, 1456, 1305, 1172, 1093 cm$^{-1}$.

EXAMPLE 231

3,5-Dimethyl-2-[4-[4-(4-picolyloxy)benzoyl]benzylthio]-4(3H)-quinazolinone

A solution of 2-[4-(4-hydroxybenzoyl)benzylthio]-3,5-dimethyl-4(3H)-quinazolinone (369 mg), 4-picolyl chloride hydrochloride (144 mg) and potassium carbonate (350 mg) in DMF (5 ml) was stirred at room temperature for 3 days. This reaction mixture was concentrated and the residue was dissolved in ethyl acetate, washed with water, dried, and concentrated. The residue was recrystallized from ethyl acetate-chloroform to provide the title compound as colorless solid (99 mg).

$^1$H-NMR (CDCl$_3$) δ: 2.85(3H,s), 3.55(3H,s), 4.60(2H,s), 5.18(2H,s), 7.01(2H,d,J=8.9 Hz), 7.15(1H,d,J=6.8 Hz), 7.37 (2H,d,J=5.4 Hz), 7.44(1H,d,J=8.0 Hz), 7.50–7.64(3H,m), 7.73(2H,d,J=8.2 Hz), 7.82(2H,d,J=8.9 Hz), 8.65(2H,d,J=5.4 Hz).

IR (KBr): 1670, 1600, 1554, 1471, 1305, 1170, 1093 cm$^{-1}$.

EXAMPLE 232

3,5-Dimethyl-2-[4-[4-[2-(4-methylpiperazinyl)ethoxy]benzoyl]benzylthio]-4(3H)-quinazolinone dihydrochloride A solution of 2-[4-[4-(2-chloroethoxy]benzoyl]benzylthio]-3,5-dimethyl-4(3H)-quinazolinone (173 mg) and 1-methylpiperazine (0.12 ml) in DMF (5 ml) was stirred at 100° C. for 15 hours. This reaction mixture was concentrated and the residue was dissolved in ethyl acetate, washed with water, and dried. Then, hydrogen chloride/ethyl acetate was added and the precipitated hydrochloride was collected by filtration and dried to provide the title compound as colorless solid (122 mg).

$^1$H-NMR (DMSO-d$_6$) δ: 2.76(3H,s), 3.46(3H,s), 2.80–3.70(13H,m), 4.16–4.40(2H,m), 4.65(2H,s), 7.10(2H, d,J=8.4 Hz), 7.22(1H,d,J=7.4 Hz), 7.47(1H,d,J=7.8 Hz), 7.58–7.80(7H,m).

IR (KBr): 1670, 1600, 1558, 1471, 1307, 1172, 1093, 929 cm$^{-1}$.

EXAMPLE 233

2-[4-[4-(2-Chloroethoxy)benzoyl]benzylthio]-3,5-dimethyl-4(3H)-quinazolinone

To a suspension of 3,5-dimethyl-2-[4-[4-(2-hydroxyethoxy)benzoyl]benzylthio]-4(3H)-quinazolinone (651 mg) in carbon tetrachloride (15 ml) was added triphenylphosphine (476 mg) and the mixture was refluxed for 40 hours. This reaction mixture was concentrated and the residue was purified by silica gel column chromatography (dichloromethane) and recrystallized from ethyl acetate to provide the title compound as colorless solid (391 mg).

$^1$H-NMR (CDCl$_3$) δ: 2.85(3H,s), 3.55(3H,s), 3.85(2H,t, J=5.9 Hz), 4.31(2H,t,J=5.9 Hz), 4.60(2H,s), 6.97(2H,d,J=8.9 Hz), 7.15(1H,d,J=7.0 Hz), 7.44(1H,d,J=8.2 Hz), 7.50–7.64 (3H,m), 7.73(2H,d,J=8.4 Hz), 7.82(2H,d,J=8.9 Hz).

IR (KBr): 1670, 1600, 1554, 1307, 1174, 1093, 696 cm$^{-1}$.

EXAMPLE 234

3,5-Dimethyl-2-[4-(4-phenacyloxybenzoyl)benzylthio]-4-(3H)-quinazolinone

A solution of 2-[4-(4-hydroxybenzoyl)benzylthio]-3,5-dimethyl-4(3H)-quinazolinone (413 mg), phenacyl bromide (315 mg) and potassium carbonate (436 mg) in DMF (7 ml) was stirred at room temperature for 15 hours. This reaction mixture was concentrated and the residue was dissolved in chloroform, washed with water, dried, and concentrated. The residue was recrystallized from chloroform-ethyl acetate to provide the title compound as colorless solid (313 mg).

$^1$H-NMR (CDCl$_3$) δ: 2.85(3H,s), 3.54(3H,s), 4.59(2H,s), 5.38(2H,s), 6.98(2H,d,J=8.8 Hz), 7.14(1H,d,J=7.0 Hz), 7.40–7.67(7H,m), 7.72(2H,d,J=8.4 Hz), 7.80(2H,d,J=8.8 Hz), 8.01(2H,m).

IR (KBr): 1708, 1675, 1594, 1560, 1471, 1176, 1093 cm$^{-1}$.

EXAMPLE 235

3,5-Dimethyl-2-[4-[4-[2-(4-piperidinopiperidino)-ethoxy]benzoyl]benzylthio]-4(3H)-quinazolinone dihydrochloride A solution of 2-[4-[4-(2-chloroethoxy)benzoyl]benzylthio]-3,5-dimethyl-4(3H)-quinazolinone (375 mg) and 4-piperidinopiperidine (434 mg) in DMF (5 ml) was stirred at 100° C. for 7 hours. This reaction mixture was concentrated and the residue was dissolved in ethyl acetate, washed with water, dried, and concentrated. Then, hydrogen chloride/ethyl acetate was added and the precipitated hydrochloride was recovered by filtration and dried to provide the title compound as colorless solid (368 mg).

¹H-NMR (DMSO-d₆) δ: 2.76(3H,s), 3.46(3H,s), 1.80–3.80(21H,m), 4.50(2H,br s), 4.66(2H,s), 7.15(2H,d,J= 8.8 Hz), 7.22(1H,d,J=7.4 Hz), 7.48(1H,d,J=7.6 Hz), 7.58–7.83(7H,m).

IR (KBr): 1670, 1598, 1558, 1457, 1307, 1172, 1093 cm⁻¹.

EXAMPLE 236

3,5-Dimethyl-2-[4-[4-[2-(2-dimethylaminoethylamino)ethoxy]benzoyl]benzylthio]-4(3H)-quinazolinone dihydrochloride A solution of 2-[4-[4-(2-chloroethoxy)benzoyl]-benzylthio]-3,5-dimethyl-4(3H)-quinazolinone (237 mg) and 2-dimethylaminoethylamine (1.1 ml) in DMF (5 ml) was stirred at 100° C. for 7 hours. This reaction mixture was concentrated and the residue was purified by silica gel column chromatography (dichloromethane: methanol: aqueous ammonia =9:1:0.1) and treated with hydrogen chloride/ ethyl acetate to provide the title compound as colorless solid (104 mg).

¹H-NMR (DMSO-d₆) δ: 2.75(3H,s), 2.85(6H,br s), 3.30–3.60(9H,m), 4.36–4.46(2H,br s), 4.65(2H,s), 7.10–7.25(3H,m), 7.46(1H,d,J=8.0 Hz), 7.56–7.84(7H,m), 9.58–9.82(1H,br).

IR (KBr): 1652, 1600, 1558, 1457, 1305, 1172 cm⁻¹.

EXAMPLE 237

3,5-Dimethyl-2-[4-[4-(4-phenylphenacyloxy)benzoyl]benzylthio]-4(3H)-quinazolinone A solution of 2-[4-(4-hydroxybenzoyl)benzylthio]-3,5-dimethyl-4(3H)-quinazolinone (398 mg), 4-phenylphenacyl bromide (290 mg) and potassium carbonate (440 mg) in DMF (7 ml) was stirred at room temperature for 72 hours. This reaction mixture was concentrated and the residue was purified by silica gel column chromatography (dichloromethane: ether =10:1) and recrystallized from chloroform-ethyl acetate to provide the title compound as colorless solid (217 mg).

¹H-NMR (CDCl₃) δ: 2.85(3H,s), 3.55(3H,s), 4.59(2H,s), 5.41(2H,s), 7.01(2H,d,J=9.0 Hz), 7.15(1H,d,J=7.0 Hz), 7.41–7.78(13H,m), 7.81(2H,d,J=9.0 Hz), 8.09(2H,d,J=8.6 Hz).

IR (KBr): 1675, 1600, 1558, 1471, 1305, 1093 cm¹.

EXAMPLE 238

3,5-Dimethyl-2-[4-[4-[2-(2-morpholinoethylamino)-ethoxy]benzoyl]benzylthio]-4(3H)-quinazolinone dihydrochloride A solution of 2-[4-[4-(2-(chloroethoxy)benzoyl)benzylthio]-3,5-dimethyl-4(3H)-quinazolinone (165 mg) and 4-(2-aminoethyl)morpholine (543 mg) in DMF (7 ml) was stirred at 100° C. for 7 hours. This reaction mixture was concentrated and the residue was purified by silica gel column chromatography (dichloromethane: methanol: aqueous ammonia =9:1:0.1) and treated with hydrogen chloride/ ethyl acetate to provide the title compound as colorless solid (101 mg).

¹H-NMR (DMSO-d₆) δ: 2.75(3H,s), 3.45(3H,s), 3.00–4.80(16H,m), 7.10–7.26(3H,m), 7.47(1H,d,J=8.0 Hz), 7.58–7.82(7H,m).

IR (KBr): 1646, 1602, 1558, 1307, 1174, 1147, 1108 cm⁻¹.

EXAMPLE 239

3,5-Dimethyl-2-[4-[4-[2-[N-[2-(2-pyridyl)ethyl]-N-methylamino]ethoxy]benzoyl]benzylthio]-4(3H)-quinazolinone dihydrochloride A solution of 2-[4-[4-(2-chloroethoxy)benzoyl]-benzylthio]-3,5-dimethyl-4(3H)-quinazolinone (381 mg), 2-(2-methylaminoethyl)pyridine (0.17 ml) and triethylamine (0.33 ml) in DMF (7 ml) was stirred at 100° C. for 21 hours. This reaction mixture was concentrated and the residue was purified by silica gel column chromatography (dichloromethane: methanol: aqueous ammonia =9:1:0.1) and treated with hydrogen chloride/ethyl acetate to provide the title compound as colorless solid (256 mg).

¹H-NMR (DMSO-d₆) δ; 2.75(3H,s), 2.97(3H,s), 3.45(3H, s), 3.46–4.20(6H,m), 4.56(2H,br s), 4.64(2H,s), 7.08–7.24 (3H,m), 7.46(1H,d,J=8.4 Hz), 7.56–7.80(7H,m), 7.87(1H,t, J=6.6 Hz), 7.99(1H,d,J=7.8 Hz), 8.45(1H,t,J=7.8 Hz), 8.82 (1H,d,J=5.4 Hz).

IR (KBr): 1662, 1600, 1556, 1307, 1174, 1110 cm⁻¹.

EXAMPLE 240

3,5-Dimethyl-2-[4-[4-[4-(4-methylpiperazinylcarbonyl)benzyloxy]benzoyl]benzylthio]-4(3H)-quinazolinone hydrochloride A solution of 2-[4-(4-hydroxybenzoyl)benzylthio]-3,5-dimethyl-4(3H)-quinazolinone (406 mg), 1-(4-chloromethylbenzoyl)-4-methylpiperazine hydrochloride (1.119 g) and potassium carbonate (739 mg) in DMF (10 ml) was stirred at room temperature for 40 hours. This reaction mixture was concentrated and the residue was purified by silica gel column chromatography (dichloromethane: methanol =9:1) and treated with hydrogen chloride/ethyl acetate to provide the title compound as colorless solid (86 mg).

¹H-NMR (CDCl₃) δ: 2.28–2.58(4H,m), 2.33(3H,s), 2.85 (3H,s), 3.38–3.60(2H,m), 3.54(3H,s), 3.64–3.90(2H,m), 4.59(2H,s), 5.17(2H,s), 7.01(2H,d,J=8.8 Hz), 7.14(1H,d, J=7.0 Hz), 7.40–7.62(8H,m), 7.72(2H,d,J=8.0 Hz), 7.81(1H, d,J=8.8 Hz).

IR (KBr): 1652, 1600, 1558, 1471, 1307, 1172, 1093 cm⁻¹.

EXAMPLE 241

6-Ethyl-7-methyl-1-[4-[4-(2-morpholinoethoxy)benzoyl]benzyl]imidazo[1,2-a]pyrimidin-5(1H)-one hydrochloride A solution of 6-ethyl-1-[4-(4-hydroxybenzoyl)-benzyl]-7-methylimidazo[1,2-a]pyrimidin-5(1H)-one (136 mg), 4-(2-chloroethyl)morpholine hydrochloride (154 mg) and potassium carbonate (205 mg) in DMF (7 ml) was stirred at 100° C. for 6 hours. This reaction mixture was concentrated and the residue was dissolved in ethyl acetate, washed with water, and dried. Then, hydrogen chloride/ethyl acetate was added and the precipitated hydrochloride was collected by filtration and dried to provide the title compound as colorless solid (132 mg).

¹H-NMR (CDCl₃) δ: 1.15(3H,t,J=7.4 Hz), 2.63(2H,q,J= 7.4 Hz), 2.80(3H,s), 2.96–3.21(2H,m), 3.44–3.70(4H,m), 4.01(2H,d,J=12.0 Hz), 4.30(2H,t,J=12.4 Hz), 4.72(2H,m), 6.20(2H,s), 6.98(2H,d,J=8.8 Hz), 7.10(1H,d,J=2.2 Hz), 7.58–7.84(7H,m).

IR (KBr): 1699, 1652, 1598, 1176 cm⁻¹.

EXAMPLE 242

6-Ethyl-1-[4-(4-hydroxybenzoyl)benzyl]-7-methyl-imidazo[1,2-a]pyrimidin-5(1H)-one A solution of 6-ethyl-7-methylimidazo[1,2-a]-pyrimidin-5(1H)-one (3.93 g), 4-(4-t-butyldimethylsilyloxybenzoyl)

benzyl bromide (14.79 g) and potassium carbonate (5.97 g) in DMF (25 ml)-dimethyl sulfoxide (25 ml) was stirred at room temperature for 20 hours. This reaction mixture was concentrated and the residue was extracted with ethyl acetate. The extract was washed with water, dried, and concentrated. The residue was purified by silica gel column chromatography (dichloromethane: methanol =9:1) and recrystallized from ethanol-ethyl acetate to provide the title compound as colorless solid (909 mg).

$^1$H-NMR (DMSO-d$_6$) δ: 1.03(3H,t,J=7.2 Hz), 2.34(3H,s), 2.52(2H,q,J=7.2 Hz), 5.38(2H,s), 6.88(2H,d,J=8.6 Hz), 7.45 (2H,d,J=8.2 Hz), 7.58–7.71(6H,m), 10.44(1H,s).

IR (KBr): 150 , 1596, 1456, 1168 cm$^{-1}$.

EXAMPLE 243

6-Ethyl-7-methyl-1-[4-[4-(4-picolyloxy)benzoyl]-benzyl]imidazo[1,2-a]pyrimidin-5(1H)-one hydrochloride A solution of 6-ethyl-1-[4-[4-(4-hydroxybenzoyl)-benzyl]-7-methylimidazo[1,2-a]pyrimidin-5(1H)-one (126 mg), 4-picolyl chloride hydrochloride (154 mg) and potassium carbonate (274 mg) in DMF (7 ml) was stirred at room temperature for 17 hours. This reaction mixture was concentrated and the residue was dissolved in ethyl acetate. The solution was washed with water, dried, and concentrated. The residue was purified by silica gel column chromatography (chloroform: methanol =19:1) and treated with hydrogen chloride/ethyl acetate to provide the title compound as colorless solid (140 mg).

$^1$H-NMR (DMSO-d$_6$) δ: 1.04(3H,t,J=7.2 Hz), 2.46–2.62 (5H,m), 5.46(2H,s), 6.51(2H,s), 7.21(2H,d,J=8.6 Hz), 7.50 (2H,d,J=8.0 Hz),7.62–7.88(6H,m), 8.11(2H,d,J=6.6 Hz), 8.96(2H,d,J=6.6 Hz).

IR (KBr): 1704, 1652, 1598, 1457, 1174, 929 cm$^{-1}$.

EXAMPLE 244

3-Methyl-2-[4-[4-(2-morpholinoethoxy)benzoyl] benzyloxy]-4H-pyrido[1,2-a]pyrimidin-4-one hydrochloride A solution of 2-[4-(4-hydroxybenzoyl)benzyloxy]-3-methyl-4H-pyrido[1,2-a]pyrimidin-4-one (104 mg), 4-(2-chloroethyl)morpholine hydrochloride (90 mg) and potassium carbonate (179 mg) in DMF (7 ml) was stirred at 100° C. for 20 hours. This reaction mixture was concentrated and the residue was dissolved in ethyl acetate, washed with water, dried, and concentrated. Then, hydrogen chloride-ethyl acetate was added and the precipitated hydrochloride was collected by filtration and dried to provide the title compound as colorless solid (24 mg).

$^1$H-NMR (DMSO-d$_6$) δ: 2.09(3H,s), 3.10–4.08(10H,m), 4.52(2H,m), 5.64(2H,s), 7.16(2H,d,J=8.6 Hz), 7.34(1H,dt, J=7.0&1.4 Hz), 7.56–7.84(7H,m), 7.95(1H,m), 8.97(1H,d, J=7.2 Hz).

IR (KBr): 1670, 1600, 1481, 1170, 927 cm$^{-1}$.

EXAMPLE 245

3-Methyl-2-[4-[4-(4-picolyloxy)benzoyl]benzyloxy]-4H-pyrido[1,2-a]pyrimidin-4-one hydrochloride A solution of 2-[4-(4-hydroxybenzoyl)benzyloxy]-3-methyl-4H-pyrido[1,2-a]pyrimidin-4-one (96 mg), 4-picolyl chloride hydrochloride (89 mg) and potassium carbonate (178 mg) in DMF (7 ml) was stirred at room temperature for 13 hours. This reaction mixture was concentrated and the residue was dissolved in ethyl acetate, washed with water, dried, and concentrated. The residue was purified by silica gel column chromatography (dichloromethane: methanol =20:1) and treated with hydrogen chloride/ethyl acetate to provide the title compound as colorless solid (87 mg).

$^1$H-NMR (DMSO-d$_6$) δ: 2.09(3H,s), 5.60(2H,s), 5.63(2H, s), 7.22(2H,d,J=8.8 Hz), 7.33(1H,t,J=6.9 Hz), 7.56– 7.86 (7H,m), 7.93(1H,t,J=7.4 Hz), 8.08(2H,t,J=5.8 Hz), 8.95(3H, m).

IR (KBr): 1666, 1598, 1461, 1172, 929 cm$^{-1}$.

EXAMPLE 246

2-[4-(6-Chloronicotinoyl)benzylthio]-3-methyl-4H-pyrido[1,2-a]pyrimidin-4-one

A solution of 2-mercapto-3-methyl-4H-pyrido[1,2-a] pyrimidin-4-one (599 mg), 4-(6-chloronicotinoyl)benzyl bromide (1.179 g) and potassium carbonate (1.148 g) in DMF (40 ml) was stirred at room temperature for 2 hours. This reaction mixture was concentrated and the residue was dissolved in ethyl acetate, washed with water, dried, and concentrated. The residue was recrystallized from tetrahydrofuranethyl acetate to provide the title compound as colorless solid (367 mg).

$^1$H-NMR (CDCl$_3$) δ: 2.09(3H,s), 4.65(2H,s), 7.31(11H, dt,J=7.0&1.4 Hz), 7.65–7.80(6H,m), 7.93(1H,m), 8.14(1H, dd,J=8.2&2.4 Hz), 8.69(1H,d,J=3.4 Hz), 8.89(1H,d,J=7.0 Hz).

IR (KBr): 1672, 1577, 1461, 1103, 925, 765 cm$^{-1}$.

EXAMPLE 247

3-Methyl-2-[4-[6-(4-piperidinopiperidino)nicotinoyl] benzylthio]-4H-pyrido[1,2-a]pyrimidin-4-one trihydrochloride A solution of 2-[4-(6-chloronicotinoyl)benzylthio]-3-methyl-4H-pyrido[1,2-a]-pyrimidin-4-one (287 mg), 4-piperidinopiperidine (137 mg) and potassium carbonate (194 mg) in DMF (10 ml) was stirred at 80° C. for 24 hours. This reaction mixture was concentrated and the residue was dissolved in chloroform. The solution was washed with water, dried, and concentrated. The residue was purified by silica gel column chromatography (chloroform-methanol =9:1) and treated with hydrogen chloride/ethyl acetate to provide the title compound as colorless solid (28 mg).

$^1$H-NMR (CDCl$_3$) δ: 1.40–2.14(8H,m), 2.19(3H,s), 2.32–2.46(2H,m), 2.96–3.16(2H,m), 3.26–3.76(5H,m), 4.44–4.60(2H,m), 4.68(2H,s), 7.32(1H,dt,J=6.3&1.6 Hz), 7.54(1H,d,J=9.7 Hz), 7.66–7.80(5H,m), 7.94(1H,m), 8.27 (1H,d,J=2.2 Hz), 8.36(1H,dd,J=7.0&2.2 Hz), 8.97(1H,d,J= 6.3 Hz).

IR (KBr): 1693, 1639, 1006, 765 cm$^{-1}$.

EXAMPLE 248

3-Methyl-2-[4-[4-(4-phenylpiperazinylmethyl)-benzoyl]benzylthio]-4H-pyrido[1,2-a]pyrimidin-4-one A solution of 2-mercapto-3-methyl-4H-pyrido[1,2-a] pyrimidin-4-one (298 mg), 4,4'-bis(bromomethyl) benzophenone (934 mg), phenylpiperazine hydrochloride (402 mg) and potassium carbonate (850 mg) in DMF (30 ml) was stirred at room temperature for 10 hours. This reaction mixture was concentrated and the residue was dissolved in chloroform, washed with water, dried, and concentrated. The residue was purified by silica gel column chromatography (hexane: ethyl acetate =1:1) to provide the title compound as colorless solid (146 mg).

$^1$H-NMR (CDCl$_3$) δ: 2.24(3H,s), 2.64(4H,m), 3.22(4H, m), 3.64(2H,s), 4.61(2H,s), 6.80–6.97(3H,m), 7.08(1H,dt,J= 8.8&1.8 Hz), 7.21–7.32(2H,m), 7.43–7.62(5H,m), 7.66(1H, m), 7.76(4H,d,J=8.4 Hz), 9.00(1H,d, 7.0 Hz).

IR (KBr): 1695, 1602, 1465, 1141, 763 cm$^{-1}$.

EXAMPLE 249

2-[4-(4-Hydroxybenzoyl)benzylthio]-3-methyl-4H-pyrido[1,2-a]pyrimidin-4-one

A solution of 2-mercapto-3-methyl-4H-pyrido[1,2-a] pyrimidin-4-one (292 mg), 4-(4-t-butyldimethylsilyloxybenzoyl)benzyl bromide (843 mg) and potassium carbonate (443 mg) in methanol(10 ml)-tetrahydrofuran (10 ml)-water(2 ml) was stirred at room temperature for 48 hours. This reaction mixture was concentrated and the residue was washed with ethyl acetate and water and recrystallized from methanol-tetrahydrofuran-ethyl acetate to provide the title compound as light-yellow solid (276 mg).

$^1$H-NMR (DMSO-d$_6$) δ: 2.10(3H,s), 4.63(2H,s), 6.46(2H, d,J=8.8 Hz), 7.31(1H,dt,J=6.9&1.6 Hz), 7.44–7.62(6H,m), 7.70(1H,m), 7.94(1H,m), 8.90(1H,m).

IR (KBr): 1660, 1600, 1556, 1452, 765 cm$^{-1}$.

EXAMPLE 250

3-Methyl-2-[4-[4-(2-morpholinoethoxy)benzoyl] benzylthio]-4H-pyrido[1,2-a]pyrimidin-4-one A solution of 2-[4-(4-hydroxybenzoyl)benzylthio]-3-methyl-4H-pyrido[1,2-a]pyrimidin-4-one (214 mg), 4-(2-chloroethyl)morpholine hydrochloride (157 mg) and potassium carbonate (247 mg) in DMF (7 ml) was stirred at 80° C. for 4 hours. This reaction mixture was concentrated and the residue was dissolved in ethyl acetate, washed with water, and dried. Then, hydrogen chloride/ethyl acetate was added and the precipitated hydrochloride was recovered by filtration and dried to provide the title compound as colorless solid (182 mg).

$^1$H-NMR (CDCl$_3$) δ: 2.10(3H,s), 3.10–4.07(10H,m), 4.51 (2H,s), 4.65(2H,s), 7.14(2H,d,J=7.0 Hz), 7.32(1H,m), 7.58–7.82(7H,m), 7.94(1H,m), 8.89(1H,d,J=7.0 Hz).

IR (KBr): 1658, 1600, 1463, 1172, 1143 cm$^{-1}$.

EXAMPLE 251

3-Methyl-2-[4-(4-hydroxybenzoyl)benzyloxy]-4H-pyrido[1,2-a]pyrimidin-4-one

A solution of 2-hydroxy-3-methyl-4H-pyrido[1,2-a] pyrimidin-4-one (3.158 g), 4-(4-t-butyldimethylsilyloxybenzoyl)benzyl bromide (12.24 g) and potassium carbonate (5.07 g) in DMF (50 ml) was stirred at room temperature for 24 hours. This reaction mixture was concentrated and the residue was purified by silica gel column chromatography (dichloromethane: ethyl acetate =1:2) and recrystallized from chloroform-methanol-ethyl acetate to provide the title compound as colorless solid (325 mg).

$^1$H-NMR (DMSO-d$_6$) δ: 2.09(3H,s), 5.62(2H,s), 6.89(2H, d,J=8.8 Hz), 7.33(1H,dt,J=7.0&1.6 Hz), 7.54–7.80(7H,m), 7.94(1H,m), 8.96(1H,d,J=6.8 Hz).

IR (KBr): 1646, 1604, 1575, 1475, 1170, 929 cm$^{-1}$.

EXAMPLE 252

7-[4-(4-Chlorobenzoyl)benzyl]-3-ethyl-2-methylthio-7H-pyrrolo[2,3-d]pyrimidin-4-one Under argon gas, 2-methylthio-7H-pyrrolo[2,3-a]-pyrimidin-4(3H)-one (1.82 g) was dissolved in DMF (60 ml) with warming. Then, anhydrous potassium carbonate (1.38 g) and ethyl iodide (1.2 ml) were added and the mixture was stirred at 55° C. for 3.5 hours. This reaction mixture was filtered to remove insolubles and the solvent was then distilled off under reduced pressure. The residue was diluted with methanol, sonicated, and collected by filtration. It was then washed with water, methanol and ether, and dried to provide a mixture of 3-ethyl-2-methylthio-7H-pyrrolo[2,3-d]pyrimidin-4-one and 4-ethoxy-2-methylthio-7H-pyrrolo [2,3-d]pyrimidine (55:45; 1.34 g). This mixture was not further purified but submitted as it was to the next reaction.

Under argon gas, the above mixture (1.14 g) was dissolved in anhydrous DMF (10 ml) and, after addition of anhydrous 1,2-dimethoxyethane (DME; 40 ml), 60% sodium hydride-oil (250 mg) was added. After 30 minutes of stirring, a solution of 4-(4-chlorobenzoyl)benzyl bromide (2.19 g) in DME (10 ml) was added dropwise and the mixture was stirred at room temperature for 15 hours. Then, ethyl acetate and saturated aqueous NaCl solution were added. The organic layer was dried over anhydrous sodium sulfate and the solvent was distilled off under reduced pressure. The residue was purified by flash column chromatography (silica gel; ethyl acetate: hexane =1:4) to provide 7-[4-(4-chlorobenzoyl)benzyl]-4-ethoxy-2-methylthio-7H-pyrrolo[2,3-d]pyrimidine (725 mg) and the title compound (994 mg). $^1$H-NMR (CDCl$_3$) δ: 1.46(3H,t,J=7.0 Hz), 2.60 (3H,s), 4.59(2H,q,J=7.0 Hz), 5.45(2H,s), 6.50(1H,d,J=3.4 Hz), 6.87(1H,d,J=3.4 Hz), 7.30(2H,d,J=8.2 Hz), 7.45(2H,d, J=8.4 Hz), 7.72(2H,d,J=8.4 Hz), 7.73(2H,d,J=8.2 Hz).

EXAMPLE 253

7-[4-(4-Chlorobenzoyl)benzyl]-2-methylthio-3-propyl7H-pyrrolo[2,3-d]pyrimidin-4-one Under argon gas, 2-methylthio-7H-pyrrolo[2,3-a]-pyrimidin-4(3H)-one (0.91 g) was dissolved in DMF (30 ml) with warming. Then, anhydrous potassium carbonate (0.691 g) and propyl iodide (0.729 ml) were added and the mixture was stirred at 60° C. for 4 hours. This reaction mixture was filtered to remove insolubles and the solvent was distilled off under reduced pressure. The residue was diluted with methanol, sonicated, and collected by filtration. It was then washed with water, methanol and ether serially and dried to provide a mixture of 2-methylthio-3-propyl-7H-pyrrolo[2, 3-d]pyrimidin-4-one and 2-methylthio-4-propoxy-7H-pyrrolo[2,3-d]pyrimidine (45:55; 603 mg). This mixture was not further purified but submitted as it was to the next reaction.

Under argon gas, the above mixture (538 mg) was dissolved in anhydrous DME (10 ml) and, then, 60% sodium hydride-oil (106 mg) was added. After 30 minutes of stirring, a solution of 4-(4-chlorobenzoyl)-benzyl bromide (966 mg) in DME (2 ml) was added dropwise. The mixture was stirred at room temperature for 13 hours, after which ethyl acetate and saturated aqueous NaCl solution were added. The organic layer was dried over anhydrous sodium sulfate and the solvent was distilled off under reduced pressure. The residue was purified by flash column chromatography (silica gel; ethyl acetate: hexane =1:4) to provide 7-[4-(4-chlorobenzoyl)benzyl]-2-methylthio-4-propoxy-7H-pyrrolo[2,3-d]pyrimidine (353 mg) and the title compound (360 mg).

¹H-NMR (CDCl₃) δ: 1.01(3H,t,J=7.2 Hz), 1.70–1.89(2H, m), 2.57(3H,s), 4.11(2H,t,J=7.2 Hz), 5.36(2H,s), 6.65(1H,d, J=3.4 Hz), 6.75(1H,d,J=3.4 Hz), 7.32(2H,d,J=8.4 Hz), 7.45 (2H,d,J=8.6 Hz), 7.73(2H,d,J=8.6 Hz), 7.74(2H,d,J=8.4 Hz).

EXAMPLE 254

3-Acetoxyethyl-7-[4-(4-chlorobenzoyl)benzyl]-2-methylthio-7H-pyrrolo[2,3-d]pyrimidin-4-one Under argon gas, 2-methylthio-7H-pyrrolo[2,3-d]-pyrimidin-4(3H)-one (1.82 g) was dissolved in DMF (60 ml) with warming. Then, anhydrous potassium carbonate (2.07 g) and bromoethyl acetate (3.34 g) were added and the mixture was stirred at 70° C. for 7 hours. This reaction mixture was filtered to remove insolubles and the solvent was distilled off under reduced pressure. The residue was diluted with methanol, disrupted by sonication, and collected by filtration. It was then washed serially with water, methanol and ether and finally dried to provide a mixture of 3-acetoxyethyl-2-methylthio-7H-pyrrolo[2,3-d]pyrimidin-4-one and 4-acetoxyethoxy-2-methylthio-7H-pyrrolo[2,3-d] pyrimidine (1:2; 1.71 g). This product was not further purified but submitted as it was to the next reaction.

Under argon gas, the above mixture (1.34 g) was dissolved in anhydrous DME (30 ml) followed by addition of 60% sodium hydride-oil (220 mg). After 30 minutes of stirring, a solution of 4-(4-chlorobenzoyl)benzyl bromide (2.02 g) in DME (2 ml) was added dropwise and the mixture was stirred at room temperature for 15 hours, at the end of which time it was diluted with ethyl acetate and saturated aqueous NaCl solution. The organic layer was dried over anhydrous sodium sulfate and the solvent was distilled off under reduced pressure. The residue was purified by flash column chromatography (silica gel; ethyl acetate: hexane =1:4-3:7) to provide 4-acetoxyethoxy-7-[4-(4-chlorobenzoyl)benzyl]-2-methylthio-7H-pyrrolo[2,3-d] pyrimidine (900 mg) and the title compound (460 mg).

¹H-NMR (CDCl₃) δ: 2.06(3H,s), 2.58(3H,s), 4.43(4H,s), 5.37(2H,s), 6.66(1H,d,J=3.6 Hz), 6.77(1H,d,J=3.6 Hz), 7.32 (2H,d,J=8.4 Hz), 7.46(2H,d,J=8.6 Hz), 7.73(2H,d,J=8.6 Hz), 7.75(2H,d,J=8.4 Hz).

EXAMPLE 255

7-[4-(4-Chlorobenzoyl)benzyl]-3-hydroxyethyl-2-methylthio-7H-pyrrolo[2,3-d]pyrimidin-4-one To a solution of 3-acetoxyethyl-7-[4-(4-chlorobenzoyl) benzyl]-2-methylthio-7H-pyrrolo[2,3-d]pyrimidin-4-one (410 mg) in methanol (8 ml)-DME (4 ml) was added 1N-aqueous sodium hydroxide solution (1.64 ml) and the mixture was stirred for 2 hours. This reaction mixture was neutralized with 1N-hydrochloric acid (1.64 ml) and the precipitate was collected by filtration, washed serially with water, methanol and ether, and dried to provide the title compound (295 mg).

¹H-NMR (CDCl₃) δ: 2.59(3H,s), 2.98(1H,t,J=5.4 Hz), 3.99(2H,q,J=5.4 Hz), 4.43(2H,t,J=5.4 Hz), 5.38(2H,s), 6.67 (1H,d,J=3.4 Hz), 6.79(1H,d,J=3.4 Hz), 7.32(2H,d,J=7.8 Hz), 7.46(2H,d,J=8.2 Hz), 7.74(2H,d,J=8.6 Hz), 7.75(2H,d,J=8.4 Hz).

EXAMPLE 256

7-[4-(4-Chlorobenzoyl)benzyl]-3-methyl-7H-pyrrolo-[2,3-d]pyrimidin-4-one

In a mixture of DME (15 ml) and ethanol (1.5 ml) was dissolved 7-[4-(4-chlorobenzoyl)benzyl]-3-methyl-2-methylthio-7H-pyrrolo[2,3-d]pyrimidin-4-one (221 mg) followed by addition of acetic acid (185 mg), and the mixture was warmed to 40° C. Then, Raney nickel was added until disappearance of the starting compound could be verified by thin-layer chromatography (TLC). The catalyst was then filtered off and the solvent was distilled off under reduced pressure. The residue was dissolved in ethyl acetate, washed with saturated aqueous NaHCO₃ solution and saturated aqueous NaCl solution in the order mentioned, and dried over anhydrous magnesium sulfate. The solvent was then distilled off under reduced pressure and the residue was allowed to stand, whereupon crystals separated out. This crystal crop was harvested by filtration, rinsed with ethanol and hexane, and dried to provide the title compound (149 mg).

¹H-NMR (CDCl₃) δ: 3.61(3H,s), 5.42(2H,s), 6.76(1H,d, J=3.4 Hz), 6.88(1H,d,J=3.4 Hz), 7.27(2H,d,J=8.4 Hz), 7.45 (2H,d,J=8.4 Hz), 7.72(2H,d,J=8.4 Hz), 7.73(2H,d,J=8.4 Hz), 7.90(1H,s).

EXAMPLE 257

7-[4-(4-Chlorobenzoyl)benzyl]-3-ethyl-7H-pyrrolo-[2,3-d]pyrimidin-4-one

In a mixture of DME (15 ml) and ethanol (1.5 ml) was dissolved 7-[4-(4-chlorobenzoyl)benzyl]-3-ethyl-2-methylthio-7H-pyrrolo[2,3-d]pyrimidin-4-one (221 mg) followed by addition of acetic acid (185 mg), and the mixture was warmed to 40° C. Then, Raney nickel was added until disappearance of the starting compound could be verified by TLC. The catalyst was then filtered off and the solvent was removed under reduced pressure. The residue was dissolved in ethyl acetate, washed with saturated aqueous NaHCO₃ solution and saturated aqueous NaCl solution in the order mentioned, and dried over anhydrous magnesium sulfate. The solvent was then distilled off under reduced pressure and the residue was allowed to stand, whereupon crystals separated out. This crystal crop was harvested by filtration, rinsed with ethanol and hexane, and dried to provide the title compound (141 mg).

¹H-NMR (CDCl₃) δ: 1.41(3H,t,J=7.2 Hz), 4.09(2H,q,J= 7.2 Hz), 5.42(2H,s), 6.76(1H,d,J=3.4 Hz), 6.87(1H,d,J=3.4 Hz), 7.28(2H,d,J=8.4 Hz), 7.45(2H,d,J=8.4 Hz), 7.73(2H,d, J=8.4 Hz), 7.74(2H,d,J=8.4 Hz), 7.89(1H,s).

EXAMPLE 258

7-[4-(4-Chlorobenzoyl)benzyl]-3-propyl-7H-pyrrolo-[2,3-d]pyrimidin-4-one

Under argon gas, 3-propyl-7H-pyrrolo[2,3-d]pyrimidin-4-one (249 mg) was dissolved in anhydrous DME (6 ml) and, under ice-cooling and stirring, 60% sodium hydride-oil (62 mg) was added. The mixture was stirred for 30 minutes, after which a solution of 4-(4-chlorobenzoyl)benzyl bromide (564 mg) in anhydrous DME (2 ml) was added. The mixture was further stirred at room temperature for 2 hours. The solvent was then distilled off under reduced pressure and the residue was dissolved in ethyl acetate, washed with saturated aqueous NaCl solution, and dried over anhydrous sodium sulfate. The solvent was then distilled off under reduced pressure and the residue was purified by flash column chromatography (silica gel, 21 g; hexane: ethyl acetate =4:1–3:2) to provide the title compound as colorless powder (507 mg).

¹H-NMR (CDCl₃) δ: 0.99(3H,t,J=7.4 Hz), 1.74–1.93(2H, m), 3.99(2H,t,J=7.4 Hz), 5.42(2H,s), 6.76(1H,d,J=3.4 Hz), 6.87(1H,d,J=3.4 Hz), 7.28(2H,d,J=8.6 Hz), 7.45(2H,d,J=8.6 Hz), 7.73(2H,d,J=8.4 Hz), 7.74(2H,d,J=8.4 Hz), 7.87(1H,s).

EXAMPLE 259

7-[4-(4-Chlorobenzoyl)benzyl]-3-isopropyl-7H-pyrrolo[2,3-d]pyrimidin-4-one

Under argon gas, 3-isopropyl-7H-pyrrolo[2,3-d]-pyrimidin-4-one (89 mg) was dissolved in anhydrous DME (2 ml) and, under ice-cooling and stirring, 60% sodium hydride-oil (22 mg) was added. The mixture was stirred for 30 minutes, after which a solution of 4-(4-chlorobenzoyl) benzyl bromide (201 mg) in anhydrous DME (1 ml) was added. Then, the mixture was stirred at room temperature for 2 hours. The solvent was distilled off under reduced pressure and the residue was dissolved in ethyl acetate, washed with saturated aqueous NaCl solution, and dried over anhydrous sodium sulfate. The solvent was then distilled off under reduced pressure and the residue was purified by flash column chromatography (silica gel, 12 g; hexane: ethyl acetate =4:1–3:2) to provide the title compound as colorless powder (181 mg).

$^1$H-NMR (CDCl$_3$) δ: 1.47(6H,d,J=7.0 Hz), 5.30(1H,q,J= 7.0 Hz), 5.42(2H,s), 6.76(1H,d,J=3.4 Hz), 6.88(1H,d,J=3.4 Hz), 7.29(2H,d,J=8.8 Hz), 7.45(2H,d,J=8.8 Hz), 7.73(2H,d, J=8.4 Hz), 7.74(2H,d,J=8.4 Hz), 7.95(1H,s).

EXAMPLE 260

2-[4-(4-Fluorobenzoyl)benzyl]thio-6-methylthiazolo [4,5-d]pyridazin-7(6H)-one

In DMF (10 ml) was dissolved 5-amino-4-chloro-2-methyl-3(2H)-pyridazinone (638 mg) followed by addition of 60% sodium hydride (384 mg), and the mixture was stirred at room temperature for 10 minutes. Then, carbon disulfide (365 mg) was added and the mixture was further stirred at 80° C. for 1 hour. Thereafter, 4-(4-fluorobenzoyl) benzyl bromide (1.4 g) was added and the mixture was stirred at room temperature for 1 hour. This reaction mixture was extracted with ethyl acetate-THF and the organic layer was washed serially with water and saturated aqueous NaCl solution, dried over anhydrous magnesium sulfate, and concentrated. The residue was purified by silica gel chromatography (hexane: ethyl acetate =1:1) to provide 1.2 g of white powder.

$^1$H-NMR (CDCl$_3$) δ: 3.88(3H,s), 4.66(2H,s), 7.17(2H,dd, J=8.8&8.8 Hz), 7.57(2H,d,J=8.2 Hz), 7.76(2H,d,J=8.2 Hz), 7.84(2H,dd,J=8.8&5.6 Hz), 8.34(1H,s).

EXAMPLE 261

2-[2-[4-(4-Chlorobenzoyl)phenyl]vinyl]-3,5-dimethyl-4(3H)-quinazolinone

To a mixture of 2,3,5-trimethyl-4(3H)-quinazolinone (376 mg) and 4-(4-chlorobenzoyl)benzaldehyde (1.1 g) was added acetic anhydride (0.5 ml) and the mixture was stirred at 140° C. for 2 hours. This reaction mixture was concentrated and the residue was washed with diethyl ether and dried to provide 504 mg of yellow powder.

$^1$H-NMR (DMSO-d$_6$) δ: 2.81(3H,s), 3.68(3H,s), 7.27(1H, d,J=7.8 Hz), 7.54(1H,d,J=7.8 Hz), 7.63(1H,d,J=15.2 Hz), 7.66(1H,dd,J=7.8&7.8 Hz), 7.66(2H,d,J=8.4 Hz), 7.80(2H, d,J=8.4 Hz), 7.81(2H,d,J=8.4 Hz), 7.97(1H,d,J=15.2 Hz), 8.02(2H,d,J=8.4 Hz).

EXAMPLE 262

2-[2-[4-(4-Chlorobenzoyl)phenyl]ethyl]-3,5-dimethyl-4(3H)-quinazolinone

To a solution of 2-[2-[4-(4-chlorobenzoyl)phenyl]-vinyl] -3,5-dimethyl-4(3H)-quinazolinone (104 mg) in THF-ethyl acetate-methanol (2:1:1) (20 ml) was added 10% Pd/C (50% hydrous) (10 mg) and the mixture was stirred under hydrogen at room temperature for 2 hours. The catalyst was then filtered off and the filtrate was concentrated. The residue was washed with ethyl acetate-methanol and dried to provide 53 mg of white powder.

$^1$H-NMR (CDCl$_3$) δ: 2.88(3H,s), 3.05–3.18(2H,m), 3.25–3.38(2H,m), 3.56(3H,s), 7.18–7.30(2H,m), 7.43(2H,d,J=8.6 Hz), 7.46(2H,d,J=8.6 Hz), 7.54(1H,dd,J=7.6&7.6 Hz), 7.74 (4H,d,J=8.6 Hz).

EXAMPLE 263

3,5-Dimethyl-2-[2-[4-(4-trifluoromethylbenzoyl)-phenyl]vinyl]-4(3H)-quinazolinone To a mixture of 2,3,5-trimethyl-4(3H)-quinazolinone (508 mg) and 4-(4-trifluoromethylbenzoyl)benzaldehyde (751 mg) was added acetic anhydride (1.0 ml) and the mixture was stirred at 140° C. for 2 hours. This reaction mixture was concentrated and the residue was washed with n-hexane-diethyl ether and dried to provide 898 mg of yellow powder.

$^1$H-NMR (DMSO-d$_6$) δ: 2.81(3H,s), 3.69(3H,s), 7.26(1H, d,J=7.6 Hz), 7.53(1H,d,J=7.6 Hz), 7.63(1H,d,J=15.8 Hz), 7.65(1H,dd,J=7.6&7.6 Hz), 7.84(2H,d,J=8.4 Hz), 7.96(4H, s), 7.97(1H,d,J=15.8 Hz), 8.02(2H,d,J=8.4 Hz).

EXAMPLE 264

3,5-Dimethyl-2-[2-[4-(4-trifluoromethylbenzoyl)-phenyl]ethyl]-4(3H)-quinazolinone To a solution of 3,5-dimethyl-2-[2-[4-(4-trifluoromethylbenzoyl)phenyl]vinyl]-4(3H)-quinazolinone (897 mg) in THF: ethyl acetate: methanol (1:1:1) (60 ml) was added 10% Pd/C (50% hydrous) (179 mg) and the mixture was stirred under hydrogen at room temperature for 2 hours. The catalyst was then filtered off and the filtrate was concentrated. The residue was purified by silica gel column chromatography (n-hexane: ethyl acetate =2:1) and recrystallized from ethyl acetate-methanol to provide 307 mg of white powder.

$^1$H-NMR (CDCl$_3$) δ: 2.88(3H,s), 3.06–3.19(2H,m), 3.24–3.38(2H,m), 3.56(3H,s), 7.19–7.30(2H,m), 7.45(2H,d, J=8.4 Hz), 7.54(1H,dd,J=7.4&7.4 Hz), 7.75(2H,d,J=8.2 Hz), 7.77(2H,d,J=8.4 Hz), 7.88(2H,d,J=8.2 Hz).

EXAMPLE 265

2-[2-[4-(4-Acetoxybenzoyl)phenyl]vinyl]-3,5-dimethyl-4(3H)-quinazolinone

To a mixture of 2,3,5-trimethyl-4(3H)-quinazolinone (376 mg) and 4-(4-acetoxybenzoyl)benzaldehyde (537 mg) was added acetic anhydride (0.5 ml) and the mixture was stirred at 140° C for 2 hours. This reaction mixture was concentrated and the residue was washed with n-hexane-diethyl ether and dried to provide 653 mg of yellow powder.

$^1$H-NMR (DMSO-d$_6$) δ: 2.33(3H,s), 2.80(3H,s), 3.68(3H, s), 7.25(1H,d,J=7.6 Hz), 7.35(2H,d,J=8.6 Hz), 7.52(1H,d,J= 7.6 Hz), 7.60(1H,d,J=15.0 Hz), 7.64(1H,dd,J=7.6&7.6 Hz), 7.81(2H,d,J=8.2 Hz), 7.84(2H,d,J=8.6 Hz), 7.96(1H,d,J= 15.0 Hz), 8.00(2H,d,J=8.2 Hz).

EXAMPLE 266

3,5-Dimethyl-2-[2-[4-(4-hydroxybenzoyl)phenyl]-ethyl]-4(3H)-quinazolinone

To a solution of 2-[2-[4-(4-acetoxybenzoyl)phenyl]vinyl] -3,5-dimethyl-4(3H)-quinazolinone (631 mg) in THF-ethyl acetate-methanol (1:1:1) (50 ml) was added 10% Pd/C (50% hydrous) (126 mg) and the mixture was stirred under hydrogen at room temperature for 2 hours. The catalyst was then filtered off and the filtrate was concentrated. After the residue was suspended in ethanol (10 ml), 1N-aqueous sodium hydroxide solution (2.9 ml) was added and the mixture was stirred at room temperature for 2 hours. This reaction mixture was concentrated and the residue was suspended in water (20 ml) and neutralized with 1N-hydrochloric acid (2.9 ml). The precipitate was collected by filtration, washed with water, and dried to provide 538 mg of white powder.

$^1$H-NMR (CDCl$_3$) δ: 2.88(3H,s), 3.05–3.19(2H,m), 3.23–3.36(2H,m), 3.58(3H,s), 6.91(2H,d,J=8.4 Hz), 7.18–7.32(2H,m), 7.38(2H,d,J=8.4 Hz), 7.58(1H,dd,J=7.6&7.6 Hz), 7.72(2H,d,J=8.4 Hz), 7.78(2H,d,J=8.4 Hz).

EXAMPLE 267

3,5-Dimethyl-2-[2-[4-[4-(2-dimethylaminoethoxy)-benzoyl]phenyl]ethyl]-4(3H)-quinazolinone hydrochloride To a solution of 3,5-dimethyl-2-[2-[4-(4-hydroxybenzoyl)phenyl]ethyl]-4(3H)-quinazolinone (534 mg) in DMF (10 ml) were added 2-dimethylaminoethyl chloride (695 mg) and potassium carbonate (677 mg) and the mixture was stirred at 80° C. for 4 hours. This reaction mixture was concentrated and extracted with ethyl acetate. The organic layer was serially washed with water and saturated aqueous NaCl solution, dried over anhydrous magnesium sulfate, and concentrated to 20 ml. To this organic solution was added 1N-hydrochloric acid (2 ml) and the mixture was extracted with water. The aqueous layer was diluted with saturated aqueous NaHCO3 solution and extracted with ethyl acetate. The organic layer was washed with saturated aqueous NaCl solution and dried over anhydrous magnesium sulfate. After concentration to 10 ml, 4N-hydrogen chloride/ethyl acetate (0.5 ml) was added, and the precipitate was collected by filtration, washed with water, and dried to provide 240 mg of white powder.

$^1$H-NMR (DMSO-d6) δ: 2.79(3H,s), 2.85(3H,s), 2.88(3H,s), 3.16–3.37(4H,m), 3.55(3H,s), 3.51–3.61(2H,m), 4.44–4.44(2H,m), 7.16(2H,d,J=8.8 Hz), 7.31(1H,d,J=7.2 Hz), 7.52–7.62(2H,m), 7.62(2H,d,J=8.8 Hz), 7.68(2H,d,J=8.4 Hz), 7.77(2H,d,J=8.4 Hz).

EXAMPLE 268

2-[2-[4-(6-Chloronicotinoyl)phenyl]vinyl]-3,5-dimethyl-4(3H)-quinazolinone

To a mixture of 2,3,5-trimethyl-4(3H)-quinazolinone (1.1 g) and 4-(6-chloronicotinoyl)benzaldehyde (1.5 g) was added acetic anhydride (2 ml) and the mixture was stirred at 140° C for 2 hours. This reaction mixture was concentrated and the residue was washed with toluene-diethyl ether and dried to provide 1.4 g of yellow powder.

$^1$H-NMR (CDCl$_3$) δ: 2.90(3H,s), 3.74(3H,s), 7.20–7.30 (1H,m), 7.24(1H,d,J=15.6 Hz), 7.51(1H,d,J=8.4 Hz), 7.58–7.61(2H,m), 7.76(2H,d,J=8.4 Hz), 7.87(2H,d,J=8.4 Hz), 8.02(1H,d,J=15.6 Hz), 8.12(1H,dd,J=2.6&8.4 Hz), 8.79(1H,d,J=2.6 Hz).

EXAMPLE 269

3,5-Dimethyl-2-[2-[4-[6-(2-dimethylaminoethoxy)-nicotinoyl]phenyl]vinyl]-4(3H)-quinazolinone To a solution of 2-dimethylaminoethanol (53 mg) in DMF (3 ml) was added 60% sodium hydride (29 mg) and the mixture was stirred at room temperature for 10 minutes. Then, 2-[2-[4-(6-chloronicotinoyl)phenyl]vinyl]-3,5-dimethyl-4(3H)-quinazolinone (208 mg) was added and the mixture was further stirred at room temperature for 2 hours. This reaction mixture was extracted with ethyl acetate and the organic layer was washed serially with water and saturated aqueous NaCl solution, dried over anhydrous magnesium sulfate, and concentrated to 10 ml. To this organic was added 1N-hydrochloric acid (2 ml) and the mixture was extracted with water. The aqueous layer was diluted with saturated aqueous NaHCO$_3$ solution and extracted with ethyl acetate. The organic layer was washed with saturated aqueous NaCl solution, dried over anhydrous magnesium sulfate, and concentrated to dryness to provide 169 mg of yellow powder.

$^1$H-NMR (CDCl$_3$) δ: 2.35(6H,s), 2.75(2H,t,J=5.7 Hz), 2.90(3H,s), 3.73(3H,s), 4.52(2H,t,J=5.7 Hz), 6.91(1H,d,J=8.7 Hz), 7.18–7.28(1H,m), 7.23(1H,d,J=15.3 Hz), 7.57–7.60 (2H,m), 7.73(2H,d,J=8.3 Hz), 7.83(2H,d,J=8.3 Hz), 8.01 (1H,d,J=15.3 Hz), 8.11(1H,dd,J=2.4&8.7 Hz), 8.62(1H,d,J=2.4 Hz).

EXAMPLE 270

3,5-Dimethyl-2-[2-[4-[6-(2-dimethylaminoethoxy)-nicotinoyl]phenyl]ethyl]-4(3H)-quinazolinone dihydrochloride To a solution of 3,5-dimethyl-2-[2-[4-[6-(2-dimethylaminoethoxy)nicotinoyl]phenyl]vinyl]-4(3H)-quinazolinone (167 mg) in ethyl acetate-methanol-acetic acid (10:10:1) (10.5 ml) was added 10% Pd/C (50% hydrous) (34 mg) and the mixture was stirred under hydrogen at room temperature for 2 hours. The catalyst was then filtered off and the filtrate was concentrated. The residue was diluted with saturated aqueous NaHCO$_3$ solution and extracted with ethyl acetate. The organic layer was washed with saturated aqueous NaCl solution, dried over anhydrous magnesium sulfate, and concentrated to 10 ml. To the residue was added 4N-hydrogen chloride/ethyl acetate (0.1 ml) and the precipitate was collected by filtration, washed with ethyl acetate-ethanol, and dried to provide 85 mg of white powder.

$^1$H-NMR (DMSO-d$_6$) δ: 2.79(3H,s), 2.86(6H,s), 3.13–3.40(4H,m), 3.56(3H,s), 3.51–3.61(2H,m), 4.73(2H,t,J=5.4 Hz), 7.05(1H,d,J=8.6 Hz), 7.33(1H,d,J=7.5 Hz), 7.55–7.66(2H,m), 7.60(2H,d,J=8.7 Hz), 7.72(2H,d,J=8.7 Hz), 8.12(1H,dd,J=2.2&8.6 Hz), 8.55(1H,d,J=2.2 Hz).

EXAMPLE 271

3,5-Dimethyl-2-[2-[4-[6-(4-phenyl-1-piperazinyl)-nicotinoyl]phenyl]vinyl]-4(3H)-quinazolinone To a solution of 2-[2-[4-(6-chloronicotinoyl)-phenyl] vinyl]-3,5-dimethyl-4(3H)-quinazolinone (333 mg) in pyridine (5 ml) was added 1-phenylpiperazine (156 ml) and the mixture was stirred at 90° C. for 4 hours. This reaction mixture was concentrated and extracted with ethyl acetate. The organic layer was washed serially with water and saturated aqueous NaCl solution, dried over anhydrous magnesium sulfate, and concentrated. The residue was purified by silica gel column chromatography (n-hexane: ethyl acetate (1:1)) to provide 162 mg of yellow powder.

$^1$H-NMR (CDCl$_3$) δ: 2.90(3H,s), 3.33(4H,t, J=5.2 Hz), 3.74(3H,s), 3.92(4H,t,J=5.2 Hz), 6.75(1H,d,J=9.1 Hz), 6.92 (1H,t,J=8.3 Hz), 6.98(2H,d,J=8.3 Hz), 7.18–7.26(1H,m), 7.21(1H,d,J=15.5 Hz), 7.33(2H,d,J=8.3 Hz), 7.57–7.60(2H, m), 7.72(2H,d,J=8.2 Hz), 7.82(2H,d,J=8.2 Hz), 8.01(1H,d, J=15.5 Hz), 8.09(1H,dd,J=2.5&9.1 Hz), 8.65(1H,d,J=2.5 Hz).

EXAMPLE 272

3,5-Dimethyl-2-[2-[4-[6-(4-phenyl-1-piperazinyl)-nicotinoyl]phenyl]ethyl]-4(3H)-quinazolinone dihydrochloride To a solution of 3,5-dimethyl-2-[2-[4-[6-(4-phenyl-1-piperazinyl)nicotinoyl]phenyl]vinyl]-4(3H)-quinazolinone (160 mg) in THF-ethyl acetate-methanol-acetic acid (10:5:5:1) (21 ml) was added 10% Pd/C (50% hydrous) (64 mg) and the mixture was stirred under hydrogen at room temperature for 6 hours. The catalyst was then filtered off and the filtrate was concentrated. The residue was diluted with saturated aqueous $NaHCO_3$ solution and extracted with ethyl acetate. The organic layer was washed with saturated aqueous NaCl solution, dried over anhydrous magnesium sulfate, and concentrated. The residue was purified by silica gel, column chromatography (n-hexane: ethyl acetate =1:1). The active fraction was concentrated to 10 ml and treated with 4N-hydrogen chloride/ethyl acetate (0.15 ml). The precipitate was recovered by filtration, washed with ethyl acetate-ethanol, and dried to provide 129 mg of white powder.

$^1$H-NMR (DMSO-$d_6$) δ: 2.80(3H,s), 3.16–3.54(8H,m), 3.60(3H,s), 3.91–4.08(4H,m), 6.99(1H,t,J=8.3 Hz), 7.10–7.42(6H,m), 7.59–7.77(6H,m), 8.01(1H,dd,J=2.2&8.0 Hz), 8.48(1H,d,J=2.2 Hz).

EXAMPLE 273

7-[4-(4-Chlorobenzoyl)benzyl]-3-methyl-1-propylxanthine

A solution of 3-methyl-7-[4-(4-chlorobenzoyl)benzyl]xanthine (657 mg), potassium carbonate (242 mg) and propyl iodide (427 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (hexane-ethyl acetate =1:1) and recrystallized from ethyl acetate to provide the title compound as colorless solid (352 mg).

$^1$H-NMR (CDCl$_3$) δ: 0.95(3H,t,J=7 Hz), 1.66(2H,q,J=8 Hz), 3.60(3H,s), 3.96(2H,t,J=7 Hz), 5.59(2H,s), 7.42(2H,d, J=7 Hz), 7.46(2H,d,J=8 Hz), 7.75(5H,m).

IR (KBr): 1700, 1665, 1650 cm$^{-1}$.

EXAMPLE 274

1,7-Bis[4-(4-chlorobenzoyl)benzyl]-3-methylxanthine

A solution of 3-methylxanthine (204 mg), potassium carbonate (340 mg) and 4-(4-chlorobenzoyl)benzyl bromide (754 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (hexane: ethyl acetate =1:1) and recrystallized from ethyl acetate-hexane to provide the title compound as colorless solid (184 mg).

$^1$H-NMR (CDCl$_3$) δ: 3.61(3H,s), 5.27(2H,s), 5.61(2H,s), 7.46(7H,m), 7.67(1H,s), 7.71(9H,m).

IR (KBr): 1700, 1660, 1645 cm$^{-1}$.

EXAMPLE 275

7-[4-(4-Chlorobenzoyl)benzyl]-1-isopropyl-3-methylxanthine

A solution of 3-methyl-7-[4-(4-chlorobenzoyl)-benzyl]xanthine (544 mg), potassium carbonate (202 mg) and isopropyl iodide (356 mg) in DMF (10 ml) was stirred at 60° C. for 5 hours. This reaction mixture was poured in water and extracted with ethyl acetate. The extract was washed with water, dried and concentrated. The residue was purified by silica gel column chromatography (hexane: ethyl acetate =1:1) and recrystallized from acetone-hexane to provide the title compound as colorless solid (38 mg).

$^1$H-NMR (CDCl$_3$) δ: 1.50(6H,d,J=6 Hz), 3.56(3H,s), 5.29 (1H,spt,J=6 Hz), 5.60(2H,s), 7.49(4H,m), 7.72(1H,s), 7.76 (4H,m).

IR (KBr): 1700, 1665, 1650 cm$^{-1}$.

EXAMPLE 276

7-[4-(4-Chlorobenzoyl)benzyl]-1-butyl-3-methylxanthine

A solution of 3-methyl-7-[4-(4-chlorobenzoyl)-benzyl] xanthine (612 mg), potassium carbonate (228 mg) and butyl iodide (430 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (hexane: ethyl acetate =1:1) and recrystallized from ethyl acetate to provide the title compound as colorless solid (147 mg).

$^1$H-NMR (CDCl$_3$) δ: 0.95(3H,t,J=7 Hz), 1.39(2H,sec,J=7 Hz), 1.63(2H,pent,J=7 Hz), 3.63(3H,s), 4.01(2H,t,J=7 Hz), 5.64(2H,s), 7.46(4H,d,J=9 Hz), 7.74(5H,d,J=9 Hz).

IR (KBr): 1700, 1680, 1655 cm$^{-1}$.

EXAMPLE 277

7-[4-(4-Chlorobenzoyl)benzyl]-1-fluoromethyl-3-methylxanthine

A solution of 3-methyl-7-[4-(4-chlorobenzoyl)-benzyl] xanthine (975 mg), sodium hydride (61 mg) and fluoromethyl bromide (121 mg) in DMF (10 ml) was stirred at 10° C. for 1 hour. This reaction mixture was poured in water and extracted with ethyl acetate. The extract was washed with water, dried, and concentrated. The residue was purified by silica gel column chromatography (hexane-ethyl acetate =1:2) and recrystallized from ethyl acetate to provide the title compound as colorless solid (121 mg).

$^1$H-NMR (CDCl$_3$) δ: 3.61(3H,s), 5.58(2H,s), 6.14(2H,d, J=50 Hz), 7.44(4H,dd,J=8 Hz), 7.70(1H,s), 7.76(4H,dd,J=8 Hz).

IR (KBr): 1715, 1665, 1650 cm$^{-1}$.

EXAMPLE 278

7-[4-(4-Hydroxybenzoyl)benzyl]-1,3-dimethylxanthine

A solution of 1,3-dimethylxanthine (742 mg), potassium carbonate (569 mg) and 4-(4-t-butyldimethylsiloxybenzoyl) benzyl bromide (2292 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (hexane: ethyl acetate =1:3) and recrystallized from chloroform-isopropyl ether to provide the title compound as colorless solid (1763 mg).

¹H-NMR (CDCl₃) δ: 3.42(3H,s), 3.62(3H,s), 5.59(2H,s), 6.90(2H,d,J=8.8 Hz), 7.40(2H,d,J=8.3 Hz), 7.68(1H,s), 7.74 (2H,d,J=8.4 Hz).

IR (KBr): 1700, 1655, 1645 cm⁻¹.

EXAMPLE 279

7-[4-(6-Chloronicotinoyl)benzyl]-1,3-dimethylxanthine

A solution of 1,3-dimethylxanthine (712 mg), potassium carbonate (578 mg) and 4-(6-chloronicotinoyl)benzyl bromide (1515 mg) in DMF (10 ml) was stirred at 60° C. for 5 hours. This reaction mixture was poured in water and extracted with ethyl acetate. The extract was washed with water, dried, and. concentrated. The residue was purified by silica gel column chromatography (hexane: ethyl acetate =1:3) and recrystallized from chloroform-isopropyl ether to provide the title compound as colorless solid (1562 mg).

¹H-NMR (CDCl₃) δ: 3.40(3H,s), 3.61(3H,s), 5.61(2H,s), 7.45(1H,d,J=8.1 Hz), 7.48(2H,d,J=8.1 Hz), 7.67(1H,s), 7.80 (2H,d,J=8.1 Hz), 8.08(1H,dd,J=2.4,8.1 Hz), 8.74(1H,d,J=2.3 Hz).

IR (KBr): 1700, 1650 cm⁻¹.

EXAMPLE 280

7-[4-(4-Bromomethylbenzoyl)benzyl]-1,3-dimethylxanthine

A solution of 1,3-dimethylxanthine (990 mg), potassium carbonate (1348 mg) and 4-(4-bromomethylbenzoyl)benzyl bromide (2007 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (hexane: ethyl acetate =1:5) and recrystallized from ethyl acetate-isopropyl ether to provide the title compound as colorless solid (1021 mg).

¹H-NMR (CDCl₃) δ: 3.41(3H,s), 3.61(3H,s), 4.53(2H,s), 5.60(2H,s), 7.44(4H,m), 7.66(1H,s), 7.78(4H,m).

IR (KBr): 1700 1650 cm⁻¹.

EXAMPLE 281

1,3-Dimethyl-7-[4-[4-(2-morpholinoethoxy)benzoyl]-benzyl]xanthine

A solution of 7-[4-(4-hydroxybenzoyl)benzyl]-1,3-dimethylxanthine (170 mg), potassium carbonate (200 mg) and 1-chloro-2-morpholinoethane hydrochloride (87 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (chloroform: ethyl acetate: acetone =1:1:1) to provide the title compound (93 mg).

¹H-NMR (CDCl₃) δ: 2.59(4H,dd,J=4.7 Hz), 2.84(2H,t,J=7.0 Hz), 3.41(3H,s), 3.61(3H,s), 3.75(4H,dd,J=4.7 Hz), 4.19 (2H,t,J=7.0 Hz), 5.59(2H,s), 6.96(2H,d,J=9.0 Hz), 7.43(2H, d,J=8.0 Hz), 7.66(1H,s), 7.75(2H,d,J=8.0 Hz), 7.79(2H,d,J=9.0 Hz).

IR (KBr): 1695, 1650 cm⁻¹.

EXAMPLE 282

1,3-Dimethyl-7-[4-[6-(4-piperidinopiperidino)-nicotinoyl]benzyl]xanthine

A solution of 7-[4-(6-chloronicotinoyl)benzyl]-1,3-dimethylxanthine (196 mg) and 4-piperidinopiperidine (102 mg) in pyridine (10 ml) was stirred at 60° C. for 5 hours. This reaction mixture was poured in water and extracted with ethyl acetate. The extract was washed with water, dried and concentrated. The residue was purified by silica gel column chromatography (ethyl acetate: acetone: triethylamine 1:1:0.1) to provide the title compound (108 mg).

¹H-NMR (CDCl₃) δ: 1.4–1.6(7H,m,br), 1.8–2.0(6H,m, br), 2.56(4H,m,br), 2.95(2H,m), 3.42(3H,s), 3.61(3H,s), 4.56(2H,m), 5.58(2H,s), 6.68(1H,d,J=9.1 Hz), 7.41(2H,d,J=8.1 Hz), 7.65(1H,s), 7.74(2H,d,J=8.1 Hz), 8.00(1H,dd,J=2.4,9.1 Hz), 8.54(1H,d,J=2.4 Hz).

IR (KBr): 1695, 1660, 1590 cm⁻¹.

EXAMPLE 283

1,3-Dimethyl-7-[4-(4-phenylpiperazinylmethylbenzoyl)benzyl]xanthine

A solution of 7-[4-(4-bromomethylbenzoyl)benzyl]-1,3-dimethylxanthine (232 mg), potassium carbonate (109 mg) and 1-phenylpiperazine (92 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (ethyl acetate: hexane: triethylamine =3:1:0.1) and recrystallized from chloroform-isopropyl ether to provide the title compound as colorless solid (20 mg).

¹H-NMR (CDCl₃) δ: 2.64(4H,t,J=5.0 Hz), 3.22(4H,t,J=5.0 Hz), 3.41(3H,s), 3.61(3H,s), 3.65(2H,s), 5.60(2H,s), 6.91(3H,m), 7.27(2H,m), 7.42(2H,d,J=8.2 Hz), 7.48(2H,d, J=8.2 Hz), 7.66(1H,s), 7.76(2H,d,J=8.2 Hz), 7.81(2H,d,J=8.2 Hz).

IR (KBr): 1695, 1650 cm⁻¹.

EXAMPLE 284

7-[4-(4-Methylbenzoyl)benzyl]-1,3-dimethylxanthine

A solution of 1,3-dimethylxanthine (99 mg), potassium carbonate (135 mg), 4-(4-methylbenzoyl)benzyl bromide (201 mg) in DMF (10 ml) was stirred at 60° C. for 5 hours. This reaction mixture was poured in water and extracted with ethyl acetate. The extract was washed with water, dried, and concentrated. The residue was purified by silica gel column chromatography (hexane: ethyl acetate =1:5) and recrystallized from ethyl acetate-isopropyl ether to provide the title compound as colorless solid (98 mg).

¹H-NMR (CDCl₃) δ: 2.44(3H,s), 3.41(3H,s), 3.60(3H,s), 5.59(2H,s), 7.27(2H,d,J=8.2 Hz), 7.41(2H,d,J=8.2 Hz), 7.68 (1H,s), 7.69(2H,d,J=8.2 Hz), 7.77(2H,d,J=8.2 Hz).

IR (KBr): 1700, 1655 cm¹.

EXAMPLE 285

7-[4-(4-Fluorobenzoyl)benzyloxy]-3,6-dimethyl-5H-thiazolo[3,2-a]pyrimidin-5-one

To a solution of 3,6-dimethyl-2-hydroxy-5H-thiazolo[3, 2-a]pyrimidin-5-one (513 mg) and potassium carbonate (741 mg) in DMF (10 ml) was added 4-(4-fluorobenzoyl) benzyl bromide (782 mg) and the mixture was stirred at 80° C. for 2 hours. This reaction mixture was concentrated and the residue was diluted with water-ethyl acetate and extracted with ethyl acetate. The extract was purified by silica gel column chromatography (hexane: ethyl acetate =2:1) and recrystallized from ethyl acetate to provide the title compound as colorless solid (76 mg).

¹H-NMR (CDCl₃) δ: 2.05(3H,s), 2.82(3H,d,J=1.2 Hz), 5.50(2H,s), 6.35(1H,d,J=1.2 Hz), 7.17(2H,dd,J=8.6 Hz), 7.45(2H,d,J=8.1 Hz), 7.79(2H,d,J=8.1 Hz), 7.86(2H,dd,J=5.5,8.6 Hz).

IR (KBr): 1640, 1590, 1385, 1340, 1300, 1270, 1245, 1145 cm⁻¹.

EXAMPLE 286

7-[4-(4-Methoxybenzoyl)benzyloxy]-3,6-dimethyl-5H-thiazolo[3,2-a]pyrimidin-5-one To a solution of 3,6-dimethyl-7-hydroxy-5H-thiazolo[3,2-a]pyrimidin-5-one (537 mg) and potassium carbonate (745 mg) in DMF (10 ml) was added 4-(4-methoxybenzoyl)benzyl bromide (970 mg) and the mixture was stirred at 80° C. for 2 hours. This reaction mixture was concentrated and the residue was diluted with water-ethyl acetate and extracted with ethyl acetate. The extract was purified by silica gel column chromatography (hexane: ethyl acetate =2:1) and recrystallized from ethyl acetate to provide the title compound as colorless solid (106 mg).

¹H-NMR (CDCl₃) δ: 2.05(3H,s), 2.82(3H,s), 3.90(3H,s), 5.49(2H,s), 6.35(1H,s), 6.97(2H,d,J=8.5 Hz), 7.52(2H,d,J=8.4 Hz), 7.78(2H,d,J=8.4 Hz), 7.84(2H,d,J=8.5 Hz).

IR (KBr): 1660, 1645, 1595, 1570, 1490 cm⁻¹.

EXAMPLE 287

7-[4-(4-Nitrobenzoyl)benzyloxy]-3,6-dimethyl-5H-thiazolo[3,2-a]pyrimidin-5-one

To a solution of 3,6-dimethyl-7-hydroxy-5H-thiazolo[3,2-a]pyrimidin-5-one (537 mg) and potassium carbonate (618 mg) in DMF (10 ml) was added 4-(4-nitrobenzoyl)benzyl bromide (909 mg) and the mixture was stirred at 80° C. for 2 hours. This reaction mixture was concentrated and the residue was diluted with water-ethyl acetate and extracted with ethyl acetate. The extract was purified by silica gel column chromatography (hexane: ethyl acetate =2:1) and recrystallized from ethyl acetate to provide the title compound as colorless solid (105 mg).

¹H-NMR (CDCl₃) δ: 2.05(3H,s), 2.82(3H,s), 5.51(2H,s), 6.36(1H,s), 7.57(2H,d,J=8.1 Hz), 7.83(2H,d,J=8.1 Hz), 7.94(2H,d,J=8.2 Hz), 8.35(2H,d,J=8.2 Hz).

IR (KBr): 1665, 1515, 1500 cm⁻¹.

EXAMPLE 288

7-[4-(6-Chloronicotinoyl)benzyloxy]-3,6-dimethyl-5H-thiazolo[3,2-a]pyrimidin-5-one To a solution of 3,6-dimethyl-7-hydroxy-5H-thiazolo[3,2-a]pyrimidin-5-one (526 mg) and potassium carbonate (574 mg) in DMF (10 ml) was added 4-(6-chloronicotinoyl)benzyl bromide (852 mg) and the mixture was stirred at 80° C. for 2 hours. This reaction mixture was concentrated and the residue was diluted with water-ethyl acetate and extracted with ethyl acetate. The extract was purified by silica gel column chromatography (hexane: ethyl acetate =2:1) and recrystallized from ethyl acetate to provide the title compound as colorless solid (300 mg).

¹H-NMR (CDCl₃) δ: 2.05(3H,s), 2.82(3H,s), 5.51(2H,s), 6.35(1H,s), 7.49(1H,d,J=8.4 Hz), 7.57(2H,d,J=8.1 Hz), 7.82(2H,d,J=8.1 Hz), 8.10(1H,dd,J=2.2,8.4 Hz), 8.78(1H,d,J=2.2 Hz).

IR (KBr): 1665, 1640, 1570, 1490 cm⁻¹.

EXAMPLE 289

7-[4-(4-Chlorobenzoyl)benzyloxy]-3-ethyl-6-methyl-5H-thiazolo[3,2-a]pyrimidin-5-one To a solution of 3-ethyl-6-methyl-7-hydroxy-5H-thiazolo[3,2-a]pyrimidin-5-one (298 mg) and potassium carbonate (363 mg) in DMF (10 ml) was added 4-(4-chlorobenzoyl)benzyl bromide (450 mg) and the mixture was stirred at 80° C. for 2 hours. This reaction mixture was concentrated and the residue was diluted with water-ethyl acetate and extracted with ethyl acetate. The extract was recrystallized from ethyl acetate to provide the title compound as colorless solid (205 mg).

¹H-NMR (CDCl₃) δ: 1.31(3H,t,J=7.2 Hz), 2.06(3H,s), 3.34(2H,q,J=7.2 Hz), 5.50(2H,s), 6.39(1H,s), 7.47(2H,d,J=8.1 Hz), 7.54(2H,d,J=8.1 Hz), 7.77(2H,d,J=8.1 Hz), 7.80(2H,d,J=8.1 Hz).

IR (KBr): 1670, 1640, 1570, 1490 cm⁻¹.

EXAMPLE 290

2-[4-(6-Chloronicotinoyl)benzylthio]-3,5-dimethyl-4(3H)-quinazolinone

The above titled compound was obtained by subjecting to reaction and process in the same manner as in Example 1.

¹H-NMR (CDCl₃): δ: 2.84(3H,s), 3.54(3H,s), 4.60(2H,s), 7.15(1H,d,J=7.8 Hz), 7.43(1H,d,J=7.8 Hz), 7.47(1H,d,J=8.2 Hz), 7.54(1H,dd,J=7.8&7.8 Hz), 7.64(2H,d,J=8.2 Hz), 7.76(2H,d,J=8.2 Hz), 8.07(1H,dd,J=2.2&8.2 Hz), 8.75(1H,d,J=2.2 Hz).

EXAMPLE 291

3,5-Dimethyl-2-[4-[6-(4-methyl-1-pyperazinyl)nicotinoyl]benylthio]-4(3H)-quinazolinone-2 hydrochloride The above titled compound was obtained by subjecting to reaction and process in the same manner as in Example 197.

m.p. 187°–189° C.

¹H-NMR (DMSO-d₆) δ:2.75(3H,s), 2.85(3H,s), 2.96–3.20(2H,m), 3.45(3H,s), 3.30–3.59(4H,m), 4.51–4.63(2H,m), 4.64(2H,s), 7.06(1H,d,J=9.3 Hz), 7.21(1H,d,J=7.7 Hz), 7.47(1H,d,J=7.7 Hz), 7.63(1H,dd,J=7.7&7.7 Hz), 7.65(2H,d,J=8.6 Hz), 7.71(2H,d,J=8.6 Hz), 7.97(1H,dd,J=2.2&9.3 Hz), 8.50(1H,d,J=2.2 Hz).

IR (KBr): 3450, 1660, 1640, 1600, 1550 cm⁻¹.

EXAMPLE 292

3,5-Dimethyl-2-[4-[6-(4-piperidino-1-piperizinyl)nicotinoyl]benzylthio]-4-(3H)-quinazolionone-2 hydrochloride The above titled compound was obtained by subjecting to reaction and process in the same manner as in Example 197.

m.p. 140°–142° C.

¹H-NMR (DMSO-d₆) δ:1.28–2.03(8H,m), 2.13–2.30(2H,m), 2.75(3H,s), 2.79–3.13(4H,m), 3.29–3.56(3H,m), 3.45(3H,s), 4.65–4.75(2H,m), 4.65(2H,s), 7.10(1H,d,J=9.0 Hz), 7.21(1H,d,J=7.9 Hz), 7.47(1H,d,J=7.9 Hz), 7.63(1H,dd,J=7.9&7.9 Hz), 7.66(2H,d,J=8.4 Hz), 7.71(2H,d,J=8.4 Hz), 7.96(1H,dd,J=1.8&9.0 Hz), 8.42(1H,d,J=1.8 Hz).

IR (KBr): 3400, 1710, 1660, 1640, 1600, 1550 cm⁻¹.

EXAMPLE 293

3,5-Dimethyl-2-[4-[6-(2-pyrimidinylthio)nicotinoyl]benzylthio]-4(3H)-quinazolinone 2-[4-(6-Chloronicotinoyl)benzylthio]-3,5-dimethyl-4(3H)-quinazolinone (214 mg) was dissolved in DMF (3 ml) followed by addition of 2-mercaptopyrimidine (66 mg) and N,N-diisopropylethylamine (96 mg), and the mixture was stirred at 100° C. for 8 hours. The reaction mixture was extracted with ethyl acetate and the organic layer was washed serially with water and saturated aqueous NaCl solution, drid over anhydrous magnesium sulfate, and concentrated. The residue was purified by silica gel chromatography (n-hexane: ethyl acetate (1:1)), washed with diethyl ether, and dried to provide 87 mg of white powder.

$^1$H-NMR (CDCl$_3$) :δ 2.85(3H,s), 3.55(3H,s), 4.60(2H,s), 7.11(1H,d,J=4.8 Hz), 7.15(1H,d,J=7.7 Hz), 7.43(1H,d,J=7.7 Hz), 7.55(1H,dd,J=7.7&7.7 Hz), 7.64(2H,d,J=8.3 Hz), 7.81 (2H,d,J=8.3 Hz), 8.02(1H,d,J=8.3 Hz), 8.12(1H,dd,J= 2.2&8.3 Hz), 8.60(2H,d,J=4.8 Hz), 8.93(1H,d,J=2.2 Hz).

IR (KBr): 1660, 1580, 1550 cm$^{-1}$.

EXAMPLE 294

5-[4-(4-Chlorobenzoyl)benzyl]-1,3,6-trimethylpyrrolo[3,2-d]pyrimidine-2,4-dione

To a solution of 1,3,6-trimethylpyrrolo[3,2-d]-pyrimidine-2,4-dione (0.120 g, 0.622 mmol) and 4-(4-chlorobenzoyl)benzyl bromide (0.153 g, 0.494 mmol) in DMF (10 ml) was added potassium carbonate (0.121 g, 0.875 mmol) and the mixture was stirred at room temperature overnight. The solvent was then removed under reduced pressure and the residue was diluted with water and extracted with ethyl acetate. The organic layer was washed with saturated aqueous NaCl solution, dried over MgSO$_4$, and concentrated under reduced pressure. The residue was recrystallized from ethyl acetate to provide colorless prisms. 0.080 g (38%)

1H-NMR (CDCl$_3$) δ: 2.25(3H,s), 3.39(3H,s), 3.47(3H,s), 5.72(2H,s), 5.83(1H,s), 7.12(2H,d,J=8.3 Hz), 7.44(2H,d,J= 8.6 Hz), 7.71(2H,d,J=8.3 Hz), 7.72(2H,d,J=8.6 Hz).

IR (KBr): 1691, 1648, 1547, 1506, 1406, 1281, 1086, 928, 748 cm$^{-1}$.

EXAMPLE 295

3,5-Dimethyl-2-[4-[6-[1-(2-dimethylaminoethyl)-5-tetrazolylthio]nicotinoyl]benzylthio]-4(3H)-quinazolinone The above titled compound was obtained by subjecting to reaction and process in the same manner as in Example 293.

m.p. 134°–135° C.

$^1$H-NMR (CDCl$_3$) δ:2.21(6H,s), 2.80(2H,t,J=6.2 Hz), 2.84(3H,s), 3.54(3H,s), 4.51(2H,t,J=6.2 Hz), 4.59(2H,s), 7.15(1H,d,J=7.8 Hz), 7.42(1H,d,J=7.8 Hz), 7.49(1H,d,J=8.4 Hz), 7.54(1H,dd,J=7.8&7.8 Hz), 7.63(2H,d,J=8.2 Hz), 7.73 (2H,d,J=8.2 Hz), 8.02(1H,dd,J=2.2&8.4 Hz), 8.71(1H,d,J= 2.2 Hz).

IR (KBr): 1660, 1575, 1550 cm$^{-1}$.

EXAMPLE 296

2-[4-(4-Chlorobenzoyl)phenylthiomethyl]-3,5-dimethyl-4(3H)-quinazolinone

The above titled compound was obtained by subjecting to reaction and process in the same manner as in Example 1.

m.p. 131.5°–132.5° C.

$^1$H-NMR (CDCl$_3$) δ:2.87(3H,s), 3.70(3H,s), 4.32(2H,s), 7.22(1H,d,J=7.8 Hz), 7.43(1H,d,J=7.8 Hz), 7.44(2H,d,J=8.8 Hz), 7.55(1H,dd,J=7.8&7.8 Hz), 7.59(2H,d,J=8.5 Hz), 7.68 (2H,d,J=8.8 Hz), 7.69(2H,d,J=8.5 Hz).

IR (KBr): 1670, 1650, 1585, 1560 cm$^{-1}$.

EXAMPLE 297

3,5-Dimethyl-2-[4-[4-[1-(2-dimethylaminoethyl)-5-tetrazolylthioethoxy]benzoyl]benzylthio]-4(3H)-quinazolinone 2-[4-[4-(2-Chloroethoxy)benzoyl]benzylthio]-3,5-dimethyl-4(3H)-quinazolinone (240 mg) was dissolved in DMF (3 ml) followed by addition of sodium iodide (75 mg), and the mixture was stirred at 90° C. for 30 minutes. Then, 1-(2-dimethylaminoethyl)-5-mercaptotetrazole (104 mg) and N,N-diisopropylethylamine (97 mg) were added and the mixture was stirred at 90° C. for 3 hours. The reaction mixture was then extracted with ethyl acetate and the organic layer was washed serially with water and saturated aqueous NaCl solution, dried over anhydrous magnesium sulfate and concentrated. The residue was washed with diethyl ether-ethyl acetate and dried to provide 100 mg of white powder.

$^1$H-NMR (CDCl$_3$) δ:2.26(6H,s), 2.77(2H,t,J=6.4 Hz), 2.85(3H,s), 3.55(3H,s), 3.73(2H,t,J=6.0 Hz), 4.32(2H,t,J= 6.4 Hz), 4.44(2H,t,J=6.0 Hz), 4.60(2H,s), 6.97(2H,d,J=8.9 Hz), 7.16(1H,d,J=7.7 Hz), 7.45(1H,d,J=7.7 Hz), 7.55(1H, dd,J=7.7&7.7 Hz), 7.59(2H,d,J=8.4 Hz), 7.72(2H,d,J=8.4 Hz), 7.81(2H,d,J=8.9 Hz).

IR (KBr): 1670, 1600, 1550 cm$^{-1}$.

EXAMPLE 298

2-[4-(4-Chlorobenzoyl)benzylthio]-3-methyl-4H-pyrido[1,2-a]pyrimidin-4-one

The above titled compound was obtained by subjecting to reaction and process in the same manner as in Example 1.

$^1$H-NMR (CDCl$_3$) δ:2.24(3H,s), 4.60(2H,s), 7.08(1H,dd, J=7.1&7.1 Hz), 7.45(1H,d,J=8.6 Hz), 7.53(1H,d,J=7.1 Hz), 7.57(2H,d,J=8.0 Hz), 7.68(1H,dd,J=7.1&7.1 Hz), 7.73(2H, d,J=8.0 Hz), 7.73(2H,d,J=8.6 Hz), 9.00(1H,d,J=7.1 Hz).

IR (KBr): 1660, 1630, 1510 cm$^{-1}$.

EXAMPLE 299

3,5-Dimethyl-2-[4-(4-(2,2,2-trifluoroethylcarbonyl)benzoyl)benzylthio]-4(3H)-quinazolinone The above titled compound was obtained by subjecting to reaction and process in the same manner as in Example 206.

$^1$H-NMR (CDCl3) δ: 2.84(3H,s), 3.55(3H,s), 4.16(2H,dq, J=9.0&6.8 Hz), 6.46(1H,t,J=6.8 Hz), 7.15(1H,d,J=7.0 Hz), 7.43(1H,d,J=7.0 Hz), 7.54(1H,t,J=7.0 Hz), 7.62(2H,d,J=8.4 Hz), 7.76(2H,d,J=8.4 Hz), 7.84(2H,d,J=8.4 Hz), 7.90(2H,d, J=8.4 Hz).

IR (KBr): 3207, 1660, 1554, 1495, 1360, 1282, 1236, 1070, 930, 835, 746 cm$^{-1}$.

EXAMPLE 300

6-Ethyl-7-methyl-1-[4-(4-trifluoromethylbenzoyl)benzyl]-imidazo[1,2-a]pyrimidin-5(1H)-one The above titled compound was obtained by subjecting to reaction and process in the same manner as in Example 163.

$^1$H-NMR (DMSO-d$_6$) δ: 1.04(t,3H,J=7.4 Hz), 2.35(s,3H), 3.69(q,2H,J=7.4 Hz), 5.43(s,2H), 7.50(d,1H,J=2.8 Hz), 7.60 (d,1H,J=2.8 Hz), 7.65(d,1H,J=2.8 Hz), 7.77(d,2H,J=7.6 Hz), 7.90(s,4H).

IR (KBr): 3097, 2971, 2489, 1695, 1658, 1596, 1450, 1410, 1331, 1279, 1180, 1132, 1066, 860, 773, 687 cm$^{-1}$.

EXAMPLE 301

2-[4-(4-Chlorobenzoyl)benzyloxy]-3,6-dimethyl-4H-pyrido[1,2-a]pyrimidin-4-one

The above titled compound was obtained by subjecting to reaction and process in the same manner as in Example 121.

$^1$H-NMR (CDCl$_3$) δ: 2.21(s,3H), 3.10(s,3H), 5.57(s,2H), 6.63(d,1H,J=7.0 Hz), 7.24(d,1H,J=9.0 Hz), 7.39(dd,1H,J=9.0 Hz&7.0 Hz), 7.47(d,2H,J=8.3 Hz), 7.57(d,2H,J=8.1 Hz), 7.76(d,2H,J=8.3 Hz), 7.47(d,2H,J=8.1 Hz).

IR (KBr): 1672, 1589, 1547, 1484, 1331, 1279, 1163 cm$^{-1}$.

EXAMPLE 302

3,6-Dimethyl-2-[4-(4-fluorobenzoyl)benzyloxy]-4H-pyrido[1,2-a]pyrimidin-4-one

The above titled compound was obtained by subjecting to reaction and process in the same manner as in Example 121.

$^1$H-NMR (CDCl$_3$) δ: 2.12(s,3H), 3.10(st3H), 5.57(s,2H), 6.63(d,1H,J=6.7 Hz), 7.14(d,1H,J=8.5 Hz), 7.23(d,2H,J=9.5 Hz), 7.39(dd,1H,J=8.5&6.7 Hz), 7.57(d,2H,J=8.0 Hz), 7.79 (d,2H,J=8.0 Hz), 7.85(dd,2H,J=9.5&5.7 Hz).

IR (KBr): 1672, 1593, 1547, 1485, 1331, 1279, 1279, 1230, 1161, 928, 854, 797, 760 cm$^1$.

EXAMPLE 303

2-[4-(6-Chloronicotinoyl)benzyloxy]-3,6-dimethyl-4H-pyrido[1,2-a]pyrimidin-4-one The above titled compound was obtained by subjecting to reaction and process in the same manner as in Example 121.

$^1$H-NMR (CDCl$_3$) δ: 2.12(s,3H), 3.10(S.3H), 5.58(s,2H), 6.62(d,1H,J=7.4 Hz), 7.23(d,1H,J=8.6 Hz), 7.39(dd,1H,J=8.6&7.4 Hz), 7.48(d,1H,J=8.4 Hz), 7.60(d,2H,J=8.4 Hz), 7.81(d,2H,J=8.4 Hz), 8.09(dd,1H,J=8.4&2.6 Hz), 8.77(d, 1H,J=2.6 Hz).

IR (KBr): 1666, 1585, 1485, 1331, 1282, 1163 cm$^{-1}$.

EXAMPLE 304

3,6-Dimethyl-2-[4-(4-hydroxybenzoyl)benzyloxy]-4H-pyrido[1,2-a]pyrimidin-4-one

The above titled compound was obtained by subjecting to reaction and process in the same manner as in Example 121.

$^1$H-NMR (CDCl$_3$) δ: 2.13(3H,s), 3.11(3H,s), 5.25(2H,s), 6.65(1H,d,J=6.6 Hz), 7.04(2H,d,J=8.7 Hz), 7.27(1H,d,J=8.8 Hz), 7.41(1H,dd,J=8.8&6.6 Hz), 7.54(2H,d,J=8.4 Hz), 7.76 (2H,d,J=8.4 Hz), 7.77(2H,d,J=8.7 Hz).

IR (KBr): 3410, 2921, 1645, 1591, 1481, 1282, 1165, 926, 731 cm$^{-1}$.

EXAMPLE 305

2-[4-(6-Chloronicotinoyl)benzylthio]-5-ethyl-3-methyl]-4(3H)-quinazolinone

The above titled compound was obtained by subjecting to reaction and process in the same manner as in Example 1.

$^1$H-NMR (CDCl$_3$) δ: 1.27(3H,t,J=7.4 Hz), 3.30(2H,q,J=7.4 Hz), 3.56(3H,s), 4.60(2H,s), 7.19(1H,d,J=7.4 Hz), 7.46 (1H,t,J=7.4 Hz), 7.47(1H,d,J=8.2 Hz), 7.57(1H,d,J=7.4 Hz), 7.65(2H,d,J=8.4 Hz), 7.77(2H,d,J=8.4 Hz), 8.08(1H,dd,J=8.4&2.4 Hz), 8.75(1H,d,J=2.4 Hz).

IR (KBr): 1666, 1552, 1462, 1281, 1159, 1099, 926 cm$^{-1}$.

EXAMPLE 306

3,6-Dimethyl-2-[4-[6-(4-piperidino)benzoyl) benzyloxy]-4H-pyrido[1,2-a]pyrimidin-4-one-3 hydrochloride The above titled compound was obtained by subjecting to reaction and process in the same manner as in Example 197.

$^1$H-NMR (DMSO-d$_6$) δ: 1.60–1.97(5H,m), 1.98(3H,s), 2.10–2.30(2H,m), 2.80–3.10(4H,m), 2.98(3H,s), 3.30–3.50 (2H,m), 3.60–3.70(4H,m), 5.60(2H,s), 6.87(1H,d,J=7.2 Hz), 7.00–7.09(2H,m), 7.30(1H,d,J=9.00 Hz), 7.62(2H,d,J=7.6 Hz), 7.71(2H,d,J=7.6 Hz), 7.95(1H,dd,J=7.6&2.2 Hz), 8.46 (1H,d,J=2.2 Hz).

IR (KBr): 3423, 2937, 1643, 1549, 1483, 1446, 1331, 1282, 1238, 1177, 1003 cm$^{-1}$.

EXAMPLE 307

3,6-Dimethyl-2-[4-[6-(4-phenylpiperazinyl) nicotinoyl)benzyloxy]-4H-pyrido[1,2-a]pyrimidin-4-one3 hydrochloride The above titled compound was obtained by subjecting to reaction and process in the same manner as in Example 197.

$^1$H-NMR (DMSO-d$_6$) δ: 1.19(3H,s), 2.99(3H,s), 3.39(4H, m), 3.89(4H,m), 5.58(2H,s), 6.88(1H,d,J=8.0 Hz), 6.95(1H, m), 7.07–7.20(3H,m), 7.28–7.35(3H,m), 7.60(1H,m), 7.62 (2H,d,J=8.4 Hz), 7.73(1H,d,J=8.4 Hz), 8.00(1H,dd,J=8.8&2.2 Hz), 8.49(1H,d,J=2.2 Hz).

IR (KBr): 3456, 1664, 1637, 1559, 1487, 1439, 1288, 1261, 1187 cm$^{-1}$.

EXAMPLE 308

3,6-Dimethyl-2-[4-[4-(2-morpholinoethoxy) benzoyloxy]-4H-pyrido[1,2-a]pyrimidin-4-one hydrochloride The above titled compound was obtained by subjecting to reaction and process in the same manner as in Example 156.

$^1$H-NMR (CDCl$_3$) δ: 2.12(3H,s), 2.60(4H,t,J=4.8 Hz), 2.85(2H,t,J=6.0 Hz), 3.75(4H,t,J=4.8 Hz), 4.20(2H,t,J=6.0 Hz), 5.56(2H,s), 6.63(1H,d,J=6.8 Hz), 6.97(2H,d,J=8.8 Hz), 7.25(1H,d,J=8.7 Hz), 7.39(1H,dd,J=8.7&6.8 Hz), 7.55(2H, d,J=8.0 Hz), 7.77(2H,d,J=8.0 Hz), 7.82(2H,d,J=8.8 Hz).

IR (KBr): 1649, 1599, 1483, 1282, 1255, 1167, 928 cm$^{-1}$.

EXAMPLE 309

5-Ethyl-3-methyl-2-[4-[6-(4-piperidino)benzoyl) benzylthio]-4(3H)-quinazolinone-3 hydrochloride $^1$H-NMR (DMSO-d$_6$) δ: 1.18(3H,t,J=7.2H), 1.50–1.90 (7H,m), 2.10–2.30(2H,m), 2.80–3.10(4H,m), 3.22(2H,q,J= 7.2 Hz), 3.30–3.50(4H,m), 3.48(3H,s), 4.65(2H,s), 4.70(1H, m), 7.02(1H,d,J=8.4 Hz), 7.22(1H,d,J=8.6 Hz), 7.48(1H,d, J=9.0 Hz), 7.64(1H,d,J=8.7 Hz), 7.66(1H,dd,J=8.6&8.4 Hz), 7.71(2H,d,J=8.7 Hz), 8.13(1H,dd,J=9.0&2.6 Hz), 8.45(1H, d,J=2.6 Hz).

IR (KBr): 3377, 2933, 2646, 2519, 1647, 1551, 1442, 1317, 1279, 1241, 1180, 1093, 1003, 926, 822, 748 cm$^{-1}$.

EXAMPLE 310

5-Ethyl-3-methyl-2-[4-[6-(4-phenylpiperazinyl) nicotinoyl)benzylthio]-4(3H)-quinazotinone- 3 hydrochloride The above titled compound was obtained by subjecting to reaction and process in the same manner as in Example 197.

¹H-NMR (DMSO-d₆) δ: 1.18(3H,t,J=7.2H), 3.22(2H,q,J=7.2 Hz), 3.40(4H,m), 3.48(3H,s), 3.89(4H,m), 4.65(2H,s), 6.90–7.40(6H,m), 7.48(2H,d,J=8.0 Hz), 7.64(2H,d,J=8.0 Hz), 7.62–7.80(3H,m), 8.00(1H,m), 8.46(1H,m).

IR (KBr): 3406, 1968, 1637, 1605, 1552, 1435, 1313, 1255, 1182, 1091, 760, 696 cm⁻¹.

EXAMPLE 311

3-Acetoxyethyl-7-[4-(4-chlorobenzoyl)benzyl]-5-methyl-7H-pyrrolo[2,3-d]pyrimidin-4-one The above titled compound was obtained by subjecting to reaction and process in the same manner as in Example 49.

¹H-NMR (CDCl₃) δ: 2.06(3H,s), 2.42(3H,s), 4.22–4.28 (2H,m), 4.37–4.43(2H,m), 5.34(2H,s), 6.59(1H,s), 7.27(2H,d,J=8.2 Hz), 7.45(2H,d,J=8.6 Hz), 7.73(2H,d,J=8.6 Hz), 7.74(2H,d,J=8.2 Hz), 7.80(1H,s).

EXAMPLE 312

7-[4-(4-Chlorobenzoyl)benzyl]-3-hydroxyethyl-5-methyl-7H-pyrrolo[2,3-d]pyrimidin-4-one 3-Acetoxyethyl-7-[4-(4-chlorobenzoyl)benzyl]-5-methyl-7H-pyrrolo[2,3-d]pyrimidin-4-one (464 mg) was dissolved in methanol (12 ml) followed by addition of 1N-sodium hydroxide (2 ml). To this mixture was added DME (6 ml) to prepare a homogeneous solution. After 4 hours of stirring, 1N-HCl (2 ml) was added and the solvent was distilled off under reduced pressure. The residue was diluted with water and triturated and the resulting powder was rinsed with water and methanol and dried to provide the title compound as crystalline powder (402 mg).

¹H-NMR (CDCl₃) δ: 2.42(3H,d,J=1.0 Hz), 2.86(1H,t,J=4.4 Hz), 3.97(2H,q,J=4.4 Hz), 4.18(2H,t,J=4.4 Hz), 5.34 (2H,s), 6.60(1H,d,J=1.0 Hz), 7.27(2H,d,J=8.2 Hz), 7.45(2H,d,J=8.6 Hz), 7.73(4H,d,J=8.4 Hz), 7.80(1H,s).

EXAMPLE 313

5-[4-(6-Chloronicotinoyl)benzyl]-1,3-dimethyl-pyrrolo[3,2-d]pyrimidin-2,4-dione

The above titled compound was obtained by subjecting to reaction and process in the same manner as in Example 163.

¹H-NMR: (CDCl₃) δ: 3.39(3H,s), 3.49(3H,s), 5.67(2H,s), 6.01(1H,d,J=3.0 Hz), 7.02(1H,d,J=3.0 Hz), 7.32(2H,d,J=8.4 Hz), 7.46(1H,d,J=8.1 Hz), 7.75(1H,d,J=8.4 Hz), 8.06(1H,dd,J=8.1&2.2 Hz), 8.74(1H,d,J=2.2 Hz).

IR (KBr): 1695, 1655, 1551, 1467, 1275, 1099, 922, 758 cm⁻¹.

EXAMPLE 314

1,3-Dimethyl-5-[4-(4-fluorobenzoyl)benzyl]-pyrrolo[3,2-d]pyrimidin-2,4-dione

The above titled compound was obtained by subjecting to reaction and process in the same manner as in Example 163.

¹H-NMR: (CDCl₃) δ: 3.40(3H,s), 3.49(3H,s), 5.66(2H,s), 6.01(1H,d,J=2.9 Hz), 7.02(1H,d,J=2.9 Hz), 7.15(2H,t,J=8.6 Hz), 7.30(2H,d,J=8.2 Hz), 7.73(2H,d,J=8.2 Hz), 7.82(2H,dd,J=8.6&5.4 Hz).

IR (KBr): 1686, 1647, 1601, 1551, 1468, 1412, 1275, 1244, 1153, 1061, 928, 856, 746 cm⁻¹.

EXAMPLE 315

1,3-Dimethyl-5-[4-[6-(4-pyperidino)nicotinoyl)benzyl]-pyrrolo[3,2-d]pyrimidin-2,4-dione-2 hydrochloride The above titled compound was obtained by subjecting to reaction and process in the same manner as in Example 197.

¹H-NMR: (DMSO-d6) δ: 1.40(2H,m), 1.68–1.82(8H,m), 2.20–2.26(2H,m), 2.80–3.00(5H,m), 3.22(3H,s), 3.39(3H,s), 4.64–4.69(2H,m), 4.64(2H,s), 6.24(1H,d,J=2.4 Hz), 7.10 (1H,d,J=9.1 Hz), 7.34(2H,d,J=8.4 Hz), 7.52(1H,d,J=2.4 Hz), 7.65(2H,d,J=8.4 Hz), 7.96(1H,dd,J=9.1&2.2 Hz), 8.40(1H,d,J=2.4 Hz).

IR (KBr): 3417, 1689, 1641, 1551, 1464, 1269, 746 cm⁻¹.

EXAMPLE 316

1,3-Dimethyl-5-[4-[6-(4-phenylpyperazino)nicotinoyl)benzyl]-pyrrolo[3,2-d]pyrimidin-2,4-dione-2 hydrochloride The above titled compound was obtained by subjecting to reaction and process in the same manner as in Example 197.

¹H-NMR: (DMSO-d₆) δ: 3.22(3H,s), 3.39(4H,m), 3.57 (3H,s), 5.65(2H,s), 6.24(1H,d,J=3.0 Hz), 6.90–7.30(6H,m), 7.34(2H,d,J=8.0 Hz), 7.52(1H,d,J=3.0 Hz), 7.66(2H,d,J=8.0 Hz), 7.98(1H,dd,J=9.0&2.2 Hz), 8.44(1H,d,J=2.2 Hz).

IR (KBr): 3413, 1691, 1641, 1549, 1464, 1255, 750 cm⁻¹.

EXAMPLE 317

2-[4-(6-Chloronicotinoyl)benzylthio]-6-hydroxy-3-methyl-4(3H)-quinazolinone

The above titled compound was obtained by subjecting to reaction and process in the same manner as in Example 1.

¹H-NMR: (DMSO-d6) δ: 3.48(3H,s), 4.63(2H,m), 7.27 (1H,dd,J=8.8&2.6 Hz), 7.38(1H,d,J=2.7 Hz), 7.52(1H,d,J=8.8 Hz), 7.69(1H,d,J=8.2 Hz), 7.75(4H,s), 8.13(1H,dd,J=8.2&2.4 Hz), 8.69(1H,d,J=2.4 Hz).

IR (KBr): 3209, 1660, 1554, 1495, 1360, 1281, 1236, 1105, 1070, 928, 835, 748 cm⁻¹.

EXAMPLE 318

2-[4-(4-Fluorobenzoyl)benzylthio]-6-hydroxy-3-methyl-4(3H)-quinazolinone

The above titled compound was obtained by subjecting to reaction and process in the same manner as in Example 1.

¹H-NMR: (CDCl₃) δ: 3.61(3H,s), 4.59(2H,s), 5.46(1H, brs), 6.51(1H,brs), 7.15(2H,t,J=8.8 Hz), 7.30(1H,dd,J=8.8&2.6 Hz), 7.54(2H,d,J=8.8 Hz), 7.60(2H,d,J=8.0 Hz), 7.74(2H,d,J=8.0 Hz), 7.78(1H,m), 7.82(1H,dd,J=5.4&2.6 Hz).

IR (KBr): 3200, 1654, 1602, 1552, 1494, 1363, 1277, 1232, 1147, 1666, 833 cm⁻¹.

EXAMPLE 319

6-Hydroxy-2-[4-(4-trifluoromethylbenzoyl)benzylthio]-3-methyl-4(3H)-quinazolinone The above titled compound was obtained by subjecting to reaction and process in the same manner as in Example 1.

¹H-NMR: (CDCl₃) δ: 3.61(3H,s), 4.59(2H,s), 7.29(1H,dd,J=8.9&3.0 Hz), 7.53(1H,d,J=8.9 Hz), 7.62(1H,d,J=8.2 Hz), 7.72–7.79(6H,m), 7.87(2H,d,J=8.0 Hz).

IR (KBr): 3346, 1678, 1610, 1556, 1493, 1323, 1143, 1063, 928, 833 cm⁻¹.

EXAMPLE 320

3-Methyl-6-(2,2,2-trifluoroethylaminocarbonyloxy)-2-[4-(4-trifluoromethylbenzoyl)benzylthio]-4(3H)-quinazolinone In DMF (5.0 ml) was dissolved 6-hydroxy-3-methyl-2-[4-(4-trifluoromethylbenzoyl)benzyl]thio-4(3H)- quinazolinone (0.300 g, 0.638 mmol) followed by addition of 4-nitrophenyl chlorocarbonate (0.196 g, 0.973 mmol) and triethylamine (0.25 ml), and the mixture was stirred at room temperature for 1 hour. Then, 2,2,2-trifluoroethylamine (0.148 g, 0.989 mmol) was further added and the mixture was stirred for an additional 14 hours. The solvent was then distilled off and the residue was dissolved in ethyl acetate and washed with saturated aqueous NaCl solution. The organic layer was dried over $MgSO_4$ and concentrated under reduced pressure. The residue was purified by silica gel column chromatography (isopropyl ether: acetone =10:1) and recrystallized from hexane-isopropyl ether to provide 0.080 g (21%) of colorless needles.

$^1$H-NMR: ($CDCl_3$) δ: 3.60(3H,s), 3.92(2H,m), 4.60(2H, s), 5.46(1H,brs), 7.51(1H,dd,J=8.5&2.5 Hz), 7.61(1H,d,J=8.8 Hz), 7.62(2H,d,J=8.0 Hz), 7.74(2H,d,J=8.4 Hz), 7.77 (2H,d,J=8.0 Hz), 7.87(2H,d,J=8.4 Hz), 7.94(1H,d,J=2.5 Hz).

IR (KBr): 3305, 1726, 1674, 1552, 1483, 1412, 1333, 1284, 1246, 1159, 1111, 1068, 1016, 933, 837, 773, 686 $cm^{-1}$.

EXAMPLE 321

2-(4-Benzoylbenzylthio)-3,5-dimethyl-4(3H)-quinazolinone

The above titled compound was obtained by subjecting to reaction and process in the same manner as in Example 1.

$^1$H-NMR: ($CDCl_3$) δ: 2.85(3H,s), 3.55(3H,s), 4.60(2H,s), 7.15(1H,d,J=7.2 Hz), 7.44–7.62(7H,m), 7.76–7.81(4H,m).

IR (KBr): 1659, 1552, 1308, 1277, 1088, 931, 858, 802, 702 $cm^{-1}$.

EXAMPLE 322

2-[4-(4-Chlorobenzoyl)benzylthio]-5-methoxymethyl-3-methyl-4(3H)-quinazolinone

The above titled compound was obtained by subjecting to reaction and process in the same manner as in Example 1.

$^1$H-NMR: ($CDCl_3$) δ: 3.55(3H,s), 3.56(3H,s), 4.60(2H,s), 5.14(2H,s), 7.45(2H,d,J=8.6 Hz), 7.52(1H,dd,J=7.4&1.8 Hz), 7.59–7.66(3H,m), 7.70–7.77(5H,m).

IR (KBr): 1660, 1552, 1435, 1404, 1308, 1281, 1086, 924, 804, 741, 687 $cm^{-1}$.

EXAMPLE 323

2-[4-(4-Fluorobenzoyl)benzylthio]-5-methoxymethyl-3-methyl-4(3H)-quinazolinone

The above titled compound was obtained by subjecting to reaction and process in the same manner as in Example 1.

$^1$H-NMR: ($CDCl_3$) δ: 3.55(3H,s), 3.56(3H,s), 4.60(2H,s), 5.14(2H,s), 7.15(2H,t,J=9.0 Hz), 7.52(1H,dd,J=7.6&2.0 Hz), 7.60(2H,d,J=8.4 Hz), 7.64(1H,m), 7.68(1H,t,J=7.6 Hz), 7.74(2H,d,J=8.4 Hz), 7.83(2H,dd,J=9.0&5.4 Hz).

IR (KBr): 1663, 1589, 1555, 1439, 1408, 1308, 1279, 1234, 1084, 924, 852, 746, 687, 575 $cm^{-1}$.

EXAMPLE 324

2-[4-(4-Chlorobenzoyl)benzylthio]-3-methyl-5-(2,2,2-trifluoroethoxymethyl)-4(3H)-quinazolinone The above titled compound was obtained by subjecting to reaction and process in the same manner as in Example 1.

$^1$H-NMR: ($CDCl_3$) δ: 3.55(3H,s), 4.05(2H,q,J=8.4 Hz), 4.60(2H,s), 5.36(2H,s), 7.45(2H,d,J=8.4 Hz), 7.54(1H,d,J=6.6 Hz), 7.60(2H,d,J=8.4 Hz), 7.61(1H,d,J=6.6 Hz), 7.68 (1H,t,J=6.6 Hz), 7.73(2H,d,J=8.4 Hz), 7.74(2H,d,J=8.4 Hz).

IR (KBr): 1676, 1645, 1558, 1443, 1409, 1309, 1157, 1088, 806, 693 $cm^{-1}$.

EXAMPLE 325

2-[4-(4-Fluorobenzoyl)benzylthio]-3-methyl-5-(2,2,2-trifluoroethoxymethyl)-4(3H)-quinazolinone The above titled compound was obtained by subjecting to reaction and process in the same manner as in Example 1.

$^1$H-NMR: ($CDCl_3$) δ: 3.55(3H,s), 4.04(2H,q,J=8.6 Hz), 4.60(2H,s), 5.36(2H,s), 7.15(2H,t,J=8.8 Hz), 7.53–7.67(5H, m), 7.73(2H,d,J=8.4 Hz), 7.84(2H,dd,J=8.8&5.4 Hz).

IR (KBr): 1662, 1603, 1558, 1443, 1412, 1279, 1161, 1088, 964, 928, 851, 690 $cm^{-1}$.

EXAMPLE 326

5-Methoxymethyl-3-methyl-2-[4-(4-trifluoromethylbenzoyl)benzylthio]-4(3H)-quinazolinone The above titled compound was obtained by subjecting to reaction and process in the same manner as in Example 1.

$^1$H-NMR: ($CDCl_3$) δ: 3.55(3H,s), 4.60(2H,s), 5.14(2H,s), 7.50(1H,d,J=8.4 Hz), 7.62(2H,d,J=8.0 Hz), 7.68(1H,d,J=8.4 Hz), 7.72–7.79(5H,m), 7.87(2H,d,J=8.0 Hz).

IR (KBr): 1660, 1560, 1408, 1315, 1279, 1161, 1134, 1086, 1063 $cm^{-1}$.

EXAMPLE 327

3-Methyl-5-(2,2,2-trifluoroethoxymethyl)-2-[4-(4-trifluoromethylbenzoyl)benzylthio]-4(3H)-quinazolinone The above titled compound was obtained by subjecting to reaction and process in the same manner as in Example 1.

$^1$H-NMR: ($CDCl_3$) δ: 3.55(3H,s), 4.05(2H,q,J=8.8 Hz), 4.61(2H,s), 5.36(2H,s), 7.55(1H,d,J=7.8 Hz), 7.62(2H,d,J=8.0 Hz), 7.66(1H,d,J=7.8 Hz), 7.72–7.79(5H,m).

IR (KBr): 1678, 1659, 1554, 1331, 1282, 1169, 1128, 1090 $cm^{-1}$.

EXAMPLE 328

1-[4-(4-Fluorobenzoyl)benzyl]-6,7,8,9-tetrahydroimidazo[2,1-b]quinazolin-5(1H)-one The above titled compound was obtained by subjecting to reaction and process in the same manner as in Example 163.

$^1$H-NMR: ($CDCl_3$) δ: 1.82(4H,m), 2.65(2H,t,J=5.6 Hz), 2.74(2H,t,J=5.6 Hz), 5.33(2H,s), 6.85(1H,d,J=2.6 Hz), 7.17 (2H,d,J=8.2 Hz), 7.40(2H,d,J=8.0 Hz), 7.55(1H,d,J=2.6 Hz), 7.78(2H,d,J=8.0 Hz), 7.83(2H,dd,J=8.2&4.8 Hz).

IR (KBr): 1657, 1589, 1527, 1418, 1277, 1213, 1159, 928 $cm^{-1}$.

EXAMPLE 329

1-[4-(4-Trifluorobenzoyl)benzyl]-6,7,8,9-tetrahydroimidazo[2,1-b]quinazolin-5(1H)-one The above titled compound was obtained by subjecting to reaction and process in the same manner as in Example 163.

$^1$H-NMR: ($CDCl_3$) δ: 1.79–1.83(4H,m), 2.65(2H,t,J=5.8 Hz), 2.73(2H,t,J=5.8 Hz), 5.34(2H,s), 6.84(1H,d,J=2.6 Hz), 7.42(2H,d,J=8.2 Hz), 7.55(1H,d,J=2.6 Hz), 7.76(2H,d,J=8.2 Hz), 7.81(2H,d,J=8.4 Hz), 7.88(2H,d,J=8.2 Hz).

IR (KBr): 1659, 1583, 1527, 1417, 1321, 1277, 1168, 1128, 1064, 928 cm$^{-1}$.

EXAMPLE 330

3,6-Dimethyl-2-[4-(4-trifluoromethylbenzoyl) benzyloxy]-4H-pyrido[1,2-a]pyrimidin-4-one The above titled compound was obtained by subjecting to reaction and process in the same manner as in Example 40.

$^1$H-NMR: (CDCl$_3$) δ: 2.12(3H,s), 3.10(3H,s), 5.58(2H,s), 6.62(1H,d,J=6.4 Hz), 7.24(1H,d,J=9.0 Hz), 7.38(1H,dd,J=9.0&6.4 Hz), 7.58(2H,d,J=8.4 Hz), 7.75(2H,d,J=8.4 Hz), 7.82(2H,d,J=8.4 Hz), 7.89(2H,d,J=8.4 Hz).

IR (KBr): 1672, 1599, 1549, 1487, 1331, 1276, 1167, 1113, 1063, 928, 802, 766 cm$^{-1}$.

EXAMPLE 331

3,6-Dimethyl-2-[4-(4-(4-fluorophenyl) piperazinocarbonyl)benzyloxy]-4H-pyrido[1,2-a] pyrimidin-4-one The above titled compound was obtained by subjecting to reaction and process in the same manner as in Example 40.

$^1$H-NMR: (CDCl$_3$) δ: 2.10(3H,s), 3.10(3H,s), 3.11(4H,brs), 3.63(2H,brs), 3.87(2H,brs), 5.51(2H,s), 6.62(1H,d,J=7.2 Hz), 6.88(2H,dd,J=8.7&4.8 Hz), 6.96(2H,d,J=8.0 Hz), 7.24(1H,d,J=7.0 Hz), 7.39(1H,dd,J=7.2&6.6 Hz), 7.44(2H,d,J=8.0 Hz), 7.49(2H,d,J=8.7 Hz).

IR (KBr): 1678, 1632, 1595, 1487, 1444, 1331, 1282, 1234, 1163, 1012, 808 cm$^{-1}$.

EXAMPLE 332

3,6-Dimethyl-2-[4-(4-(2-pyridyl)piperazinocarbonyl) benzyloxy]-4H-pyrido[1,2-a]pyridin-4-one The above titled compound was obtained by subjecting to reaction and process in the same manner as in Example 40.

$^1$H-NMR: (CDCl$_3$) δ: 2.10(3H,s), 3.10(3H,s), 3.59(6H, brs), 3.85(2H,brs), 5.52(2H,s), 6.61–6.71(3H,m), 7.24(1H, d,J=9.0 Hz), 7.35–7.59(6H,m), 8.20(1H,d,J=5.4 Hz), 7.39 (1H,dd,J=7.2&6.6 Hz), 7.44(2H,d,J=8.0 Hz), 7.49(2H,d,J=8.7 Hz).

IR (KBr): 1674, 1632, 1595, 1551, 1485, 1435, 1375, 1332, 1279, 1238, 1163, 1010, 764 cm$^1$.

EXAMPLE 333

1-[4-(4-Chlorobenzoyl)benzyl]-1,6,7,8,9,10-hexahydrocyclopento[d]imidazo[1,2-a]pyrimidin-5-one The above titled compound was obtained by subjecting to reaction and process in the same manner as in Example 163.

$^1$H-NMR: (CDCl$_3$) δ: 1.50–1.80(5H,m), 1.84(1H,m), 2.80–2.91(4H,m), 5.34(2H,s), 6.85(1H,d,J=2.6 Hz), 7.40 (2H,d,J=8.0 Hz), 7.46(2H,d,J=8.4 Hz), 7.56(1H,d,J=2.6 Hz), 7.74(2H,d,J=8.4 Hz), 7.77(2H,d,J=8.0 Hz).

IR (KBr): 2918, 1655, 1584, 1520, 1308, 1277, 1190, 1090, 928, 696 cm$^{-1}$.

EXAMPLE 334

1-[4-(4-Trifluoromethylbenzoyl)benzyl]-1,6,7,8-tetrahydro-5H-cyclopento[d]-imidazo[1,2-a] pyrimidin-5-one The above titled compound was obtained by subjecting to reaction and process in the same manner as in Example 163.

$^1$H-NMR: (CDCl$_3$) δ: 2.15(2H,m), 2.90(2H,t,J=6.4 Hz), 2.94(2H,t,J=7.4 Hz), 5.37(2H,s), 6.89(1H,d,J=2.6 Hz), 7.41 (2H,d,J=8.2 Hz), 7.63(1H,d,J=2.6 Hz), 7.76(2H,d,J=8.2 Hz), 7.82(2H,d,J=8.2 Hz), 7.88(2H,d,J=8.2 Hz).

IR (KBr): 1657, 1570, 1520, 1475, 1327, 1277, 1167, 1128, 1063, 700 cm$^{-1}$.

EXAMPLE 335

1-[4-(4-Fluorobenzoyl)benzyl]-1,6,7,8-tetrahydro-5H-cyclopento[d]imidazo[1,2-a]pyrimidin-5-one The above titled compound was obtained by subjecting to reaction and process in the same manner as in Example 163.

$^1$H-NMR: (CDCl$_3$) δ: 2.13(2H,m), 2.90(2H,t,J=7.1 Hz), 2.94(2H,t,J=7.1 Hz), 5.36(2H,s), 6.88(1H,d,J=2.6 Hz), 7.17 (2H,d,J=8.7 Hz), 7.39(1H,d,J=7.8 Hz), 7.62(1H,d,J=2.6 Hz), 7.65(2H,d,J=7.8 Hz), 7.83(2H,dd,J=8.7&5.4 Hz).

IR (KBr): 1664, 1581, 1525, 1410, 1279, 1225, 1151, 928, 852, 736 cm$^{-1}$.

EXAMPLE 336

1-[4-(4-Fluorobenzoyl)benzyl-1,6,7,8,9,10-hexahydrocyclopento[d]imidazo[1,2-a]pyrimidin-5-one The above titled compound was obtained by subjecting to reaction and process in the same manner as in Example 163.

$^1$H-NMR: (CDCl$_3$) δ: 1.50–1.72(4H,m), 1.80–2.00(2H, m), 2.86–2.91(4H,m), 5.34(2H,s), 6.86(1H,d,J=2.6 Hz), 7.16(2H,d,J=8.8 Hz), 7.41(2H,d,J=7.8 Hz), 7.56(1H,d,J=2.6 Hz), 7.78(2H,d,J=7.8 Hz), 7.83(2H,dd,J=8.8&5.6 Hz).

IR (KBr): 1655, 1587, 1522, 1277, 1227, 930, 860, 739, 704 cm$^{-1}$.

EXAMPLE 337

1-[4-(4-Chlorobenzoyl)benzyl]-7-methylimidazo[1, 2-a]pyrimidin-5(1H)-one

The above titled compound was obtained by subjecting to reaction and process in the same manner as in Example 163.

$^1$H-NMR (CDCl$_3$) δ: 2.39(3H,s), 5.36(2H,s), 5.97(1H,s), 6.88(1H,d,J=2.8 Hz), 7.41(2H,d,J=8.2 Hz), 7.46(2H,d,J=9.0 Hz), 7.59(1H,d,J=2.8 Hz), 7.71(2H,d,J=9.0 Hz), 7.78(2H,d, J=8.2 Hz).

IR (KBr): 1676, 1657, 1580, 1533, 1423, 1277, 1165, 1088, 926, 835, 746, 685 cm$^{-1}$.

EXAMPLE 338

1-[4-(4-Chlorobenzoyl)benzyl]-6,7-diethylimidazo [1,2-a]pyrimidin-5(1H)-one

The above titled compound was obtained by subjecting to reaction and process in the same manner as in Example 163.

$^1$H-NMR (CDCl$_3$) δ: 1.16(3H,t,J=7.4 Hz), 1.28(3H,t,J=7.4 Hz), 2.66(2H,q,J=7.4 Hz), 2.71(2H,q,J=7.4 Hz), 5.33 (2H,s), 6.87(1H,d,J=2.6 Hz), 7.44(2H,d,J=8.0 Hz), 7.46(2H, d,J=8.4 Hz), 7.54(1H,d,J=2.6 Hz), 7.73(2H,d,J=8.0 Hz), 7.77(2H,d,J=8.4 Hz).

IR (KBr): 1655, 1576, 1460, 1412, 1360, 1275, 1207, 1169, 1084, 933, 734, 698 cm$^{-1}$.

EXAMPLE 339

6,7-Diethyl-1-[4-(4-trifluorimethylbenzoyl)benzyl]-imidazol[-2-a]pyrimidin-5(1H)-one The above titled compound was obtained by subjecting to reaction and process in the same manner as in Example 163.

¹H-NMR (CDCl₃) δ: 1.16(3H,t,J=7.4 Hz), 1.28(3H,t,J=7.4 Hz), 2.66(2H,q,J=7.4 Hz), 2.71(2H,q,J=7.4 Hz), 5.33 (2H,s), 6.87(1H,d,J=2.6 Hz), 7.46(2H,d,J=8.4 Hz), 7.54(1H, d,J=2.6 Hz), 7.75(2H,d,J=8.4 Hz), 7.81(2H,d,J=8.4 Hz), 7.88(2H,d,J=8.4 Hz).

IR (KBr): 1668, 1585, 1514, 1410, 1331, 1115, 1066, 931, 847, 769, 706 cm⁻¹.

EXAMPLE 340

1-[4-(4-Chlorobenzoyl)benzyl]-7-methyl-6-propyl-imidazo[1,2-a]pyrimidin-5(1H)-one The above titled compound was obtained by subjecting to reaction and process in the same manner as in Example 163.

¹H-NMR (CDCl₃) δ: 1.00(3H,t,J=7.4 Hz), 1.58(2H,m), 2.43(3H,s), 2.60(2H,t,J=7.0 Hz), 5.33(2H,s), 6.84(1H,d,J=2.6 Hz), 7.41(2H,d,J=8.0 Hz), 7.46(2H,d,J=8.8 Hz), 7.54 (1H,d,J=2.6 Hz), 7.74(2H,d,J=8.8 Hz), 7.78(2H,d,J=8.0 Hz).

IR (KBr): 1655, 1585, 1518, 1412, 1273, 1213, 1086, 924, 733, 698 cm⁻¹.

EXAMPLE 341

7-Methyl-6-propyl-1-[4-(4-trifluoromethylbenzoyl)benzyl]-imidazo[1,2-a]pyrimidin-5(1H)-one The above titled compound was obtained by subjecting to reaction and process in the same manner as in Example 163.

¹H-NMR (CDCl₃) δ: 1.00(3H,t,J=7.8 Hz), 1.55(2H,m), 2.43(3H,s), 2.60(2H,t,J=7.6 Hz), 5.34(2H,s), 6.85(1H,d,J=2.6 Hz), 7.42(2H,d,J=8.4 Hz), 7.54(1H,d,J=2.6 Hz), 7.75 (2H,d,J=8.4 Hz), 7.81(2H,d,J=8.0 Hz), 7.88(2H,d,J=8.0 Hz).

IR (KBr): 1655, 1578, 1520, 1414, 1321, 1279, 1221, 1176, 1140, 1065, 931, 708 cm⁻¹.

EXAMPLE 342

3,5-Dimethyl-2-[4-(4-formylpiperazinylcarbonyl)benzylthio]-4(3H)-quinazolinone

The above titled compound was obtained by subjecting to reaction and process in the same manner as in Example 1.

¹H-NMR (CDCl₃) δ: 2.85(3H,s), 3.27–3.82(8H,m), 3.54 (3H,s), 4.56(2H,s), 7.16(1H,d,J=6.7 Hz), 7.34–7.60(6H,m), 8.11(1H,s).

IR (KBr): 1670, 1558, 1458, 1095, 1004 cm⁻¹.

EXAMPLE 343

3,5-Dimethyl-2-[4-(4-methylpiperazinylcarbonyl)benzylthio]-4(3H)-quinazolinone

The above titled compound was obtained by subjecting to reaction and process in the same manner as in Example 1.

¹H-NMR (CDCl₃) δ: 2.82(3H,s), 2.85(3H,s), 3.53(3H,s), 2.60–4.21(8H,m), 4.55(2H,s), 7.16(1H,d,J=7.4 Hz), 7.35–7.47(3H,m), 7.50–7.63(3H,m).

IR (KBr): 1683, 1473, 1307, 1093 cm⁻¹.

EXAMPLE 344

3,5-Dimethyl-2-[4-[4-(2-hydroxyethyl)piperazinylcarbonyl]benzylthio]-4(3H)-quinazolinone The above titled compound was obtained by subjecting to reaction and process in the same manner as in Example 1.

¹H-NMR (CDCl₃) δ: 2.75(3H,s), 3.00–3.86(15H,m), 4.60 (2H,s), 7.21(1H,d,J=7.2 Hz), 7.38–7.68(6H,m).

IR (KBr): 1668, 1558, 1471, 1093, 989, 806 cm⁻¹.

EXAMPLE 345

3,5-Dimethyl-2-[4-[4-(2-pyridyl)piperazinylcarbonyl]benzylthio]-4(3H)-quinazolinone The above titled compound was obtained by subjecting to reaction and process in the same manner as in Example 1.

¹H-NMR (CDCl₃) δ: 2.85(3H,s), 3.30–4.06(8H,m), 3.54 (3H,s), 4.56(2H,s), 6.68(2H,m), 7.15(1H,d,J=6.6 Hz), 7.36–7.60(7H,m), 8.20(1H,m).

IR (KBr): 1677, 1625, 1592, 1305, 1095, 1012 cm⁻¹.

EXAMPLE 346

3,5-Dimethyl-2-[4-(4-piperonylpiperazinylcarbonyl)benzylthio]-4(3H)-quinazolinone The above titled compound was obtained by subjecting to reaction and process in the same manner as in Example 1.

¹H-NMR (CDCl₃) δ: 2.26–2.58(4H,m), 2.84(3H,s), 3.30–3.56(2H,brs), 3.43(2H,s), 3.53(3H,s), 3.62–3.84(2H, brs), 4.54(2H,s), 5.94(2H,s), 6.73(2H,s), 6.84(1H,s), 7.14 (1H,d,J=7.6 Hz), 7.35(2H,d,J=8.2 Hz), 7.39–7.58(4H,m).

IR (KBr): 1675, 1556, 1307, 1093, 1039 cm⁻¹.

EXAMPLE 347

2-[4-(4-Benzylpiperazinylcarbonyl)benzylthio]-3,5-dimethyl-4(3H)-quinazolinone

The above titled compound was obtained by subjecting to reaction and process in the same manner as in Example 1.

¹H-NMR (CDCl₃) δ: 2.30–2.58(4H,m), 2.84(3H,s), 3.30–3.60(2H,m), 3.53(5H,s), 3.66–3.86(2H,m), 4.53(2H,s), 7.14(1H,d,J=7.0 Hz), 7.24–7.58(11H,m).

IR (KBr): 1675, 1616, 1456, 1305, 1095, 993 cm⁻¹.

EXAMPLE 348

3,5-Dimethyl-2-[4-[4-(4-fluorophenyl)piperazinylcarbonyl]benzylthio]-4(3H)-quinazolinone The above titled compound was obtained by subjecting to reaction and process in the same manner as in Example 1.

¹H-NMR (CDCl₃) δ: 2.85(3H,s), 2.80–3.24(4H,m), 3.54 (3H,s), 3.30–4.04(4H,m), 4.55(2H,s), 6.83–7.04(4H,m), 7.15(1H,d,J=6.6 Hz), 7.36–7.60(6H,m).

IR (KBr): 1683, 1629, 1095, 1014 cm⁻¹.

EXAMPLE 349

3,5-Dimethyl-2-[4-[4-(2-pyrimidyl)piperazinylcarbonyl]benzylthio]-4(3H)-quinazolinone The above titled compound was obtained by subjecting to reaction and process in the same manner as in Example 1.

¹H-NMR (CDCl₃) δ: 2.85(3H,s), 3.38–4.02(8H,m), 3.54 (3H,s), 4.56(2H,s), 6.55(1H,t,J=4.7 Hz), 7.15(1H,d,J=6.6 Hz), 7.41(2H,d,J=8.2 Hz), 7.44(1H,d,J=8.2 Hz), 7.50–7.59 (3H,m), 8.33(2H,d,J=4.7 Hz).

IR (KBr): 1675, 1627, 1585, 1510, 1307, 1089 cm⁻¹.

EXAMPLE 350

3,5-Dimethyl-2-(4-morpholinocarbonylbenzylthio)-4(3H)-quinazolinone

The above titled compound was obtained by subjecting to reaction and process in the same manner as in Example 1.

¹H-NMR (CDCl₃) δ: 2.85(3H,s), 3.30–3.89(8H,m), 3.53 (3H,s), 4.54(2H,s), 7.15(1H,d,J=6.6 Hz), 7.37(2H,d,J=8.4 Hz), 7.43(1H,d,J=8.0 Hz), 7.49–7.59(3H,m).

IR (KBr): 1670, 1629, 1550, 1427, 1112, 894 cm⁻¹.

EXAMPLE 351

3,5-Dimethyl-2-[3-(4-methylpiperazinylcarbonyl) benzylthio]-4(3H)-quinazolinone

The above titled compound was obtained by subjecting to reaction and process in the same manner as in Example 1.

¹H-NMR (CDCl₃) δ: 2.28(3H,s), 2.10–2.58(4H,m), 2.84 (3H,s), 3.26–3.55(2H,m), 3.53(3H,s), 3.86–3.60(2H,m), 4.54(2H,s), 7.14(1H,d,J=7.2 Hz), 7.26–7.58(6H,m).

IR (KBr): 1685, 1579, 1560, 1461, 1423, 1089 cm⁻¹.

EXAMPLE 352

2-(4-(4-Hydroxymethylpiperidylcarbonyl) benzylthio)-3,5-dimethyl-4(3H)-quinazolinone In THF (25 ml) was dissolved 2-[4-(4-ethoxycarbonylpiperidylcarbonyl)benzylthio]-3,5-dimethyl-4(3H)-quinazolinone (3.593 g) followed by addition of LiBH₄ (254 mg), and the mixture was stirred for 30 minutes. This reaction mixture was washed with 1N-HCl and saturated aqueous NaCl solution in that order, dried, and concentrated. The residue was rinsed with ethyl acetate to provide the title compound as colorless-solid (1.871 g).

¹H-NMR (CDCl₃) δ: 1.04–1.90(6H,m), 2.85(3H,s), 2.66–3.20(2H,m), 3.53(5H,s), 3.56–3.96(1H,s), 4.54(2H,s), 4.55–5.00(1H,m), 7.15(1H,d,J=7.0 Hz), 7.35(2H,d,J=8.2 Hz), 7.43(2H,d,J=7.2 Hz), 7.46–7.58(6H,m).

IR (KBr): 1668, 1601, 1558, 1471, 1450, 1307, 1097cm⁻¹.

EXAMPLE 353

2-(4-(4-Bromomethylpiperidylcarbonyl)benzylthio)-3,5-dimethyl-4(3H)-quinazolinone In dichloromethane (25 ml) was dissolved 2-[4-(4-hydroxymethylpiperidylcarbonyl)benzylthio]-3,5-dimethyl-4(3H)-quinazolinone (1.081 g) followed by addition of carbon tetrabromide (1.050 g). Then, triphenylphosphine (982 mg) was added over 10 minutes and the mixture was stirred at room temperature for 2 hours. The salt was filtered off and the filtrate was concentrated. The residue was purified by silica gel chromatography (hexane-ethyl acetate =1:1) and rinsed with ether to provide the title compound as colorless solid (496 mg).

¹H-NMR (CDCl₃) δ: 1.08–1.50(2H,m), 1.75–2.06(3H, m), 2.85(3H,s), 2.50–3.14(2H,m), 3.32(2H,d,J=5.8 Hz), 3.53(3H,s), 3.64–3.96(1H,m), 4.55(2H,s), 4.60–4.90(1H,m), 7.15(1H,d,J=7.0 Hz), 7.34–7.60(6H,m).

IR (KBr): 1666, 1550, 1435, 1305, 1095, 964 cm⁻¹.

EXAMPLE 354

3,5-Dimethyl-2-(4-(4-isonicotinoyloxymethylpiperidylcarbonyl) benzylthio)-4(3H)-quinazolinone In DMF (15 ml) was dissolved 2-[4-(4-hydroxymethylpiperidylcarbonyl)benzylthio]-3,5-dimethyl-4(3H)-quinazolinone (415 mg), and following addition of isonicotinyl chloride hydrochloride (270 mg), triethylamine (0.40 ml) was added over 5 minutes. The mixture was stirred at room temperature for 3 hours, after which it was concentrated. The residue was washed with water, saturated aqueous NaHCO₃ solution, and saturated aqueous NaCl solution in that order, dried, and concentrated. The residue was recrystallized from hexane/ethyl acetate to provide the title compound as colorless solid (241 mg).

¹H-NMR (CDCl₃) δ: 1.16–2.22(5H,m), 2.85(3H,s), 2.56–3.20(2H,m), 3.53(3H,s), 3.55–4.04(1H,m), 4.26(2H,d, J=6.4 Hz), 4.55(2H,s), 4.40–5.00(1H,m), 7.15(1H,d,J=7.2 Hz), 7.31–7.60(6H,m), 7.83(2H,d,J=5.8 Hz), 8.80(2H,d,J= 5.8 Hz).

IR (KBr): 1718, 1668, 1560, 1295, 1099 cm⁻¹.

EXAMPLE 355

3,5-Dimethyl-2-(4-(4-(4-(4-fluorophenyl) piperazinylcarbonyl)piperidylcarbonyl) benzylthio)-4(3H)-quinazolinone The above titled compound was obtained by subjecting to reaction and process in the same manner as in Example 184.

¹H-NMR (CDCl₃) δ: 1.54–1.92(6H,m), 2.85(3H,s), 2.70–3.16(7H,m), 3.53(3H,s), 3.60–3.82(4H,m), 4.54(2H,s), 6.84–7.04(4H,m), 7.14(1H,d,J=8.8 Hz), 7.33–7.59(6H,m).

IR (KBr): 1672, 1550, 1434, 1307, 1226 cm⁻¹.

EXAMPLE 356

3,5-Dimethyl-2-(4-(4-morpholinocarbonylpiperidylcarbonyl)benzylthio)-4 (3H)-quinazolinone The above titled compound was obtained by subjecting to reaction and process in the same manner as in Example 184.

¹H-NMR (CDCl₃) δ: 1.54–1.94(6H,m), 2.85(3H,s), 2.60–3.12(3H,m), 3.53(3H,s), 3.67(9H,m), 4.54(2H,m), 7.15(1H,d,J=7.2 Hz), 7.33–7.59(6H,m).

IR (KBr): 1731, 1681, 1556, 1411, 1272, 1085 cm⁻¹.

EXAMPLE 357

2-(5-(2-(4-(3-Trifluoromethylphenyl) piperadynylcarbonyl)pyradyl) methylthio)-3,5-dimethyl-2-mercapto-4(3H)-quinazolinone The above titled compound was obtained by subjecting to reaction and process in the same manner as in Example 184.

¹H-NMR (CDCl₃) δ: 2.84(3H,s), 3.22(2H,m), 3.34(2H, m), 3.81(2H,m), 3.97(2H,m), 4.67(2H,s), 7.00–7.20(4H,m), 7.30–7.48(2H,m), 7.55(1H,t,J=7.6 Hz), 8.87(1H,s), 8.96 (1H,s).

IR (KBr): 1675, 1558, 1448, 1307, 1116 cm¹.

EXAMPLE 358

8-(4-(4-Chlorobenzoyl)benzyloxy)-3,4-dihydro-7-methyl-2H,6H-pyrimido[2,1-b][1,3]thiazin-6-one The above titled compound was obtained by subjecting to reaction and process in the same manner as in Example 40.

¹H-NMR (CDCl₃) δ: 1.99(3H,s), 2.26(2H,m), 3.17(2H,t, J=5.9 Hz), 4.10(2H,t,J=5.9 Hz), 5.42(2H,s), 7.49(4H,m), 7.77(4H,m).

IR (KBr): 1649, 1589, 1500, 1390, 1274 cm⁻¹.

EXAMPLE 359

3,4-Dihydro-8-(4-(4-fluorobenzoyl)benzyloxy)-7-methyl-2H,6H-pyrimido[2,1-b][1,3]thiazin-6-one The above titled compound was obtained by subjecting to reaction and process in the same manner as in Example 40.

¹H-NMR (CDCl₃) δ: 1.99(3H,s), 2.59(2H,m), 3.17(2H,t, J=5.9 Hz), 4.10(2H,t,J=5.9 Hz), 5.42(2H,s), 7.17(2H,m), 7.52(2H,d,J=8.6 Hz), 7.82(4H,m).

IR (KBr): 1652, 1580, 1500, 1266, 1118 cm⁻¹.

EXAMPLE 360

3,4-Dihydro-7-methyl-8-(4-(4-trifluoromethylbenzoyl)benzyloxy)-2H,6H-pyrido[2,1-b][1,3]thiazin-6-one The above titled compound was obtained by subjecting to reaction and process in the same manner as in Example 40.

¹H-NMR (CDCl₃) δ: 1.99(3H,s), 2.26(2H,m), 3.17(2H,t, J=5.8 Hz), 4.10(2H,t,J=5.8 Hz), 5.43(2H,s), 7.54(2H,d,J=8.4 Hz), 7.84(6H,m).

IR (KBr): 1654, 1591, 1498, 1326, 1187, 1122 cm⁻¹.

EXAMPLE 361

3-Methyl-2-[4-[4-(4-fluorophenyl)piperadylcarbonyl]benzylthio]-4H-pyrido[1,2-a]pyrimidin-4-one The above titled compound was obtained by subjecting to reaction and process in the same manner as in Example 40.

¹H-NMR (CDCl₃) δ: 2.21(3H,s), 2.90–3.26(4H,m), 3.42–4.04(4H,m), 5.57(2H,s), 6.82–7.16(5H,m), 7.50(5H, m), 7.70(1H,m), 9.08(1H,m).

IR (KBr): 1673, 1633, 1510, 1284, 1236, 1170 cm⁻¹.

EXAMPLE 362

3-Methyl-2-[4-[4-(2-pyridyl)piperazinylcarbonyl]benzyloxy]-4H-pyrido[1,2-a]pyrimidin-4-one The above titled compound was obtained by subjecting to reaction and process in the same manner as in Example 40.

¹H-NMR (CDCl₃) δ: 2.22(3H,s), 3.44–4.06(8H,m), 5.57 (2H,s), 6.69(2H,m), 7.11(1H,m), 7.48(6H,m), 7.71(1H,m), 8.21(1H,m), 9.08(1H,d,J=6.4 Hz).

IR (KBr): 1679, 1627, 1484, 1284, 1170 cm⁻¹.

EXAMPLE 363

3-Methyl-2-[4-[4-(2-pyridyl)piperazinylcarbonyl]benzyloxy]-6,7,8,9-tetrahydro-4H-pyrido[1,2-a]pyrimidin-4-one The above titled compound was obtained by subjecting to reaction and process in the same manner as in Example 40.

¹H-NMR (CDCl₃) δ: 1.80–2.08(4H,m), 2.01(3H,s), 2.84 (2H,t,J=6.1 Hz), 3.40–4.04(8H,m), 3.95(2H,t,J=6.1 Hz), 5.40(2H,s), 6.69(2H,m), 7.40–7.58(5H,m), 8.21(1H,dd,J= 1.8,5.6 Hz).

IR (KBr): 1660, 1527, 1479, 1241, 1155 cm⁻¹.

EXAMPLE 364

8-(4-(4-Chlorobenzoyl)benzylthio)-3,4-dihydro-7-methyl-2H,6H-pyrimido[2,1-b][1,3]thiazin-6-one The above titled compound was obtained by subjecting to reaction and process in the same manner as in Example 40.

¹H-NMR (CDCl₃) δ: 2.00(3H,s), 2.26(2H,m), 3.17(2H,t, J=5.8 Hz), 4.07(2H,t,J=5.8 Hz), 4.40(2H,s), 7.40–7.56(4H, m), 7.68–7.80(4H,m).

IR (KBr): 1647, 1496, 1398, 1286 cm⁻¹.

EXAMPLE 365

3,4-Dihydro-7-methyl-8-(4-(4-trifluoromethylbenzoyl)benzylthio)-2H,6H-pyrimido[2,1-b][1,4]thiazin-6-one The above titled compound was obtained by subjecting to reaction and process in the same manner as in Example 40.

¹H-NMR (CDCl₃) δ: 2.00(3H,s), 2.26(2H,m), 3.17(2H,t, J=5.8 Hz), 4.07(2H,t,J=5.8 Hz), 4.40(2H,s), 7.53(2H,d,J=8.2 Hz), 7.76(4H,d,J=8.2 Hz), 7.89(2H,d,J=8.2 Hz).

IR (KBr): 1641, 1546, 1494, 1326, 1166, 1130 cm⁻¹.

EXAMPLE 366

3,4-Dihydro-8-(4-(4-fluorobenzoyl)benzylthio)-7-methyl-2H,6H-pyrimido[2,1-b][1,3]thiazin-6-one The above titled compound was obtained by subjecting to reaction and process in the same manner as in Example 40.

¹H-NMR (CDCl₃) δ: 2.00(3H,s), 2.26(2H,m), 3.17(2H,t, J=5.8 Hz), 4.07(2H,t,J=5.8 Hz), 4.40(2H,s), 7.08–7.23(2H, m), 7.51(2H,d,J=8.3 Hz), 7.72(2H,d,J=8.3 Hz), 7.76–7.96 (2H,m).

IR (KBr): 1646, 1596, 1498, 1396, 1155 cm⁻¹.

EXAMPLE 367

3,5-Dimethyl-2-(4-(4-(2-(2-pyridyl)ethyl-N-methylaminocarbonyl)piperidylcarbonyl)benzylthio)-4(3H)-quinazolinone The above titled compound was obtained by subjecting to reaction and process in the same manner as in Example 184.

¹H-NMR (CDCl₃) δ: 1.48–1.84(7H,m), 2.85(3H,s), .2.97(3H,s), 2.46–3.10(4H,m), 3.53(3H,s), 3.77(2H, m), 4.54(2H,s), 7.06–7.25(2H,m), 7.30–7.66(8H,m), 8.54(1H,m).

IR (KBr): 1675, 1556, 1434, 1307 cm⁻¹.

EXAMPLE 368

1-(4-(4-Trifluorobenzoyl)benzyl)-1,6,7,8,9,10-hexahydrocyclopento[d]imidazo[1,2-a]pyrimidin-5-one The above titled compound was obtained by subjecting to reaction and process in the same manner as in Example 163.

¹H-NMR (CDCl₃) δ: 1.50–1.95(6H,m), 2.88(4H,m), 5.35 (2H,s), 6.87(1H,d,J=2.7 Hz), 7.43(2H,d,J=8.4 Hz), 7.57(1H, d,J=2.7 Hz), 7.72–7.92(6H,m).

IR (KBr): 1654, 1581, 1326, 1278 cm⁻¹.

EXAMPLE 369

3,4-Dihydro-8-(4-(4-methoxybenzoyl)benzyloxy)-7-methyl-2H,6H-pyrimido[2,1-b][1,3]thiazin-6-one The above titled compound was obtained by subjecting to reaction and process in the same manner as in Example 40.

¹H-NMR (CDCl₃) δ: 1.99(3H,s), 2.26(2H,m), 3.17(2H,t, J=5.8 Hz), 3.89(3H,s), 4.10(2H,t,J=5.8 Hz), 5.42(2H,s), 6.97(2H,d,J=8.3 Hz), 7.51(2H,d,J=8.3 Hz), 7.73–7.84(4H, m).

IR (KBr): 1654, 1504, 1257, 1170, 1128 cm⁻¹.

EXAMPLE 370

3-Methyl-2-(4-(4-cyanobenzoyl)benzyloxy)-6,7,8,9-tetrahydro-4H-pyrido[1,2-a]pyrimidin-4-one The above titled compound was obtained by subjecting to reaction and process in the same manner as in Example 40.

EXAMPLE 371

6-Methyl-7-[4-(4-cyanobenzoyl)benzyloxy]-2,3-dihydro-5H-thiazolo[1,2-a]pyrimidin-5-one The above titled compound was obtained by subjecting to reaction and process in the same manner as in Example 40.

$^1$H-NMR (CDCl$_3$) δ: 1.78–2.03(4H,m), 2.02(3H,s), 2.83 (2H,t,J=6.4 Hz), 3.95(2H,t,J=6.2 Hz), 5.46(2H,s), 7.55(2H, d,J=8.4 Hz), 7.75–7.93(6H,m).

IR (KBr): 2227, 1658, 1535, 1276, 1149 cm$^{-1}$.

EXAMPLE 372

3,4-Dihydro-8-(4-(4-hydroxybenzoyl)benzyloxy)-7-methyl-2H,6H-pyrimido[2,1-b][1,3]thiazin-6-one The above titled compound was obtained by subjecting to reaction and process in the same manner as in Example 40.

$^1$H-NMR (CDCl$_3$) δ: 1.97(3H,s), 3.47(2H,t,J=7.7 Hz), 4.47(2H,t,J=7.7 Hz), 5.44(2H,s), 7.53(2H,d,J=8.0 Hz), 7.75–7.92(6H,m).

IR (KBr): 2231, 1600, 1523, 1392, 1278, 1143 cm$^{-1}$.

EXAMPLE 373

3,4-Dihydro-8-[4-[4-(N,N-dimethylcarbamoyloxy)benzoyl]benzyloxy]-7-methyl-2H,6H-pyrimido[2,1-b][1,3]thiazin-6-one The above titled compound was obtained by subjecting to reaction and process in the same manner as in Example 40.

$^1$H-NMR (DMSO-d$_6$) δ: 1.85(3H,s), 2.14(2H,m), 3.21 (2H,m), 3.95(2H,m), 5.40(2H,s), 6.89(2H,d,J=8.6 Hz), 7.54 (2H,d,J=8.4 Hz), 7.64–7.72(4H,m).

IR (KBr): 1645, 1585, 1498, 1278 cm$^{-1}$.

EXAMPLE 374

3-Methyl-2-(4-(4-acetoxybenzoyl)benzyloxy)-6,7,8,9-tetrahydro-4H-pyrido[1,2-a]pyrimidin-4-one The above titled compound was obtained by subjecting to reaction and process in the same manner as in Example 40.

$^1$H-NMR (CDCl$_3$) δ: 1.99(3H,s), 2.26(2H,m), 3.05(3H,s), 3.13(3H,s), 3.17(2H,m), 4.10(2H,t,J=5.6 Hz), 5.42(2H,s), 7.25(2H,d,J=9.0 Hz), 7.52(2H,d,J=8.4 Hz), 7.82(4H,m).

IR (KBr): 1718, 1654, 1502, 1390, 1270 cm$^{-1}$.

EXAMPLE 374

3-Methyl-2-(4-(4-acetoxybenzoyl)benzyloxy)-6,7,8,9-tetrahydro-4H-pyrido[1,2-a]pyrimidin-4-one The above titled compound was obtained by subjecting to reaction and process in the same manner as in Example 40.

$^1$H-NMR (CDCl$_3$) δ: 1.89(4H,m), 2.02(3H,s), 2.35(3H,s), 2.84(2H,t,J=6.2 Hz), 3.94(2H,t,J=6.2 Hz), 5.45(2H,s), 5.42 (2H,s), 7.22(2H,d,J=8.8 Hz), 7.52(2H,d,J=8.4 Hz), 7.76–7.90(4H,m).

IR (KBr): 1758, 1646, 1527, 1199 cm$^{-1}$.

EXAMPLE 375

3-Methyl-2-(4-(4-hydroxybenzoyl)benzyloxy)-6,7,8,9-tetrahydro-4H-pyrido[1,2-a]pyrimidin-4-one The above titled compound was obtained by subjecting to reaction and process in the same manner as in Example 40.

$^1$H-NMR (DMSO-d$_6$) δ: 1.81(4H,m), 1.87(3H,s), 2.81 (2H,t,J=6.3 Hz), 3.79(2H,t,J=5.9 Hz), 5.46(2H,s), 6.90(2H, d,J=8.6 Hz), 7.56(2H,d,J=8.2 Hz), 7.62–7.73(4H,m).

IR (KBr): 1735, 1635, 1510, 1280, 1149 cm$^{-1}$.

EXAMPLE 376

3-Methyl-2-[4-[4-(N,N-dimethylcarbamoyloxy)benzoyl]benzyloxy]-6,7,8,9-tetrahydro-4H-pyrido[1,2-a]pyrimidin-4-one The above titled compound was obtained by subjecting to reaction and process in the same manner as in Example 228.

$^1$H-NMR (CDCl$_3$) δ: 1.92(4H,m), 2.03(3H,s), 2.84(2H,t, J=6.3 Hz), 3.05(3H,s), 3.14(3H,s), 3.95(2H,t,J=6.3 Hz), 5.45(2H,s), 7.25(2H,d,J=8.5 Hz), 7.52(2H,d,J=8.5 Hz), 7.82 (4H,m).

IR (KBr): 1716, 1658, 1602, 1527, 1396 cm$^{-1}$.

EXAMPLE 377

3-Methyl-2-[4-(4-methylpiperazinylcarbonyl)benzylthio]-thieno[3,2-d]pyrimidin-4(3H)-one-hydrochloride The above titled compound was obtained by subjecting to reaction and process in the same manner as in Example 1.

$^1$H-NMR (DMSO-d$_6$) δ: 2.80(3H,brs), 3.00–3.90(8H,m), 3.51(3H,s), 4.59(2H,s), 7.37(1H,d,J=5.2 Hz), 7.43(2H,d,J= 8.2 Hz), 7.62(2H,d,J=8.2 Hz), 8.16(1H,d,J=5.2 Hz).

IR (KBr): 1665, 1640, 1530, 1500, 1410, 1280, 1260cm$^{-1}$.

EXAMPLE 378

3,6-Dimethyl-7-[4-(4-methylpiperazinylcarbonyl)benzyloxy]-5H-thiazolo[3,2-a]pyrimidin-5-one-hydrochloride The above titled compound was obtained by subjecting to reaction and process in the same manner as in Example 40.

$^1$H-NMR (CDCl$_3$) δ: 1.90(3H,s), 2.69(3H,d,J=1.2 Hz), 3.78(3H,s), 3.00–3.90(8H,m), 5.44(2H,s), 6.98(1H,d,J=1.2 Hz), 7.48(2H,d,J=8.2 Hz), 7.54(2H,d,J=8.2 Hz).

IR (KBr): 1680, 1650, 1630, 1565, 1500 cm$^{-1}$.

EXAMPLE 379

3-Methyl-2-[4-(4-methylpiperazinylcarbonyl)benzyloxy]-4H-pyrido[1,2-a]pyrimidin-4-one-hydrochloride The above titled compound was obtained by subjecting to reaction and process in the same manner as in Example 40.

$^1$H-NMR (DMSO-d$_6$) δ: 2.07(3H,s), 2.80(3H,s), 3.00–3.85(8H,m), 5.57(2H,s), 7.15–7.70(6H,m), 8.00(1H, m), 5.97(1H,d,J=7.4 Hz).

IR (KBr): 1670, 1630, 1470, 1420 cm$^{-1}$.

EXAMPLE 380

3,5-Dimethyl-2-[4-[4-(2-piperidinoethyl)piperazinylcarbonyl]benzylthiol-4(3H)-quinazolinone-2 hydrochloride The above titled compound was obtained by subjecting to reaction and process in the same manner as in Example 1.

$^1$H-NMR (DMSO-d$_6$+D$_2$O) δ: 1.50–1.85(6H,m), 2.75 (3H,s), 2.95–4.15(16H,m), 3.59(3H,s), 4.59(2H,s), 7.22(1H, d,J=7.0 Hz), 7.37–7.70(6H,m).

IR (KBr): 1675, 1640, 1550, 1450, 1420 cm$^1$.

EXAMPLE 381

3,5-Dimethyl-2-[4-(4-cinnamylpiperazinylcarbonyl)benzylthio]-4(3H)-quinazolinone-hydrochloride The above titled compound was obtained by subjecting to reaction and process in the same manner as in Example 1.

$^1$H-NMR (DMSO-d$_6$) δ: 2.75(3H,s), 2.90–3.55(8H,m), 3.44(3H,s), 3.90(2H,m), 4.60(2H,s), 6.39(1H,dt,J=15.8&7.0 Hz), 6.83(1H,d,J=15.8 Hz), 7.21(1H,d,J=7.4 Hz), 7.30–7.70 (11H,m).

IR (KBr): 1675, 1630, 1550, 1420 cm⁻¹.

EXAMPLE 382

2-[4-(4-Chlorobenzoyl)benzylthio]-5-methyl-4(3H)-quinazolinone

The above titled compound was obtained by subjecting to reaction and process in the same manner as in Example 1.

¹H-NMR (DMSO-d₆) δ: 2.73(3H,s), 4.57(2H,s), 7.18(1H, d,J=7.2 Hz), 7.44(1H,d,J=7.2 Hz), 7.55–7.80(5H,m), 12.40 (1H,brs).

IR (KBr): 1670, 1585, 1560 cm⁻¹.

EXAMPLE 383

2-[4-(4-Chlorobenzoyl)benzyloxy]-3-methyl-6,7,8,9-tetrahydro-4H-pyrido[1,2=a]pyrimidin-4-one The above titled compound was obtained by subjecting to reaction and process in the same manner as in Example 40.

¹H-NMR (CDCl₃) δ: 1.75–2.05(4H,m), 2.02(3H,s), 2.83 (2H,t,J=6.8 Hz), 3.95(2H,t,J=6.0 Hz), 5.46(2H,s), 7.47(2H, d,J=8.6 Hz), 7.52(2H,d,J=8.4 Hz), 7.76(2H,d,J=8.6 Hz), 7.78(2H,d,J=8.4 Hz).

IR (KBr): 1650, 1640, 1595, 1520, 1135 cm⁻¹.

EXAMPLE 384

2-[4-(4-Fluorobenzoyl)benzyloxy]-3-methyl-6,7,8,9-tetrahydro-4H-pyrido[1,2-a]pyrimidin-4-one The above titled compound was obtained by subjecting to reaction and process in the same manner as in Example 40.

¹H-NMR (CDCl₃) δ: 1.80–2.05(4H,m), 2.02(3H,s), 2.84 (2H,t,J=6.4 Hz), 3.95(2H,t,J=6.0 Hz), 5.46(2H,s), 7.17(2H, t,J=8.6 Hz), 7.52(2H,d,J=8.4 Hz), 7.78(2H,d,J=8.4 Hz), 7.86 (2H,dd,J=8.6&5.6 Hz).

IR (KBr): 1650, 1640, 1590, 1525, 1270, 1130 cm⁻¹.

EXAMPLE 385

3-Methyl-2-[4-(4-trifluoromethylbenzoyl)benzyloxy]-6,7,8,9-tetrahydro-4H-pyrido[1,2-a]pyrimidin-4-one The above titled compound was obtained by subjecting to reaction and process in the same manner as in Example 40.

¹H-NMR (CDCl₃) δ: 1.80–2.00(4H,m), 2.02(3H,s), 2.83 (2H,t,J=6.6 Hz), 3.95(2H,t,J=6.0 Hz), 5.47(2H,s), 7.54(2H, d,J=8.0 Hz), 7.76(2H,d,J=8.6 Hz), 7.82(2H,d,J=8.6 Hz), 7.90(2H,d,J=8.0 Hz).

IR (KBr): 1655, 1605, 1325, 1145 cm¹.

EXAMPLE 386

2-[4-(4-Chlorobenzoyl)benzyloxy]-3,6-dimethyl-6,7,8,9-tetrahydro-4H-pyrido[1,2-a]pyrimidin-4-one The above titled compound was obtained by subjecting to reaction and process in the same manner as in Example 40.

¹H-NMR (CDCl₃) δ: 1.34(3H,d,J=6.6 Hz), 1.80–2.05(4H, m), 2.02(3H,s), 2.86(2H,m), 4.95(1H,m), 5.44(2H,s), 7.47 (2H,d,J=8.6 Hz), 7.52(2H,d,J=8.6 Hz), 7.76(2H,d,J=8.6 Hz), 7.78(2H,d,J=8.6 Hz).

IR (KBr): 1650, 1640, 1600, 1520, 1135 cm⁻¹.

EXAMPLE 387

3,6-Dimethyl-2-[4-(4-fluorobenzoyl)benzyloxy]-6,7,8,9-tetrahydro-4H-pyrido[1,2-a]pyrimidin-4-one The above titled compound was obtained by subjecting to reaction and process in the same manner as in Example 40.

¹H-NMR (CDCl₃) δ: 1.34(3H,d,J=6.6 Hz), 1.80–2.05(4H, m), 2.02(3H,s), 2.65–3.00(2H,m), 4.96(1H,m), 5.44(2H,s), 7.16(2H,t,J=8.6 Hz), 7.52(2H,d,J=8.4 Hz), 7.77(2H,d,J=8.4 Hz), 7.85(2H,dd,J=8.6&5.4 Hz).

IR (KBr): 1650, 1595, 1520, 1270, 1135 cm⁻¹.

EXAMPLE 388

3,6-Dimethyl-2-[4-(4-trifluoromethylbenzoyl)benzyloxy]- 6,7,8,9-tetrahydro-4H-pyrido[1,2-a]pyrimidin-4-one The above titled compound was obtained by subjecting to reaction and process in the same manner as in Example 40.

¹H-NMR (CDCl₃) δ: 1.34(3H,d,J=6.6 Hz), 1.80–2.05(4H, m), 2.02(3H,s), 2.65–3.00(2H,m), 4.96(1H,m), 5.45(2H,s), 7.54(2H,d,J=8.0 Hz), 7.76(2H,d,J=8.6 Hz), 7.82(2H,d,J=8.6 Hz), 7.90(2H,d,J=8.0 Hz).

IR (KBr): 1655, 1645, 1605, 1525, 1325, 1130 cm⁻¹.

EXAMPLE 389

7-[4-(4-Fluorobenzoyl)benzyloxy]-6-methyl-2,3-dihydro-5H-thiazolo[1,2-a]pyrimidin-5-one The above titled compound was obtained by subjecting to reaction and process in the same manner as in Example 40.

¹H-NMR (CDCl₃) δ: 1.98(3H,s), 3.47(2H,t,J=7.8 Hz), 4.47(2H,t,J=7.8 Hz), 5.44(2H,s), 7.17(2H,t,J=8.6 Hz), 7.51 (2H,d,J=8.2 Hz), 7.78(2H,d,J=8.2 Hz), 7.86(2H,dd,J= 8.6&5.4 Hz).

IR (KBr): 1650, 1640, 1590, 1510, 1390, 1345, 1285, 1220 cm⁻¹.

EXAMPLE 390

7-[4-(4-Methoxybenzoyl)benzyloxy]-6-methyl-2,3-dihydro-5H-thiazolo[1,2-a]pyrimidin-5-one The above titled compound was obtained by subjecting to reaction and process in the same manner as in Example 40.

¹H-NMR (CDCl₃) δ: 1.98(3H,s), 3.47(2H,t,J=7.8 Hz), 3.90(3H,s), 4.47(2H,t,J=7.8 Hz), 5.43(2H,s), 6.97(2H,t,J= 8.8 Hz), 7.49(2H,d,J=8.4 Hz), 7.77(2H,d,J=8.4 Hz), 7.84 (2H,d,J=8.8 Hz).

IR (KBr): 1650, 1640, 1595, 1515, 1390, 1255 cm⁻¹.

EXAMPLE 391

6-Methyl-7-[4-(3,4,5-trimethoxybenzoyl)benzyloxy]-2,3-dihydro-5H-thiazolo[1,2-a]pyrimidin-5-one The above titled compound was obtained by subjecting to reaction and process in the same manner as in Example 40.

¹H-NMR (CDCl₃) δ: 1.98(3H,s), 3.47(2H,t,J=7.8 Hz), 3.88(6H,s), 3.94(3H,s), 4.47(2H,t,J=7.8 Hz), 5.44(2H,s), 7.07(2H,s), 7.51(2H,d,J=8.4 Hz), 7.81(2H,d,J=8.4 Hz).

IR (KBr): 1645, 1595, 1580, 120, 1390, 1330, 1230, 1125 cm⁻¹.

EXAMPLE 392

7-[4-(4-Chlorobenzoyl)benzylthio]-6-methyl-2,3-dihydro-5H-thiazolo[1,2-a]pyrimidin-5-one The above titled compound was obtained by subjecting to reaction and process in the same manner as in Example 1.

¹H-NMR (CDCl₃) δ: 1.99(3H,s), 3.45(2H,t,J=7.6 Hz), 4.41(2H,s), 4.45(2H,t,J=7.6 Hz), 7.45(2H,d,J=8.2 Hz), 7.49 (2H,d,J=8.0 Hz), 7.72(2H,d,J=8.0 Hz), 7.74(2H,d,J=8.2 Hz).

EXAMPLE 393

7-[4-(4-Fluorobenzoyl)benzylthio]-6-methyl-2,3-dihydro-5H-thiazolo[1,2-a]pyrimidin-5-one The above titled compound was obtained by subjecting to reaction and process in the same manner as in Example 1.

$^1$H-NMR (CDCl$_3$) δ: 1.99(3H,s), 3.45(2H,t,J=7.6 Hz), 4.42(2H,s), 4.45(2H,t,J=7.6 Hz), 7.16(2H,t,J=8.6 Hz), 7.48 (2H,d,J=8.2 Hz), 7.72(2H,d,J=8.2 Hz), 7.84(2H,dd,J=8.6&5.4 Hz).

IR (KBr): 1645, 1600, 1595, 1550, 1500 cm$^{-1}$.

EXAMPLE 394

2-[4-(4-Chlorobenzoyl)benzylthio]-3-methyl-6,7,8,9-tetrahydro-4H-pyrido[1,2-a]pyrimidin-4-one The above titled compound was obtained by subjecting to reaction and process in the same manner as in Example 1.

$^1$H-NMR (CDCl$_3$) δ: 1.72-2.10(4H,m), 2.03(3H,s), 2.89 (2H,t,J=6.2 Hz), 3.92(2H,t,J=6.0 Hz), 4.44(2H,s), 7.45(2H,d,J=8.6 Hz), 7.50(2H,d,J=8.4 Hz), 7.72(2H,d,J=8.4 Hz), 7.74(2H,d,J=8.6 Hz).

IR (KBr): 1645, 1605, 1560, 1520 cm$^{-1}$.

EXAMPLE 395

3-Methyl-2-[4-(4-trifluoromethylbenzoyl)benzylthio]-6,7,8,9-tetrahydro-4H-pyrido[1,2-a]pyrimidin-4-one The above titled compound was obtained by subjecting to reaction and process in the same manner as in Example 1.

$^1$H-NMR (CDCl$_3$) δ: 1.75-2.10(4H,m), 2.04(3H,s), 2.89 (2H,t,J=6.3 Hz), 3.92(2H,t,J=6.0 Hz), 4.45(2H,s), 7.53(2H,d,J=8.2 Hz), 7.75(4H,d,J=8.2 Hz), 7.88(2H,d,J=8.2 Hz).

IR (KBr): 1645, 1560, 1520, 1320, 1160, 1120 cm$^{-1}$.

EXAMPLE 396

2-[4-(4-Fluorobenzoyl)benzylthio]-3-methyl-6,7,8,9-tetrahydro-4H-pyrido[1,2-a]pyrimidin-4-one The above titled compound was obtained by subjecting to reaction and process in the same manner as in Example 1.

$^1$H-NMR (CDCl$_3$) δ: 1.80-2.10(4H,m), 2.04(3H,s), 2.90 (2H,t,J=6.4 Hz), 3.93(2H,t,J=5.9 Hz), 4.45(2H,s), 7.16(2H,t,J=8.6 Hz), 7.51(2H,d,J=8.4 Hz), 7.72(2H,d,J=8.4 Hz), 7.94 (2H,dd,J=8.6&5.4 Hz).

IR (KBr): 1640, 1595, 1560, 1520, 1270, 1225 cm$^{-1}$.

EXAMPLE 397

6-Methyl-7-[4-(4-trifluoromethylbenzoyl)benzylthio]-2,3-dihydro-5H-thiazolo[1,2-a]pyridin-5-one The above titled compound was obtained by subjecting to reaction and process in the same manner as in Example 1.

$^1$H-NMR (CDCl$_3$) δ: 1.99(3H,s), 3.46(2H,t,J=7.7 Hz), 4.43(2H,s), 4.45(2H,t,J=7.7 Hz), 7.51(2H,d,J=8.4 Hz), 7.75 (2H,d,J=8.2 Hz), 7.76(2H,d,J=8.4 Hz), 7.89(2H,d,J=8.2 Hz).

IR (KBr): 1655, 1600, 1555, 1505, 1385, 1325, 1275, 1120, 1060 cm$^{-1}$.

EXAMPLE 398

3,6-Dimethyl-7-[4-(4-trifluoromethylbenzoyl)benzylthio]-5H-thiazolo[1,2-a]pyrimidin-5-one The above titled compound was obtained by subjecting to reaction and process in the same manner as in Example 1.

$^1$H-NMR (CDCl$_3$) δ: 2.06(3H,s), 2.80(3H,d,J=1.2 Hz), 4.49(2H,s), 6.35(1H,q,J=1.2 Hz), 7.54(2H,d,J=8.2 Hz), 7.75 (2H,d,J=8.6 Hz), 7.76(2H,d,J=8.2 Hz), 7.88(2H,d,J=8.6 Hz).

IR (KBr): 1660, 1650, 1530, 1485, 1320, 1170, 1110 cm$^{-1}$.

EXAMPLE 399

2-[2-[4-(4-Chlorobenzoyl)phenyl)ethyl]-3-methyl-6,7,8,9-tetrahydro-4H-pyrido[1,2-a]pyrimidin-4-one $^1$H-NMR (CDCl$_3$) δ: 1.75-2.00(4H,m), 1.99(3H,s), 2.80-3.08(6H,m), 3.95(2H,t,J=6.0 Hz), 7.33(2H,d,J=8.2 Hz), 7.46(2H,d,J=8.6 Hz), 7.71(2H,d,J=8.2 Hz), 7.74(2H,d,J=8.6 Hz).

IR (KBr): 1650, 1600, 1530 cm$^{-1}$.

EXAMPLE 400

7-[2-[4-(4-Chlorobenzoyl)phenyl]ethyl]-6-methyl-2,3-dihydro-5H-thiazolo[1,2-a]pyridin-5-one The above titled compound was obtained by subjecting to reaction and process in the same manner as in Example 399.

$^1$H-NMR (CDCl$_3$) δ: 2.06(3H,s), 2.80(3H,d,J=1.2 Hz), 4.49(2H,s), 6.35(1H,q,J=1.2 Hz), 7.54(2H,d,J=8.2 Hz), 7.75 (2H,d,J=8.6 Hz), 7.76(2H,d,J=8.2 Hz), 7.88(2H,d,J=8.6 Hz).

IR (KBr): 1650, 1510 cm$^{-1}$.

EXAMPLE 401

8-[2-[4-(4-Chlorobenzoyl)phenyl]ethyl]-7-methyl-3,4-dihydro-2H,6H-pyrimido[2,1-b][1,3]thiazin-6-one The above titled compound was obtained by subjecting to reaction and process in the same manner as in Example 399.

$^1$H-NMR (CDCl$_3$) δ: 1.96(3H,s), 2.28(2H,m), 2.85(2H,m), 3.01(2H,m), 3.18(2H,t,J=6.0 Hz), 4.10(2H,t,J=5.6 Hz), 7.33(2H,d,J=8.2 Hz), 7.47(2H,d,J=8.2 Hz), 7.71(2H,d,J=8.2 Hz), 7.74(2H,d,J=8.2 Hz).

IR (KBr): 1645, 1500 cm$^{-1}$.

EXAMPLE 402

6-Methyl-7-[4-(4-trifluoromethylbenzoyl)benzyloxy]-2,3-dihydro-5H-thiazolo[1,2-a]pyrimidin-5-one The above titled compound was obtained by subjecting to reaction and process in the same manner as in Example 40.

$^1$H-NMR (CDCl$_3$) δ: 1.98(3H,s), 3.48(2H,t,J=7.8 Hz), 4.47(2H,t,J=7.8 Hz), 5.45(2H,s), 7.53(2H,d,J=8.6 Hz), 7.60-7.93(6H,m).

IR (KBr): 1655, 1590, 1510, 1325, 1140 cm$^{-1}$.

EXAMPLE 403

2-[4-(4-Methoxybenzoyl)benzyloxy]-3-methyl-6,7,8,9-tetrahydro-4H-pyrido[1,2-a]pyrimidin-4-one The above titled compound was obtained by subjecting to reaction and process in the same manner as in Example 40.

$^1$H-NMR (CDCl$_3$) δ: 1.80-2.12(4H,m), 2.02(3H,s), 2.84 (2H,t,J=6.4 Hz), 3.90(3H,s), 3.95(2H,t,J=6.0 Hz), 5.45(2H,s), 6.97(2H,d,J=8.8 Hz), 7.51(2H,d,J=8.2 Hz), 7.77(2H,d,J=8.2 Hz), 7.84(2H,d,J=8.8 Hz).

IR (KBr): 1660, 1645, 1600, 1530, 1283, 1255, 1150 cm$^{-1}$.

EXAMPLE 404

3-Methyl-2-[4-(4-methylbenzoyl)benzyloxy]-6,7,8,9-tetrahydro-4H-pyrido[1,2-a]pyrimidin-4-one The above titled compound was obtained by subjecting to reaction and process in the same manner as in Example 40.

$^1$H-NMR (CDCl$_3$) δ: 1.80–2.05(4H,m), 2.02(3H,s), 2.45 (3H,s), 2.84(2H,t,J=6.5 Hz), 3.94(2H,t,J=6.0 Hz), 5.45(2H, s), 7.28(2H,d,J=8.4 Hz), 7.50(2H,d,J=8.0 Hz), 7.72(2H,d,J= 8.0 Hz), 7.79(2H,d,J=8.4 Hz).

IR (KBr): 1650, 1600, 1530, 1270, 1145 cm$^{-1}$.

EXAMPLE 405

6-Methyl-7-[4-(4-methylbenzoyl)benzyloxy]-2,3-dihydro-5H-thiazolo[1,2-a]pyrimidin-5-one The above titled compound was obtained by subjecting to reaction and process in the same manner as in Example 40.

$^1$H-NMR (CDCl$_3$) δ: 1.98(3H,s), 2.45(3H,s), 3.47(2H,t, J=7.7 Hz), 4.47(2H,t,J=7.7 Hz), 5.43(2H,s), 7.29(2H,d,J=8.4 Hz), 7.49(2H,d,J=8.4 Hz), 7.73(2H,d,J=8.4 Hz), 7.79(2H,d, J=8.4 Hz).

IR (KBr): 1655, 1600, 1590, 1515, 1390, 1270 cm$^{-1}$.

EXAMPLE 406

7-Methyl-8-[4-(4-methylbenzoyl)benzyloxy]-3,4-dihydro-2H,6H-pyrimido[2,1-b][1,3]thiazin-6-one The above titled compound was obtained by subjecting to reaction and process in the same manner as in Example 40.

$^1$H-NMR (CDCl$_3$) δ: 1.99(3H,s), 2.20–2.38(2H,m), 2.45 (3H,s), 3.17(2H,t,J=6.0 Hz), 4.10(2H,t,J=5.6 Hz), 5.42(2H, s), 7.29(2H,d,J=8.2 Hz), 7.51(2H,d,J=8.2 Hz), 7.73(2H,d,J= 8.2 Hz), 7.79(2H,d,J=8.2 Hz).

IR (KBr): 1645, 1585, 1495 cm$^{-1}$.

EXAMPLE 407

3-Ethyl-2-methylthio-7-[4-(3,4,5-trimethoxybenzoyl)benzyl]-7H-pyrrolo[2,3-d]pyrimidin-4-one The above titled compound was obtained by subjecting to reaction and process in the same manner as in Example 49.

$^1$H-NMR (CDCl$_3$) δ: 1.36(3H,t,J=7.2 Hz), 2.58(3H,s), 3.87(6H,s), 3.95(3H,s), 4.22(2H,q,J=7.2 Hz), 5.37(2H,s), 6.65(1H,d,J=3.4 Hz), 6.77(1H,d,J=3.4 Hz), 7.04(2H,s), 7.34 (2H,d,J=8.4 Hz), 7.78(2H,d,J=8.4 Hz).

EXAMPLE 408

7-[4-(4-t-Butyldimethylsilyloxybenzoyl)benzyl)-3-ethyl-2-methylthio-7H-pyrrolo[2,3-d]pyrimidin-4-one The above titled compound was obtained by subjecting to reaction and process in the same manner as in Example 49.

$^1$H-NMR (CDCl$_3$) δ: 0.24(6H,s), 0.99(9H,s), 1.36(3H,t, J=7.2 Hz), 2.57(3H,s), 4.22(2H,q,J=7.2 Hz), 5.35(2H,s), 6.65(1H,d,J=3.4 Hz), 6.75(1H,d,J=3.4 Hz), 6.89(2H,d,J=8.6 Hz), 7.30(2H,d,J=8.4 Hz), 7.73(2H,d,J=8.4 Hz), 7.74(2H,d, J=8.6 Hz).

EXAMPLE 409

3-Ethyl-7-[4-(4-hydroxybenzoyl)benzyl]-2-methylthio-7H-pyrrolo[2,3-d]pyrimidin-4-one In THF (76.8 ml) was dissolved 7-[4-(4-t-butyldimethylsilyloxybenzoyl)benzyl]-3-ethyl-2-methylthio-7H-pyrrolo[2,3-d]pyrimidin-4-one (4.10 g) followed by addition of 1M-tetrabutylammonium fluoride-THF (7.68 ml), and the mixture was stirred for 30 minutes. To this reaction mixture was added water and the THF was distilled off. Then, ethyl acetate was added to the residue and the organic layer was separated. The organic layer was washed with saturated aqueous NaCl solution and dried over anhydrous sodium sulfate and the solvent was then distilled off under reduced pressure. The residue was triturated with ether and the resulting powder was collected by filtration, rinsed with ether, methanol and hexane, and dried to provide the title compound as crystalline powder (3.0 g)

$^1$H-NMR (DMSO-d$_6$) δ: 1.24(3H,t,J=7.2 Hz), 2.60(3H,s), 4.08(2H,q,J=7.2 Hz), 5.41(2H,s), 6.47(1H,d,J=3.4 Hz), 6.87 (2H,d,J=8.6 Hz), 7.19(1H,d,J=3.4 Hz), 7.44(2H,d,J=8.0 Hz), 7.63(2H,d,J=8.6 Hz), 7.65(2H,d,J=8.0 Hz).

EXAMPLE 410

7-[4-(4-Dimethylaminoethoxybenzoyl)benzyl]-3-ethyl-2-methylthio-7H-pyrrolo[2,3-d]pyrimidin-4-one The above titled compound was obtained by subjecting to reaction and process in the same manner as in Example 156.

$^1$H-NMR (CDCl$_3$) δ: 1.36(3H,t,J=7.2 Hz), 2.35(6H,s), 2.58(3H,s), 2.76(2H,t,J=5.6 Hz), 4.14(2H,t,J=5.6 Hz), 4.22 (2H,q,J=7.2 Hz), 5.35(2H,s), 6.65(1H,d,J=3.4 Hz), 6.75(1H, d,J=3.4 Hz), 6.97(2H,d,J=8.8 Hz), 7.30(2H,d,J=8.2 Hz), 7.72(2H,d,J=8.2 Hz), 7.79(2H,d,J=8.8 Hz).

EXAMPLE 411

3-Ethyl-2-methylthio-7-[4-(4-nicotinoylmethoxybenzoyl)benzyl]-7H-pyrrolo[2,3-d]pyrimidin-4-one The above titled compound was obtained by subjecting to reaction and process in the same manner as in Example 237.

$^1$H-NMR (CDCl$_3$) δ: 1.23(3H,t,J=7.2 Hz), 2.60(3H,s), 4.08(2H,q,J=7.2 Hz), 5.42(2H,s), 5.78(2H,s), 6.47(1H,d,J= 3.4 Hz), 7.14(2H,d,J=8.8 Hz), 7.20(1H,d,J=3.4 Hz), 7.46 (2H,d,J=8.2 Hz), 7.59–7.64(1H,m), 7.69(2H,d,J=8.2 Hz), 7.72(2H,d,J=8.8 Hz), 8.32–8.39(1H,m), 8.86(1H,dd,J=1.6, 4.8 Hz), 9.20(1H,d,J=1.6 Hz).

EXAMPLE 412

3-Ethyl-2-methylthio-7-[4-(4-morpholinoethoxybenzoyl)benzyl]-7H-pyrrolo[2,3-d]pyrimidin-4-one-hydrochloride The above titled compound was obtained by subjecting to reaction and process in the same manner as in Example 156.

$^1$H-NMR (CDCl$_3$) δ: 1.36(3H,t,J=7.0 Hz), 2.58(3H,s), 2.59(4H,t,J=4.7 Hz), 2.84(2H,t,J=5.6 Hz), 3.74(4H,t,J=4.7 Hz), 4.19(2H,t,J=5.6 Hz), 4.22(2H,q,J=7.0 Hz), 5.35(2H,s), 6.66(1H,d,J=3.4 Hz), 6.75(1H,d,J=3.4 Hz), 6.96(2H,d,J=8.8 Hz), 7.30(2H,d,J=8.2 Hz), 7.72(2H,d,J=8.2 Hz), 7.80(2H,d, J=8.8 Hz).

EXAMPLE 413

3-Ethyl-2-methylthio-7-[4-(4-piperidinoethoxybenzoyl)benzyl]-7H-pyrrolo[2,3-d]pyrimidin-4-one-hydrochloride The above titled compound was obtained by subjecting to reaction and process in the same manner as in Example 156.

$^1$H-NMR (CDCl$_3$) δ: 1.36(3H,t,J=7.2 Hz), 1.37–1.52(2H, m), 1.54–1.68(4H,m), 2.51(4H,t,J=5.6 Hz), 2.58(3H,s), 2.80 (2H,t,J=6.2 Hz), 4.18(2H,t,J=6.2 Hz), 4.21(2H,q,J=7.2 Hz), 5.35(2H,s), 6.65(1H,d,J=3.4 Hz), 6.76(1H,d,J=3.4 Hz), 6.96 (2H,d,J=9.0 Hz), 7.31(2H,d,J=8.4 Hz), 7.72(2H,d,J=8.4 Hz), 7.79(2H,d,J=9.0 Hz).

EXAMPLE 414

7-[4-(4-Fluorobenzoyl)benzyl]-5-methyl-7H-pyrrolo[2,3-d]pyrimidin-4(3H)-one

7-[4-(4-Fluorobenzoyl)benzyl]-5-methyl-2-methylthio-7H-pyrrolo[2,3-d]pyrimidin-4(3H)-one (775 mg) was dissolved in a mixture of DME (100 ml), ethyl acetate (100 ml) and methanol (80 ml). After addition of acetic acid (2.5 ml), Raney nickel was added. After confirming disapperance of the starting compound, the catalyst was filtered off. The solvent was then distilled off under reduced pressure. The residue was pulverized with ether, and the crystalline powder was collected by filtration, rinsed with ether, and dried to provide the title compound (529 mg).

$^1$H-NMR (DMSO-$d_6$+$D_2O$) 5: 2.29(3H,s), 5.39(2H,s), 6.96(1H,s), 7.33(2H,d,J=8.1 Hz), 7.37(2H,d,J=8.8 Hz), 7.69 (2H,d,J=8.1 Hz), 7.80(2H,dd,J=5.6,8.8 Hz), 7.86(1H,s).

EXAMPLE 415

3-Ethyl-7-[4-(4-hydroxybenzoyl)benzyl]-5-methyl-7H-pyrrolo[2,3-d]pyrimidin-4-one The above titled compound was obtained by subjecting to reaction and process in the same manner as in Example 49.

$^1$H-NMR (DMSO-$d_6$+$D_2O$) δ: 1.25(3H,t,J=7.2 Hz), 2.30 (3H,s), 3.96(2H,q,J=7.2 Hz), 5.36(2H,s), 6.87(2H,d,J=8.6 Hz), 6.97(1H,s), 7.33(2H,d,J=8.2 Hz), 7.63(4H,d,J=8.6 Hz), 8.19(1H,s), 10.43(1H,s).

EXAMPLE 416

7-[4-(6-Chloronicotinoyl)benzyl]-3-ethyl-5-methyl-7H-pyrrolo[2,3-d]pyrimidin-4-one The above titled compound was obtained by subjecting to reaction and process in the same manner as in Example 49.

$^1$H-NMR (CDCl$_3$) δ: 1.41(3H,t,J=7.2 Hz), 2.44(3H,d,J=1.0 Hz), 4.05(2H,q,J=7.2 Hz), 5.36(2H,s), 6.60(1H,d,J=1.0 Hz), 7.30(2H,d,J=8.2 Hz), 7.47(1H,d,J=8.4 Hz), 7.75(2H,d, J=8.2 Hz), 7.84(1H,s), 8.07(1H,dd,J=2.4,8.4 Hz), 8.74(1H, d,J=2.4 Hz).

EXAMPLE 417

3-Ethyl-5-methyl-7-[4-(4-trifluoromethylbenzoyl) benzyl]-7H-pyrrolo[2,3-d]pyrimidin-4-one The above titled compound was obtained by subjecting to reaction and process in the same manner as in Example 49.

$^1$H-NMR (CDCl$_3$) 5: 1.41(3H,t,J=7.2 Hz), 2.43(3H,s), 4.05(2H,q,J=7.2 Hz), 5.35(2H,s), 6.59(1H,s), 7.28(2H,d,J= 8.6 Hz), 7.74(2H,d,J=8.0 Hz), 7.76(2H,d,J=8.0 Hz), 7.83 (1H,s), 7.87(2H,d,J=8.6 Hz).

EXAMPLE 418

3-Ethyl-5-methyl-7-[4-(4-phenylpiperazinomethyl benzoyl)benzyl]-7H-pyrrolo[2,3-d]pyrimidin-4-one The above titled compound was obtained by subjecting to reaction and process in the same manner as in Example 49.

$^1$H-NMR (CDCl$_3$) δ: 1.41(3H,t,J=7.2 Hz), 2.44(3H,d,J=1.0 Hz), 2.64(4H,t,J=5.1 Hz), 3.22(4H,t,J=5.1 Hz), 3.64(2H, s), 4.06(2H,q,J=7.2 Hz), 5.34(2H,s), 6.60(1H,d,J=1.0 Hz), 6.86(1H,t,J=8.0 Hz), 6.93(2H,d,J=8.0 Hz), 7.26(2H,d,J=8.4 Hz), 7.27(2H,d,J=8.0 Hz), 7.47(2H,d,J=8.2 Hz), 7.76(2H,d, J=8.4 Hz), 7.77(2H,d,J=8.2 Hz), 7.83(1H,s).

EXAMPLE 419

3-Ethyl-5-methyl-7-[4-(4-morpholinoethoxybenzoyl) benzyl]-7H-pyrrolo[2,3-d]pyrimidin-4-one hydrochloride The above titled compound was obtained by subjecting to reaction and process in the same manner as in Example 156.

$^1$H-NMR (CDCl$_3$) δ: 1.40 (3H,t,J=7.2 Hz), 2.43(3H,d,J= 1.2 Hz), 2.59(4H,t,J=4.7 Hz), 2.84(2H,t,J=5.7 Hz), 3.74(4H, t,J=4.7 Hz), 4.05(2H,q,J=7.2 Hz), 4.19(2H,t,J=5.7 Hz), 5.33 (2H,s), 6.60(1H,d,J=1.2 Hz), 6.95(2H,d,J=8.8 Hz), 7.26(2H, d,J=8.2 Hz), 7.71(2H,d,J=8.2 Hz), 7.79(2H,d,J=8.8 Hz), 7.84(1H,s).

EXAMPLE 420

3-Ethyl-5-methyl-7-[4-(6-piperidinopyperidinylnicotinoyl)benzyl]-7H-pyrrolo(2,3-d]pyrimidin-4-one-2hydrochloride The above titled compound was obtained by subjecting to reaction and process in the same manner as in Example 158.

$^1$H-NMR (CDCl$_3$) δ: 1.41(3H,t,J=7.2 Hz), 1.46–2.02 (10H,m), 2.43(3H,s), 2.54(4H,t,J=5.1 Hz), 2.55–2.67(1H, m), 2.93(2H,dt,J=2.6&13.0 Hz), 4.06(2H,q,J=7.2 Hz), 4.54 (2H,d,J=13.0 Hz), 5.33(2H,s), 6.58(1H,s), 6.67(1H,d,J=9.0 Hz), 7.25(2H,d,J=8.2 Hz), 7.69.(2H,d,J=8.2 Hz), 7.83(1H, s), 8.00(1H,dd,J=2.2&8.2 Hz), 8.55(1H,d,J=2.2 Hz).

EXAMPLE 421

7-[4-[4-(4-N-t-Butoxycarbonylpiperidylmethoxy) benzoyl]benzyl]-1,3-dimethyl-xanthine The above titled compound was obtained by subjecting to reaction and process in the same manner as in Example 156. m.p. 163°–165° C.

$^1$H-NMR (CDCl$_3$) δ: 1.2–1.4(2H,m), 1.47(9H,s), 1.7–2.1 (3H,m), 2.76(2H,t,J=12.7 Hz), 3.41(3H,s), 3.61(3H,s), 4.1–4.3(2H,brm), 5.59(2H,s), 6.93(2H,ABq,J=8.6 Hz), 7.40 (2H,ABq,J=7.9 Hz), 7.65(1H,s), 7.74(2H,ABq,J=7.9 Hz), 7.78(2H,ABq,J=8.6 Hz).

IR (KBr): 1699, 1664, 1655, 1599, 1257 cm$^{-1}$.

EXAMPLE 422

1,3-Dimethyl-7-[4-[4-(4-piperidylmethoxy)benzoyl]-benzyl]xanthine monohydrochloride In tetrahydrofuran (5 ml) was dissolved 7-[4-[4-(4-N-tert-butoxycarbonylpiperidylmethoxy)benzoyl]-benzyl]-1,3-dimethylxanthine (366 mg), followed by dropwise addition of 4N-HCl/ethyl acetate (0.78 ml) under ice-cooling. The mixture was stirred at 50° C. overnight and, then refluxed for 8 hours. The reaction mixture was concentrated and the solid residue was collected by filtration and rinsed with ethyl acetate to provide the title compound as white powder (227 mg).

m.p. 243°–245° C.

$^1$H-NMR (DMSO-$d_6$) δ: 1.3–1.7(2H,m), 1.8–2.2(3H,m), 2.8–3.0(2H,m), 3.2–3.5(2H,m), 3.22(3H,s), 3.45(3H,s), 3.98 (2H,d,J=6.0 Hz), 5.61(2H,s), 7.08(2H,ABq,J=8.8 Hz), 7.46

(2H,ABq,J=8.2 Hz), 7.66(2H,ABq,J=8.2 Hz), 7.72(2H, ABq,J=8.8 Hz), 8.35(1H,s).

IR (KBr): 1707, 1662, 1599, 1259, 1171 cm$^{-1}$.

EXAMPLE 423

1,3-Dimethyl-7-[4-[4-(4-N-methylpiperidylmethoxy) benzyl]xanthine

The above titled compound was obtained by subjecting to reaction and process in the same manner as in Example 156.

m.p. 128°–130° C.

$^1$H-NMR (CDCl$_3$) δ: 1.2–2.2(7H,m), 2.35(3H,s), 2.9–3.1 (2H,m), 3.41(3H,s), 3.61(3H,s), 3.89(2H,d,J=5.4 Hz), 5.59 (2H,s), 6.92(2H,ABq,J=8.8 Hz), 7.40(2H,ABq,J=8.2 Hz), 7.65(1H,s), 7.7–7.9(4H,m).

IR (KBr): 1713, 1664, 1597, 1252, 1173, 758 cm$^{-1}$.

EXAMPLE 424

7-[4-[4-[1-(4-N-t-Butoxycarbonylpiperidyl)ethoxy] benzoyl]benzyl-1,3-xanthine

The above titled compound was obtained by subjecting to reaction and process in the same manner as in Example 156.

m.p. 149°–151° C.

$^1$H-NMR (CDCl$_3$) δ: 1.1–1.3(3H,brm), 1.6–1.8(4H,brm), 1.46(9H,s), 2.71(2H,t,J=13.7 Hz), 3.42(3H,s), 3.61(3H,s), 4.0–4.2(4H,brm), 5.59(2H,s), 6.93(2H,ABq,J=8.8 Hz), 7.40 (2H,ABq,J=8.0 Hz), 7.65(1H,s), 7.74(2H,ABq,J=8.0 Hz), 7.78(2H,ABq,J=8.8 Hz).

IR (KBr): 1705, 1664, 1254, 1176 cm$^{-1}$.

EXAMPLE 425

1,3-Dimethyl-7-[4-[4-[1-(4-piperidyl)ethoxy] benzoyl]benzyl]xanthine-hydrochloride 1,3-Dimethyl-7-[4-[4-[1-(4-piperidyl)ethoxy]benzoyl] benzyl]xanthine monohydrochloride In tetrahydrofuran (10 ml) was dissolved 7-[4-[4-[1-(4-N-tert-butoxycarbonylpiperidyl)ethoxy]benzoyl]benzyl-1, 3-xanthine (454 mg) followed by dropwise addition of 4N-HCl/ethyl acetate (0.94 ml) under ice-cooling. The mixture was stirred at 50° C. overnight and then refluxed for 2 days. This reaction mixture was concentrated and the solid residue was collected by filtration and rinsed with ethyl acetate-ether to provide the title compound as white powder (403 mg).

m.p. 240°–242° C.

$^1$H-NMR (DMSO-d$_6$) δ: 1.2–2.0(7H,brm), 2.7–3.0(2H, brm), 3.21(3H,s), 3.2–3.3(2H,m), 3.44(3H,s), 4.1–4.2(2H, brm), 5.61(2H,s), 7.06(2H,ABq,J=9.0 Hz), 7.45(2H,ABq,J= 8.1 Hz), 7.66(2H,ABq,J=8.1 Hz), 7.71(2H,ABq,J=9.0 Hz), 8.33(1H,s), 8.4–8.8(2H,brm).

IR (KBr): 1684, 1653, 1601, 1257 cm$^{-1}$.

EXAMPLE 426

1,3-Dimethyl-7-[4-[4-[1-(4-N-methylpiperidyl)-ethoxy]benzoyl]benzyl]xanthine

In acetonitrile-methanol (4 ml-2 ml) was dissolved 1,3-dimethyl-7-[4-[4-[1-(4-piperidyl)ethoxy]benzoyl]-benzyl] xanthine monohydrochloride (202 mg), and followed by addition of 37% formalin (0.045 ml), sodium cyanoborohydride (38 mg) was further added under ice-cooling. The mixture was stirred at room temperature for 1.5 hours, then adjusted to pH 5 with acetic acid, and concentrated. To the residue were added ethyl acetate and aqueous NaHCO$_3$ solution. The ethyl acetate layer was washed with aqueous NaCl solution, dried over anhydrous magnesium sulfate, and concentrated. The residue was purified by silica gel column chromatography to provide the title compound as white powder (34 mg, 18%).

m.p. 213–214° C.

$^1$H-NMR (CDCl$_3$) δ: 1.2–2.1(9H,m), 2.29(3H,s), 2.8–3.0 (2H,brm), 3.42(3H,s), 3.61(3H,s), 4.08(2H,t,J=6.3 Hz), 5.59 (2H,s), 6.93(2H,ABq,J=8.8 Hz), 7.40(2H,ABq,J=7.6 Hz), 7.65(1H,s), 7.75(2H,ABq,J=7.6 Hz), 7.79(2H,ABq,J=8.8 Hz).

IR (KBr): 1716, 1662, 1525, 1255 cm$^{-1}$.

EXAMPLE 427

7-[4-(4-Chlorobenzoyl)benzyloxy]-6-methyl-2,3-dihydro-5H-thiazolo[3,2-a]pyrimidin-5-one To a solution of 7-hydroxy-6-methyl-2,3-dihydro-5H-thiazolo[3,2-a]pyrimidin-5-one (1.0 g) and potassium carbonate (750 mg) in DMF (15 ml) was added 4-(4-chlorobenzoyl)benzyl bromide (2.0 g) and the mixture was stirred at 60° C. for 2 hours. This reaction mixture was concentrated and the residue was purified by silica gel column chromatography (hexane-ethyl acetate =1:1) and recrystallized from isopropyl ether to provide the title compound as colorless solid (200 mg).

$^1$H-NMR (CDCl$_3$) δ: 1.97(3H,s), 3.47(2H,t,J=7.8 Hz), 4.46(2H,t,J=7.8 Hz), 5.43(2H,s), 7.46(2H,d,J=8.0 Hz), 7.50 (2H,d,J=8.0 Hz), 7.76(2H,d,J=8.0 Hz), 7.78(2H,d,J=8.0 Hz).

IR (KBr): 1650, 1515, 1390 cm$^{-1}$.

Formulation Example 1 (amount per tablet)

(1) Compound of Example 15 10.0 mg
(2) Lactose 60.0 mg
(3) Corn starch 35.0 mg
(4) Gelatin 3.0 mg
(5) Magnesium stearate 2.0 mg Using 0.03 ml of a 10 wt. % aqueous solution of gelatin (3.0 mg as gelatin), a mixture of 10.0 mg of the compound of Example 15, 60.0 mg of lactose and 35.0 mg of corn starch was passed through a 1 mm sieve, granulated, dried at 40° C., and resieved. The resulting granules were mixed with 2.0 mg of magnesium stearate and the mixture was compressed. The resulting core tablet was sugar-coated with a suspension comprising sucrose, titanium dioxide, talc and gum arabic and, then, glazed with beeswax to provide a coated tablet.

Formulation Example 2 (amount per tablet)

(1) Compound of Example 15 10.0 mg
(2) Lactose 70.0 mg
(3) Corn starch 50.0 mg
(4) Soluble starch 7.0 mg
(5) Magnesium stearate 3.0 mg Using 0.07 ml of an aqueous solution of soluble starch (7.0 mg as soluble starch), a mixture of 10.0 mg of the compound of Example 15 and 3.0 mg of magnesium stearate was granulated, dried, and blended with 70.0 mg of lactose and 50.0 mg of corn starch. The mixture was compressed to provide a tablet.

TEST EXAMPLE 1

In vitro prostate carcinoma cell proliferation inhibition assay

Prostate carcinoma cell line PC-3 cells were suspended in Ham's F-12K medium (Flow Laboratories or Dainippon Pharmaceutical Co., Ltd) supplemented with 10% fetal calf serum, and seeded in a 96-well microtiter plate (5000 cells/50 or 75 µl/well). The plate was then incubated in a 5% $CO_2$ incubator at 37° C. On the following day, a 3-fold dilution series with the medium with serum of the test compound in N,N-dimethylformamide (DMF) (50 or 25 µl/well) were added (final volume 100 µl/cell) and the plate was incubated for another 3 days. Following addition of a thiazolyl-tetrazolium (MTT) solution, absorbance based on the viable cell number was determined "Tada et al., Journal of Immunological Methods, 93, 157 (1986)". With the estimated cell number in the control group to which the test compound solution was not added being taken as 100%, the percentage of the estimated cell number in each test group was determined and the concentration ($IC_{50}$ value) of the test compound which was required for 50% inhibition of the estimated viable cell number in the control group was calculated. The results are presented in Table 1.

TABLE 1

| Compound (Example No.) | $IC_{50}$ (nM) PC-3 |
| --- | --- |
| 37 | 6 |
| 50 | 9 |
| 55 | <1.52 |
| 57(A) | 5 |
| 57(B) | 9 |
| 62(A) | <1.52 |
| 66 | 8 |
| 84(A) | 2 |
| 94 | 2 |
| 96 | <1.52 |
| 124 | 8 |
| 129(A) | <1.52 |
| 132(A) | 2 |
| 138 | <1.52 |
| 144 | <1.52 |
| 148 | <1.52 |
| 158 | 4.5 |
| 169 | <1.52 |
| 181 | 3 |
| 184 | <1.52 |
| 189 | 1.9 |
| 193 | 2 |
| 214 | 5.2 |
| 217 | <1.52 |
| 228 | 7 |
| 234 | 7 |
| 252 | <1.52 |
| 329 | 2.6 |
| 365 | 6.2 |
| 385 | 4.6 |
| 406 | 0.94 |

It is apparent from Table 1 that the compounds of the present invention show a potent cell proliferation-inhibitory effect on prostate carcinoma cell line PC-3.

TEST EXAMPLE 2

Inhibitory action of the test compounds against the growth of subcutaneously implanted tumor The human prostatic carcinoma cells PC-3, which are maintained in vitro, were harvested using 0.05% trypsin, washed with Ham's F12K medium containing 10% serum, and then suspended in PBS (phosphate-buffered saline) at a concentration of $3\times10^7$ cells/ml. The aliquot of 100 µl was transplanted into the right central flank region of a 7-week old, male BALB/c nu/nu mouse using a syringe with a 25 gauge needle. After the size of the resulting tumor mass was measured on the 25th day after the transplantation, the mice were divided into groups of five animals (the average tumor volume of each group was between 162 and 176 mm), and then the treatment with test compounds was commenced. Tumor volume was calculated according to the formulation: tumor volume =0.5×(the longest diameter)×(the shortest diameter)$^2$ after two-dimensional measurement of the tumor mass by a caliper. The test compounds were suspended in 0.5% methylcellulose/physiological saline, and subcutaneously injected at a volume of 10 µl/g body weight.

Thereafter the test compounds were administered every Monday, Wednesday and Friday for 3 weeks. The inhibitory action was assessed on the 46th day after the transplanation by the ratio of tumor volume gain of treated groups to that of the control group(T/C %). The dosage of the test compounds was expressed as mg/kg/shot.

TABLE 2

| Example No. | Dosage (mg/kg) | No. of animals | Tumor volume gain (mm³) | T/C (%) |
| --- | --- | --- | --- | --- |
| control | — | 5 | 902 ± 149* | 100 |
| 7 | 80 | 5 | 445 ± 110 | 49 |
| 42 | 80 | 5 | 329 ± 252 | 36 |

*mean ± SD

The results are shown in Table 2. All the test compounds suppressed the growth of human prostatic carcinoma cell strain PC-3 transplanted into nude mice.

Since the antitumor agents of this invention exhibits activity for suppressing the tumor growth in vivo, it is useful for the therapy of intractable solid tumors including, for example, prostatic cancer.

TEST EXAMPLE 3

Inhibitory action of the test compound against the growth of subcutaneously implanted tumor The human prostatic carcinoma cells PC-3, which are maintained in vitro, were harvested using 0.05% trypsin, washed with Ham's F12K medium containing 10% serum, and then suspended in PBS (phosphate-buffered saline) at a concentration of $3\times10^7$ cells/ml. The aliquot of 100 µl was transplanted into the right central flank region of a 7-week old, male BALB/c nu/nu mouse using a syringe with a 25 guage needle. After the size of the resulting tumor mass was measured on the 32nd day after the transplantation, the mice were divided into groups of five animals (the average tumor volume of each group was between 273 and 293 mm³), and then the treatment with test compound was commenced. Tumor volume was calculated according to the formulation: tumor volume =0.5×(the longest diameter)×(the shortest diameter)2 after two-dimensional measurement of the tumor mass by a caliper. The test compound was suspended in 0.5% methylcellulose/physiological saline, and orally administered at a volume of 10 µl/g body weight. Thereafter the test compound was administered once a day for 3 weeks. The inhibitory action was assessed on the 53rd day after the transplanation, the first day after the last administration, by the ratio of tumor volume gain of treated groups to that of the control group (T/C %). The dosage of the test compounds was expressed as mg/kg/shot.

TABLE 3

| Example No. | Dosage (mg/kg) | No. of animals | Tumor volume gain (mm³) | T/C (%) |
|---|---|---|---|---|
| control | — | 5 | 1317 ± 204* | 100 |
| 189 | 75 | 5 | 697 ± 199 | 53 |

*mean ± SD

The results are shown in Table 3. The test compound suppressed the growth of human prostatic carcinoma cell strain PC-3 transplanted into nude mice.

Since the antitumor agents of this invention exhibits activity for suppressing the tumor growth in vivo, it is useful for the therapy of intractable solid tumors including, for example, prostatic cancer.

TEST EXAMPLE 4

Inhibitory action of the test compound against the growth of subcutaneously implanted tumor The human prostatic carcinoma cells PC-3, which are maintained in vitro, were harvested using 0.05% trypsin, washed with Ham's F12K medium containing 10% serum, and then suspended in PBS (phosphate-buffered saline) at a concentration of $3 \times 10^7$ cells/ml. The aliquot of 100 μl was transplanted into the right central flank region of a 7-week old, male BALB/c nu/nu mouse using a syringe with a 25 gauge needle. After the size of the resulting tumor mass was measured on the 31st day after the transplanation, the mice were divided into groups of five animals (the average tumor volume of each group was between 273 and 293 mm³), and then the treatment with test compound was commenced. Tumor volume was calculated according to the formulation: tumor volume=0.5×(the longest diameter)×(the shortest diameter)² after two-dimensional measurement of the tumor mass by a caliper. The test compound was suspended in 0.5% methylcellulose/physiological saline, and orally administered at a volume of 10 μl/g body weight. Thereafter the test compound was administered once a day for 3 weeks. The inhibitory action was assessed on the 52nd day after the transplanation, the first day after the last administration, by the ratio of tumor volume gain of treated groups to that of the control group (T/C %). The dosage of the test compound is expressed as mg/kg/shot.

TABLE 4

| Example No. | Dosage (mg/kg) | No. of animals | Tumor volume gain (mm³) | T/C (%) |
|---|---|---|---|---|
| control | — | 5 | 1410 ± 434* | 100 |
| 385 | 25 | 5 | 893 ± 247 | 63 |
| 385 | 50 | 5 | 732 ± 156 | 52 |
| 385 | 75 | 5 | 596 ± 176 | 42 |

*mean ± SD

The results are shown in Table 4. The test compound suppressed the growth of human prostatic carcinoma cell strain PC-3 transplanted into nude mice in a dose-dependent manner.

Since the antitumor agents of this invention exhibits activity for suppressing the tumor growth in vivo, it is useful for the therapy of intractable solid tumors including, for example, prostatic cancer.

The compound of the present invention has excellent antitumoral activity and displays potent efficacy in the treatment of refractory carcinomas and prevention of metastases to remote organs.

What is claimed is:

1. A compound of the formula:

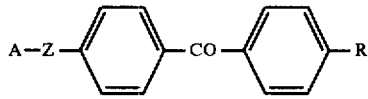

wherein A is the formula:

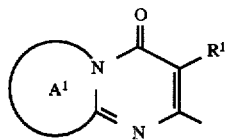

wherein $A^1$ is pyridine ring or piperidine ring which may be substituted with methyl and $R^1$ is methyl; Z is —O—CH$_2$; R is halogen, $C_{1-6}$ alkyl, halo-$C_{1-6}$ alkyl, $C_{1-6}$ alkoxy, or halo-$C_{1-6}$ alkoxy, or a salt thereof.

2. 3-Methyl-2-[4-(4-trifluoromethylbenzoyl)benzyloxy]-6,7,8,9-tetrahydro-4H-pyrido[1,2-a]pyrimidin-4-one, or a salt thereof.

3. A process for producing a compound of claim 1, which comprises reacting:

a) A—Y$^n$, or a salt thereof with Y—Ph—CO—Ph—R, or a salt thereof, b) A—X, or a salt thereof with HZ—Ph—CO—Ph—R, or a salt thereof, c) A$^a$, or a salt thereof with A$^b$—Z—Ph—CO—Ph—R, or a salt thereof, or d) A—Z—Ph—H, or a salt thereof with X—CO—Ph—R, or a salt thereof, wherein Y and Y$^a$ react to form a divalent group represented by Z in claim 1; A$^a$ and A$^b$ are, taken together, an optionally substituted condensed ring represented by A; Ph is 4-phenylene; and X is a reactive group.

4. A composition comprising compound according to claim 1 and a pharmaceutically acceptable carrier.

5. Method for treating a tumor in mammals which comprises administrating to a subject in need an effective amound of a compound according to claim 1.

6. A method for the manufacture of a medicament for the treatment of a tumor comprising the steps of selecting a compound according to claim 1 and blending said compound with a pharmaceutically acceptable excipient.

* * * * *

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

Page 1 of 15

It is certified that error appears in the above-identified patent and that said Letters Patent is hereby corrected as shown below:

[57] ABSTRACT

Line 2, "A—Z—Ar$^1$1'CO—Ar$^2$" should read --A—Z—Ar$^1$—CO—Ar$^2$

COLUMN 1

Line 15, "postperative" should read --postoperative--.
Line 33, "denvatives" should read --derivatives--.
Line 39, "is described" should be deleted.
Line 63, "-agents" should read --agents--.

COLUMN 3

Line 45, "consisiting" should read --consisting--.

COLUMN 4

Line 41, "A$^2$" should read --A$^1$--.
Line 65, "R" should read --R$^1$--.

COLUMN 5

Line 48, "AR$^2$1'" should read --AR$^2$--.
Line 60, "A$^2$" should read --A$^1$--.

UNITED STATES PATENT AND TRADEMARK OFFICE
CERTIFICATE OF CORRECTION

PATENT NO. : 5,753,664
DATED : May 19, 1998
INVENTOR(S): TETSUYA AONO ET AL.

Page 2 of 15

It is certified that error appears in the above-identified patent and that said Letters Patent is hereby corrected as shown below:

COLUMN 6

Line 41, "Za" should read --$Z^a$--.

COLUMN 8

Line 24, "(R" should read --$(R^3$--.
Line 38, "$C_{7-14}$ aralkyl," should read
--$C_{7-4}$ aralkyl,--.
Line 52, "$A^2$" should read --$A^1$--.
Line 58, " 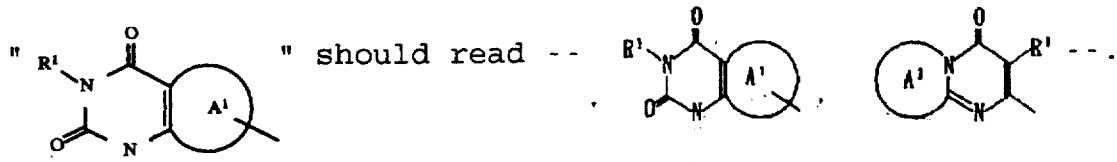 " should read --

COLUMN 9

Line 23, "D-Alk-E-Ar1-CO-Ar$^2$" should read
--D-Alk-E-$Ar^1$-CO-$Ar^2$--.
Line 59, "amound" should read --amount--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 10

Line 12, ".1" should read --1--.
Line 21, "includes" should read --include--.
Line 38, "pyrido[1,2-*a]" should read
    --pyrido[1,2-a]--.
Line 58-59, "can be used the same one" should read
    --are the same as--.
Line 61, "includes" should read --include--.

COLUMN 11

Line 6, "pyrimidin-one"" should read
    --pyrimidinone"--.
Line 66, "such" should read --such as--.

COLUMN 14

Line 60, "$C_{14\ 10}$ alkylthio," should read
    --$C_{1-10}$ alkylthio,--.

COLUMN 15

Line 11, "$C_{-6}$ alkyl," should read --$C_{1-6}$ alkyl,--.

COLUMN 16

Line 1, "$A^2$" should read --$A^1$--.

UNITED STATES PATENT AND TRADEMARK OFFICE
CERTIFICATE OF CORRECTION

PATENT NO. : 5,753,664
DATED : May 19, 1998
INVENTOR(S): TETSUYA AONO ET AL.

Page 4 of 15

It is certified that error appears in the above-identified patent and that said Letters Patent is hereby corrected as shown below:

COLUMN 17

Line 66, ".ring" should read --ring--.

COLUMN 18

Line 11, ".methylthio," should read --methylthio,--.
    Line 59, "contains" should read --contain--.

COLUMN 19

Line 19, "follow:" should read --follows:--.
    Line 20, "(A-2),(B-1),(C-2),(D-1)" should read
      --(A-2),(B-1),(C-2),(D-1)/--.
    Line 22, "(A-7),(B-2),(C-2),(D-1)/" should read
      --(A-7),(B-1),(C-2),(D-1)/--.
    Line 64, "B—Z—Ar—CO—Ar$^2$" should read
      --B—Z—Ar$^1$—CO—Ar$^2$--.

COLUMN 20

Line 2, "$^6$-oxopurine," should read --6-oxopurine,--.
    Line 12, "1,$^2$,$^4$-triazolo" should read --1,2,4-triazolo--.
    Line 14, "$^7$H-cyclopenta" should read --7H-cyclopenta--.
    Line 16, "pryido[3,$^4$-d]" should read --pyrido [3,4-d]--.
    Line 48, "Cl≅3" should read --$C_{1-3}$--.
    Line 58, "—Z—Arl—CO—Ar$^2$" should read ----Z—Ar$^1$—CO—Ar$^2$--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 22

Line 8, "goes" should read --go--.
   Line 35, "A" should read --$A^b$--.

COLUMN 23

Line 4, "$C_{16}$" should read --$C_{1-6}$--.
   Line 67, "hydrochloride.," should read
      --hydrochloride,--.

COLUMN 26

Line 26, "δ1.98" should read --δ: 1.98--.
   Line 40, "δ3.6" should read --δ: 3.60--.

COLUMN 27

Line 6, "δ5.76" should read --δ: 5.76--.

COLUMN 28

Line 9, "δ:5.85" should read --δ: 5.85--.
   Line 66, "H-NMR" should read --$^1$H-NMR--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 32

Line 37, "mixtrue" should read --mixture--.

COLUMN 33

Line 20, "6:" should read --$\delta$:--.

COLUMN 35

Line 7, "6:" should read --$\delta$:--.
   Line 38, "E:" should read --$\delta$:--.
   Line 50, "8:" should read --$\delta$:--.
   Line 64, "was-dissolved" should read --was dissolved--.

COLUMN 36

Line 64, "5:" should read --$\delta$:--.

COLUMN 37

Line 14, "8:" should read --$\delta$:--
   Line 59, "8:" should read --$\delta$:--

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 39

Line 17, "1.4;5" should read --1.45--.
    Line 32, "This-reaction" should read --This reaction--.
    Line 55, "$cm^{-1}$" should read --$cm^{-1}$.--.

COLUMN 40

Line 3, "8:" should read --$\delta$:--.
    Line 20, "IH-NMR" should read --$^{1}$H-NMR--.

COLUMN 41

Line 44, ",7.65" should read --7.65--.

COLUMN 42

Line 7, "8:" should read --$\delta$:--.
    Line 50, "H-NMR" should read --$^{1}$H-NMR--; and
      "6:" should read --$\delta$:--.
    Line 56, "8:" should read --$\delta$:--.

COLUMN 43

Line 7, "8:" should read --$\delta$:--.
    Line 45, "6:" should read --$\delta$:--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

Page 8 of 15

It is certified that error appears in the above-identified patent and that said Letters Patent is hereby corrected as shown below:

COLUMN 44

Line 10, "8:" should read --$\delta$:--.
    Line 31, "cm$^{-1}$" should read --cm$^{-1}$.--.
    Line 46, "6:" should read --$\delta$:--.

COLUMN 45

Line 11, "E:" should read --$\delta$:--.

COLUMN 49

Line 32, "8:" should read --$\delta$:--.

COLUMN 50

Line 63, "iN-sodium" should read --1N - sodium--.

COLUMN 51

Line 26, "(4H,m)-IR" should read --(4H,m). ¶IR--.

COLUMN 52

Line 39, "8:" should read --$\delta$:--.
    Line 54, "4,41-thiobis" should read --4,4'-thiobis--.
    Line 61, "(0.405g)" should read --(0.405g).--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 53

Line 64, "1H-NMR" should read --$^1$H-NMR--; and "6:" should read --$\delta$:--.

COLUMN 57

Line 49, "1H-NMR" should read --$^1$H-NMR--.

COLUMN 58

Line 8, "$^2$H-NMR" should read --$^1$H-NMR--.

COLUMN 62

Line 8, "(1H,s)" should read --1H,s).--.

COLUMN 64

Line 20, "E:" should read --$\delta$:--.

COLUMN 66

Line 20, "n-hexaneethyl" should read --n-hexane: ethyl--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 67

Line 3, "n-hexaneethyl" should read
      --n-hexane: ethyl--.
    Line 5, "n-hexanediethyl" should read
      --n-hexane-diethyl--.
    Line 42, "n-hexanediethyl" should read
      --n-hexane-diethyl--.
    Line 60, "2-thione," should read --2-thione--.

COLUMN 70

Line 10, "1:5.6-1:2.3)" should read
      --1:5.6→1:2.3)--.
    Line 33, "1:5.6-1:2.3)" should read
      --1:5.6→1:2.3)--.

COLUMN 72

Line 15, "1:4—1:1-" should read --1:4→1:1→--.
    Line 35, (hexaneethyl" should read --hexane-ethyl--;
      and "4:1—3:2)" should read --4:1→3:2)--.
    Line 44, "pyrrole" should read --pyrrolo--.

COLUMN 73

Line 11, "1:49-ethanol" should read --1:49→ethanol--.
    Line 12, "1:19-1:9)" should read --1:19→1:9)--.
    Line 37, "chloroform-ethanol:" should read
      --chloroform→ethanol:--.

UNITED STATES PATENT AND TRADEMARK OFFICE
CERTIFICATE OF CORRECTION

PATENT NO. : 5,753,664
DATED : May 19, 1998
INVENTOR(S) : TETSUYA AONO ET AL.

It is certified that error appears in the above-identified patent and that said Letters Patent is hereby corrected as shown below:

COLUMN 74

Line 7, "1:0-9:1)" should read --1:0→9:1)--.
　　Line 26, "1:0-9:1;" should read --1:0→9:1;--

COLUMN 81

Line 18, "(1.235g)" should read --(1.235g).--

COLUMN 89

Line 34, "-7-yl)" should read ---7-yl)---.

COLUMN 90

Line 42, "(4-phenylpiperazinylmethyl)" should read
　　　--(4-phenylpiperazinylmethyl)---.

COLUMN 91

Line 21, "fro" should read --for--.
　　Line 34, "(4-piperidinopiperidinyl)" should read
　　　--(4-piperidinopiperidinyl)---.

COLUMN 95

Line 11, "(2H,d,J=8.4 Hz)" should read --2H,d,J=8.4Hz),--.

UNITED STATES PATENT AND TRADEMARK OFFICE
CERTIFICATE OF CORRECTION

PATENT NO. : 5,753,664

DATED : May 19, 1998

INVENTOR(S) : TETSUYA AONO ET AL.

It is certified that error appears in the above-identified patent and that said Letters Patent is hereby corrected as shown below:

COLUMN 102

Line 13, "butoxycarbonyhmethyl)" should read --butoxycarbonylmethyl)--.

COLUMN 107

Line 14, "900C" should read --90°C--.

COLUMN 114

Line 23, "(CDC13)" should read --(CDCl$_3$)--.

COLUMN 115

Line 35, "6:" should read --δ:--.
    Line 53, "6:" should read --δ:--.

COLUMN 116

Line 46, "6:" should read --δ:--.

COLUMN 118

Line 14, "6;" should read --δ:--.

COLUMN 123

Line 36, "=1:4-3:7)" should read --=1:4→3:7)--.

UNITED STATES PATENT AND TRADEMARK OFFICE
CERTIFICATE OF CORRECTION

PATENT NO. : 5,753,664

DATED : May 19, 1998

INVENTOR(S) : TETSUYA AONO ET AL.

Page 13 of 15

It is certified that error appears in the above-identified patent and that said Letters Patent is hereby corrected as shown below:

COLUMN 124

Line 16, "5:" should read --$\delta$:--.
    Line 63, "=4:1-3:2)" should read --=4:1$\rightarrow$3:2)--.

COLUMN 125

Line 19, "=4:1-3:2)" should read --=4:1$\rightarrow$3:2)--.

COLUMN 127

Line 33, "NaHCO3" should read --$NaHCO_3$--.

COLUMN 131

Line 39, "5:" should read --$\delta$:--.

COLUMN 132

Line 7, "5:" should read --$\delta$:--.

COLUMN 134

Line 21, "($CDCl_3$):" should read --($CDCl_3$)--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

COLUMN 135

Line 9, "(CDCl$_3$):8" should read --(CDCl$_3$) δ:--.

COLUMN 137

Line 24, "(st3H)," should read --(s,3H),--.

COLUMN 138

Line 23, "one3" should read --one-3--.
Line 64, "quinazotinone- 3" should read
    --quinazolinone-3--.

COLUMN 153

Line 63, "Dinethyl" should read --Dimethyl--.

COLUMN 159

Line 19, "5:" should read δ:--.
Line 54, "5:" should read δ:--.

COLUMN 164

Line 24, "ᵃmean±SD" should read --a:mean±SD--.
Line 57, "diameter)2" should read --diameter)$^2$--.

UNITED STATES PATENT AND TRADEMARK OFFICE
CERTIFICATE OF CORRECTION

PATENT NO. : 5,753,664

DATED : May 19, 1998

INVENTOR(S): TETSUYA AONO ET AL.

It is certified that error appears in the above-identified patent and that said Letters Patent is hereby corrected as shown below:

<u>COLUMN 165</u>

Line 9, "$^a$mean±SD" should read --a:mean±SD--.
Line 53, "$^a$mean±SD" should read --a:mean±SD--.

<u>COLUMN 166</u>

Line 35, "a)A-Y$^n$," should read --a)A-Y$^a$,--.
Line 53, "amound" should read --amount--.

Signed and Sealed this

Tenth Day of August, 1999

Attest:

*Attesting Officer*

Q. TODD DICKINSON

*Acting Commissioner of Patents and Trademarks*